US012735481B2

(12) United States Patent
Chongyang Li et al.

(10) Patent No.: US 12,735,481 B2
(45) Date of Patent: Sep. 15, 2026

(54) BISPECIFIC ANTIBODIES WITH ALTERNATIVELY MATCHED INTERCHAIN CYSTEINES AND USES THEREOF

(71) Applicant: Phanes Therapeutics, Inc., San Diego, CA (US)

(72) Inventors: Jack Chongyang Li, San Diego, CA (US); Minghan Wang, San Diego, CA (US); Hui Zou, Hinsdale, IL (US); Haiqun Jia, San Diego, CA (US)

(73) Assignee: Phanes Therapeutics, Inc., San Diego, CA (US)

( * ) Notice: Subject to any disclaimer, the term of this patent is extended or adjusted under 35 U.S.C. 154(b) by 930 days.

(21) Appl. No.: 17/755,742

(22) PCT Filed: Dec. 3, 2020

(86) PCT No.: PCT/US2020/063066

§ 371 (c)(1),
(2) Date: May 6, 2022

(87) PCT Pub. No.: WO2021/126538

PCT Pub. Date: Jun. 24, 2021

(65) Prior Publication Data

US 2022/0411497 A1 Dec. 29, 2022

Related U.S. Application Data

(60) Provisional application No. 62/706,511, filed on Aug. 21, 2020, provisional application No. 62/704,973, filed on Jun. 5, 2020, provisional application No. 63/007,996, filed on Apr. 10, 2020, provisional application No. 62/988,144, filed on Mar. 11, 2020, provisional application No. 62/952,747, filed on Dec. 23, 2019, provisional application No. 62/948,953, filed on Dec. 17, 2019.

(51) Int. Cl.

| | |
|---|---|
| ***C07K 16/28*** | (2006.01) |
| ***A61P 35/00*** | (2006.01) |
| ***C12N 15/63*** | (2006.01) |

(52) U.S. Cl.

CPC .......... *C07K 16/2803* (2013.01); *A61P 35/00* (2018.01); *C12N 15/63* (2013.01); *C07K 2317/24* (2013.01); *C07K 2317/31* (2013.01); *C07K 2317/522* (2013.01); *C07K 2317/56* (2013.01)

(58) Field of Classification Search

CPC ............ C07K 16/2803; C07K 2317/24; C07K 2317/31; C07K 2317/522; C07K 2317/56; C07K 16/00; C07K 2317/52; C07K 16/28; A61P 35/00; C12N 15/63; A61K 2039/505

See application file for complete search history.

(56) References Cited

U.S. PATENT DOCUMENTS

| | | | | |
|---|---|---|---|---|
| 9,527,927 | B2 | 12/2016 | Chowdhury | |
| 10,344,099 | B2 | 7/2019 | Enami | |
| 11,214,615 | B2 * | 1/2022 | Wang | A61K 39/001111 |
| 11,299,550 | B2 * | 4/2022 | Wang | A61P 35/00 |
| 11,306,151 | B2 * | 4/2022 | Wang | G01N 33/57492 |
| 11,365,242 | B2 * | 6/2022 | Wang | G01N 33/74 |
| 11,390,679 | B2 * | 7/2022 | Wang | G01N 33/577 |
| 11,401,329 | B2 * | 8/2022 | Wang | A61P 35/00 |
| 11,873,335 | B2 * | 1/2024 | Wang | C07K 16/28 |
| 12,037,391 | B2 * | 7/2024 | Wang | A61P 37/02 |
| 2009/0182127 | A1 | 7/2009 | Kjaergaard | |
| 2010/0015133 | A1 | 1/2010 | Igawa | |
| 2010/0028637 | A1 | 2/2010 | Tavsanli | |
| 2011/0123532 | A1 | 5/2011 | Gurney | |
| 2012/0149876 | A1 | 6/2012 | Von Kreudenstein | |
| 2013/0195849 | A1 | 8/2013 | Spreter Von Kreudenstein | |
| 2014/0303354 | A1 | 10/2014 | Masternak | |
| 2017/0037130 | A1 * | 2/2017 | Raum | A61K 39/39558 |
| 2018/0177873 | A1 * | 6/2018 | Carter | G16B 20/50 |
| 2018/0355065 | A1 | 12/2018 | Masternak | |
| 2019/0248899 | A1 | 8/2019 | Yan | |

FOREIGN PATENT DOCUMENTS

| | | | | |
|---|---|---|---|---|
| EP | 2915819 | | 9/2015 | |
| JP | 2019530434 | A | 10/2019 | |
| WO | 2006028936 | | 3/2006 | |
| WO | 2011131746 | | 10/2011 | |
| WO | WO-2017205014 | A1 * | 11/2017 | C07K 16/2818 |
| WO | 2018027204 | A1 | 2/2018 | |

(Continued)

OTHER PUBLICATIONS

Dall'Acqua et al. "Antibody humanization by framework shuffling" Methods 2005; 36:43-60 (Year: 2005).*

Almagro and Fransson "Humanization of antibodies" Frontiers in Bioscience 2008; 13:1619-33). (Year: 2008).*

Briney et al. "Commonality despite exceptional diversity in the baseline human antibody repertoire" Nature 2019; 566: 393-397. (Year: 2019).*

Avanzino et al. "A T-cell engaging bispecific antibody with a tumor-selective bivalent folate receptor alpha binding arm for the treatment of ovarian cancer." Oncoimmunology 2022, 11, 1; e2113697, 1-12 (Year: 2022).*

(Continued)

*Primary Examiner* — Misook Yu
*Assistant Examiner* — Grace H Lunde
(74) *Attorney, Agent, or Firm* — Ice Miller LLP

(57) ABSTRACT

Engineered bispecific antibodies with shifted interchain disulfide bond on one arm while maintaining the native interchain disulfide bond on the second arm are described. Also described are anti-CD47/FRα bispecific antibodies and antigen-binding fragments thereof. Also described are nucleic acids encoding the antibodies, compositions comprising the antibodies, and methods of producing the antibodies and using the antibodies for treating or preventing diseases, such as cancer and/or associated complications.

19 Claims, 105 Drawing Sheets

Specification includes a Sequence Listing.

(56) References Cited

FOREIGN PATENT DOCUMENTS

| | | |
|---|---|---|
| WO | 2019040791 | 2/2019 |
| WO | 2019177854 | 9/2019 |
| WO | 2019178539 | 9/2019 |
| WO | 2019183406 | 9/2019 |
| WO | 2019196522 | 10/2019 |
| WO | 2019204398 | 10/2019 |
| WO | 2019217145 | 11/2019 |
| WO | 2020102647 | 5/2020 |
| WO | 2021126538 | 6/2021 |

OTHER PUBLICATIONS

Nagai et al. "Advances in the study of CD47-based bispecific antibody in cancer immunotherapy." Monoclonal Antibodies Immunodiagn. Immunother. 2015 34, 3; 181-190). (Year: 2015).*

Piccione et al. "A bispecific antibody targeting CD47 and CD20 selectively binds and eliminates dual antigen expressing lymphoma cells." mAbs 2015 7:5, 946-956 (Year: 2015).*

Zhang et al. "Advances in the study of CD47-based bispecific antibody in cancer immunotherapy." Immunology 2022, 167; 15-27 (Year: 2022).*

Boogerd, Leonora S.F., et al., "Concordance of folate receptor-a expression between biopsy, primary tumor and metastasis in breast cancer and lung cancer patients", Oncotarget, vol. 7, No. 14, 2016, 17442-17454.

Cheung, Anthony et al., "Targeting folate receptor alpha for cancer treatment", Oncotarget, vol. 7, No. 32, 2016, 52553-52574.

International Preliminary Report on Patentability issued in App. No. PCT/US20/63066, mailing date May 17, 2022, 9 pages.

International Search Report and Written Opinion issued in App. No. PCT/US20/63066, mailing date Apr. 22, 2021, 13 pages.

Merchant, Margaret A. , et al. "An efficient route to human bispecific IgG," Nature Biotechnology, vol. 16, Jul. 1998, pp. 677-681.

Salazar, Marcela D'Alincourt et al. "The folate receptor: What does it promise in tissue-targeted therapeutics?," Cancer Metastasis, vol. 26, 2007, pp. 141-152.

Toffoli, Giuseppe et al., "Overexpression of folate binding protein in ovarian cancers", Int J Cancer, 74, 1997, 193-198.

Weitman, Steven D., et al., "Distribution of the Folate Receptor GP38 in Normal and Malignant Cell Lines and Tissues", Cancer Res 52, 1992, 3396-3401.

* cited by examiner

| Region | FR1 | | | | | | | | | | | | | | | | | | | | | | |
|---|---|---|---|---|---|---|---|---|---|---|---|---|---|---|---|---|---|---|---|---|---|---|---|
| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| mAb 1 | Q | V | Q | L | V | Q | S | G | A | E | V | K | K | P | G | A | S | V | K | V | S | C | K | A |
| mAb 2 | E | V | Q | L | V | E | T | G | G | G | L | I | Q | P | G | G | S | L | R | L | S | C | A | A |

| Region | FR1 | | | | | | CDR1 | | | | | FR2 | | | | | | | | | | | | |
|---|---|---|---|---|---|---|---|---|---|---|---|---|---|---|---|---|---|---|---|---|---|---|---|---|
| Kabat number | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 |
| mAb 1 | S | G | Y | T | F | T | S | Y | W | M | H | W | V | R | Q | A | P | G | Q | G | L | E | W | I |
| mAb 2 | S | G | F | T | F | S | D | F | G | M | H | W | I | R | Q | A | P | G | K | G | L | E | W | V |

| Region | FR2 | CDR2 | | | | | | | | | | | | | | | | FR3 | | | | | |
|---|---|---|---|---|---|---|---|---|---|---|---|---|---|---|---|---|---|---|---|---|---|---|---|
| Kabat number | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 |
| mAb 1 | G | N | I | D | P | S | D | S | E | T | H | Y | A | Q | K | F | Q | G | R | V | T | L | T | V |
| mAb 2 | A | Y | M | S | Y | T | P | G | T | F | H | Y | A | D | T | V | K | D | R | F | T | I | S | R |

| Region | FR3 | | | | | | | | | | | | | | | | | | | | | | |
|---|---|---|---|---|---|---|---|---|---|---|---|---|---|---|---|---|---|---|---|---|---|---|---|
| Kabat number | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 |
| mAb 1 | D | K | S | T | S | T | V | Y | M | E | L | S | S | L | R | S | E | D | T | A | V | Y | Y | C |
| mAb 2 | D | N | S | K | N | T | L | Y | L | Q | M | N | S | L | R | A | E | D | T | A | V | Y | Y | C |

| Region | FR3 | | CDR3 | | | | | | | | FR4 | | | | | | | | | | |
|---|---|---|---|---|---|---|---|---|---|---|---|---|---|---|---|---|---|---|---|---|---|
| Kabat number | 93 | 94 | 95 | 96 | 97 | 98 | 99 | 100 | 101 | 102 | 103 | 104 | 105 | 106 | 107 | 108 | 109 | 110 | 111 | 112 | 113 |
| mAb 1 | A | G | T | D | L | - | - | - | A | Y | W | G | Q | G | T | L | V | T | V | S | S |
| mAb 2 | A | R | V | H | V | G | T | V | D | Y | W | G | Q | G | T | L | V | T | V | S | S |

FIG. 2A

| Region | CH1 | | | | | | | | | | | | | | | | | | | | | | | |
|---|---|---|---|---|---|---|---|---|---|---|---|---|---|---|---|---|---|---|---|---|---|---|---|---|
| EU number | 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 |
| mAb 1 | A | S | T | K | G | P | S | V | F | P | L | A | P | S | S | K | S | T | S | G | G | T | A | A |
| mAB 2 | A | S | T | K | G | P | S | V | F | P | L | A | P | S | S | K | S | T | S | G | G | T | A | A |

| Region | CH1 | | | | | | | | | | | | | | | | | | | | | | | |
|---|---|---|---|---|---|---|---|---|---|---|---|---|---|---|---|---|---|---|---|---|---|---|---|---|
| EU number | 142 | 143 | 144 | 145 | 146 | 147 | 148 | 149 | 150 | 151 | 152 | 153 | 154 | 155 | 156 | 157 | 158 | 159 | 160 | 161 | 162 | 163 | 164 | 165 |
| mAb 1 | L | G | C | L | V | K | D | Y | F | P | E | P | V | T | V | S | W | N | S | G | A | L | T | S |
| mAb 2 | L | G | C | L | V | K | D | Y | F | P | E | P | V | T | V | S | W | N | S | G | A | L | T | S |

| Region | CH1 | | | | | | | | | | | | | | | | | | | | | | | |
|---|---|---|---|---|---|---|---|---|---|---|---|---|---|---|---|---|---|---|---|---|---|---|---|---|
| EU number | 166 | 167 | 168 | 169 | 170 | 171 | 172 | 173 | 174 | 175 | 176 | 177 | 178 | 179 | 180 | 181 | 182 | 183 | 184 | 185 | 186 | 187 | 188 | 189 |
| mAb 1 | G | V | H | T | F | P | A | V | L | Q | S | S | G | L | Y | S | L | S | S | V | V | T | V | P |
| mAb 2 | G | V | H | T | F | P | A | V | L | Q | S | S | G | L | Y | S | L | S | S | V | V | T | V | P |

| Region | CH1 | | | | | | | | | | | | | | | | | | | | | | | |
|---|---|---|---|---|---|---|---|---|---|---|---|---|---|---|---|---|---|---|---|---|---|---|---|---|
| EU number | 190 | 191 | 192 | 193 | 194 | 195 | 196 | 197 | 198 | 199 | 200 | 201 | 202 | 203 | 204 | 205 | 206 | 207 | 208 | 209 | 210 | 211 | 212 | 213 |
| mAb 1 | S | S | S | L | G | T | Q | T | Y | I | C | N | V | N | H | K | P | S | N | T | K | V | D | K |
| mAb 2 | S | S | S | L | G | T | Q | T | Y | I | C | N | V | N | H | K | P | S | N | T | K | V | D | K |

| Region | CH1 | | | | | | |
|---|---|---|---|---|---|---|---|
| EU number | 214 | 215 | 216 | 217 | 218 | 219 | 220 |
| mAb 1 | K* | V | E | P | K | S | C |
| mAb 2 | K* | V | E | P | K | S | C |

FIG. 2B

| Region | FR1 | | | | | | | | | | | | | | | | | | | | | | CDR1 |
|---|---|---|---|---|---|---|---|---|---|---|---|---|---|---|---|---|---|---|---|---|---|---|---|
| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| mAb 1 | E | I | V | L | T | Q | S | P | G | T | L | S | L | S | P | G | E | R | A | T | L | S | C | H |
| mAb 2 | E | V | V | L | T | Q | S | P | A | T | L | S | L | S | P | G | E | R | A | T | L | S | C | R |

| Region | CDR1 | | | | | | | | | | FR2 | | | | | | | | | | | | | |
|---|---|---|---|---|---|---|---|---|---|---|---|---|---|---|---|---|---|---|---|---|---|---|---|---|
| Kabat number | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 |
| mAb 1 | A | S | Q | N | I | N | V | W | L | S | W | Y | Q | Q | K | P | G | Q | A | P | R | L | L | I |
| mAb 2 | A | S | Q | N | I | N | N | N | L | H | W | F | Q | Q | K | P | G | Q | A | P | R | L | L | I |

| Region | CRD2 | CDR2 | | | | | | | FR3 | | | | | | | | | | | | | | | |
|---|---|---|---|---|---|---|---|---|---|---|---|---|---|---|---|---|---|---|---|---|---|---|---|---|
| Kabat number | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 |
| mAb 1 | Y | K | A | S | N | L | H | T | G | I | P | D | R | F | S | G | S | G | S | G | T | D | F | T |
| mAb 2 | K | Y | A | S | Q | S | I | S | G | I | P | A | R | F | S | G | S | G | S | G | T | D | F | T |

| Region | FR3 | | | | | | | | | | | | | | | | CDR3 | | | | | | | |
|---|---|---|---|---|---|---|---|---|---|---|---|---|---|---|---|---|---|---|---|---|---|---|---|---|
| Kabat number | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 95a |
| mAb 1 | L | T | I | S | R | L | E | P | E | D | F | A | V | Y | Y | C | Q | Q | G | Q | S | Y | P | - |
| mAb 2 | L | T | I | S | S | L | E | P | E | D | F | A | V | Y | F | C | Q | Q | S | N | S | W | P | A |

| Region | CDR3 | | FR4 | | | | | | | | | |
|---|---|---|---|---|---|---|---|---|---|---|---|---|
| Kabat number | 96 | 97 | 98 | 99 | 100 | 101 | 102 | 103 | 104 | 105 | 106 | 107 |
| mAb 1 | F | T | F | G | Q | G | T | K | V | E | I | K |
| mAb 2 | L | T | F | G | Q | G | T | K | V | E | I | K |

FIG. 2C

| Region | CL | | | | | | | | | | | | | | | | | | | | | | |
|---|---|---|---|---|---|---|---|---|---|---|---|---|---|---|---|---|---|---|---|---|---|---|---|
| EU number | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 | 131 |
| mAb 1 | R | T | V | A | A | P | S | V | F | I | F | P | P | S | D | E | Q | L | K | S | G | T | A | S |
| mAb 2 | R | T | V | A | A | P | S | V | F | I | F | P | P | S | D | E | Q | L | K | S | G | T | A | S |

| Region | CL | | | | | | | | | | | | | | | | | | | | | | |
|---|---|---|---|---|---|---|---|---|---|---|---|---|---|---|---|---|---|---|---|---|---|---|---|
| EU number | 132 | 133 | 134 | 135 | 136 | 137 | 138 | 139 | 140 | 141 | 142 | 143 | 144 | 145 | 146 | 147 | 148 | 149 | 150 | 151 | 152 | 153 | 154 | 155 |
| mAb 1 | V | V | C | L | L | N | N | F | Y | P | R | E | A | K | V | Q | W | K | V | D | N | A* | L | Q |
| mAb 2 | V | V | C | L | L | N | N | F | Y | P | R | E | A | K | V | Q | W | K | V | D | N | A* | L | Q |

| Region | CL | | | | | | | | | | | | | | | | | | | | | | |
|---|---|---|---|---|---|---|---|---|---|---|---|---|---|---|---|---|---|---|---|---|---|---|---|
| EU number | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
| mAb 1 | S | G | N | S | Q | E | S | V | T | E | Q | D | S | K | D | S | T | Y | S | L | S | S | T | L |
| mAb 2 | S | G | N | S | Q | E | S | V | T | E | Q | D | S | K | D | S | T | Y | S | L | S | S | T | L |

| Region | CL | | | | | | | | | | | | | | | | | | | | | | |
|---|---|---|---|---|---|---|---|---|---|---|---|---|---|---|---|---|---|---|---|---|---|---|---|
| EU number | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 |
| mAb 1 | T | L | S | K | A | D | Y | E | K | H | K | V* | Y | A | C | E | V | T | H | Q | G | L | S | S |
| mAb 2 | T | L | S | K | A | D | Y | E | K | H | K | V* | Y | A | C | E | V | T | H | Q | G | L | S | S |

| Region | CL | | | | | | | | | | |
|---|---|---|---|---|---|---|---|---|---|---|---|
| EU number | 204 | 205 | 206 | 207 | 208 | 209 | 210 | 211 | 212 | 213 | 214 |
| mAb 1 | P | V | T | K | S | F | N | R | G | E | C |
| mAb 2 | P | V | T | K | S | F | N | R | G | E | C |

FIG. 2D

| Region | CH1 | | | | | | | | | | | | | | | | | | | | | | |
|---|---|---|---|---|---|---|---|---|---|---|---|---|---|---|---|---|---|---|---|---|---|---|---|
| EU number | 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 |
| IgG2 | A | S | T | K | G | P | S | V | F | P | L | A | P | C | S | R | S | T | S | E | S | T | A | A |
| IgG3 | A | S | T | K | G | P | S | V | F | P | L | A | P | C | S | R | S | T | S | G | G | T | A | A |
| IgG4 | A | S | T | K | G | P | S | V | F | P | L | A | P | C | S | R | S | T | S | E | S | T | A | A |

| EU number | 142 | 143 | 144 | 145 | 146 | 147 | 148 | 149 | 150 | 151 | 152 | 153 | 154 | 155 | 156 | 157 | 158 | 159 | 160 | 161 | 162 | 163 | 164 | 165 |
|---|---|---|---|---|---|---|---|---|---|---|---|---|---|---|---|---|---|---|---|---|---|---|---|---|
| IgG2 | L | G | C | L | V | K | D | Y | F | P | E | P | V | T | V | S | W | N | S | G | A | L | T | S |
| IgG3 | L | G | C | L | V | K | D | Y | F | P | E | P | V | T | V | S | W | N | S | G | A | L | T | S |
| IgG4 | L | G | C | L | V | K | D | Y | F | P | E | P | V | T | V | S | W | N | S | G | A | L | T | S |

| Region | CH1 | | | | | | | | | | | | | | | | | | | | | | |
|---|---|---|---|---|---|---|---|---|---|---|---|---|---|---|---|---|---|---|---|---|---|---|---|
| EU number | 166 | 167 | 168 | 169 | 170 | 171 | 172 | 173 | 174 | 175 | 176 | 177 | 178 | 179 | 180 | 181 | 182 | 183 | 184 | 185 | 186 | 187 | 188 | 189 |
| IgG2 | G | V | H | T | F | P | A | V | L | Q | S | S | G | L | Y | S | L | S | S | V | V | T | V | P* |
| IgG3 | G | V | H | T | F | P | A | V | L | Q | S* | S | G | L | Y | S | L | S | S | V | V | T | V | P |
| IgG4 | G | V | H | T | F | P | A | V | L | Q | S | S | G | L | Y | S | L | S | S | V | V | T | V | P |

| Region | CH1 | | | | | | | | | | | | | | | | | | | | | | |
|---|---|---|---|---|---|---|---|---|---|---|---|---|---|---|---|---|---|---|---|---|---|---|---|
| EU number | 190 | 191 | 192 | 193 | 194 | 195 | 196 | 197 | 198 | 199 | 200 | 201 | 202 | 203 | 204 | 205 | 206 | 207 | 208 | 209 | 210 | 211 | 212 | 213 |
| IgG2 | S | S | N* | F* | G | T | Q | T | Y | T | C | N | V | D | H | K | P | S | N | T | K | V | D | K |
| IgG3 | S | S | S* | L* | G | T | Q | T | Y | T | C | N | V | N | H | K | P | S | N | T | K | V | D | K |
| IgG4 | S | S | S | L | G | T | K | T | Y | T | C | N | V | D | H | K | P | S | N | T | K | V | D | K |

| Region | CH1 | | | | | | | |
|---|---|---|---|---|---|---|---|---|
| EU number | 214 | 215 | 216 | 217 | 218 | | | 219 | 220 |
| IgG2 | T | V | E | R | K | | | C | C |
| IgG3 | R | V | E | L | K | T | P | L | G |
| IgG4 | R | V | E | S | K | Y | G | | |

FIG. 2E

| Region | CL | | | | | | | | | | | | | | | | | | | | | | | |
|---|---|---|---|---|---|---|---|---|---|---|---|---|---|---|---|---|---|---|---|---|---|---|---|---|
| EU number | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 | 131 |
| Lambda CL | Q | P | K | A | A* | P | S* | V | T | L | F | P | P | S | S | E | E | L | Q | A | N | K | A | T |

| Region | CL | | | | | | | | | | | | | | | | | | | | | | | |
|---|---|---|---|---|---|---|---|---|---|---|---|---|---|---|---|---|---|---|---|---|---|---|---|---|
| EU number | 132 | 133 | 134 | 135 | 136 | 137 | 138 | 139 | 140 | 141 | 142 | 143 | 144 | 145 | 146 | 147 | 148 | 149 | 150 | 151 | 152 | 153 | | 154 |
| Lambda CL | L | V | C | L | I | S | D | F | Y | P | G | A | V | T | V | A | W | K | A | D | S* | S | P | V |

| Region | CL | | | | | | | | | | | | | | | | | | | | | | | |
|---|---|---|---|---|---|---|---|---|---|---|---|---|---|---|---|---|---|---|---|---|---|---|---|---|
| EU number | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 |
| Lambda CL | K | A | G | | | V | E | T | T | T* | P | S | K | Q | S | N | N | K | Y | A | A | S | S | Y |

| Region | CL | | | | | | | | | | | | | | | | | | | | | | | |
|---|---|---|---|---|---|---|---|---|---|---|---|---|---|---|---|---|---|---|---|---|---|---|---|---|
| EU number | 179 | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 |
| Lambda CL | L | S | L | T | P | E | Q | W | K | S | H | R* | S | Y | S | C | Q | V | T | H | E | G | | |

| Region | CL | | | | | | | | | | | |
|---|---|---|---|---|---|---|---|---|---|---|---|---|
| EU number | 203 | 204 | 205 | 206 | 207 | 208 | 209 | 210 | 211 | 212 | 213 | 214 |
| Lambda CL | S | T | V | E | K | T | V | A | P | T | E | C |

FIG. 2F

Mutant mAb with bsAb 12 design
Reducing
mAU
Time [min]

Mutant mAb with bsAb 12 design
Non-reducing
mAU
Time [min]

| Temperature | % HMW | % MMW | % LMW |
|---|---|---|---|
| 55°C | 0 | 100 | 0 |
| 60°C | 0 | 100 | 0 |
| 65°C | 3.95 | 96.05 | 0 |
| 70°C | 45.91 | 54.09 | 0 |
| 75°C | 93.87 | 4.48 | 1.65 |

| Temperature | % HMW | % MMW | % LMW |
|---|---|---|---|
| 55°C | 0 | 99.14 | 0.86 |
| 60°C | 0 | 100 | 0 |
| 65°C | 19.56 | 80.44 | 0 |
| 70°C | 86.24 | 13.76 | 0 |
| 75°C | 90.25 | 3.25 | 6.50 |

mAU
M2 design
75°C
70°C
65°C
60°C
55°C
min

| Temperature | % HMW | % MMW | % LMW |
|---|---|---|---|
| 55°C | 0 | 100 | 0 |
| 60°C | 0 | 100 | 0 |
| 65°C | 2.37 | 97.63 | 0 |
| 70°C | 41.80 | 58.20 | 0 |
| 75°C | 91.92 | 4.93 | 3.15 |

| Temperature | % HMW | % MMW | % LMW |
|---|---|---|---|
| 55°C | 0 | 100 | 0 |
| 60°C | 0 | 100 | 0 |
| 65°C | 15.91 | 84.09 | 0 |
| 70°C | 87.01 | 10.61 | 2.38 |
| 75°C | 100 | 0 | 0 |

| Temperature | % HMW | % MMW | % LMW |
|---|---|---|---|
| 55°C | 0 | 100 | 0 |
| 60°C | 0 | 100 | 0 |
| 65°C | 0.55 | 99.45 | 0 |
| 70°C | 16.12 | 83.88 | 0 |
| 75°C | 81.11 | 18.89 | 0 |

| Temperature | % HMW | % MMW | % LMW |
|---|---|---|---|
| 55°C | 0 | 100 | 0 |
| 60°C | 1.23 | 98.77 | 0 |
| 65°C | 9.73 | 89.62 | 0.65 |
| 70°C | 38.90 | 60.64 | 0.46 |
| 75°C | 95.42 | 3.68 | 0.90 |

| Temperature | % HMW | % MMW | % LMW |
|---|---|---|---|
| 55°C | 0 | 100 | 0 |
| 60°C | 0 | 100 | 0 |
| 65°C | 0.65 | 99.35 | 0 |
| 70°C | 12.98 | 87.02 | 0 |
| 75°C | 79.93 | 19.60 | 0.47 |

| Time | % HMW | % MMW | % LMW |
|---|---|---|---|
| 0 hour | 0 | 100 | 0 |
| 1 hour | 12.97 | 87.03 | 0 |
| 3 hours | 16.62 | 83.38 | 0 |
| 5 hours | 23.15 | 76.28 | 0.57 |
| 7 hours | 25.81 | 74.19 | 0 |

| Time | % HMW | % MMW | % LMW |
|---|---|---|---|
| 0 hour | 0 | 100 | 0 |
| 1 hour | 20.60 | 79.40 | 0 |
| 3 hours | 25.97 | 73.21 | 0.82 |
| 5 hours | 31.46 | 68.54 | 0 |
| 7 hours | 34.84 | 63.59 | 1.57 |

| Time | % HMW | % MMW | % LMW |
|---|---|---|---|
| 0 hour | 0.13 | 99.80 | 0.07 |
| 1 hour | 12.42 | 87.58 | 0 |
| 3 hours | 16.93 | 83.07 | 0 |
| 5 hours | 23.16 | 76.84 | 0 |
| 7 hours | 26.09 | 72.07 | 1.84 |

| Time | % HMW | % MMW | % LMW |
|---|---|---|---|
| 0 hour | 0.15 | 99.73 | 0.12 |
| 1 hour | 12.06 | 87.94 | 0 |
| 3 hours | 15.55 | 84.45 | 0 |
| 5 hours | 18.84 | 80.13 | 1.03 |
| 7 hours | 20.51 | 79.49 | 0 |

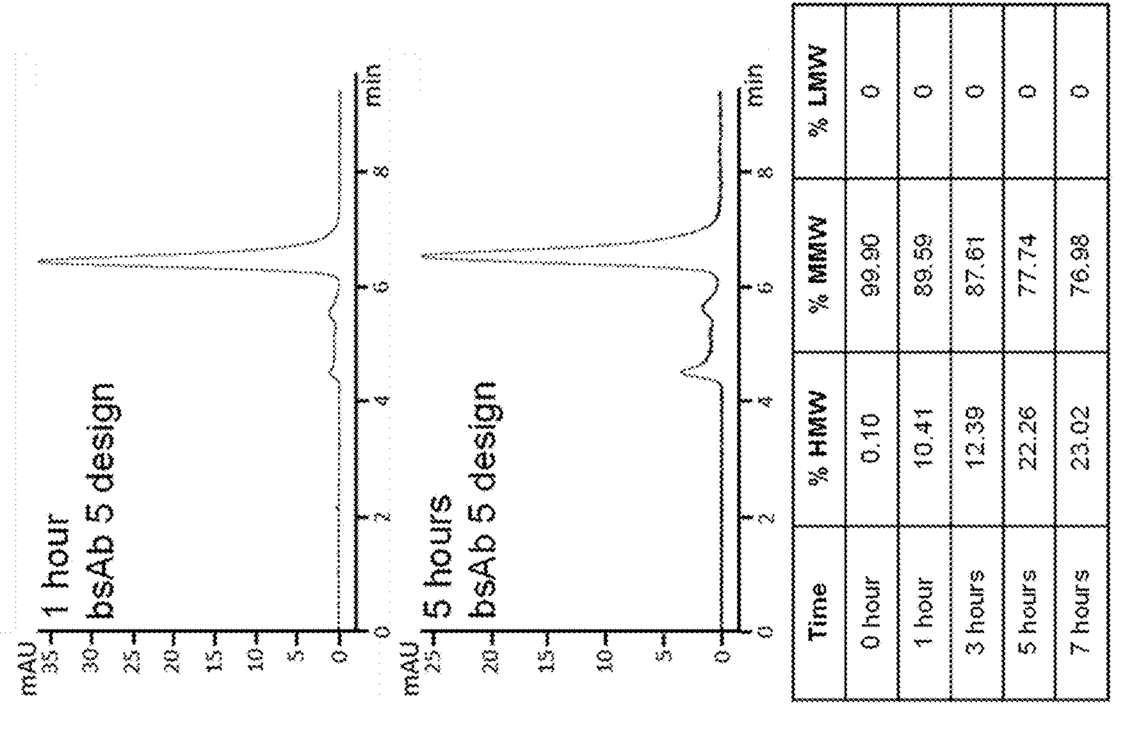
| Time | % HMW | % MMW | % LMW |
|---|---|---|---|
| 0 hour | 0.10 | 99.90 | 0 |
| 1 hour | 10.41 | 89.59 | 0 |
| 3 hours | 12.39 | 87.61 | 0 |
| 5 hours | 22.26 | 77.74 | 0 |
| 7 hours | 23.02 | 76.98 | 0 |
FIG. 6E
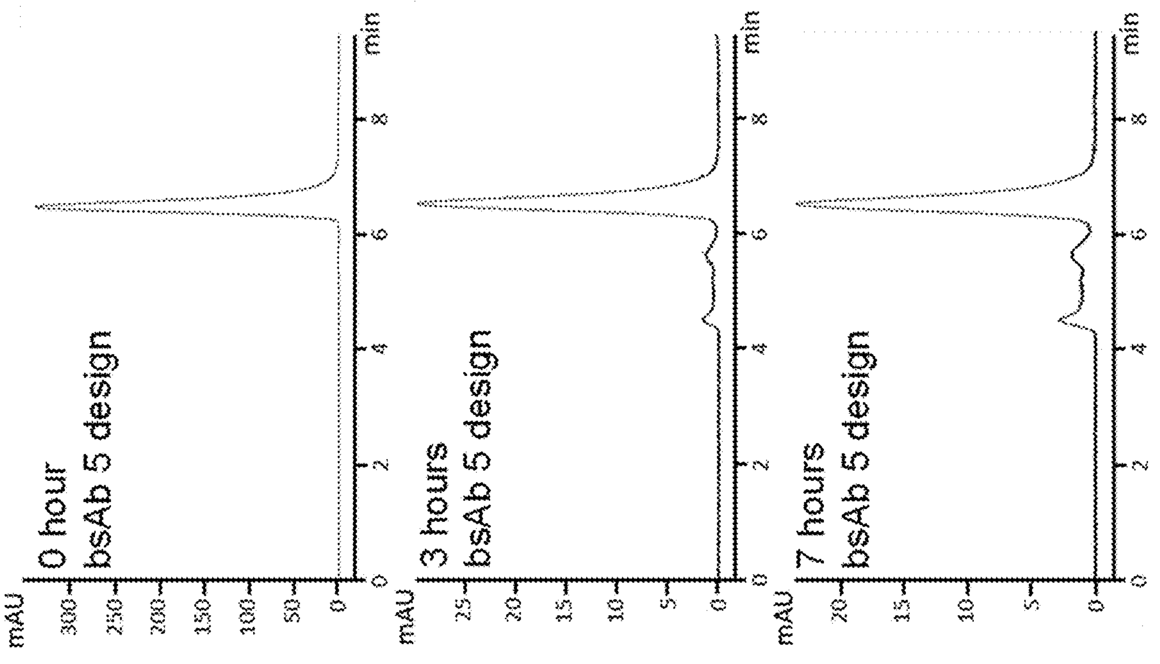

| Time | % HMW | % MMW | % LMW |
|---|---|---|---|
| 0 hour | 0 | 100 | 0 |
| 1 hour | 11.43 | 88.57 | 0 |
| 3 hours | 15.48 | 84.52 | 0 |
| 5 hours | 19.38 | 80.62 | 0 |
| 7 hours | 19.94 | 80.06 | 0 |

| Time | % HMW | % MMW | % LMW |
|---|---|---|---|
| 0 hour | 0.09 | 99.91 | 0 |
| 1 hour | 14.73 | 85.27 | 0 |
| 3 hours | 20.19 | 79.81 | 0 |
| 5 hours | 24.84 | 75.16 | 0 |
| 7 hours | 30.46 | 69.54 | 0 |

| Time | % HMW | % MMW | % LMW |
|---|---|---|---|
| 0 hour | 0.10 | 99.78 | 0.12 |
| 1 hour | 9.96 | 90.04 | 0 |
| 3 hours | 13.39 | 86.61 | 0 |
| 5 hours | 15.78 | 84.22 | 0 |
| 7 hours | 18.77 | 81.23 | 0 |

| Lane | |
|---|---|
| 1 | Markers |
| 2 | bsAb 5; non-reduced |
| 3 | bsAb 5; reduced |
| 4 | bsAb 1; non-reduced |
| 5 | bsAb 1; reduced |
| 6 | BsAb 2; reduced |
| 7 | bsAb 2; non-reduced |
| 8 | bsAb 4; reduced |
| 9 | bsAb 4; non-reduced |
| 10 | bsAb 3; reduced |
| 11 | bsAb 3; non-reduced |
| 12 | bsAb 8; reduced |
| 13 | bsAb 8; non-reduced |

| Lane | |
|---|---|
| 1 | Markers |
| 2 | bsAb 6; non-reduced |
| 3 | bsAb 6; reduced |
| 4 | bsAb 7; non-reduced |
| 5 | BsAb 7; reduced |

| Lane | |
|---|---|
| 1 | bsAb 5b (E/K) |
| 2 | bsAb 10 (E/K) |
| 3 | bsAb 12 (E/K) |
| 4 | bsAb 5b (K/E) |
| 5 | bsAb 10 (K/E) |
| 6 | bsAb 12 (K/E) |
| 7 | bsAb 5b |
| 8 | bsAb 10 |
| 9 | bsAb 12 |
| 10 | Markers |

| Lane | |
|---|---|
| 1 | bsAb 5b (E/K) |
| 2 | bsAb 10 (E/K) |
| 3 | bsAb 12 (E/K) |
| 4 | bsAb 5b (K/E) |
| 5 | bsAb 10 (K/E) |
| 6 | bsAb 12 (K/E) |
| 7 | bsAb 5b |
| 8 | bsAb 10 |
| 9 | bsAb 12 |
| 10 | Markers |

| Chain | Area% | Expected Area% |
|---|---|---|
| L1 | 15.52% | 13.54% |
| H2 | 32.33% | 36.36% |
| L2 | 14.64% | 12.40% |
| H1 | 37.51% | 37.71% |

| Chain | Area% | Expected Area% |
|---|---|---|
| L1 | 16.89% | 13.54% |
| H2 | 35.06% | 36.36% |
| L2 | 15.40% | 12.40% |
| H1 | 32.66% | 37.71% |

| Chain | Area% | Expected Area% |
|---|---|---|
| L1 | 14.62% | 13.54% |
| H2 | 33.13% | 36.36% |
| L2 | 14.96% | 12.40% |
| H1 | 37.29% | 37.71% |

| Chain | Area% | Expected Area% |
|---|---|---|
| H1 | 35.42 | 37.71 |
| L1 | 14.11 | 13.54 |
| H2 | 37.71 | 36.36 |
| L2 | 12.76 | 12.40 |

| Chain | Area% | Expected Area% |
|---|---|---|
| H1 | 33.54 | 37.71 |
| L1 | 14.80 | 13.54 |
| H2 | 38.41 | 36.36 |
| L2 | 13.26 | 12.40 |

| Chain | Area% | Expected Area% |
|---|---|---|
| H1 | 33.90 | 37.71 |
| L1 | 14.49 | 13.54 |
| H2 | 38.35 | 36.36 |
| L2 | 13.26 | 12.40 |

| Chain | Area% | Expected Area% |
|---|---|---|
| H1 | 35.87 | 37.71 |
| L1 | 13.73 | 13.54 |
| H2 | 37.63 | 36.36 |
| L2 | 12.77 | 12.40 |

| Chain | Area% | Expected Area% |
|---|---|---|
| H1 | 34.02 | 37.71 |
| L1 | 14.49 | 13.54 |
| H2 | 37.99 | 36.36 |
| L2 | 13.50 | 12.40 |

| Chain | Area% | Expected Area% |
|---|---|---|
| H1 | 35.08 | 37.71 |
| L1 | 13.80 | 13.54 |
| H2 | 37.83 | 36.36 |
| L2 | 13.29 | 12.40 |

| Chain | Area% | Expected Area% |
|---|---|---|
| H1 | 34.74 | 37.71 |
| L1 | 14.71 | 13.54 |
| H2 | 38.01 | 36.36 |
| L2 | 12.54 | 12.40 |

| Chain | Area% | Expected Area% |
|---|---|---|
| H1 | 33.04 | 37.71 |
| L1 | 15.06 | 13.54 |
| H2 | 38.80 | 36.36 |
| L2 | 13.09 | 12.40 |

| Chain | Area% | Expected Area% |
|---|---|---|
| H1 | 33.64 | 37.71 |
| L1 | 14.74 | 13.54 |
| H2 | 38.77 | 36.36 |
| L2 | 12.86 | 12.40 |

| Calculated mw (Da) | | Observed mw (Da) | |
|---|---|---|---|
| mAb1 Fab | mAb2 Fab | mAb1 Fab | mAb2 Fab |
| 47,023.33 | 47,394.89 | 47,024.70 | 47,395.72 |

| Calculated mw (Da) | | Observed mw (Da) | |
|---|---|---|---|
| mAb1 Fab | mAb2 Fab | mAb1 Fab | mAb2 Fab |
| 47,073.39 | 47,394.89 | 47,074.77 | 47,396.00 |

| Calculated mw (Da) | | Observed mw (Da) | |
|---|---|---|---|
| mAb1 Fab | mAb2 Fab | mAb1 Fab | mAb2 Fab |
| 47,030.33 | 47,394.89 | 47,031.91 | 47,396.23 |

| Charge | Calculated m/z | Observed m/z |
|---|---|---|
| 5 | 1879.91 | 1879.88 |
| 6 | 1566.76 | 1566.57 |
| 7 | 1343.08 | 1342.92 |
| 8 | 1175.32 | 1175.43 |
| 9 | 1044.84 | 1044.49 |
| 10 | 940.46 | 940.57 |

- The calculated mw of the disulfide crosslinked peptide is 9,394.49 Da.
- The observed mw of the disulfide crosslinked peptide is 9,394.57 Da.

| Charge | Calculated m/z | Observed m/z |
|---|---|---|
| 5 | 2016.62 | 2016.51 |
| 6 | 1680.69 | 1680.43 |
| 7 | 1440.73 | 1440.49 |
| 8 | 1260.77 | 1260.61 |
| 9 | 1120.79 | 1120.65 |
| 10 | 1008.82 | 1008.73 |

| Charge | Calculated m/z | Observed m/z |
|---|---|---|
| 5 | 2008.01 | 2007.76 |
| 6 | 1673.51 | 1673.40 |
| 7 | 1434.58 | 1434.56 |
| 8 | 1255.38 | 1255.30 |
| 9 | 1116.01 | 1115.97 |

| Charge | Calculated m/z | Observed m/z |
|---|---|---|
| 3 | 1051.890 | 1051.5 |
| 4 | 789.168 | 789.2 |

- The calculated mw of the disulfide bonded peptide is 3,152.7 Da.
- The observed mw of the disulfide bonded peptide is 3,152.2 Da.

| Charge | Calculated m/z | Observed m/z |
|---|---|---|
| 8 | 1638.588 | 1638.6 |
| 9 | 1456.634 | 1456.6 |
| 10 | 1311.070 | 1311.1 |
| 11 | 1191.973 | 1191.9 |
| 12 | 1092.745 | 1092.6 |
| 13 | 1008.746 | 1008.8 |

- The calculated mw of the disulfide bonded peptide is 13,100.7 Da.
- The observed mw of the disulfide bonded peptide is 13,100.7 Da.

| Charge | Calculated m/z | Observed m/z |
|---|---|---|
| 6 | 1591.279 | 1591.3 |
| 7 | 1364.096 | 1364.0 |
| 8 | 1193.709 | 1193.6 |
| 9 | 1061.186 | 1061.2 |
| 10 | 955.168 | 955.2 |

| Calculated mw of (Fab')2 (Da) | Observed mw of (Fab')2 (Da) |
|---|---|
| 96,823.07 | 96,825.35 |

- Protein A purified only antibody was digested with papain to generate Fab species.

| Species | Calculated mass | Observed mass |
|---|---|---|
| mAb 1 arm Fab | 47083.46 | 47084.95 |
| mAb 2b arm Fab | 47718.12 | 47719.50 |
| H1/L2 Fab | 46911.20 | 46912.40 |
| H2/L1 Fab | 47890.38 | 47889.04 |

- Protein A purified only antibody was digested with papain to generate Fab species.

| Species | Calculated mass | Observed mass |
|---|---|---|
| mAb 1 arm Fab | 47001.27 | 47002.91 |
| mAb 2b arm Fab | 47718.12 | 47719.76 |
| H1/L2 Fab | 46870.11 | 46871.25 |
| H2/L1 Fab | 47849.28 | ND |

- Protein A purified only antibody was digested with papain to generate Fab species.

| Species | Calculated mass | Observed mass |
| --- | --- | --- |
| mAb 1 arm Fab | 46982.27 | 46983.32 |
| mAb 2b arm Fab | 47718.12 | 47719.36 |
| H1/L2 Fab | 46870.11 | 46871.33 |
| H2/L1 Fab | 47830.28 | ND |

- Protein A and HIC purified antibody was digested by papain to generate Fab species.

| Species | Calculated mass | Observed mass |
|---|---|---|
| mAb 1 arm Fab | 46982.27 | 46983.46 |
| mAb 2b arm Fab | 47718.12 | 47719.37 |
| H1/L2 Fab | 46870.11 | ND |
| H2/L1 Fab | 47830.28 | ND |

SEQUENCE LISTING

```
<160> NUMBER OF SEQ ID NOS: 36

<210> SEQ ID NO 1
<211> LENGTH: 114
<212> TYPE: PRT
<213> ORGANISM: Artificial Sequence
<220> FEATURE:
<223> OTHER INFORMATION: bsAb1 VH

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

Trp Met His Trp Val Arg Gln Ala Pro Gly Gln Cys Leu Glu Trp Ile
35 40 45

Gly Asn Ile Asp Pro Ser Asp Ser Glu Thr His Tyr Ala Gln Lys Phe
50 55 60

Gln Gly Arg Val Thr Leu Thr Val Asp Lys Ser Thr Ser Thr Val Tyr
65 70 75 80

Met Glu Leu Ser Ser Leu Arg Ser Glu Asp Thr Ala Val Tyr Tyr Cys
85 90 95

Ala Gly Thr Asp Leu Ala Tyr Trp Gly Gln Gly Thr Leu Val Thr Val
100 105 110

Ser Ser

<210> SEQ ID NO 2
<211> LENGTH: 103
<212> TYPE: PRT
<213> ORGANISM: Artificial Sequence
<220> FEATURE:
<223> OTHER INFORMATION: bsAb 1 CH1

<400> SEQUENCE: 2

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Ser
100

<210> SEQ ID NO 3
<211> LENGTH: 107
<212> TYPE: PRT
<213> ORGANISM: Artificial Sequence
<220> FEATURE:
<223> OTHER INFORMATION: bsAb 1 VL

<400> SEQUENCE: 3

Glu Ile Val Leu Thr Gln Ser Pro Gly Thr Leu Ser Leu Ser Pro Gly
1 5 10 15

Glu Arg Ala Thr Leu Ser Cys His Ala Ser Gln Asn Ile Asn Val Trp
20 25 30

Leu Ser Trp Tyr Gln Gln Lys Pro Gly Gln Ala Pro Arg Leu Leu Ile
35 40 45

Tyr Lys Ala Ser Asn Leu His Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Gly Gln Ser Tyr Pro Phe
85 90 95

Thr Phe Gly Gln Cys Thr Lys Val Glu Ile Lys
100 105

```
<210> SEQ ID NO 4
<211> LENGTH: 107
<212> TYPE: PRT
<213> ORGANISM: Artificial Sequence
<220> FEATURE:
<223> OTHER INFORMATION: bsAb 1 CL

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105


<210> SEQ ID NO 5
<211> LENGTH: 103
<212> TYPE: PRT
<213> ORGANISM: Artificial Sequence
<220> FEATURE:
<223> OTHER INFORMATION: bsAb 5 CH1

<400> SEQUENCE: 5

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser
            100


<210> SEQ ID NO 6
<211> LENGTH: 107
<212> TYPE: PRT
<213> ORGANISM: Artificial Sequence
<220> FEATURE:
<223> OTHER INFORMATION: bsAb 5 CL

<400> SEQUENCE: 6

Arg Thr Val Ala Ala Pro Ser Val Phe Ile Phe Cys Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105


<210> SEQ ID NO 7
<211> LENGTH: 103
<212> TYPE: PRT
<213> ORGANISM: Artificial Sequence
<220> FEATURE:
<223> OTHER INFORMATION: bsAb 6 CH1

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Cys Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser
            100


<210> SEQ ID NO 8
<211> LENGTH: 107
<212> TYPE: PRT
<213> ORGANISM: Artificial Sequence
<220> FEATURE:
<223> OTHER INFORMATION: bsAb 6 CL

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Cys Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105


<210> SEQ ID NO 9
```

```
<211> LENGTH: 103
<212> TYPE: PRT
<213> ORGANISM: Artificial Sequence
<220> FEATURE:
<223> OTHER INFORMATION: bsAb 7 CH1

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Cys Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser
            100


<210> SEQ ID NO 10
<211> LENGTH: 107
<212> TYPE: PRT
<213> ORGANISM: Artificial Sequence
<220> FEATURE:
<223> OTHER INFORMATION: bsAb 7 CL

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Cys Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105


<210> SEQ ID NO 11
<211> LENGTH: 103
<212> TYPE: PRT
<213> ORGANISM: Artificial Sequence
<220> FEATURE:
<223> OTHER INFORMATION: bsAb 8 CH1

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Cys Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser
            100
```

<210> SEQ ID NO 12
<211> LENGTH: 107
<212> TYPE: PRT
<213> ORGANISM: Artificial Sequence
<220> FEATURE:
<223> OTHER INFORMATION: bsAb 8 CL

<400> SEQUENCE: 12

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Cys Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105
```

<210> SEQ ID NO 13
<211> LENGTH: 114
<212> TYPE: PRT
<213> ORGANISM: Artificial Sequence
<220> FEATURE:
<223> OTHER INFORMATION: mAb 1 VH

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asp Pro Ser Asp Ser Glu Thr His Tyr Ala Gln Lys Phe
    50                  55                  60

Gln Gly Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Gly Thr Asp Leu Ala Tyr Trp Gly Gln Gly Thr Leu Val Thr Val
            100                 105                 110

Ser Ser
```

<210> SEQ ID NO 14
<211> LENGTH: 117

```
<212> TYPE: PRT
<213> ORGANISM: Artificial Sequence
<220> FEATURE:
<223> OTHER INFORMATION: mAb 2 VH

<400> SEQUENCE: 14

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Asp Phe
            20                  25                  30

Gly Met His Trp Ile Arg Gln Ala Pro Gly Lys Gly Leu Glu Trp Val
        35                  40                  45

Ala Tyr Met Ser Tyr Thr Pro Gly Thr Phe His Tyr Ala Asp Thr Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Val Gly Thr Val Asp Tyr Trp Gly Gln Gly Thr Leu
            100                 105                 110

Val Thr Val Ser Ser
        115


<210> SEQ ID NO 15
<211> LENGTH: 103
<212> TYPE: PRT
<213> ORGANISM: Artificial Sequence
<220> FEATURE:
<223> OTHER INFORMATION: mAb 1 CH1

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100


<210> SEQ ID NO 16
<211> LENGTH: 103
<212> TYPE: PRT
<213> ORGANISM: Artificial Sequence
<220> FEATURE:
<223> OTHER INFORMATION: mAb 2 CH1

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100


<210> SEQ ID NO 17
<211> LENGTH: 107
<212> TYPE: PRT
<213> ORGANISM: Artificial Sequence
<220> FEATURE:
<223> OTHER INFORMATION: mAb 1 VL

<400> SEQUENCE: 17

Glu Ile Val Leu Thr Gln Ser Pro Gly Thr Leu Ser Leu Ser Pro Gly
1               5                   10                  15

Glu Arg Ala Thr Leu Ser Cys His Ala Ser Gln Asn Ile Asn Val Trp
            20                  25                  30

Leu Ser Trp Tyr Gln Gln Lys Pro Gly Gln Ala Pro Arg Leu Leu Ile
        35                  40                  45

Tyr Lys Ala Ser Asn Leu His Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Gly Gln Ser Tyr Pro Phe
                85                  90                  95

Thr Phe Gly Gln Gly Thr Lys Val Glu Ile Lys
            100                 105


<210> SEQ ID NO 18
<211> LENGTH: 108
<212> TYPE: PRT
<213> ORGANISM: Artificial Sequence
<220> FEATURE:
<223> OTHER INFORMATION: mAb 2 VL

<400> SEQUENCE: 18

Glu Val Val Leu Thr Gln Ser Pro Ala Thr Leu Ser Leu Ser Pro Gly
1               5                   10                  15

Glu Arg Ala Thr Leu Ser Cys Arg Ala Ser Gln Asn Ile Asn Asn Asn
            20                  25                  30

Leu His Trp Phe Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Ala
                85                  90                  95

Leu Thr Phe Gly Gln Gly Thr Lys Val Glu Ile Lys
            100                 105


<210> SEQ ID NO 19
<211> LENGTH: 107
```

<212> TYPE: PRT
<213> ORGANISM: Artificial Sequence
<220> FEATURE:
<223> OTHER INFORMATION: mAb 1 CL

<400> SEQUENCE: 19

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 20
<211> LENGTH: 107
<212> TYPE: PRT
<213> ORGANISM: Artificial Sequence
<220> FEATURE:
<223> OTHER INFORMATION: mAb 2 CL

<400> SEQUENCE: 20

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 21
<211> LENGTH: 103
<212> TYPE: PRT
<213> ORGANISM: Artificial Sequence
<220> FEATURE:
<223> OTHER INFORMATION: IgG2 CH1

<400> SEQUENCE: 21

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys
            100


<210> SEQ ID NO 22
<211> LENGTH: 105
<212> TYPE: PRT
<213> ORGANISM: Artificial Sequence
<220> FEATURE:
<223> OTHER INFORMATION: IgG3 CH1

<400> SEQUENCE: 22

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly
            100                 105


<210> SEQ ID NO 23
<211> LENGTH: 103
<212> TYPE: PRT
<213> ORGANISM: Artificial Sequence
<220> FEATURE:
<223> OTHER INFORMATION: IgG4 CH1

<400> SEQUENCE: 23

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly
            100


<210> SEQ ID NO 24
<211> LENGTH: 104
<212> TYPE: PRT
<213> ORGANISM: Artificial Sequence
<220> FEATURE:
```

```
<223> OTHER INFORMATION: lambda CL

<400> SEQUENCE: 24

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys
            100


<210> SEQ ID NO 25
<211> LENGTH: 103
<212> TYPE: PRT
<213> ORGANISM: Artificial Sequence
<220> FEATURE:
<223> OTHER INFORMATION: bsAb 9 CH1

<400> SEQUENCE: 25

Ala Ser Thr Lys Gly Pro Ser Val Phe Pro Leu Cys Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser
            100


<210> SEQ ID NO 26
<211> LENGTH: 107
<212> TYPE: PRT
<213> ORGANISM: Artificial Sequence
<220> FEATURE:
<223> OTHER INFORMATION: bsAb 9 CL

<400> SEQUENCE: 26

Arg Thr Val Ala Ala Pro Ser Val Phe Ile Phe Pro Pro Cys Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

```
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105


<210> SEQ ID NO 27
<211> LENGTH: 103
<212> TYPE: PRT
<213> ORGANISM: Artificial Sequence
<220> FEATURE:
<223> OTHER INFORMATION: bsAb 10 CH1

<400> SEQUENCE: 27

Ala Ser Thr Lys Gly Pro Ser Val Phe Pro Leu Ala Pro Ser Ser Cys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser
            100


<210> SEQ ID NO 28
<211> LENGTH: 107
<212> TYPE: PRT
<213> ORGANISM: Artificial Sequence
<220> FEATURE:
<223> OTHER INFORMATION: bsAb 10 CL

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Cys Ser Phe Asn Arg Gly Glu Ser
            100                 105


<210> SEQ ID NO 29
<211> LENGTH: 103
<212> TYPE: PRT
<213> ORGANISM: Artificial Sequence
<220> FEATURE:
<223> OTHER INFORMATION: bsAb 11 CH1

<400> SEQUENCE: 29
```

```
Ala Ser Thr Lys Gly Pro Ser Val Phe Pro Leu Ala Pro Ser Ser Cys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Ser
            100


<210> SEQ ID NO 30
<211> LENGTH: 107
<212> TYPE: PRT
<213> ORGANISM: Artificial Sequence
<220> FEATURE:
<223> OTHER INFORMATION: bsAb 11 CL

<400> SEQUENCE: 30

Arg Thr Val Ala Ala Pro Ser Val Phe Cys Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105


<210> SEQ ID NO 31
<211> LENGTH: 103
<212> TYPE: PRT
<213> ORGANISM: Artificial Sequence
<220> FEATURE:
<223> OTHER INFORMATION: bsAb 12 CH1

<400> SEQUENCE: 31

Ala Ser Thr Lys Gly Pro Ser Val Phe Pro Leu Ala Pro Ser Ser Cys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                85                  90                  95

Lys Val Glu Pro Lys Ser Ser
            100


<210> SEQ ID NO 32
<211> LENGTH: 107
<212> TYPE: PRT
<213> ORGANISM: Artificial Sequence
<220> FEATURE:
<223> OTHER INFORMATION: bsAb 12 CL

<400> SEQUENCE: 32

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Cys Asn Arg Gly Glu Ser
            100                 105


<210> SEQ ID NO 33
<211> LENGTH: 120
<212> TYPE: PRT
<213> ORGANISM: Artificial Sequence
<220> FEATURE:
<223> OTHER INFORMATION: mAb 2b VH

<400> SEQUENCE: 33

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Tyr Thr His Tyr Asn Gly Met Phe
    50                  55                  60

Lys Gly Arg Ala Ser Leu Thr Ala Asp Lys Ser Thr Ser Thr Gly Tyr
65                  70                  75                  80

Met Glu Leu Ser Ser Leu Arg Ser Glu Asp Thr Ala Val Phe Phe Cys
                85                  90                  95

Thr Arg His Gly Asp Phe Pro Tyr Trp Tyr Phe Asp Val Trp Gly Arg
            100                 105                 110

Gly Thr Leu Val Thr Val Ser Ser
        115                 120


<210> SEQ ID NO 34
<211> LENGTH: 103
<212> TYPE: PRT
<213> ORGANISM: Artificial Sequence
<220> FEATURE:
<223> OTHER INFORMATION: mAb 2b CH1

<400> SEQUENCE: 34
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100


<210> SEQ ID NO 35
<211> LENGTH: 107
<212> TYPE: PRT
<213> ORGANISM: Artificial Sequence
<220> FEATURE:
<223> OTHER INFORMATION: mAb 2b VL

<400> SEQUENCE: 35

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Asn Ile Asp Ser Tyr
            20                  25                  30

Leu Ala Trp Tyr Gln Gln Lys Pro Gly Arg Ala Pro Lys Leu Leu Val
        35                  40                  45

Tyr Ala Ala Thr Asn Leu Ala Val Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln His His Tyr Ser Thr Pro Pro
                85                  90                  95

Thr Phe Gly Gln Gly Thr Lys Leu Glu Ile Lys
            100                 105


<210> SEQ ID NO 36
<211> LENGTH: 107
<212> TYPE: PRT
<213> ORGANISM: Artificial Sequence
<220> FEATURE:
<223> OTHER INFORMATION: mAb 2b CL

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

-continued

```
Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

BISPECIFIC ANTIBODIES WITH ALTERNATIVELY MATCHED INTERCHAIN CYSTEINES AND USES THEREOF

CROSS-REFERENCE TO RELATED APPLICATION

This application is a Section 371 of International Application No. PCT/US2020/063066 filed Dec. 3, 2020, which was published in the English language on Jun. 24, 2021, under International Publication No. WO 2021/126538 A1, and claims priority to U.S. Provisional Application No. 62/948,953, filed on Dec. 17, 2019; U.S. Provisional Application No. 62/952,747, filed on Dec. 23, 2019; U.S. Provisional Application No. 62/988,144, filed on Mar. 11, 2020; U.S. Provisional Application No. 63/007,996, filed on Apr. 10, 2020; U.S. Provisional Application No. 62/704,973, filed Jun. 5, 2020; and U.S. Provisional Application No. 62/706,511, filed on Aug. 21, 2020. Each disclosure is incorporated herein by reference in its entirety.

FIELD OF THE INVENTION

This invention relates to engineered bispecific antibodies with a shifted interchain disulfide bond on one arm while maintaining the native interchain disulfide bond on the second arm. These bispecific antibodies can have stability and production advantages and can be used for therapeutic purposes. The invention relates to the bispecific antibodies, nucleic acids and expression vectors encoding the antibodies, recombinant cells containing the vectors, and compositions comprising the antibodies. Methods of making the antibodies, and methods of using the antibodies to treat diseases including cancer and/or associated complications are also provided.

REFERENCE TO SEQUENCE LISTING SUBMITTED ELECTRONICALLY

This application contains a sequence listing, which is submitted electronically via EFS-Web as an ASCII formatted sequence listing with a file name "065799.30US2 Sequence Listing" and a creation date of May 6, 2022, and having a size of 36 kb. The sequence listing submitted via EFS-Web is part of the specification and is herein incorporated by reference in its entirety.

BACKGROUND OF THE INVENTION

Antibodies (immunoglobulins) are naturally occurring proteins that play important roles in the immune system's function in defending the body against foreign objects such as bacteria and viruses. Antibodies in their native structure exist as a Y-shaped protein, consisting of two arms with each containing an identical heavy chain (HC) and an identical light chain (LC). The heavy chain contains one variable region (VH) and 3 constant regions (CH1, CH2 and CH3, respectively) that are arranged in the order of VH, CH1, CH2 and CH3 from the N-terminus to the C-terminus, and the light chain contains one variable region (VL) and one constant region (CL) that are arranged in the order of VL and CL from the N-terminus to the C-terminus. The association of the heavy chain and the light chain in each arm is usually termed "pairing," which involves VH, CH1, VL, and CL. The VH and VL physically interact with each other to form the binding domain of the antibody against its antigen so that the Y-shaped antibody has two identical binding domains with one on each arm against the same antigen, and therefore is bivalent and mono-specific, a typical characteristic of a monoclonal antibody.

As part of the antibody structure, CH1 and CL also physically interact with each other, which involves physical contacts as well as an interchain disulfide bond (also called "disulfide bridge") formed by the free thiol groups of two native cysteines on CH1 and CL, respectively. The interchain disulfide bond helps stabilize the overall structure formed by the heavy chain and light chain on each arm. In addition, inner-chain disulfide bonds are also formed as part of the native antibody structure. The C-terminus of the heavy chains (CH2 and CH3) forms a tight structure, which is important for the bivalency of the native antibody.

Monoclonal antibodies (mAbs) have been an excellent protein therapeutic platform due to their high affinity binding to antigens, the long half-life in vivo, naturally occurring stable structure, the ability to activate the immune system against drug targets, and many other aspects. However, when therapeutic strategies require targeting two separate antigens, such as two tumor-specific antigens on the same cancer cell, with one antibody, a mAb cannot serve the purpose. Under such a circumstance, a bispecific antibody is made to target two different antigens on the same cell, with one arm binding to the first antigen and the other arm binding to the second antigen. Although there is monovalency for each antigen binding, the binding to both antigens on the same cell can compensate for the lost avidity due to loss of the bivalency against each antigen. Bispecific antibodies provide increased selectivity when compared with mAbs because they have higher binding to cells expressing both antigens than cells expressing only one of the antigens. This is especially important in reducing safety concerns when normal cells or tissues express one of the two antigens. Bispecific antibodies can target two pathways simultaneously when it binds to two different cell surface antigens or soluble ligands/proteins, which is another advantage over mAbs.

If a bispecific antibody is made from two mAbs, the product would contain two different arms from the two mAbs, respectively, with each arm having a unique heavy chain and a unique light chain. The expression of the bispecific antibody in production cells during the manufacturing process requires the expression of 4 different proteins: the two different heavy chains and the two different light chains. While the goal is to have each HC pair with its corresponding LC on each arm of the bispecific antibody during production, mispairings (the LC of one arm pairs with the HC of the other arm) usually occur and generate unwanted products, making it challenging to produce and isolate the intended bispecific antibody product. Several approaches have been employed to improve the manufacturing aspect of the bispecific antibodies. One example is to identify a common light chain through protein engineering. However, domain swaps and many mutations could significantly change the native antibody structure, which can increase the risk of aggregation and/or reduce the stability.

The expression of FRα is elevated in certain solid tumors such as ovarian, lung and breast cancers (Toffoli et al., Int J Cancer 1997; 74:193-198 and Boogerd et al., Oncotarget 2016; 7:17442-17454), but its expression is at low levels in limited normal human tissues (Weitman, et al., Cancer Res 1992; 52:3396-3401). Consistent with this observation, phase 1 clinical trials conducted so far with FRα-targeting small and large molecules revealed good drug tolerability (Cheung et al., Oncotarget 2016; 7:52553-52574). Therefore, FRα is an ideal target for cancer therapies. Further, CD47 which mediates the "don't eat me" signal is overexpressed in many tumors. A bispecific antibody with one arm binding to CD47 and the other arm binding to FRα (termed anti-CD47/FRα bispecific antibody) can be used to selectively target a cell that expresses both antigens. Binding of the bispecific antibody to both antigens on the same cell can result in increased affinity compared with either arm due to avidity. The bispecific antibody is expected to have weaker activity against cells that express only CD47 (but not FRα) due to the lack of avidity when compared with a bivalent anti-CD47 mAb, which can potentially increase safety and/or tolerability margins. An anti-CD47/FRα bispecific antibody can selectively block the CD47/SIRPα interaction on a cell that express both CD47 and FRα and activate the innate immune system against the cell, such as a cancer cell. Thus, an anti-CD47/FRα bispecific antibody can be an effective therapy for ovarian cancer, and other tumors that express significant levels of both CD47 and FRα on the cell surface.

BRIEF SUMMARY OF THE INVENTION

In one general aspect, the invention relates to isolated bispecific antibodies or antigen-binding fragments thereof comprising:

a. a first heavy chain, H1;

b. a second heavy chain, H2;

c. a first light chain, L1; and d. a second light chain, L2;

wherein H1 and L1 form a first arm comprising a first antigen-binding domain that specifically binds a first antigen, preferably a first antigen of human origin, and wherein H2 and L2 form a second arm comprising a second antigen-binding domain that specifically binds a second antigen, preferably a second antigen of human origin, wherein (a) H1 comprises a CH1 region of human IgG1, IgG2, IgG3, or IgG4; and (b) L1 comprises a CL region of a human kappa light chain or a human lambda light chain;

wherein the CH1 and CL regions comprise amino acid substitutions or a native amino acid at an amino acid residue corresponding to the amino acid position of SEQ ID NO:15, 21, 22, or 23 for CH1 and SEQ ID NO:19 or 24 for CL; wherein the amino acid substitutions or the native amino acid in the CH1 and CL regions are selected from:

(1) K133C and C220X in CH1, and F209C and C214X in CL;

(2) S131C and C220X in CH1, and P119C and C214X in CL;

(3) K133C and C220X in CH1, and K207C and C214X in CL;

(4) F170C and C220X in CH1, and S176C and C214X in CL;

(5) P171C and C220X in CH1, and S162C and C214X in CL;

(6) V173C and C220X in CH1, and Q160C and C214X in CL;

(7) F170C and C131X in CH1, and S176C and C214X in CL;

(8) P171C and C131X in CH1, and S162C and C214X in CL;

(9) V173C and C131X in CH1, and Q160C and C214X in CL;

(10) A129C and C220X in CH1, and S121C and C214X in CL;

(11) K133C and C220X in CH1, and I117C and C214X in CL;

(12) C131 in CH1, and P119C and C214X in CL;

(13) A129C and C131X in CH1, and S121C and C214X in CL;

(14) R133C and C131X in CH1, and K207C and C214X in CL;

(15) R133C and C131X in CH1, and 1117C and C214X in CL;

(16) R133C and C131X in CH1, and L117C and C214X in CL;

(17) K133C and C220X in CH1, and L117C and C214X in CL;

(18) R133C and C131X in CH1, and F209C and C214X in CL;

(19) R133C and C131X in CH1, and V209C and C214X in CL; or

(20) K133C and C220X in CH1, and V209C and C214X in CL;

wherein X is selected from S, A or G.

In another general aspect, the invention relates to isolated bispecific antibodies or antigen-binding fragment thereof comprising:

a. a first heavy chain, H1;

b. a second heavy chain, H2;

c. a first light chain, L1; and d. a second light chain, L2;

wherein H1 and L1 form a first arm comprising a first antigen-binding domain that specifically binds a first antigen, preferably a first antigen of human origin, and wherein H2 and L2 form a second arm comprising a second antigen-binding domain that specifically binds a second antigen, preferably a second antigen of human origin, wherein (a) H1 comprises a CH1 region of human IgG1, IgG2, IgG3, or IgG4 and a heavy chain variable region (VH region); and (b) L1 comprises a CL region of a human kappa light chain or a human lambda light chain and a light chain variable region (VL region);

wherein the CH1 region, the VH region, the CL region, and the VL region comprise amino acid substitutions at an amino acid residue corresponding to the amino acid position of SEQ ID NO: 15, 21, 22, or 23 for CH1; SEQ ID NO: 13 for VH; SEQ ID NO: 19 or 24 for CL; and SEQ ID NO: 17 for VL;

wherein the amino acid substitutions in the CH1 region, the VH region, the CL region, and the VL region are selected from:

(1) C220X in CH1, G44C in VH, C214X in CL, and G101C in VL; or (2) C131X in CH1, G44C in VH, C214X in CL, and G101C in VL;

wherein X is selected from S, A or G.

In certain embodiments, the first antigen-binding domain is a CD47 binding domain. In certain embodiments, the VH region comprises an amino acid sequence of SEQ ID NO: 1, the CH1 region comprises an amino acid sequence of SEQ ID NO: 2, the VL region comprises an amino acid sequence of SEQ ID NO: 3, and the CL region comprises an amino acid sequence of SEQ ID NO: 4.

In certain embodiments, the second arm comprising H2 and L2 does not comprise the amino acid substitutions of the first arm comprising H1 and L1. In certain embodiments, the two heavy chains H1 and H2 each comprise a VH region, a CH1 region, and a Fc region (containing CH2 and CH3 regions), wherein the VH regions have different amino acid sequences. In certain embodiments, the two heavy chains H1 and H2 each comprise a VH region, a CH1 region, and a Fc region (containing CH2 and CH3 regions), wherein the CH1 regions have different amino acid sequences. In certain embodiments, the two heavy chains H1 and H2 each comprise a VH region, a CH1 region, and a Fc region (containing CH2 and CH3 regions), wherein the Fc regions have different amino acid sequences. In certain embodiments, the two light chains L1 and L2 each comprise a VL region and a CL region, wherein the VL regions have different amino acid sequences. In certain embodiments, the two light chains L1 and L2 each comprise a VL region and a CL region, wherein the CL regions have different amino acid sequences.

In certain embodiments, H1 and H2 form a heterodimer.

In certain embodiments, the isolated humanized anti-CD47/anti-FRα bispecific antibody or antigen-binding fragment thereof is capable of blocking binding of signal regulatory protein alpha (SIRPα) to CD47 on cancer cells that express both FRα and CD47.

In certain embodiments, the isolated humanized anti-CD47/anti-FRα bispecific antibody or antigen-binding fragment thereof is capable of inducing macrophage-mediated phagocytosis of cancer cells that express both FRα and CD47.

In certain embodiments, the isolated humanized anti-CD47/anti-FRα bispecific antibody or antigen-binding fragment thereof is capable of binding cancer cells that express both FRα and CD47 with minimal to undetectable binding to human red blood cells (RBCs).

Also provided are isolated nucleic acids encoding the isolated bispecific antibodies or antigen-binding fragments thereof of the invention disclosed herein.

Also provided are vectors comprising the isolated nucleic acids encoding the bispecific antibodies or antigen-binding fragments thereof of the invention disclosed herein.

Also provided are host cells comprising the vectors comprising the isolated nucleic acids encoding the bispecific antibodies or antigen-binding fragments thereof of the invention disclosed herein.

In certain embodiments, provided is a pharmaceutical composition comprising the isolated bispecific antibodies or antigen-binding fragments thereof of the invention and a pharmaceutically acceptable carrier.

Also provided are methods of targeting FRα and CD47 that are both expressed on a cancer cell surface in a subject in need thereof, comprising administering to the subject the pharmaceutical compositions comprising the isolated anti-CD47/anti-FRα bispecific antibodies or antigen-binding fragments thereof of the invention.

Also provided are methods of blocking binding of SIRPα to CD47 on cancer cells that express both FRα and CD47 in a subject in need thereof, comprising administering to the subject the pharmaceutical compositions comprising the isolated anti-CD47/anti-FRα bispecific antibodies or antigen-binding fragments thereof of the invention.

Also provided are methods of inducing macrophage-mediated phagocytosis of cancer cells that express both FRα and CD47 in a subject in need thereof, comprising administering to the subject the pharmaceutical compositions comprising the isolated anti-CD47/anti-FRα bispecific antibodies or antigen-binding fragments thereof of the invention.

Also provided are methods of binding cancer cells that express both FRα and CD47 by an anti-CD47/anti-FRα bispecific antibody or antigen-binding fragment with minimal to undetectable binding to human red blood cells (RBCs) in a subject in need thereof, comprising administering to the subject the pharmaceutical compositions comprising the isolated anti-CD47/anti-FRα bispecific antibodies or antigen-binding fragments thereof of the invention.

Also provided are methods of treating cancer in a subject in need thereof, comprising administering to the subject the pharmaceutical compositions of the invention. The cancer can be any liquid or solid cancer, for example, it can be selected from, but not limited to, a lung cancer, a gastric cancer, an esophageal cancer, a bile duct cancer, a cholangiocarcinoma, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Also provided are methods of producing the isolated bispecific antibody or antigen-binding fragment thereof of the invention, comprising culturing a cell comprising a nucleic acid encoding the antibody or antigen-binding fragment thereof under conditions to produce the antibody or antigen-binding fragment thereof, and recovering the antibody or antigen-binding fragment thereof from the cell or culture.

Also provided are methods of producing a pharmaceutical composition comprising the isolated bispecific antibody or antigen-binding fragment thereof of the invention, comprising combining the antibody or antigen-binding fragment thereof with a pharmaceutically acceptable carrier to obtain the pharmaceutical composition.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

In FIG. 1A, the native interchain disulfide bond between CH1 and CL (marked by the dashed line) is eliminated by converting the disulfide bond-forming native cysteines to serines; two native non-cysteine residues on CH1 and CL, respectively, were converted to cysteines to form a new interchain disulfide bond between CH1 and CL. A similar strategy was used in FIG. 1B except that the newly formed interchain disulfide bond between HC and LC of the right arm is between the VH and VL regions. H1 and L1 are the heavy chain and light chain of the mAb 1 arm, respectively, and H2 and L2 are the heavy chain and light chain of the mAb 2 arm, respectively.

FIGS. 2A-2F show sequences of various antibody components. FIGS. 2A-2D show the VH (FIG. 2A), CH1 (FIG. 2B), VL (FIG. 2C), and CL (FIG. 2D) sequences of mAb 1 (on human IgG1 heavy chain and kappa light chain) and mAb 2 (on human IgG1 heavy chain and kappa light chain), respectively (VH for mAb 1 (SEQ ID NO: 13); VH for mAb 2 (SEQ ID NO: 14); CH1 for mAb 1 (SEQ ID NO: 15); CH1 for mAb 2 (SEQ ID NO: 16); VL for mAb 1 (SEQ ID NO: 17); VL for mAb 2 (SEQ ID NO: 18); CL for mAb 1 (SEQ ID NO: 19); CL for mAb 2 (SEQ ID NO: 20)). The CDR regions determined by Kabat method are highlighted. The cysteine residues involved in the interchain disulfide bond formation between the heavy chain and the light chain of each arm are also highlighted. FIG. 2E shows the alignment of CH1 regions of human IgG2 (SEQ ID NO: 21), IgG3 (SEQ ID NO: 22), and IgG4 (SEQ ID NO: 23). FIG. 2F shows the CL region of human lambda light chain (SEQ ID NO: 24). * represents sites of known allelic variations.

FIG. 3A, 3-D model of bsAb 1; FIG. 3B, 3-D model of bsAb 2; FIG. 3C, 3-D model of bsAb 3; FIG. 3D, 3-D model of bsAb 4; FIG. 3E, 3-D model of bsAb 5; FIG. 3F, 3-D model of bsAb 6; FIG. 3G, 3-D model of bsAb 7; FIG. 3H, 3-D model of bsAb 8; FIG. 3I, 3-D model of bsAb 9; FIG. 3J, 3-D model of bsAb 10; FIG. 3K, 3-D model of bsAb 11; FIG. 3L, 3-D model of bsAb 12.

FIG. 5A, mutant mAb with M1 design; FIG. 5B, mutant mAb with M2 design; FIG. 5C, mutant mAb with Z1 design; FIG. 5D, mutant mAb with Z2 design; FIG. 5E, mutant mAb with bsAb 10 design; FIG. 5F, mutant mAb with bsAb 11 design; FIG. 5G, mutant mAb with bsAb 12 design. HMW, high molecular weight species; MMW, medium molecular weight species (the mutant mAb); LMW, low molecular weight species.

FIGS. 6A-6H show the SEC (size exclusion chromatography) profiles of mutant mAbs containing different shifted interchain disulfide bonds in a pH stability study in which the samples were incubated at pH3.0 for different time periods at room temperature. The chromatogram corresponding to each incubation period (0, 1, 3, 5, and 7 hours) is shown; the 0 hour chromatogram represents the sample that was not subject to pH3.0 incubation. The table in each FIG shows the % AUCs (area under the curves) of different peaks for each given incubation period. FIG. 6A, mutant mAb with M1 design; FIG. 6B, mutant mAb with M2 design; FIG. 6C, mutant mAb with Z1 design; FIG. 6D, mutant mAb with Z2 design; FIG. 6E, mutant mAb with bsAb 5 design; FIG. 6F, mutant mAb with bsAb 10 design; FIG. 6G, mutant mAb with bsAb 11 design; FIG. 6H, mutant mAb with bsAb 12 design. HMW, high molecular weight species; MMW, medium molecular weight species (the mutant mAb); LMW, low molecular weight species.

FIG. 7C, the SDS-PAGE was run under non-reducing conditions; FIG. 7D, the SDS-PAGE was run under reducing conditions.

FIG. 9A, SEC profile of bsAb 1; FIG. 9N, SEC profile of bsAb 12.

FIG. 10A, RP-HPLC profile of bsAb 6; FIG. 10B, RP-HPLC profile of bsAb 7; FIG. 10C, RP-HPLC profile of bsAb 8; FIG. 10D, RP-HPLC profile of bsAb 5b (E/K); FIG. 10E, RP-HPLC profile of bsAb 10 (E/K); FIG. 10F, RP-HPLC profile of bsAb 12 (E/K); FIG. 10G, RP-HPLC profile of bsAb 5b (K/E); FIG. 10H, RP-HPLC profile of bsAb 10 (K/E); FIG. 10I, RP-HPLC profile of bsAb 12 (K/E); FIG. 10J, RP-HPLC profile of bsAb 5b; FIG. 10K, RP-HPLC profile of bsAb 10; FIG. 10L, RP-HPLC profile of bsAb 12.

FIG. 11A, RP-HPLC profile of control antibody #1 assembled with H1, H2 and L1 of bsAb 7, and purified with Protein A chromatography; FIG. 11N, RP-HPLC profile of HIC purified bsAb 12. H1 and L1 represent the HC and LC, respectively, of the mAb 1 (anti-CD47) arm; H2 and L2 represent the HC and LC, respectively, of the mAb 2 (anti-Frα) arm (FIGS. 11A-11E) or the mAb 2b (anti-FRα) arm (FIGS. 11F-11N). Expected Area % represents the AUC ratio calculated based on the amino acid sequence of each chain; Area % represents the AUC ratio calculated using the AUCs of all the 4 peaks of each bispecific antibody on RP-HPLC under reducing condition.

FIG. 12A, bridging ELISA data for bsAb 6, bsAb 7 and bsAb 8; FIG. 12B, bridging ELISA data for bsAb 5b (E/K), bsAb 10 (E/K), and bsAb 12 (E/K); FIG. 12C, bridging ELISA data for bsAb 5b (K/E); FIG. 12D, bridging ELISA data for bsAb 10 (K/E); FIG. 12E, bridging ELISA data for bsAb 12 (K/E); FIG. 12F, bridging ELISA data for bsAb 5b, bsAb 10, and bsAb 12.

FIG. 14A, MS profile of papain digested bsAb 6; FIG. 14B, MS profile of papain digested bsAb 7; FIG. 14C, MS profile of papain digested bsAb 8.

FIG. 15A, MS profile of the disulfide crosslinked peptide fragment generated from trypsin digested mAb 1 arm of bsAb 6; FIG. 15B, MS profile of the disulfide crosslinked peptide fragment generated from trypsin digested mAb 1 arm of bsAb 7; FIG. 15C, MS profile of the disulfide crosslinked peptide fragment generated from trypsin digested mAb 1 arm of bsAb 8; FIG. 15D, MS profile of the disulfide crosslinked peptide fragment generated from trypsin digested mAb 1 arm of bsAb 5b; FIG. 15E, MS profile of the disulfide crosslinked peptide fragment generated from trypsin digested mAb 1 arm of bsAb 10; FIG. 15F, MS profile of the disulfide crosslinked peptide fragment generated from trypsin digested mAb 1 arm of bsAb 12.

FIG. 16A, MS profile of bsAb 6 (Fab')2; FIG. 16B, MS profile of bsAb 7 (Fab')2; FIG. 16C, MS profile of bsAb 8 (Fab')2.

FIG. 17A, bsAb 5b; FIG. 17B, bsAb 10; FIG. 17C, bsAb 12. Anti-FRα parental mAb, the mAb from which the anti-FRα arm was used to construct the bispecific antibodies bsAb 5b, bsAb 10 and bsAb 12; anti-CD47 parental mAb, the mAb from which the anti-CD47 arm was used to construct the bispecific antibodies bsAb 5b, bsAb 10 and bsAb 12; Ab, antibody. Ab concentrations used in the assay are indicated below each graph; 5,000 nM F(ab')2 was used to assess the inhibitory effect.

FIG. 19A, Protein A purified WT bispecific antibody; FIG. 19B, Protein A purified bsAb 10; FIG. 19C, Protein A purified bsAb 12. WT bispecific antibody, the bispecific antibody generated by co-expressing the mAb1 arm and mAb 2b arm with no mutations introduced (the native interchain disulfide bonds are on both arms); H1 and L1 are heavy chain and light chain of the mAb 1 arm, respectively, and H2 and L2 are heavy chain and light chain of the mAb 2b arm, respectively; H1/L2 Fab and H2/L1 Fab represent the Fab fragments of the heavy chain/light chain mismatched species. ND, not detected.

DETAILED DESCRIPTION OF THE INVENTION

Figure 1A:
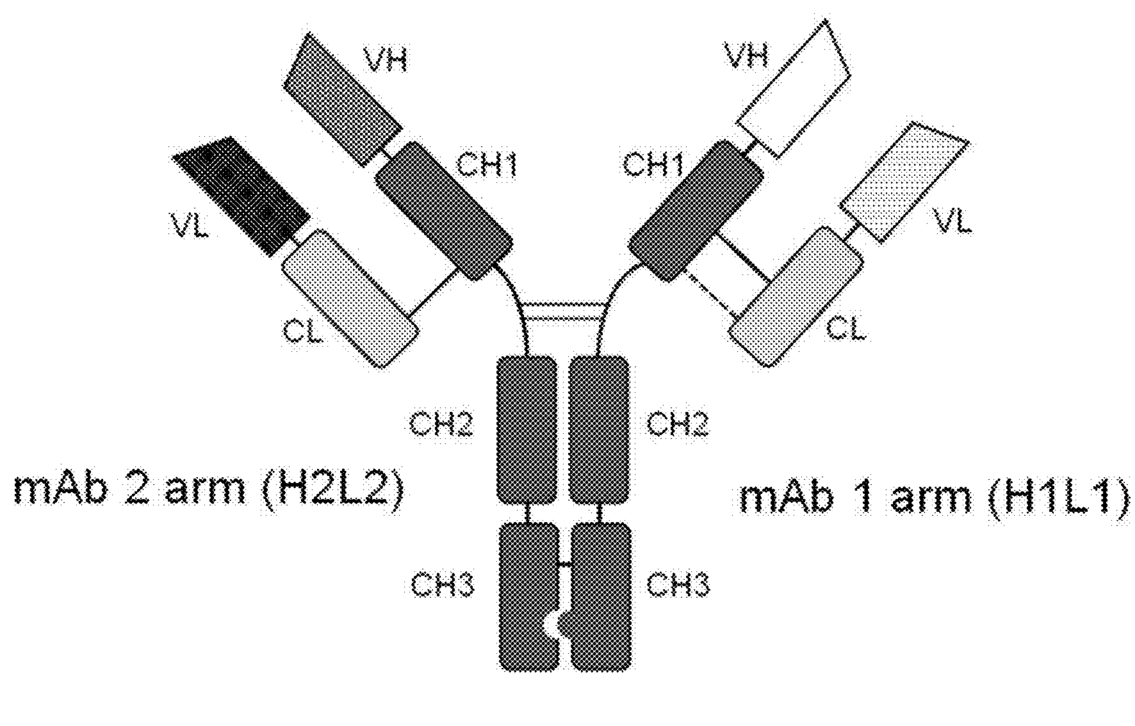
FIGS. 1A and 1B show the schematic structure of a bispecific antibody with the right arm against one antigen (such as CD47) and the left arm against a second antigen (such as FRα). Both arms have different heavy chain VH and light chain VL regions; the heavy chains (HCs) and light chains (LCs) of the bispecific antibody are in the framework of IgG1 and kappa, respectively, for the purpose of presenting an example. Knob in the hole (KiH) mutations are introduced in the CH3 regions of both HCs to promote heterodimer formation. In addition, a cysteine residue was introduced to each of the two CH3 regions, respectively, to promote the formation of an interchain disulfide bond to stabilize the heterodimer.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right," "left," "lower," and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

As used herein, the terms "different heavy chains" or "different light chains" as used throughout the specification and claims, indicate that the heavy chains or the light chains have sequences that are not identical to each other.

The terms "identical" or percent "identity," in the context of two or more nucleic acids or polypeptide sequences (e.g., bispecific antibodies, anti-FRα antibodies, anti-CD47 antibodies, anti-CD47/anti-FRα bispecific antibodies, FRα polypeptides and polynucleotides that encode them, and CD47 polypeptides and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the term "vector" is a replicon in which another nucleic acid segment can be operably inserted so as to bring about the replication or expression of the segment.

As used herein, the term "host cell" refers to a cell comprising a nucleic acid molecule of the invention. The "host cell" can be any type of cell, e.g., a primary cell, a cell in culture, or a cell from a cell line. In one embodiment, a "host cell" is a cell transfected with a nucleic acid molecule of the invention. In another embodiment, a "host cell" is a progeny or potential progeny of such a transfected cell. A progeny of a cell may or may not be identical to the parent cell, e.g., due to mutations or environmental influences that can occur in succeeding generations or integration of the nucleic acid molecule into the host cell genome.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed bispecific antibody can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The conventional one-letter or three-letter code for amino acid residues is used herein. The terms "peptide," "polypeptide," and "protein" can be used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Bispecific Antibodies

The invention generally relates to isolated bispecific antibodies in which the native cysteine residues for the interchain disulfide bond between the CH1 region of the heavy chain and the CL region of the light chain of one arm are eliminated by converting the native cysteine residues to non-cysteine residues (e.g., native cysteine residues to serine residues); concurrently or subsequently, two native non-cysteine residues in the CH1 and CL regions or in the VH and VL regions of the same arm are converted to cysteines so that a new interchain disulfide bond is formed between the heavy chain and the light chain. The two native non-cysteine residues, with one each on the CH1 region and the CL region or one each on the VH region and the VL region are identified by structural modeling for their proximity and the potential to form an interchain disulfide bond once converted to cysteines. The amino acid substitutions result in the least perturbation to the overall structure of the antigen binding domain. The overall effect of the invention is that the native interchain disulfide bond between the CH1 and CL regions in one arm of the bispecific antibody is shifted to a different site with the recombinantly introduced cysteines and the native interchain disulfide bond in the second arm is unchanged.

The invention generally also relates to isolated bispecific antibodies in which one arm has a shifted interchain disulfide bond as described above and the other arm has the native interchain disulfide bond creating a heterodimer, with one arm comprising a shifted interchain disulfide bond and the second arm comprising the native interchain disulfide bond. The bispecific antibody is capable of binding to two antigens. Bispecific antibodies formed with two different heavy chains (HCs) and light chains (LCs) are difficult to produce due to the propensity of incorrect pairing of the two heavy chains and the two light chains, which results in the production of unwanted products that are difficult to eliminate in the manufacturing process; even when the unwanted products from mispairing can be eliminated during purification, the mispairing reduces the production efficiency for the intended bispecific antibody product. Different strategies to reduce or eliminate mispairing of HCs and LCs have been attempted, but many of them involve protein engineering including domain swap and mutagenesis, leading to increased risk of aggregation and immunogenicity. By introducing a "shifted interchain disulfide bond" in one arm while maintaining the native interchain disulfide bond in the second arm, and concurrently introducing knob in the hole and disulfide bond-forming cysteine mutations in the Fc regions, the heterodimeric bispecific antibody can be produced with improved efficiency. Production of such bispecific antibodies, including, but not limited to anti-CD47/anti-FRα bispecific antibodies, can be carried out by co-expressing the two heavy chains and the two light chains.

Antibodies

The invention generally relates to isolated bispecific antibodies with a shifted interchain disulfide bond on one arm while maintaining the native interchain disulfide bond on the second arm. In particular, the invention generally relates to anti-CD47/anti-FRα bispecific antibodies, nucleic acids and expression vectors encoding the antibodies, recombinant cells containing the vectors, and compositions comprising the antibodies. Methods of making the antibodies, and methods of using the antibodies to treat diseases, including cancer, are also provided. The antibodies of the invention possess one or more desirable functional properties, including but not limited to high-affinity binding to FRα and CD47, high specificity to FRα and CD47, the ability to induce effector-mediated tumor cell lysis, the ability to stimulate complement-dependent cytotoxicity (CDC), antibody-dependent phagocytosis (ADPC), and/or antibody-dependent cellular-mediated cytotoxicity (ADCC) against cells expressing FRα and/or CD47, the ability to mediate the recruitment of conjugated drugs, and the ability to inhibit tumor growth in subjects and animal models when administered alone or in combination with other anti-cancer therapies.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

Several systems are used for the numbering of amino acid residues in antibodies. The Kabat numbering method is a scheme based on variable regions of antibodies (Elvin A. Kabat et al., Sequences of Proteins of Immunological Interest 5th ed. (1991). The EU numbering system is widely used for the constant domains (including portions of the CH1, hinge, and the Fc) (Elvin A. Kabat et al., Sequences of Proteins of Immunological Interest 5th ed. (1991).

As used herein, the term an "isolated antibody" refers to an antibody which is substantially free of other antibodies having different antigenic specificities (e.g., an isolated antibody that specifically binds to FRα is substantially free of antibodies that do not bind to FRα, an isolated antibody that specifically binds to CD47 is substantially free of antibodies that do not bind to CD47, a bispecific antibody that specifically binds to CD47 and FRα is substantially free of antibodies that do not bind to CD47 and FRα). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), a single domain antibody (sdab), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope.

As used herein, the term "FRα" refers to folate receptor α, also known as folate receptor 1 (FOLR1) or folate binding protein (FBP), which is a glycosyl-phosphatidylinositol (GPI)-anchored membrane protein on a cell surface that has high affinity for and transports the active form of folate, 5-methyltetrahydrofolate (5-MTF), and its derivatives into cells (Salazar and Ratnam, Cancer Metastasis Rev 2007; 26:141-52). FRα has become an oncology target because it is overexpressed in certain solid tumors such as ovarian, lung and breast cancers (Toffoli et al., Int J Cancer 1997; 74:193-198 and Boogerd et al., Oncotarget 2016; 7:17442-17454), but its expression is at low levels in limited normal human tissues (Weitman, et al., Cancer Res 1992; 52:3396-3401). Consistent with this observation, phase 1 clinical trials conducted so far with FRα-targeted small and large molecules revealed good drug tolerability (Cheung et al., Oncotarget 2016; 7:52553-52574). Therefore, FRα is a tumor-associated/tumor-specific antigen and anti-FRα monoclonal antibodies (mAbs) and bispecific antibodies can be potential anti-cancer therapies. Further, FRα can be used to specifically target therapeutic molecules to cancer cells. An exemplary amino acid sequence of a human FRα is represented by GenBank Accession No. NP_057937.1.

As used herein, the term "CD47" refers to a multi-spanning transmembrane receptor belonging to the immunoglobulin superfamily, which has been indicated to be involved in multiple cellular process, including cell migration, adhesion, and T cell function. CD47, also known as integrin-associated protein (IAP), ovarian cancer antigen (OA3), Rh-related antigen, and MER6, was originally identified as a tumor antigen on human ovarian cancer and was subsequently shown to be expressed on multiple human tumor types, including both hematologic and solid tumors. The interaction between CD47 and signal regulatory protein alpha (SIRPα), an inhibitory protein expressed on macrophages, prevents phagocytosis of CD47-expressing cells. CD47 is additionally expressed at low levels on virtually all non-malignant cells. The term "human CD47" refers to a CD47 originated from a human. An exemplary amino acid sequence of a human CD47 is represented in GenBank Accession No. NP_001768.1.

As used herein, an antibody that "specifically binds to CD47 and/or FRα" refers to an antibody that binds to CD47 and/or FRα, preferably human CD47 and/or human FRα, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

According to another particular aspect, the invention relates to isolated bispecific antibodies or antigen-binding fragments thereof comprising:

a. a first heavy chain, H1;

b. a second heavy chain, H2;

c. a first light chain, L1; and d. a second light chain, L2;

wherein H1 and L1 form a first arm comprising a first antigen-binding domain that specifically binds a first antigen, preferably a first antigen of human origin, and wherein H2 and L2 form a second arm comprising a second antigen-binding domain that specifically binds a second antigen, preferably a second antigen of human origin, wherein (a) H1 comprises a CH1 region of human IgG1, IgG2, IgG3, or IgG4; and (b) L1 comprises a CL region of a human kappa light chain or a human lambda light chain;

wherein the CH1 and CL regions comprise amino acid substitutions or a native amino acid at an amino acid residue corresponding to the amino acid position of SEQ ID NO:15, 21, 22, or 23 for CH1 and SEQ ID NO:19 or 24 for CL;

wherein the amino acid substitutions or the native amino acid in the CH1 and CL regions are selected from:

(1) K133C and C220X in CH1, and F209C and C214X in CL;
(2) S131C and C220X in CH1, and P119C and C214X in CL;
(3) K133C and C220X in CH1, and K207C and C214X in CL;
(4) F170C and C220X in CH1, and S176C and C214X in CL;
(5) P171C and C220X in CH1, and S162C and C214X in CL;
(6) V173C and C220X in CH1, and Q160C and C214X in CL;
(7) F170C and C131X in CH1, and S176C and C214X in CL;
(8) P171C and C131X in CH1, and S162C and C214X in CL;
(9) V173C and C131X in CH1, and Q160C and C214X in CL;
(10) A129C and C220X in CH1, and S121C and C214X in CL;
(11) K133C and C220X in CH1, and I117C and C214X in CL;
(12) C131 in CH1, and P119C and C214X in CL;
(13) A129C and C131X in CH1, and S121C and C214X in CL;
(14) R133C and C131X in CH1, and K207C and C214X in CL;
(15) R133C and C131X in CH1, and I117C and C214X in CL;
(16) R133C and C131X in CH1, and L117C and C214X in CL;
(17) K133C and C220X in CH1, and L117C and C214X in CL;
(18) R133C and C131X in CH1, and F209C and C214X in CL;
(19) R133C and C131X in CH1, and V209C and C214X in CL; or
(20) K133C and C220X in CH1, and V209C and C214X in CL;

wherein X is selected from S, A or G.

According to another particular aspect, the invention relates to isolated bispecific antibodies or antigen-binding fragment thereof comprising:

a. a first heavy chain, H1;
b. a second heavy chain, H2;
c. a first light chain, L1; and
d. a second light chain, L2;

wherein H1 and L1 form a first arm comprising a first antigen-binding domain that specifically binds a first antigen, preferably a first antigen of human origin, and wherein H2 and L2 form a second arm comprising a second antigen-binding domain that specifically binds a second antigen, preferably a second antigen of human origin, wherein (a) H1 comprises a CH1 region of human IgG1, IgG2, IgG3, or IgG4 and a heavy chain variable region (VH region); and
(b) L1 comprises a CL region of a human kappa light chain or a human lambda light chain and a light chain variable region (VL region);

wherein the CH1 region, the VH region, the CL region, and the VL region comprise amino acid substitutions at an amino acid residue corresponding to the amino acid position of SEQ ID NO: 15, 21, 22, or 23 for CH1; SEQ ID NO: 13 for VH; SEQ ID NO: 19 or 24 for CL; and SEQ ID NO: 17 for VL;

wherein the amino acid substitutions in the CH1 region, the VH region, the CL region, and the VL region are selected from:

(1) C220X in CH1, G44C in VH, C214X in CL, and G101C in VL; or
(2) C131X in CH1, G44C in VH, C214X in CL, and G101C in VL;

wherein X is selected from S, A or G.

According to another particular aspect, the first antigen-binding domain is a CD47 binding domain. In certain embodiments, the VH region comprises an amino acid sequence of SEQ ID NO: 1, the CH1 region comprises an amino acid sequence of SEQ ID NO: 2, the VL region comprises an amino acid sequence of SEQ ID NO: 3, and the CL region comprises an amino acid sequence of SEQ ID NO: 4.

According to another particular aspect, (a) the second arm comprising H2 and L2 does not comprise the amino acid substitutions of the first arm comprising H1 and L1; (b) the two heavy chains H1 and H2 each comprise a VH region, a CH1 region, and a Fc region (containing CH2 and CH3 regions), wherein the VH regions have different amino acid sequences; (c) the two heavy chains H1 and H2 each comprise a VH region, a CH1 region, and a Fc region (containing CH2 and CH3 regions), wherein the CH1 regions have different amino acid sequences; (d) the two heavy chains H1 and H2 each comprise a VH region, a CH1 region, and a Fc region (containing CH2 and CH3 regions), wherein the Fc regions have different amino acid sequences; (e) the two light chains L1 and L2 each comprise a VL region and a CL region, wherein the VL regions have different amino acid sequences; and/or (f) the two light chains L1 and L2 each comprise a VL region and a CL region, wherein the CL regions have different amino acid sequences.

In another particular aspect, H1 and H2 form a heterodimer.

In another particular aspect, (a) the VH region of H1 and the VL region of L1 have a Q39E and a Q38K substitution mutation, respectively, and the VH region of H2 and the VL region of L2 have a Q39K and a Q38E substitution mutation, respectively; or the VH region of H1 and the VL region of L1 have a Q39K and a Q38E substitution mutation, respectively, and the VH region of H2 and the VL region of L2 have a Q39E and a Q38K substitution mutation, respectively.

In another particular aspect, the isolated bispecific antibody or antigen-binding fragment thereof is an anti-CD47/anti-FRα bispecific antibody or antigen-binding fragment thereof. In certain embodiments, the anti-CD47/anti-FRα bispecific antibody or antigen-binding fragment thereof is capable of blocking binding of signal regulatory protein alpha (SIRPα) to CD47 on cancer cells that express both FRα and CD47. In certain embodiments, the isolated humanized anti-CD47/anti-FRα bispecific antibody or antigen-binding fragment thereof is capable of inducing macrophage-mediated phagocytosis of cancer cells that express both FRα and CD47. In certain embodiments, the isolated humanized anti-CD47/anti-FRα bispecific antibody or antigen-binding fragment thereof is capable of binding cancer cells that express both FRα and CD47 with minimal to undetectable binding to human red blood cells (RBCs).

In another particular aspect, the first antigen-binding domain has the VH sequence of SEQ ID: 13 and VL sequence of SEQ ID: 17, and the second antigen-binding domain has the VH sequence of SEQ ID: 33 and VL sequence of SEQ ID: 35; or the first antigen-binding domain has the VH sequence of SEQ ID: 13 and VL sequence of SEQ ID: 17, and the second antigen-binding domain has the VH sequence of SEQ ID: 14 and VL sequence of SEQ ID: 18.

Full length bispecific antibodies of the invention can be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent monospecific antibody molecule and simultaneously CH3 domains of the parent antibodies release and reform by dissociation-association. The CH3 domains of the Fab arms can be engineered to favor heterodimerization over homodimerization. The resulting product is a bispecific antibody having two Fab arms or half molecules which each bind a distinct epitope, i.e., an epitope on CD47 and an epitope on FRα.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Publ. No. WO2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob." Exemplary CH3 substitution pairs forming a knob and a hole are (expressed as modified positions in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface can be used, as described in U.S. Pat. Publ. No. 2010/0015133; U.S. Pat. Publ. No. 2009/0182127; U.S. Pat. Publ. No. 2010/028637; or U.S. Pat. Publ. No. 2011/0123532. In other strategies, heterodimerization can be promoted by the following substitutions (expressed as modified position in the first CH3 domain of the first heavy chain/modified position in the second CH3 domain of the second heavy chain): L351Y_F405AY407V/T394W, T366I_K392M_T394W/F405A_Y407V, T366L_K392M_T394W/F405A_Y407V, L351Y_Y407A/T366A_K409F, L351Y_Y407A/T366V K409F Y407A/T366A_K409F, or T350V_L351Y_F405A Y407V/T350V_T366L_K392L_T394W as described in U.S. Pat. Publ. No. 2012/0149876 or U.S. Pat. Publ. No. 2013/0195849.

In addition to methods described above, bispecific antibodies of the invention can be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in PCT Pat. Publ. No. WO2011/131746. In the methods, the first monospecific bivalent antibody and the second monospecific bivalent antibody are engineered to have certain substitutions at the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions can optionally be restored to non-reducing conditions. Exemplary reducing agents that can be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, preferably a reducing agent selected from the group consisting of: 2-mercaptoethylamine, dithiothreitol and tris (2-carboxyethyl) phosphine. For example, incubation for at least 90 minutes at a temperature of at least 20° C. in the presence of at least 25 mM 2-MEA or in the presence of at least 0.5 mM dithiothreitol at a pH from 5-8, for example at pH of 7.0 or at pH of 7.4 can be used.

In another general aspect, the invention relates to an isolated nucleic acid encoding a bispecific antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding antibodies or antigen-binding fragments thereof of the invention can be altered without changing the amino acid sequences of the proteins.

In another general aspect, the invention relates to a vector comprising an isolated nucleic acid encoding a bispecific antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention. Such techniques are well known to those skilled in the art in view of the present disclosure.

In another general aspect, the invention relates to a host cell comprising a vector comprising an isolated nucleic acid encoding a bispecific antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a bispecific antibody or antigen-binding fragment thereof of the invention, comprising culturing a cell comprising a nucleic acid encoding the bispecific antibody or antigen-binding fragment thereof under conditions to produce a bispecific antibody or antigen-binding fragment thereof of the invention, and recovering the bispecific antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated bispecific antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g., 21$^{st}$ edition (2005), and any later editions). Non-limiting examples of additional ingredients include buffers, diluents, solvents, tonicity regulating agents, preservatives, stabilizers, and chelating agents. One or more pharmaceutically acceptable carriers can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethylene glycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a bispecific antibody or antigen-binding fragment thereof of the invention, comprising combining a bispecific antibody or antigen-binding fragment thereof with a pharmaceutically acceptable carrier to obtain the pharmaceutical composition.

Methods of Use

In another general aspect, the invention relates to a method of targeting FRα and CD47 that are both expressed on a cancer cell surface in a subject in need thereof, the method comprises administering to the subject in need thereof an anti-CD47/anti-FRα bispecific antibody or antigen-binding fragment thereof or a pharmaceutical composition of the invention. Binding of the bispecific antibody or antigen-binding fragment thereof to FRα and/or CD47 can mediate complement-dependent cytotoxicity (CDC), antibody-dependent phagocytosis (ADPC), and/or antibody-dependent cellular cytotoxicity (ADCC) or other effects that result in the death of the targeted cancer cell. The bispecific antibody or antigen-binding fragment thereof can, for example, serve to recruit conjugated drugs to mediate the death of the targeted cancer cell.

In another general aspect, the invention relates to a method of blocking binding of SIRPα to CD47 on cancer cells that express both FRα and CD47 in a subject in need thereof, the method comprises administering to the subject in need thereof an anti-CD47/anti-FRα bispecific antibody or antigen-binding fragment thereof or a pharmaceutical composition of the invention.

In another general aspect, the invention relates to a method of inducing macrophage-mediated phagocytosis of cancer cells that express both FRα and CD47 in a subject in need thereof, the method comprises administering to the subject in need thereof an anti-CD47/anti-FRα bispecific antibody or antigen-binding fragment thereof or a pharmaceutical composition of the invention.

In another general aspect, the invention relates to a method of binding cancer cells that express both FRα and CD47 by a humanized anti-CD47/anti-FRα bispecific antibody or antigen-binding fragment thereof with minimal to undetectable binding to human red blood cells (RBCs) in a subject in need thereof, the method comprises administering to the subject in need thereof an isolated humanized anti-CD47/anti-FRα bispecific antibody or antigen-binding fragment thereof, or a pharmaceutical composition of the invention. The humanized anti-CD47/anti-FRα bispecific antibody or antigen-binding fragment thereof of the invention has high selectivity for cancer cells with minimal to undetectable binding to human red blood cells (RBCs).

The functional activity of bispecific antibodies and antigen-binding fragments thereof that bind both FRα and CD47 can be characterized by methods known in the art and as described herein. Methods for characterizing bispecific antibodies and antigen-binding fragments thereof that bind both FRα and CD47 include, but are not limited to, affinity and specificity assays including Biacore, ELISA, FACS and OctetRed analysis. According to particular embodiments, the methods for characterizing bispecific antibodies and antigen-binding fragments thereof that bind both FRα and CD47 include those described below.

In another general aspect, the invention relates to a method of treating a cancer in a subject in need thereof, comprising administering to the subject in need thereof an isolated humanized anti-CD47/anti-FRα bispecific antibody or antigen-binding fragment thereof or a pharmaceutical composition of the invention. The cancer can be any liquid or solid cancer, for example, it can be selected from, but not limited to, a lung cancer, a gastric cancer, an esophageal cancer, a bile duct cancer, a cholangiocarcinoma, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

According to embodiments of the invention, the pharmaceutical composition comprises a therapeutically effective amount of an anti-CD47/anti-FRα bispecific antibody or antigen-binding fragment thereof of the invention. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-CD47/anti-FRα bispecific antibodies or antigen-binding fragments thereof, a therapeutically effective amount means an amount of the anti-CD47/anti-FRα bispecific antibody or antigen-binding fragment thereof that modulates an immune response in a subject in need thereof. Also as used herein with reference to anti-CD47/anti-FRα bispecific antibodies or antigen-binding fragments thereof, a therapeutically effective amount means an amount of the anti-CD47/anti-FRα bispecific antibody or antigen-binding fragment thereof that results in treatment of a disease, disorder, or condition; prevents or slows the progression of the disease, disorder, or condition; or reduces or completely alleviates symptoms associated with the disease, disorder, or condition.

According to particular embodiments, the disease, disorder or condition to be treated is cancer, preferably a cancer selected from the group consisting of a lung cancer, a gastric cancer, an esophageal cancer, a bile duct cancer, a cholangiocarcinoma, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors. According to other particular embodiments, the disease, disorder or condition to be treated is an inflammatory disease, a metabolic disease, or any other disease where a bispecific antibody can be used as a therapy.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, provided is a composition used in the treatment of a cancer. For cancer therapy, the composition can be used in combination with another treatment including, but not limited to, a chemotherapy, an anti-TIM-3 mAb, an anti-LAG-3 mAb, an anti-CD73 mAb, an anti-apelin mAb, an anti-CTLA-4 antibody, an anti-EGFR mAb, an anti-HER-2 mAb, an anti-CD19 mAb, an anti-CD20 mAb, an anti-CD33 mAb, an anti-TIP-1 mAb, an anti-DLL3 mAb, an anti-CLDN18.2 mAb, an anti-PD-L1 antibody, an anti-PD-1 antibody, a PD-1/PD-L1 therapy, other immuno-oncology drugs, an antiangiogenic agent, a radiation therapy, an antibody-drug conjugate (ADC), a targeted therapy, or other anticancer drugs.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

EMBODIMENTS

The invention provides also the following non-limiting embodiments.

Embodiment 1 is an isolated bispecific antibody or antigen-binding fragment thereof comprising:

a. a first heavy chain, H1;
b. a second heavy chain, H2;
c. a first light chain, L1; and
d. a second light chain, L2;

wherein H1 and L1 form a first arm comprising a first antigen-binding domain that specifically binds a first antigen, preferably a first antigen of human origin, and wherein H2 and L2 form a second arm comprising a second antigen-binding domain that specifically binds a second antigen, preferably a second antigen of human origin, wherein (a) H1 comprises a CH1 region of human IgG1, IgG2, IgG3, or IgG4; and
(b) L1 comprises a CL region of a human kappa light chain or a human lambda light chain;

wherein the CH1 and CL regions comprise amino acid substitutions or a native amino acid at an amino acid residue corresponding to the amino acid position of SEQ ID NO:15, 21, 22, or 23 for CH1 and SEQ ID NO:19 or 24 for CL; wherein the amino acid substitutions or the native amino acid in the CH1 and CL regions are selected from:

(1) K133C and C220X in CH1, and F209C and C214X in CL;
(2) S131C and C220X in CH1, and P119C and C214X in CL;
(3) K133C and C220X in CH1, and K207C and C214X in CL;
(4) F170C and C220X in CH1, and S176C and C214X in CL;
(5) P171C and C220X in CH1, and S162C and C214X in CL;
(6) V173C and C220X in CH1, and Q160C and C214X in CL;
(7) F170C and C131X in CH1, and S176C and C214X in CL;
(8) P171C and C131X in CH1, and S162C and C214X in CL;
(9) V173C and C131X in CH1, and Q160C and C214X in CL;
(10) A129C and C220X in CH1, and S121C and C214X in CL;
(11) K133C and C220X in CH1, and 1117C and C214X in CL;
(12) C131 in CH1, and P119C and C214X in CL;
(13) A129C and C131X in CH1, and S121C and C214X in CL;
(14) R133C and C131X in CH1, and K207C and C214X in CL;
(15) R133C and C131X in CH1, and 1117C and C214X in CL;
(16) R133C and C131X in CH1, and L117C and C214X in CL;
(17) K133C and C220X in CH1, and L117C and C214X in CL;
(18) R133C and C131X in CH1, and F209C and C214X in CL;
(19) R133C and C131X in CH1, and V209C and C214X in CL; or
(20) K133C and C220X in CH1, and V209C and C214X in CL;

wherein X is selected from S, A, or G.

Embodiment 2 is an isolated bispecific antibody or antigen-binding fragment thereof comprising:

a. a first heavy chain, H1;
b. a second heavy chain, H2;
c. a first light chain, L1; and
d. a second light chain, L2;

wherein H1 and L1 form a first arm comprising a first antigen-binding domain that specifically binds a first antigen, preferably a first antigen of human origin, and wherein H2 and L2 form a second arm comprising a second antigen-binding domain that specifically binds a second antigen, preferably a second antigen of human origin, wherein (a) H1 comprises a CH1 region of human IgG1, IgG2, IgG3, or IgG4 and a heavy chain variable region (VH region); and
(b) L1 comprises a CL region of a human kappa light chain or a human lambda light chain and a light chain variable region (VL region);

wherein the CH1 region, the VH region, the CL region, and the VL region comprise amino acid substitutions at an amino acid residue corresponding to the amino acid position of SEQ ID NO: 15, 21, 22, or 23 for CH1; SEQ ID NO: 13 for VH; SEQ ID NO: 19 or 24 for CL; and SEQ ID NO: 17 for VL;

wherein the amino acid substitutions in the CH1 region, the VH region, the CL region, and the VL region are selected from:

(1) C220X in CH1, G44C in VH, C214X in CL, and G101C in VL; or
(2) C131X in CH1, G44C in VH, C214X in CL, and G101C in VL;

wherein X is selected from S, A, or G.

Embodiment 3 is the isolated bispecific antibody or antigen-binding fragment thereof of embodiments 1 or 2, wherein the first antigen-binding domain is a CD47 binding domain.

Embodiment 4 is the isolated bispecific antibody or antigen-binding fragment thereof of embodiment 3, wherein the VH region comprises an amino acid sequence of SEQ ID NO: 1, the CH1 region comprises an amino acid sequence of SEQ ID NO: 2, the VL region comprises an amino acid sequence of SEQ ID NO: 3, and the CL region comprises an amino acid sequence of SEQ ID NO: 4.

Embodiment 5 is the isolated bispecific antibody or antigen-binding fragment thereof of any one of embodiments 1 to 4, wherein (a) the second arm comprising H2 and L2 does not comprise the amino acid substitutions of the first arm comprising H1 and L1;

(b) the two heavy chains H1 and H2 each comprise a VH region, a CH1 region, and a Fc region (containing CH2 and CH3 regions), wherein the VH regions have different amino acid sequences;

(c) the two heavy chains H1 and H2 each comprise a VH region, a CH1 region, and a Fc region (containing CH2 and CH3 regions), wherein the CH1 regions have different amino acid sequences;

(d) the two heavy chains H1 and H2 each comprise a VH region, a CH1 region, and a Fc region (containing CH2 and CH3 regions), wherein the Fc regions have different amino acid sequences;

(e) the two light chains L1 and L2 each comprise a VL region and a CL region, wherein the VL regions have different amino acid sequences; and/or (f) the two light chains L1 and L2 each comprise a VL region and a CL region, wherein the CL regions have different amino acid sequences.

Embodiment 6 is the isolated bispecific antibody or antigen-binding fragment thereof of embodiment 5, wherein H1 and H2 form a heterodimer.

Embodiment 7 is the isolated bispecific antibody or antigen-binding fragment thereof of any one of claims 1 to 6, wherein (a) the VH region of H1 and the VL region of L1 have a Q39E and a Q38K substitution mutation, respectively, and the VH region of H2 and the VL region of L2 have a Q39K and a Q38E substitution mutation, respectively; or (b) the VH region of H1 and the VL region of L1 have a Q39K and a Q38E substitution mutation, respectively, and the VH region of H2 and the VL region of L2 have a Q39E and a Q38K substitution mutation, respectively.

Embodiment 8 is the isolated bispecific antibody or antigen-binding fragment thereof of any one of embodiments 1 to 7, wherein the isolated bispecific antibody or antigen-binding fragment is an anti-CD47/anti-FRα bispecific antibody or antigen-binding fragment thereof, wherein the first antigen-binding domain specifically binds CD47, preferably human CD47, and the second antigen-binding domain specifically binds folate receptor α (FRα), preferably human FRα.

Embodiment 9 is the isolated bispecific antibody or antigen-binding fragment thereof of any one of claims 1 to 8, wherein (a) the first antigen-binding domain has the VH sequence of SEQ ID: 13 and VL sequence of SEQ ID: 17, and the second antigen-binding domain has the VH sequence of SEQ ID: 33 and VL sequence of SEQ ID: 35; or (b) the first antigen-binding domain has the VH sequence of SEQ ID: 13 and VL sequence of SEQ ID: 17, and the second antigen-binding domain has the VH sequence of SEQ ID: 14 and VL sequence of SEQ ID: 18.

Embodiment 10 is the isolated bispecific antibody or antigen-binding fragment thereof of embodiments 8 or 9, wherein the anti-CD47/anti-FRα bispecific antibody or antigen-binding fragment thereof is capable of blocking binding of signal regulatory protein alpha (SIRPα) to CD47 on cancer cells that express both FRα and CD47, inducing macrophage-mediated phagocytosis of cancer cells that express both FRα and CD47, and/or binding cancer cells that express both FRα and CD47 with minimal to undetectable binding to human red blood cells (RBCs).

Embodiment 11 is an isolated nucleic acid encoding the bispecific antibody or antigen-binding fragment of any one of embodiments 1 to 10.

Embodiment 12 is a vector comprising the isolated nucleic acid of embodiment 11.

Embodiment 13 is a host cell comprising the vector of embodiment 12.

Embodiment 14 is a pharmaceutical composition, comprising the isolated bispecific antibody or antigen-binding fragment thereof of any one of embodiments 1 to 10 and a pharmaceutically acceptable carrier.

Embodiment 15 is a method of targeting FRα and CD47 that are both expressed on a cancer cell surface in a subject in need thereof, blocking the binding of SIRPα to CD47 on cancer cells that express both FRα and CD47 in a subject in need thereof, inducing macrophage-mediated phagocytosis of cancer cells that express both FRα and CD47 in a subject in need thereof, binding cancer cells that express both FRα and CD47 with minimal to undetectable binding to human red blood cells (RBCs) in a subject in need thereof, and/or treating cancer in a subject in need thereof, comprising administering to the subject a pharmaceutical composition comprising the isolated anti-CD47/anti-FRα bispecific antibody or antigen-binding fragment thereof of any one of embodiments 8 to 10 and a pharmaceutically acceptable carrier, optionally, the cancer is selected from the group consisting of a lung cancer, a gastric cancer, an esophageal cancer, a bile duct cancer, a cholangiocarcinoma, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Embodiment 16 is a method of producing the bispecific antibody or antigen-binding fragment thereof of any one of embodiments 1 to 10, comprising culturing a cell comprising a nucleic acid encoding the bispecific antibody or antigen-binding fragment thereof under conditions to produce the bispecific antibody or antigen-binding fragment thereof, and recovering the bispecific antibody or antigen-binding fragment thereof from the cell or culture.

Embodiment 17 is a method of producing a pharmaceutical composition comprising the bispecific antibody or antigen-binding fragment thereof of any one of embodiments 1 to 10, comprising combining the bispecific antibody or antigen-binding fragment thereof with a pharmaceutically acceptable carrier to obtain the pharmaceutical composition.

EXAMPLES

Figure 1B:
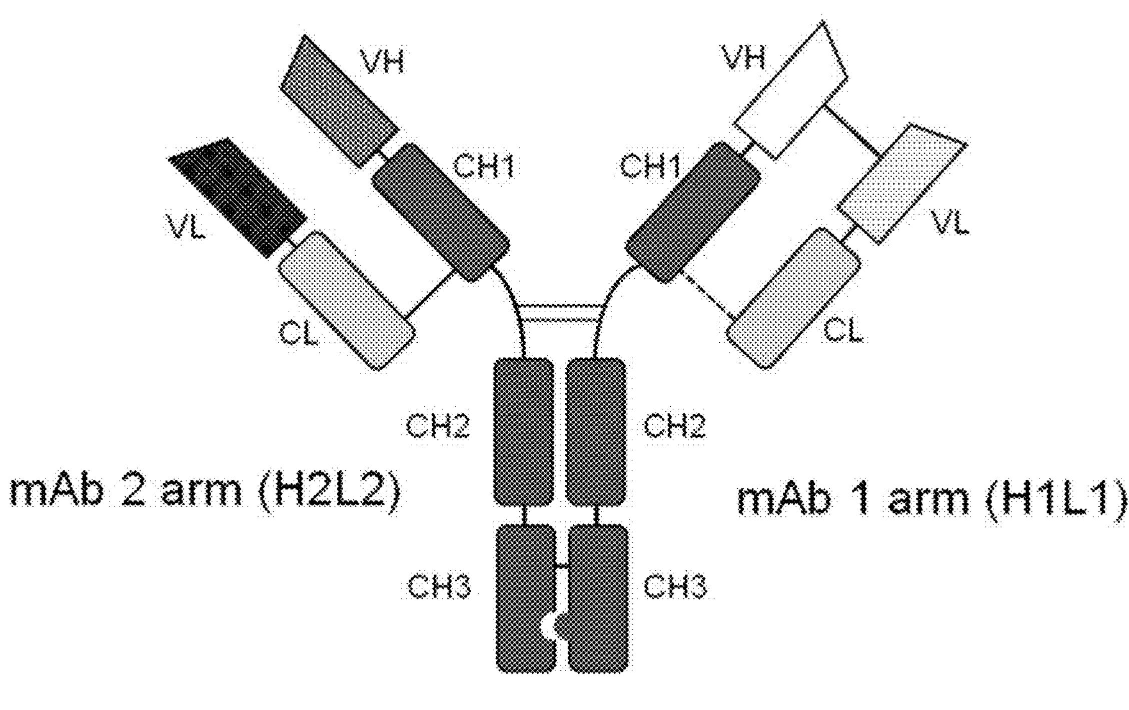
Figure 3A:
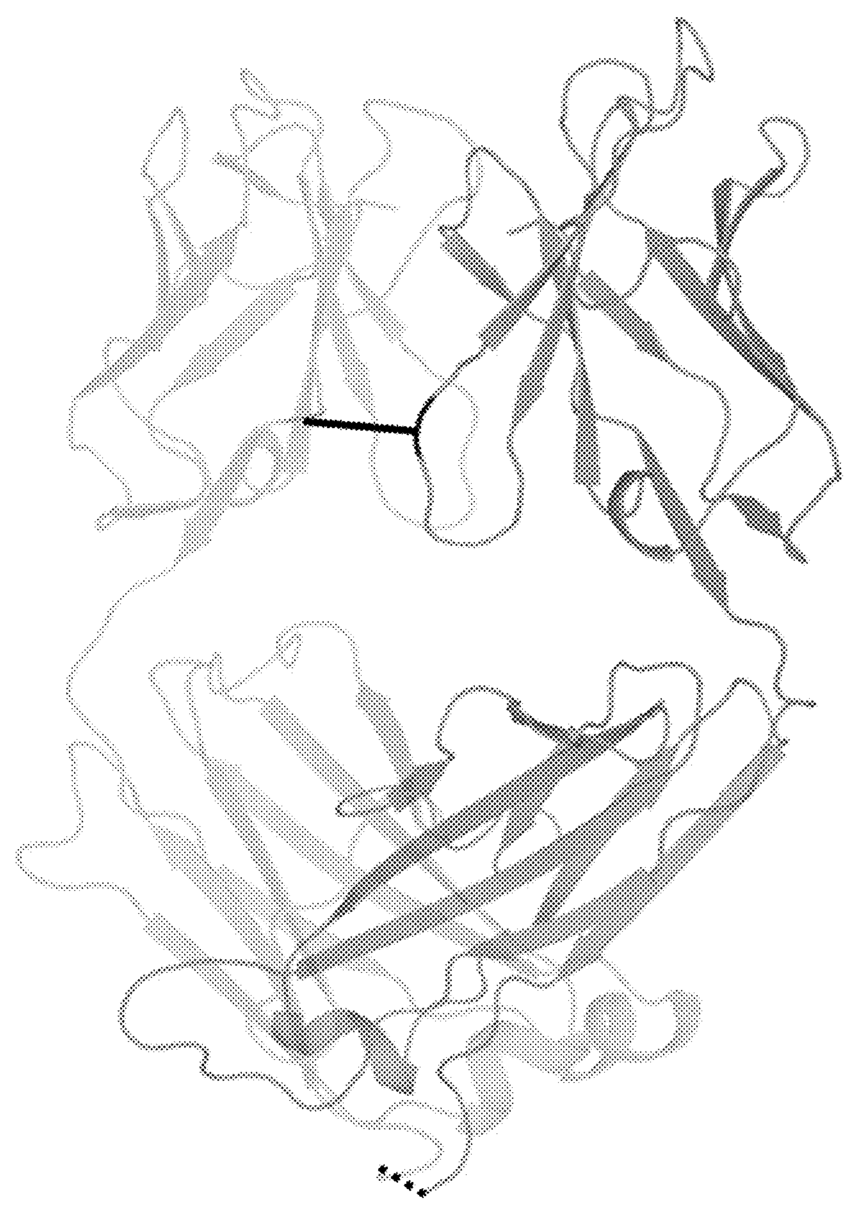
FIGS. 3A-3L show the 3-D modeling of the Fab region (containing VH, CH1, VL and CL) in a mAb 1 arm to identify potential sites for cysteine knock-ins to form a new interchain disulfide bond between the HC and LC. The dashed line represents the native interchain disulfide bond between the HC and LC (the native interchain disulfide region was not included in the models for bsAb 9, 10, 11, and 12, and, therefore, there is no dashed line in the models of these 4 bsAbs); the solid line represents the potential new interchain disulfide bond formed by the newly knocked in cysteines.
Figure 3B:
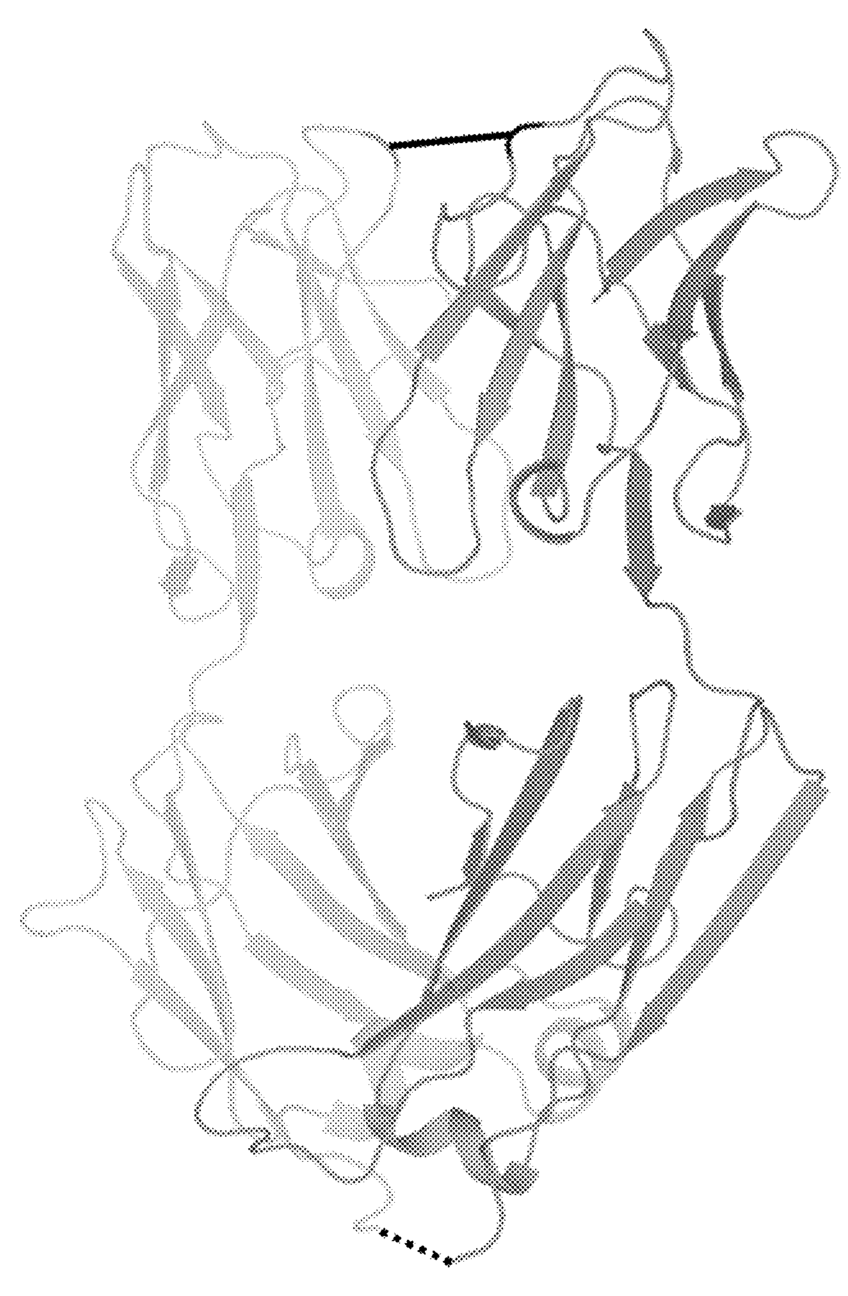
Figure 3C:
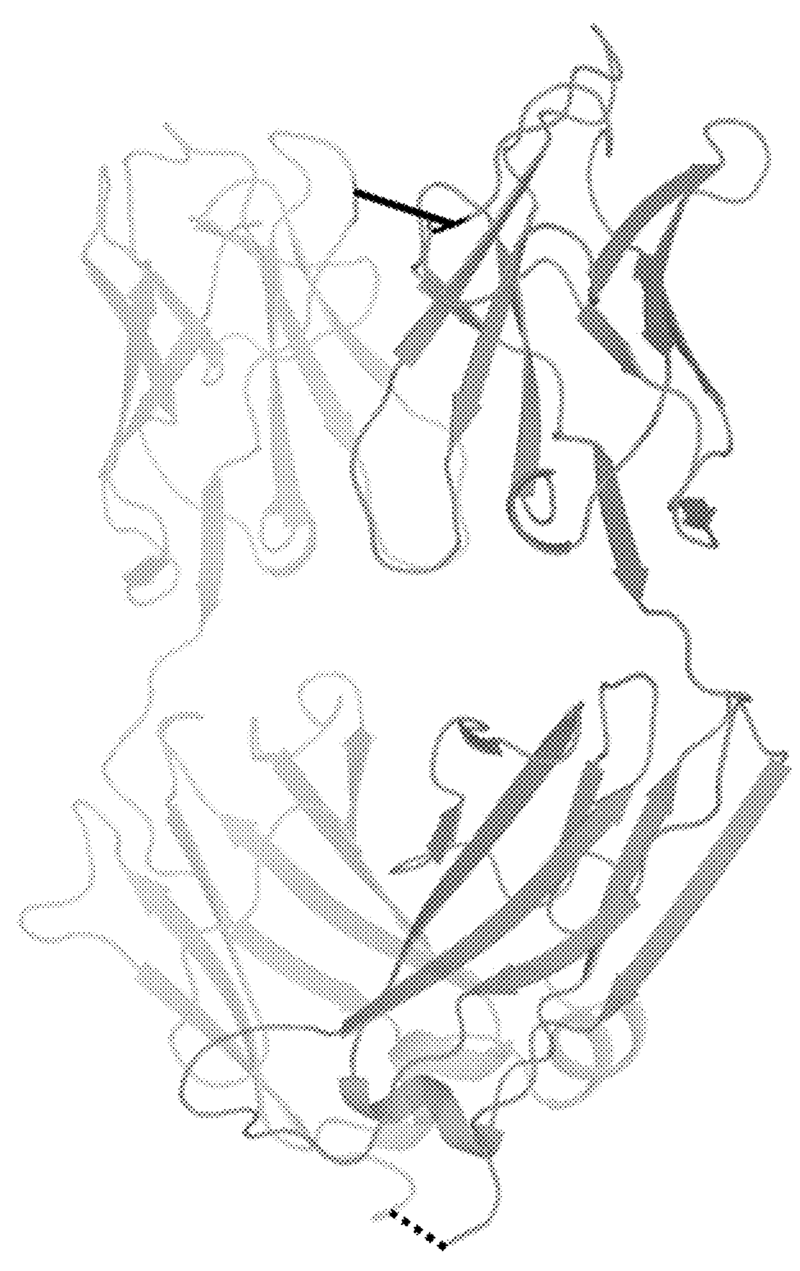
Figure 3D:
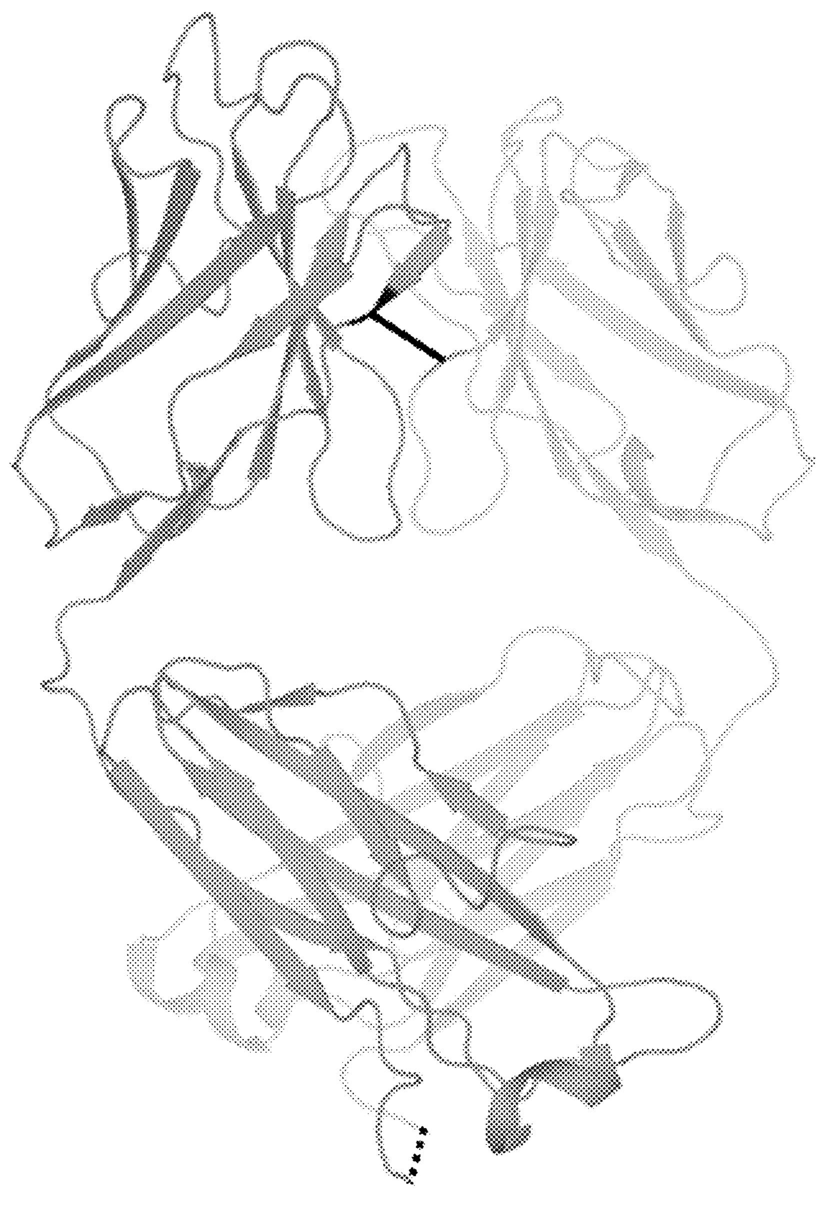
Figure 3E:
Figure 3F:
Figure 3G:
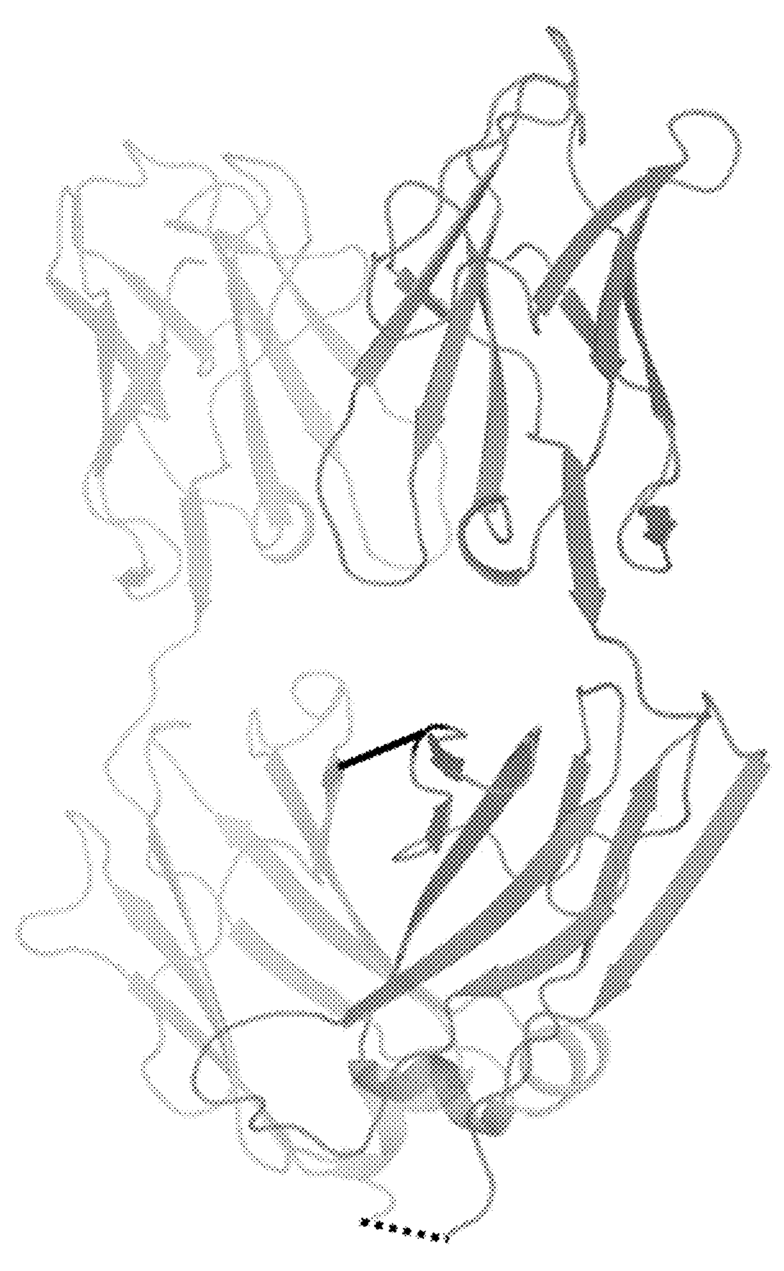
Figure 3H:
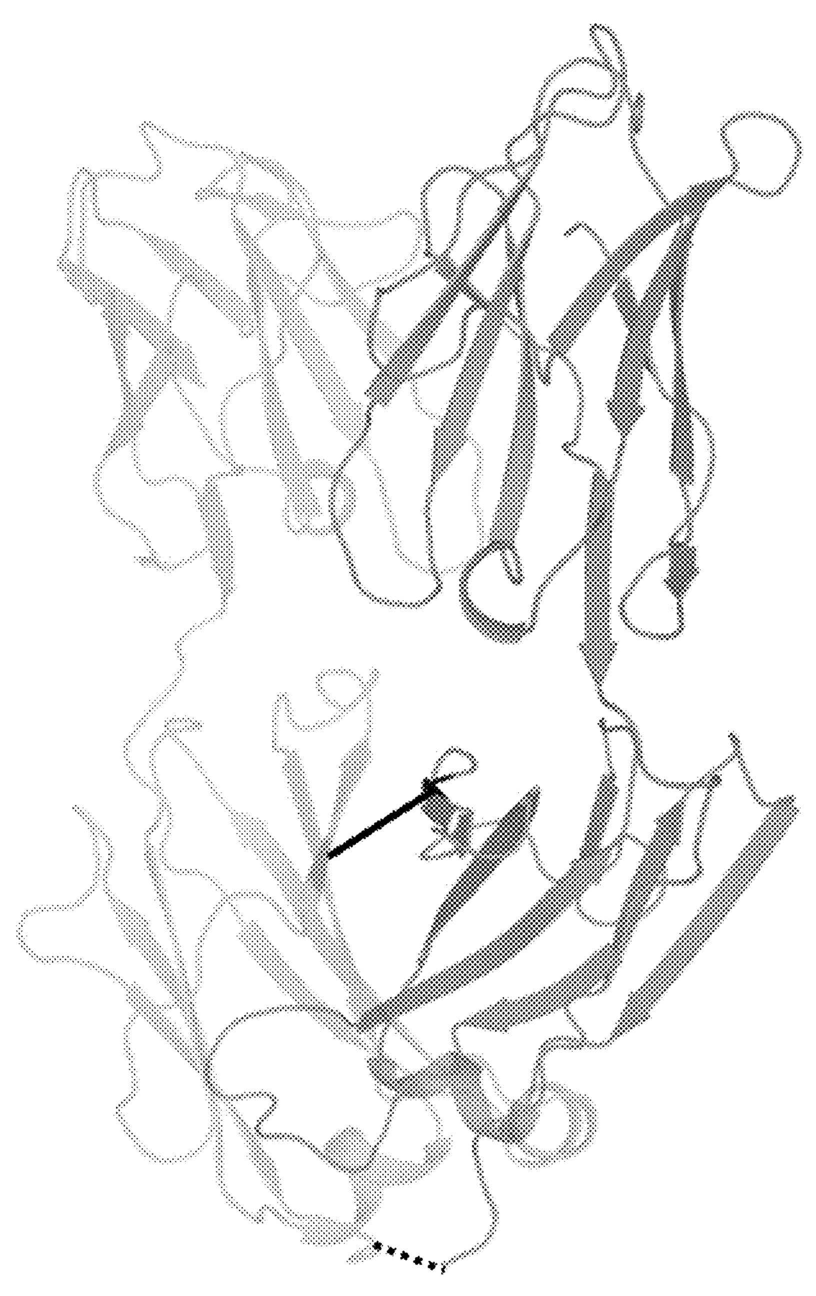
Figure 3I:
Figure 3J:
Figure 3K:
Figure 3L:

Example 1: Construction of Bispecific Antibodies with Altered Cysteine Sites FIGS. 1A and 1B illustrate a bispecific antibody with two different heavy chains and two different light chains in a heterodimer of H1H2, which can be facilitated with common approaches such as knob-in-hole and charged pairs. The two native cysteines that form the interchain disulfide bond in the H1L1 arm can be converted to non-cysteines so that the native interchain disulfide bond is eliminated (the dashed lines in FIGS. 1A and 1B); in the meantime, two native non-cysteine residues in H1L1 close to each other in the 3-D structure can be converted to cysteines to form a new interchain disulfide bond (the solid lines in FIGS. 1A and 1B). The newly formed interchain disulfide bond can be between CH1 and CL of H1L1 (FIG. 1A) or VH and VL of H1L1 (FIG. 1B). By shifting the sites for the interchain disulfide bond in H1L1, the two light chains can pair favorably with their corresponding heavy chains, respectively. Further, the asymmetric structure formed as a result of shifting the interchain disulfide bond on the mAb 1 arm can better differentiate the physical properties of the bispecific antibody and the potential impurities, facilitating the purification and production of the intended bispecific antibody. Multiple pairs of native non-cysteine residues (also called "knock-in sites") in H1L1 that can form a new interchain disulfide bond were identified. The examples below are shown with bispecific antibodies in the human IgG1 heavy chain VH and CH1, and kappa light chain VL and CL sequences. This concept can also be applied to constructing bispecific antibodies using CH1 of human IgG2, IgG3, or IgG4 heavy chain, and CL of human lambda light chain whenever conserved knock-in sites exist. Whenever a knock-in site happens to be a native cysteine (not the ones involved in forming the native interchain disulfide bond), it can be directly used to form the new interchain disulfide bond.

A humanized anti-CD47 mAb (described in International Pat. Pub. No. WO2019/217145; referred to as mAb 1 here) and two humanized anti-FRα mAbs (described in International Pat. Pub. No. WO2019/177854; referred to as mAb 2 and mAb 2b, respectively, here) were used to construct anti-CD47/anti-FRα bispecific antibodies. FIGS. 1A and 1B illustrate the structure of a desired bispecific antibody, with mAb 1 (anti-CD47) as the right arm and mAb 2 (anti-FRα) as the left arm (in some bispecific antibodies, mAb 2b rather than mAb 2 is used as the left arm). The VH and VL regions of the bispecific antibody were fused to the constant regions of human IgG1 heavy chain (HC) and kappa light chain (LC), respectively. The mAb 1 HC has the T366W (EU numbering) mutation to form a "knob" and the mAb 2 HC has the mutations T366S, L368A, and Y407V to form a "hole," so that the two heavy chains were favored to form a bispecific antibody with heterodimeric HCs (mAb 1 HC/mAb 2 HC) rather than homodimeric HCs (mAb 1 HC/mAb 1 HC or mAb 2 HC/mAb 2 HC). In addition, a S354C cysteine mutation was introduced on the mAb 1 HC and a Y349C cysteine mutation was introduced on the mAb 2 HC to stabilize the heterodimeric pairing of the heavy chains of the heterodimer (Merchant et al. Nat. Biotechnol. 16(7):677-81 (1998)). A strategy of shifting the interchain disulfide bond between the HC and the LC on the mAb 1 arm was employed to favor the expression, purification, and/or production of the intended bispecific antibody when the two HCs and two LCs were co-transfected into cells. To achieve this goal, the two native cysteines on the HC and LC of the mAb 1 arm, respectively, that form the interchain disulfide bond were converted to serine residues, and two native non-cysteine residues on the HC and LC of the mAb 1 arm, respectively, were identified through structural modeling for their close proximity, such that once cysteines were introduced into these sites (herein referred to as "knocked in cysteines" or "alternative cysteines"), the cysteine residues would potentially form a new interchain disulfide bond. The newly formed interchain disulfide bond through pairing of alternative cysteines can be between the CH1 and CL regions as shown in FIG. 1A or between the VH and VL regions as shown in FIG. 1B, where the native interchain disulfide bond between the CH1 and CL region of the mAb 1 arm is marked with the dashed line and the newly formed interchain disulfide bond by knocked in cysteines on the mAb 1 arm is marked with a solid line. No mutations were introduced to the VH, VL, CH1, or CL regions of the mAb 2 arm and therefore, the mAb 2 arm has the same native interchain disulfide bond.

The VH, CH1, VL, and CL sequences of mAb 1 and mAb 2, and the IgG2 CH1, IgG3 CH1, IgG4 CH1 and lambda CL sequences are listed in FIGS. 2A-2F and Table 1 (SEQ ID NOs: 13, 15, 17, and 19, respectively, for mAb 1; and SEQ ID NOs: 14, 16, 18, and 20, respectively, for mAb 2; and SEQ ID NOs: 21, 22, 23 and 24, respectively, for IgG2 CH1, IgG3 CH1, IgG4 CH1 and lambda CL). The VH, CH1, VL, and CL sequences of mAb 2b are listed in Table 1 (SEQ ID NOs: 33, 34, 35, and 36, respectively). The anti-CD47 antibody mAb 1 was selected as the arm with modified interchain disulfide bond. Homology models to a number of previously solved antibody structures in the public domain were generated in Schrodinger BioLuminate® (Schrodinger; New York, NY), and possible interchain disulfide bridges were identified with the Cysteine Mutation tool using a beta-carbon cutoff distance of 7 Å. Identified pairs were further analyzed individually and pairwise with the Mutagenesis tool to identify non-cysteine to cysteine mutations, which resulted in the least perturbation to the overall structure while resulting in a decrease in interchain binding affinity for single non-cysteine to cysteine mutations while not significantly affecting binding affinity for paired cysteine mutations. The top candidates were selected for expression and experimental validation. The potential disulfide bonds formed by the knock-in cysteine sites are marked with a solid line and the native interchain disulfide bonds are marked with a dashed line as shown in FIGS. 3A-3L. The native interchain disulfide region was not included in the models for bsAb 9, 10, 11, and 12 and therefore, there is no dashed line in the models of these 4 bsAbs. Each of the mAb 1 arms with different pairs of knocked in cysteines was paired with one native mAb 2 arm to form a bispecific antibody (bsAb). The amino acid substitutions on the mAb 1 arm of the mAb 1/mAb 2 bispecific antibody for shifted interchain disulfide bond are listed in Table 2.

Figure 4A:
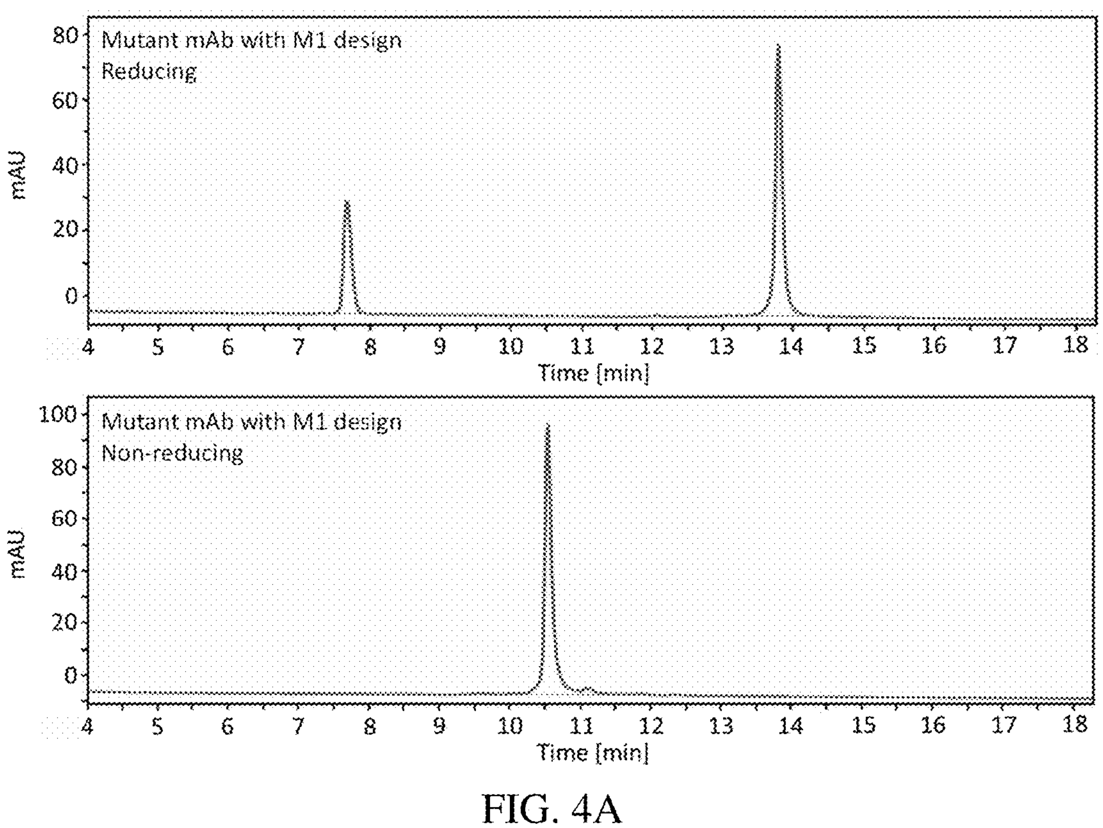
FIGS. 4A-4H show the RP-HPLC profiles of mutant mAbs containing different shifted interchain disulfide bonds under reducing or non-reducing condition.
Figure 4B:
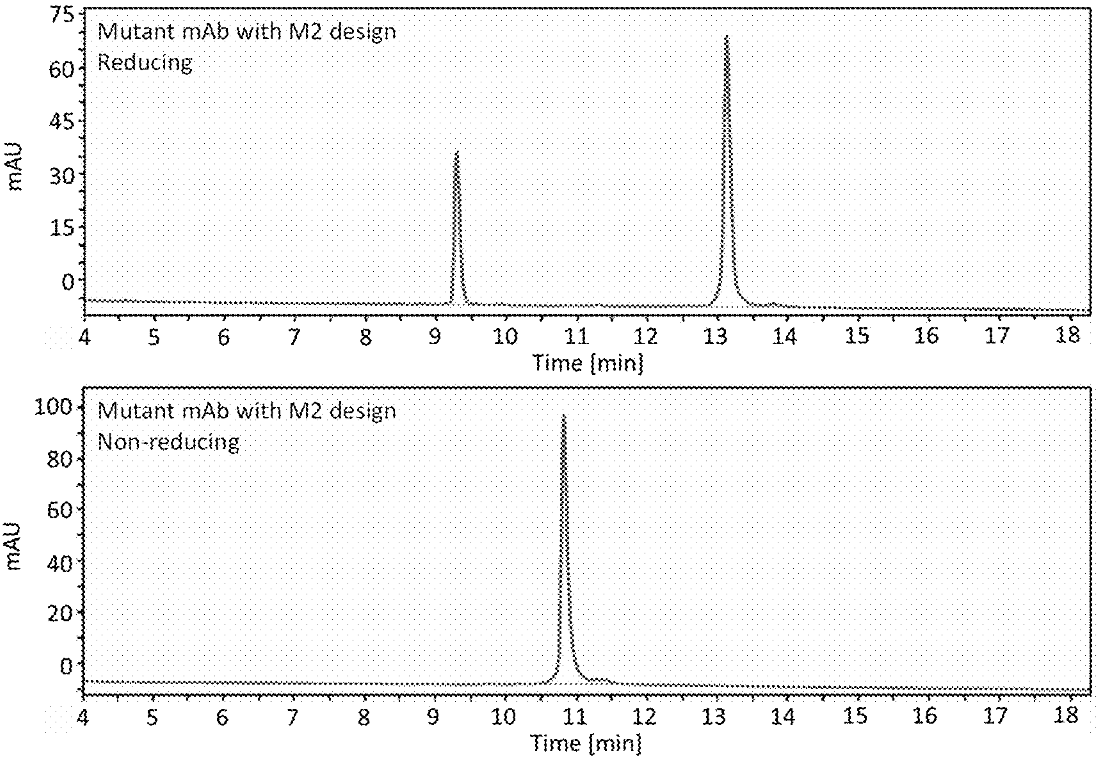
Figures 4C, 4D:
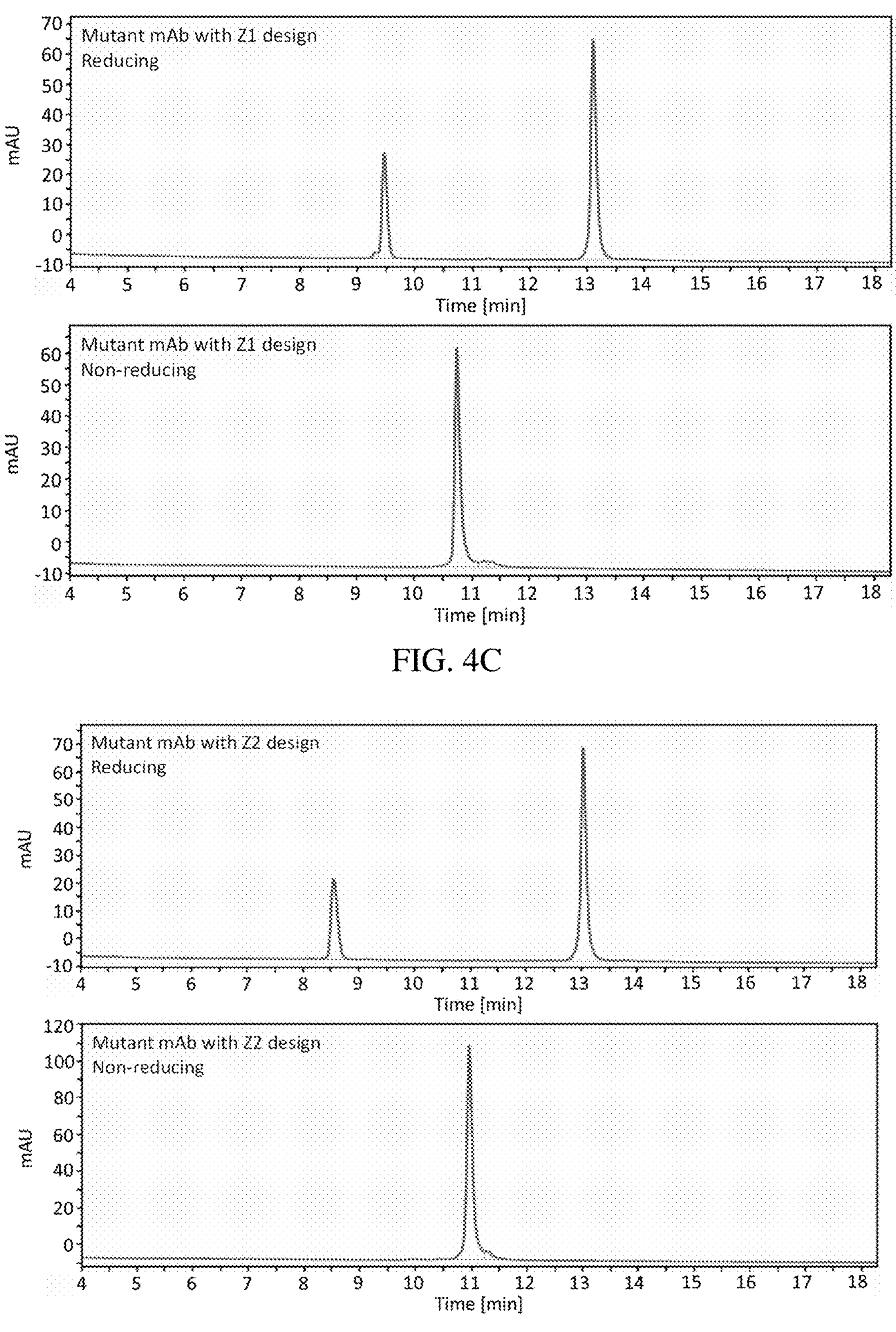
Figure 4E:
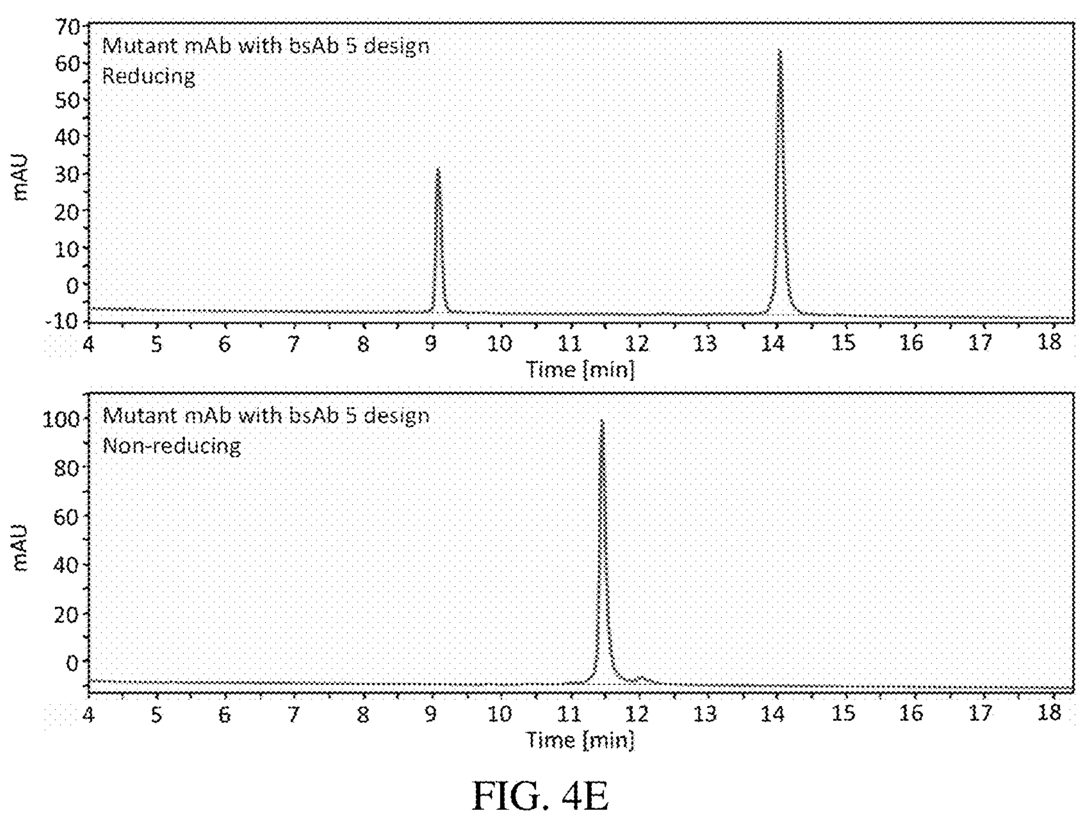
Figure 4F:
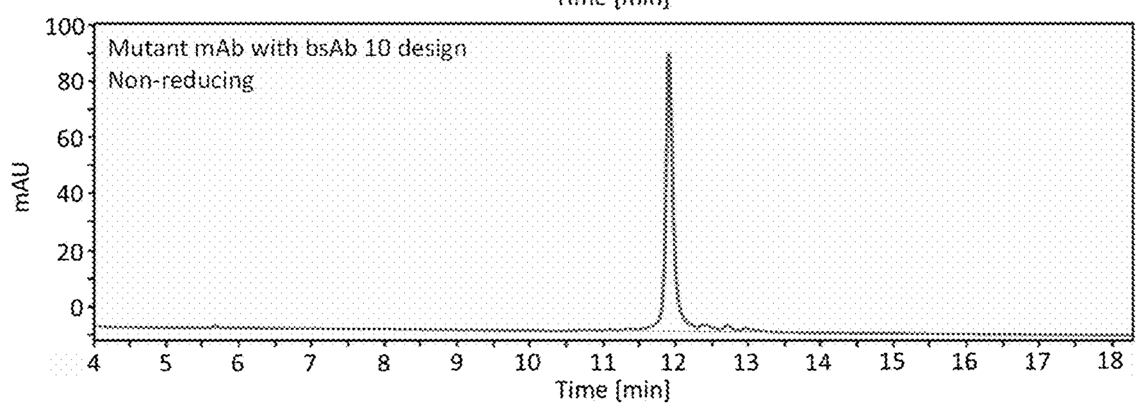
Figures 4G, 4H:
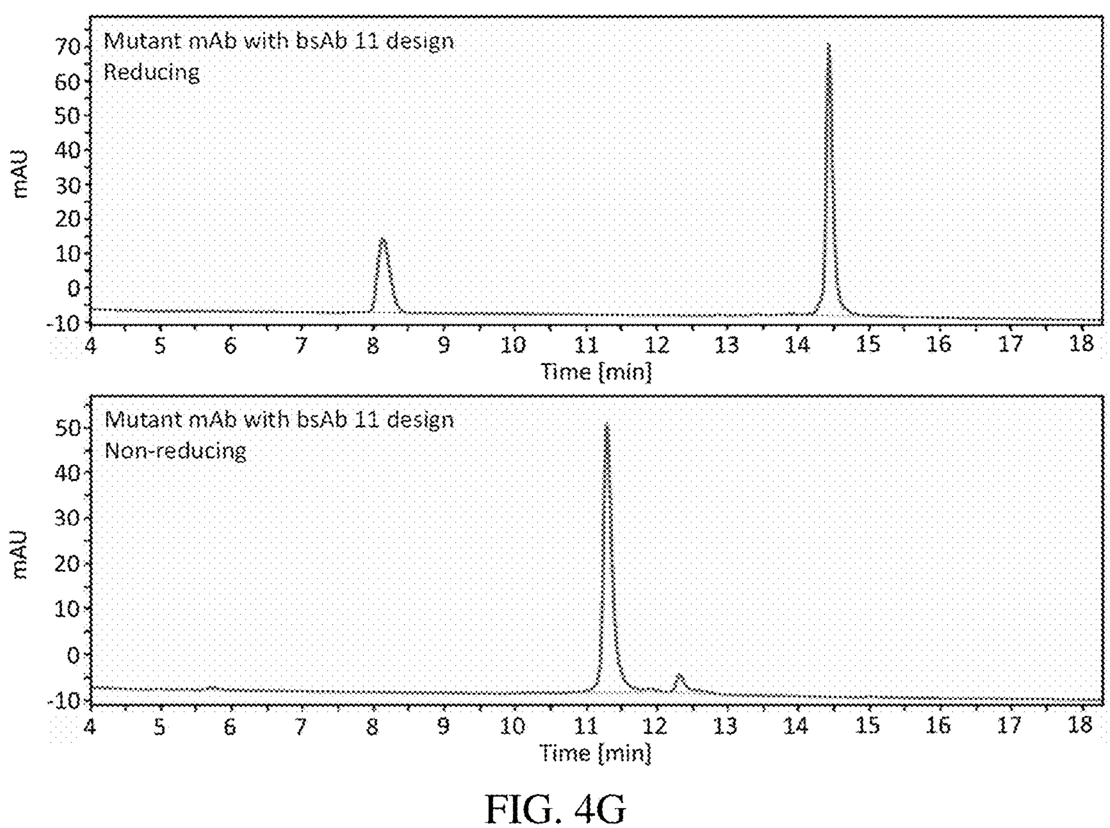
Figure 4I:
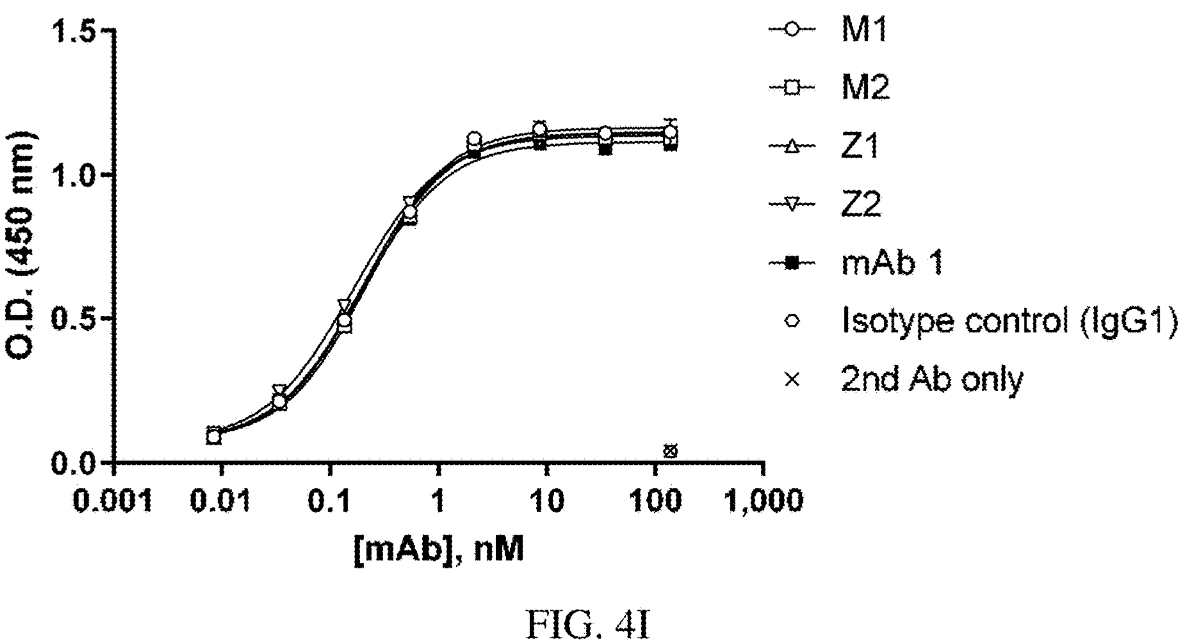
FIGS. 4I-4J show the binding of the mutant mAbs containing different shifted interchain disulfide bonds to CD47 in an ELISA assay.
Figure 4J:
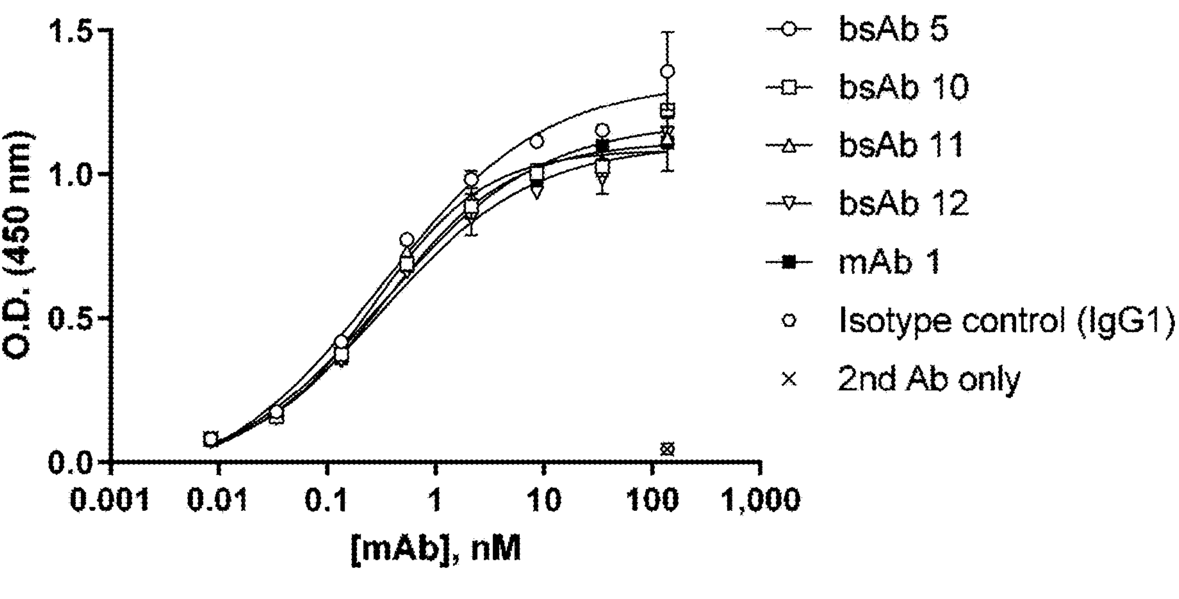
Figures 5A, 5B:
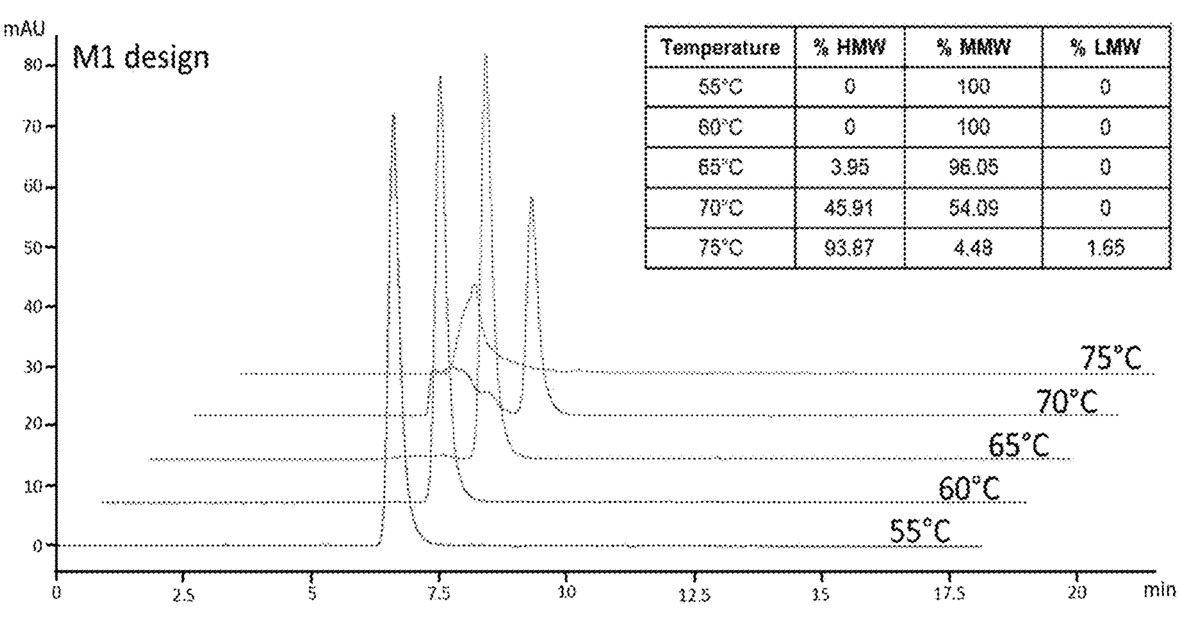
FIGS. 5A-5G show the SEC (size exclusion chromatography) profiles of mutant mAbs containing different shifted interchain disulfide bonds in a thermostability study in which the samples were incubated at different temperatures for 5 minutes. The chromatogram corresponding to each temperature is shown. The table in each FIG shows the % AUCs (area under the curves) of different peaks for each given temperature.
Figure 5C:
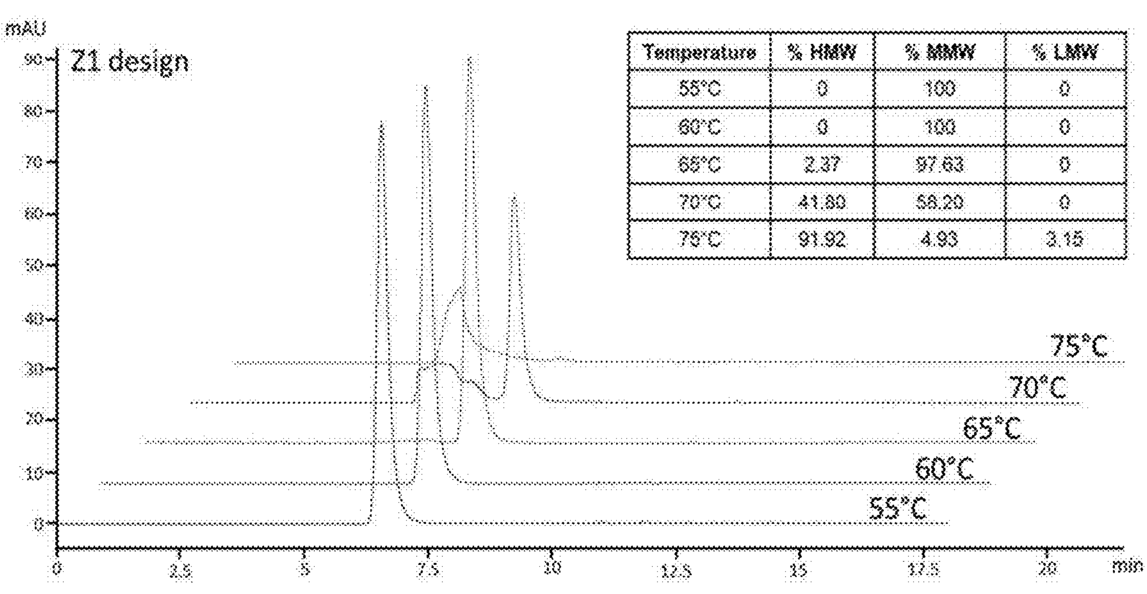
Figure 5D:
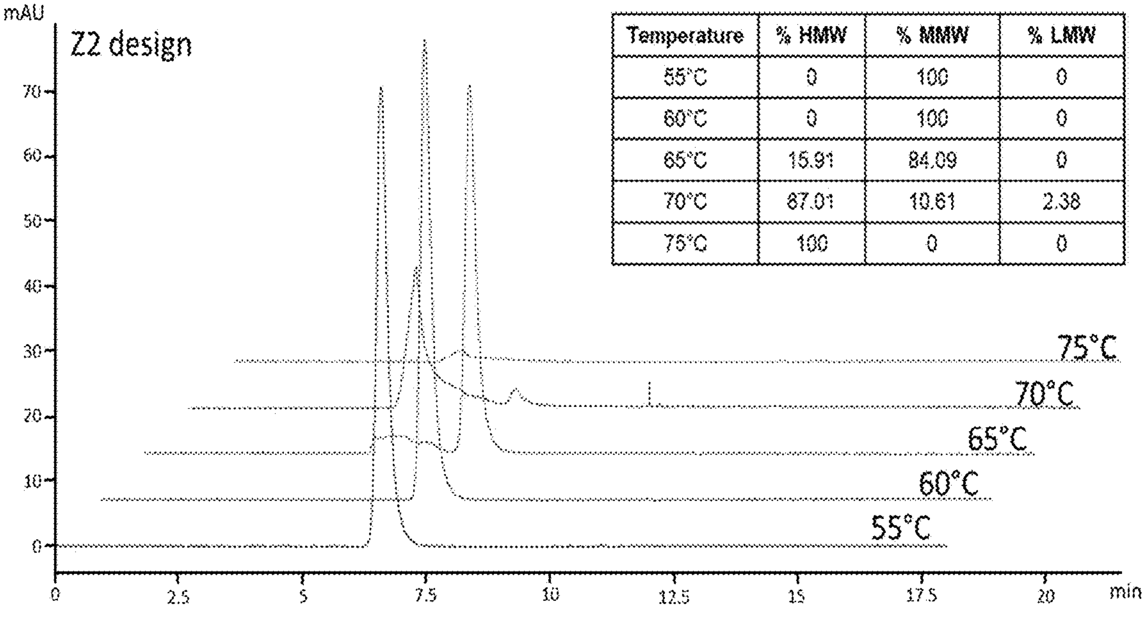
Figure 5E:
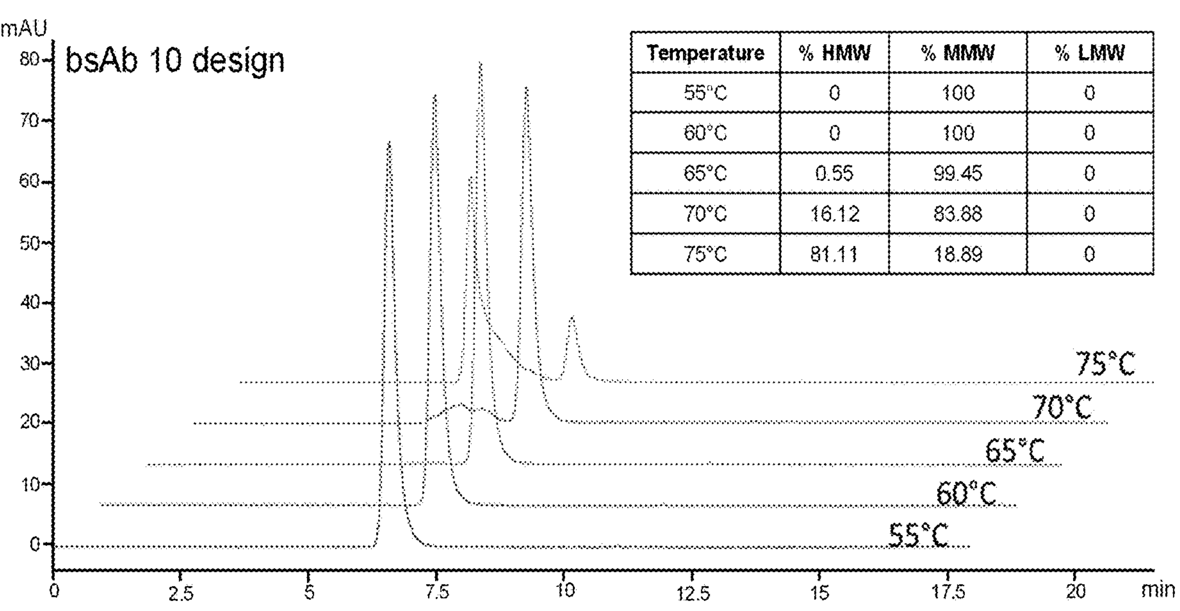
Figure 5F:
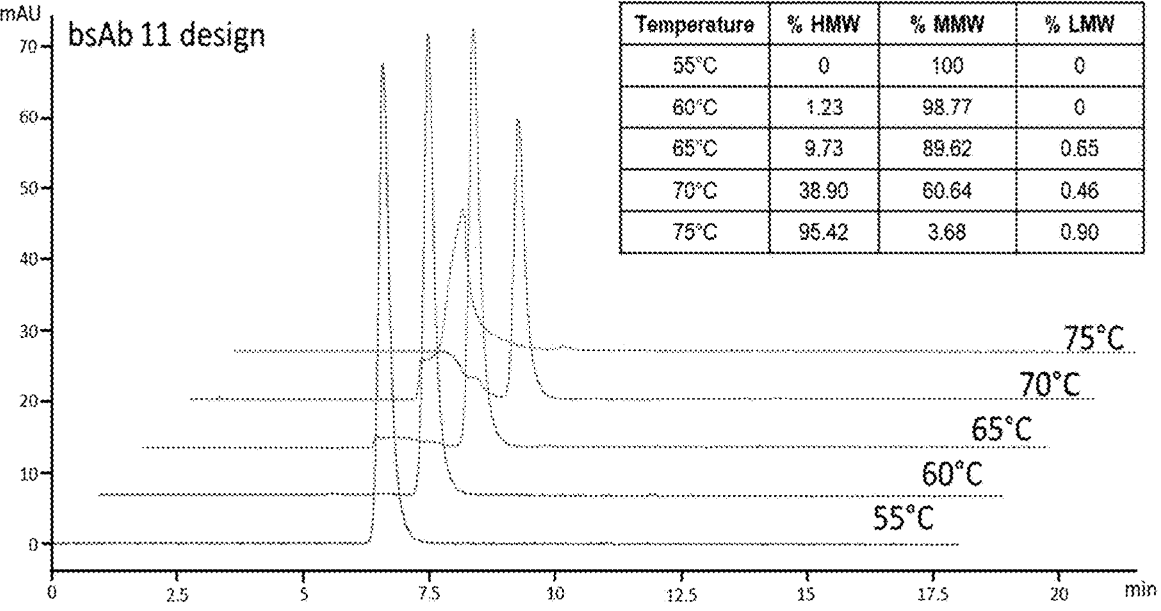
Figure 5G:
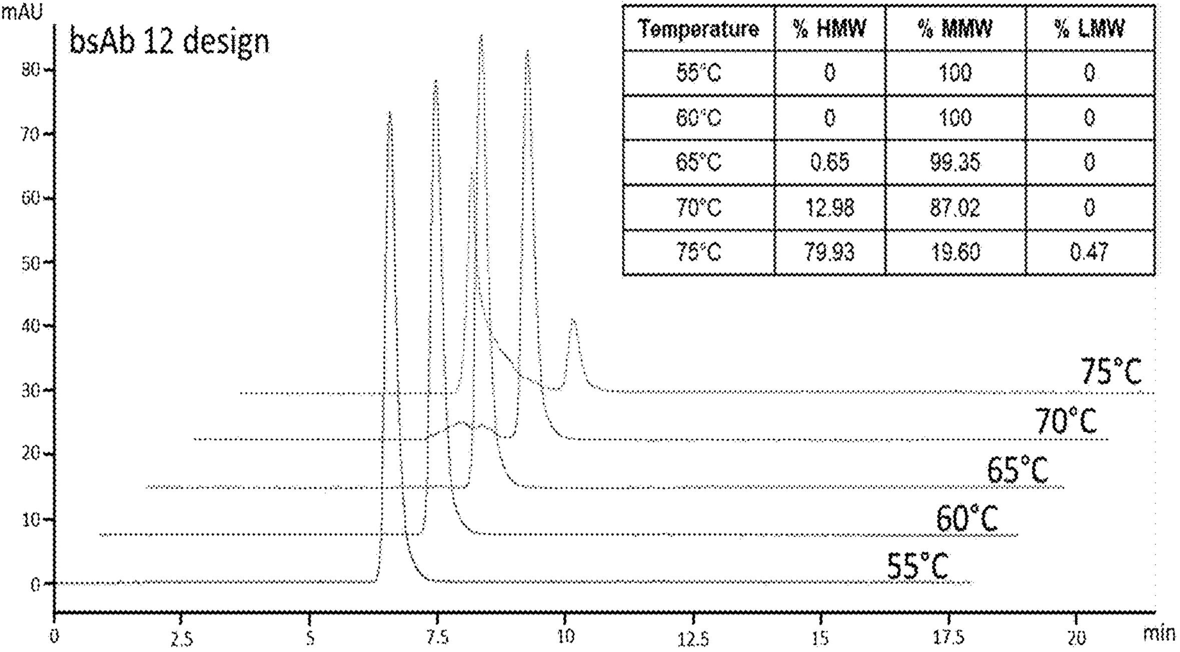
Figure 6A:
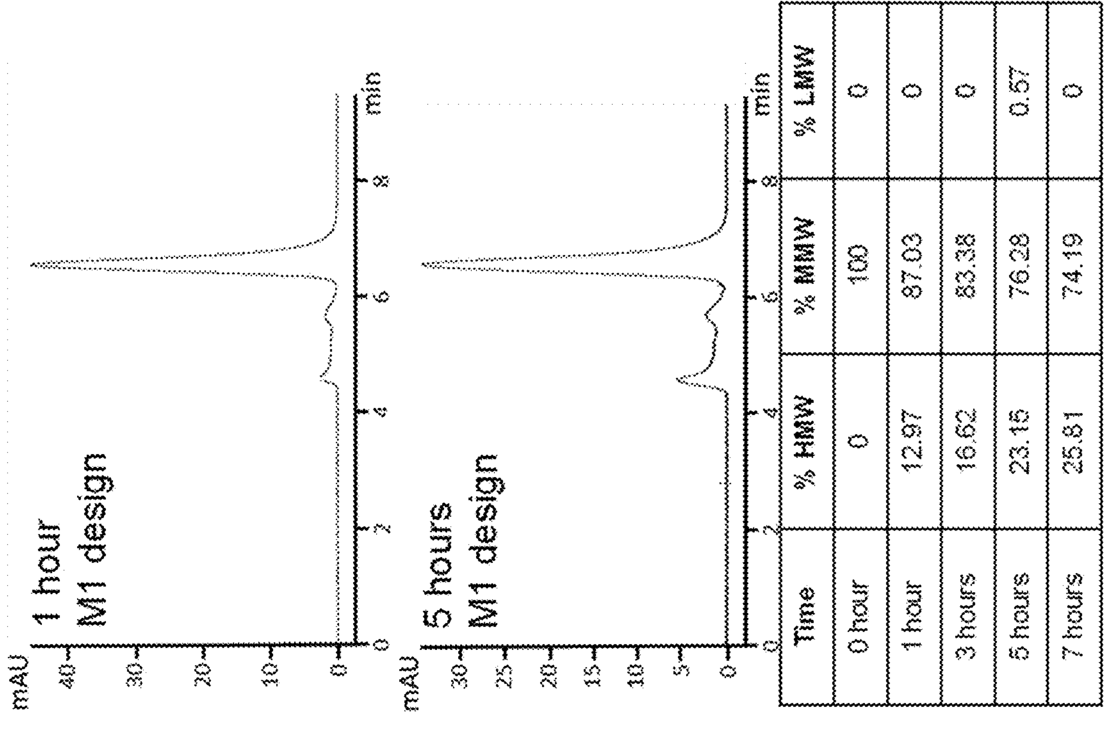
Figure 6A:
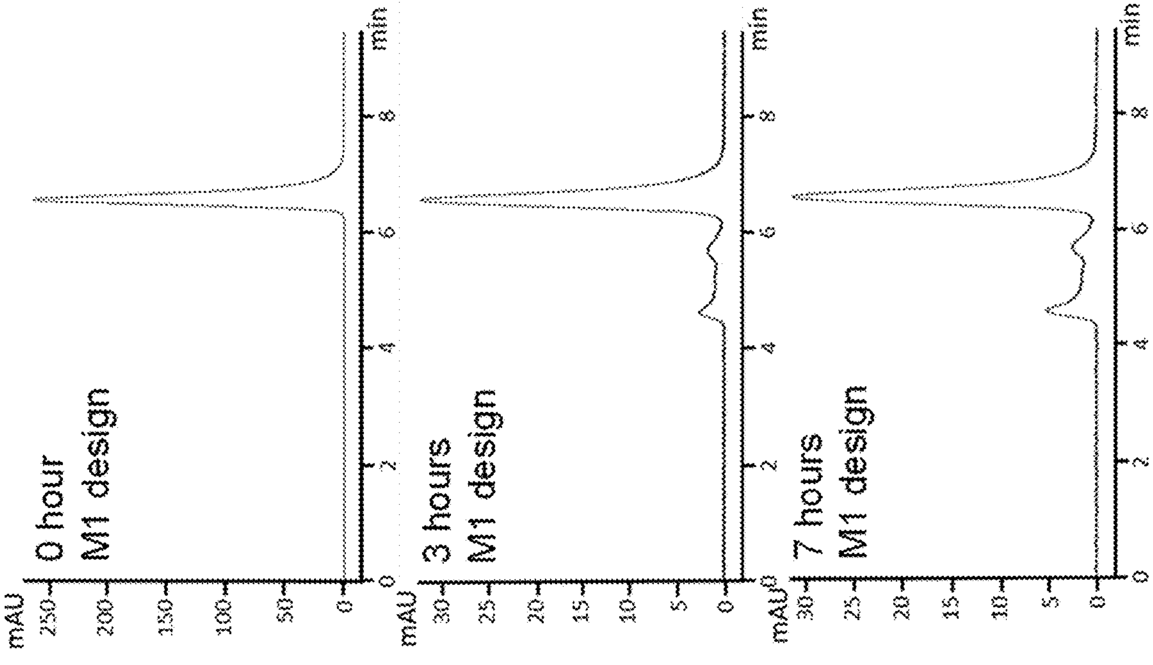
Figure 6B:
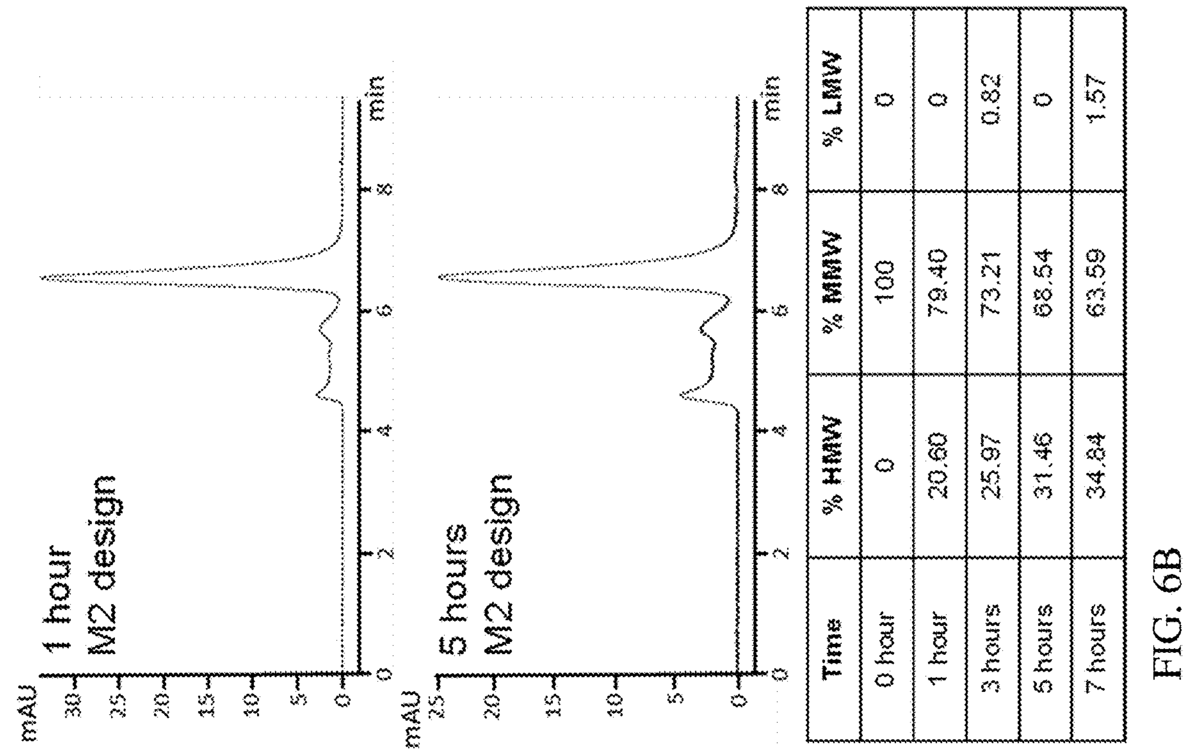
Figure 6B:
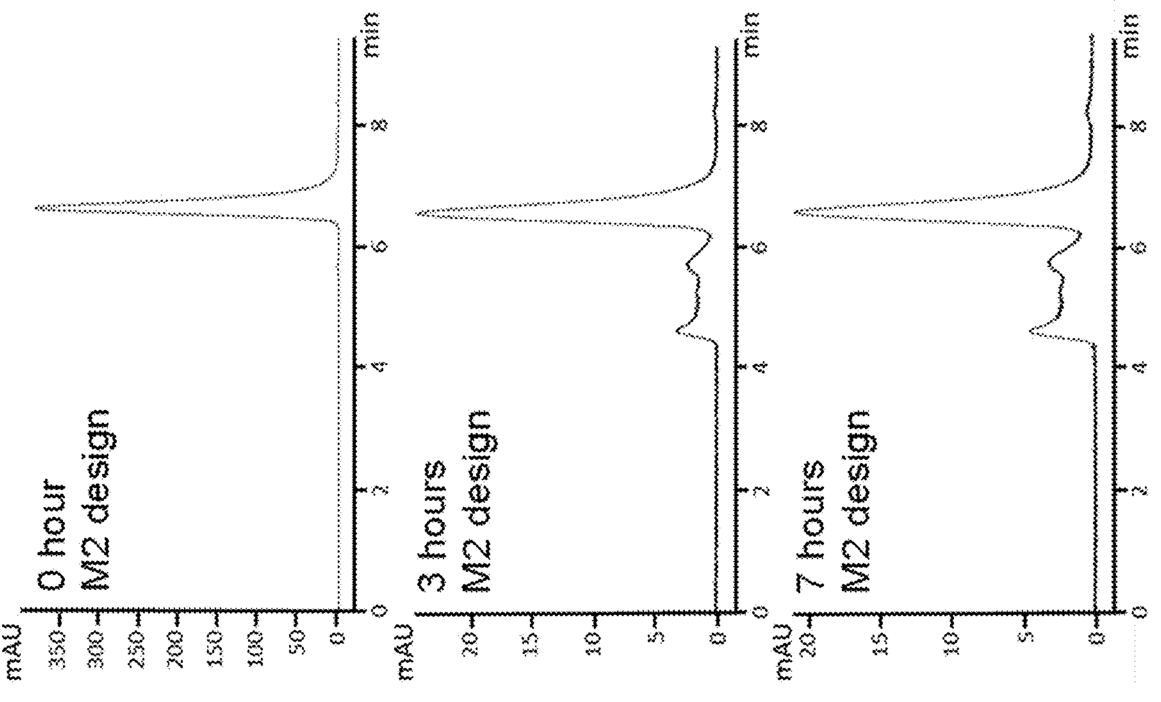
Figure 6C:
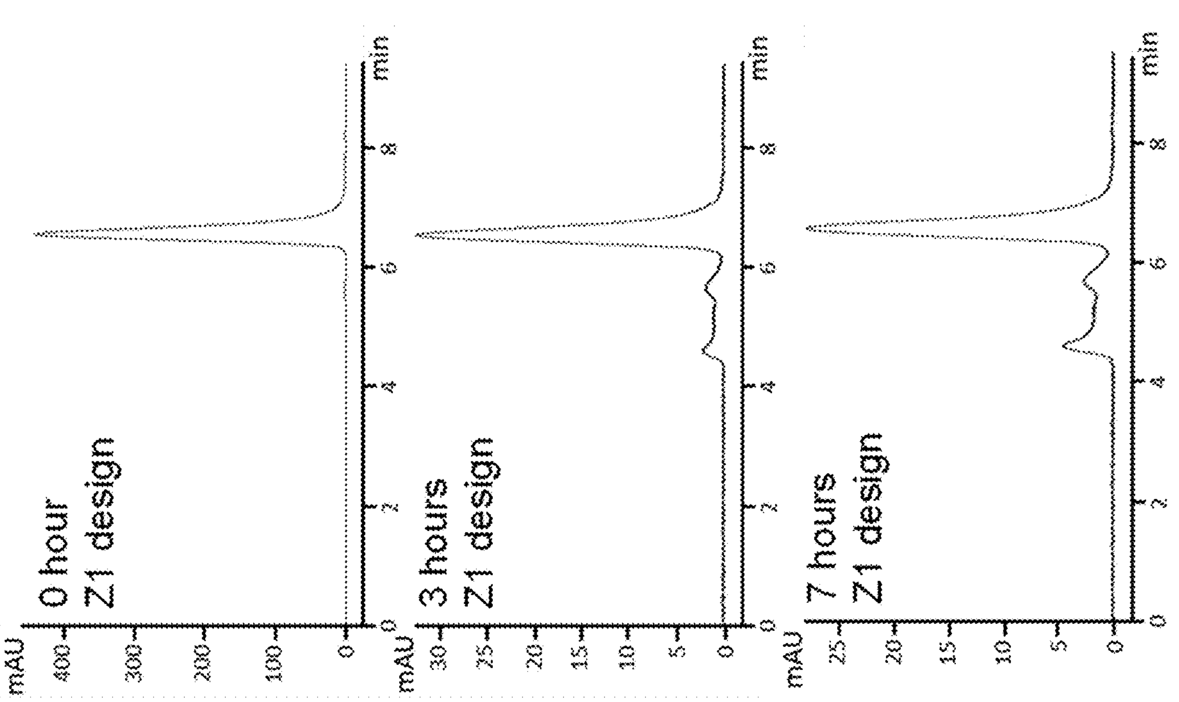
Figure 6C:
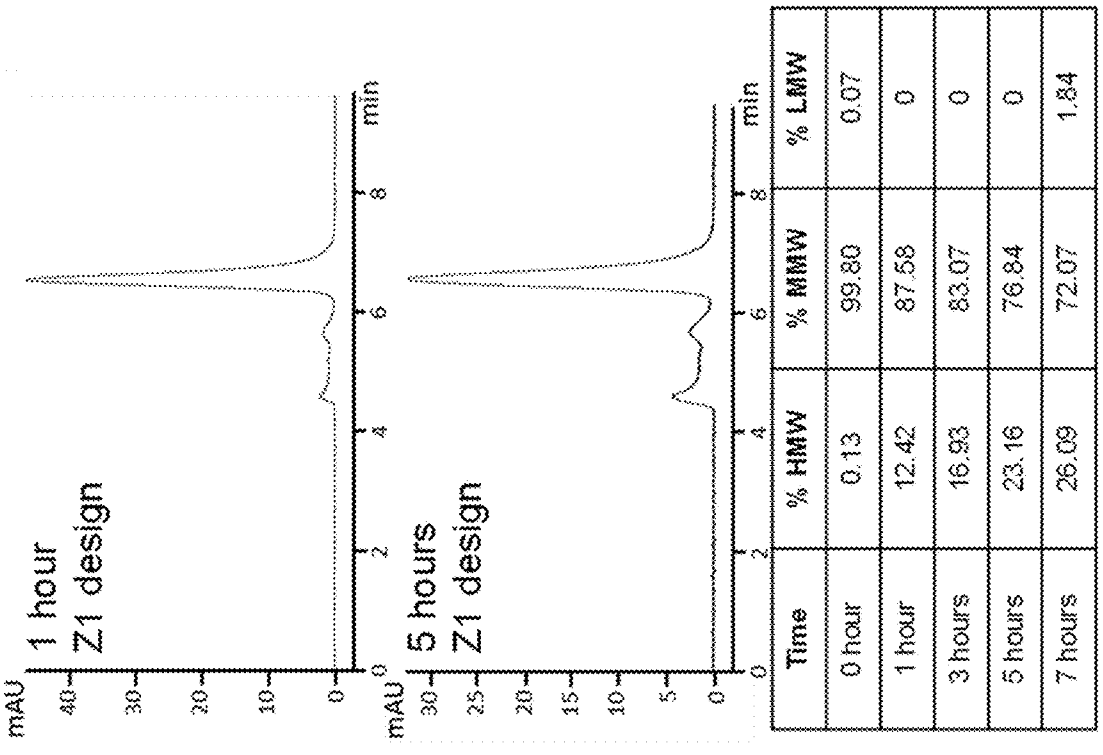
Figure 6D:
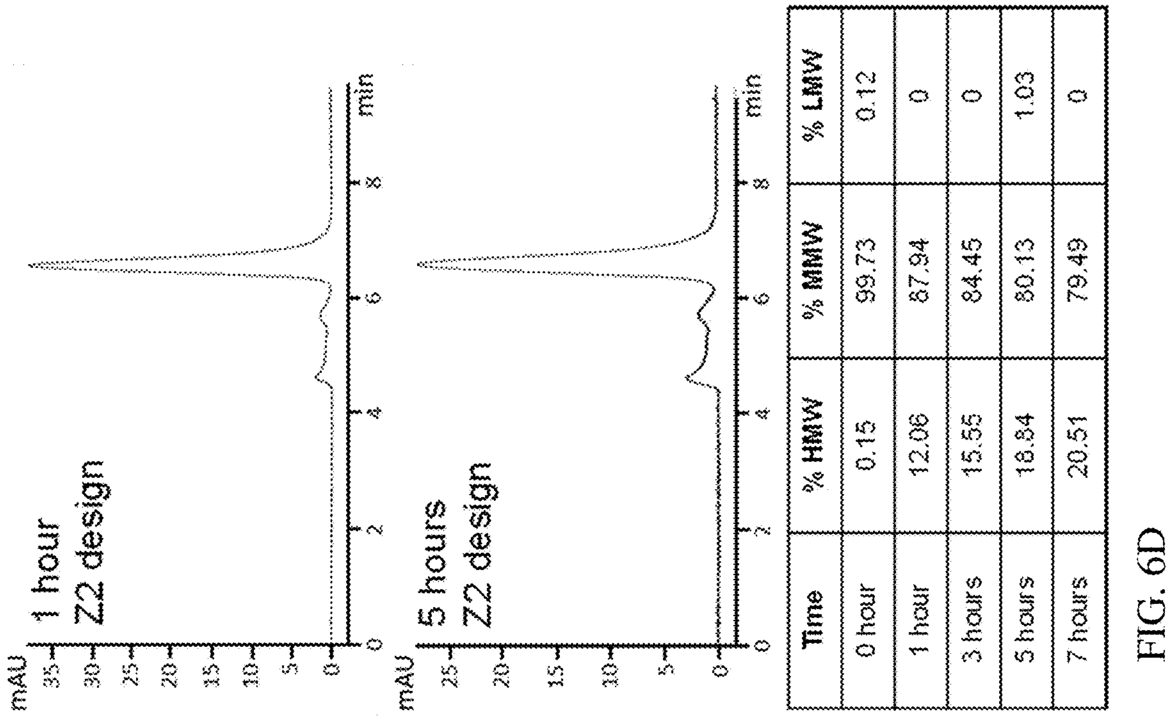
Figure 6D:
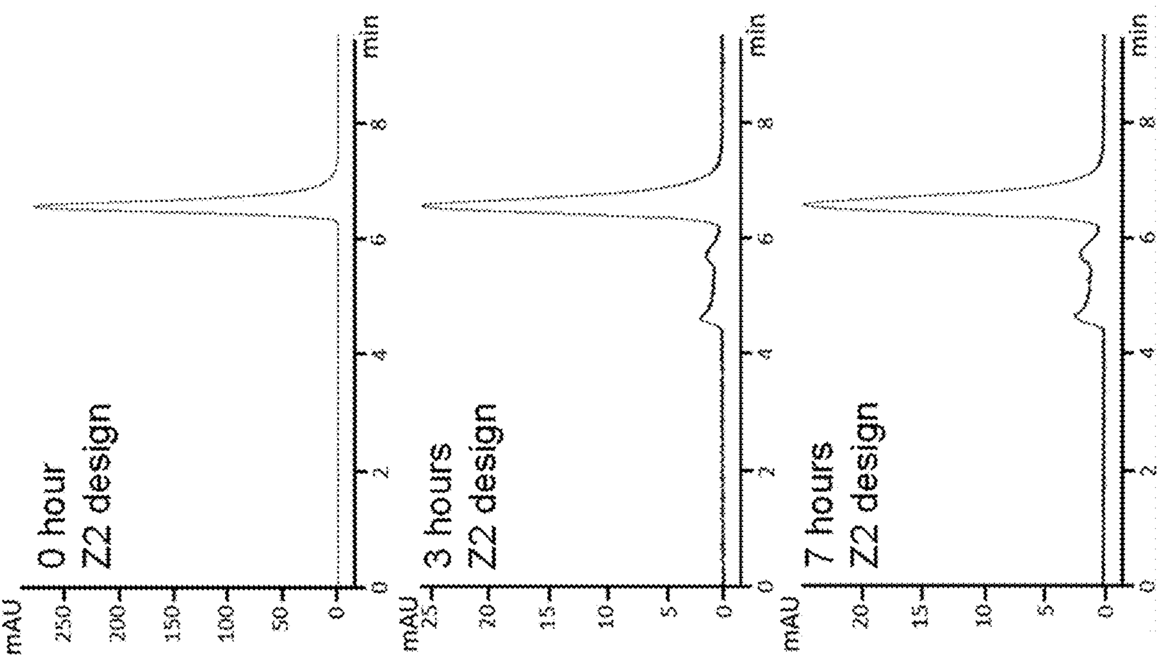
Figure 6F:
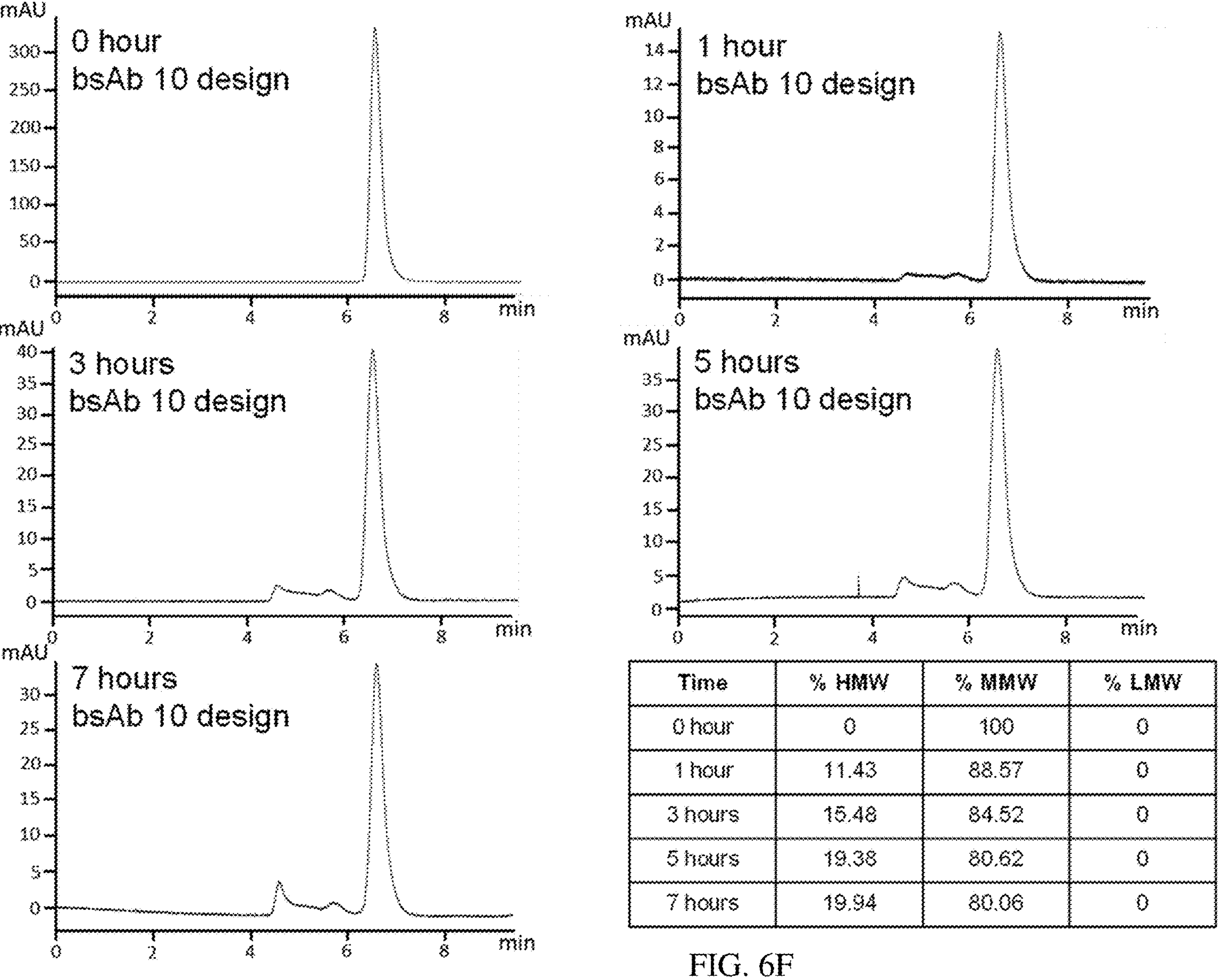
Figure 6G:
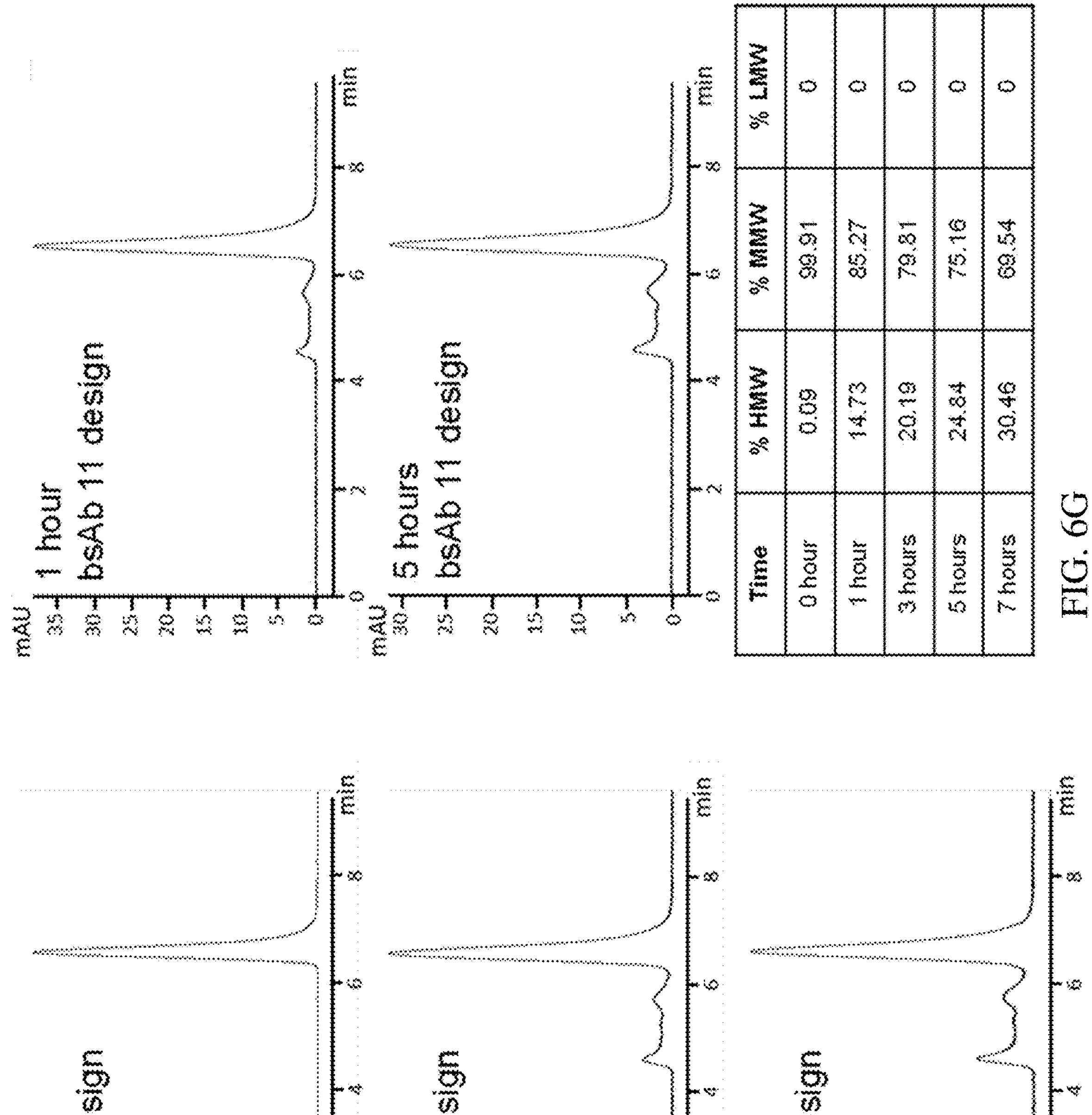
Figure 6H:
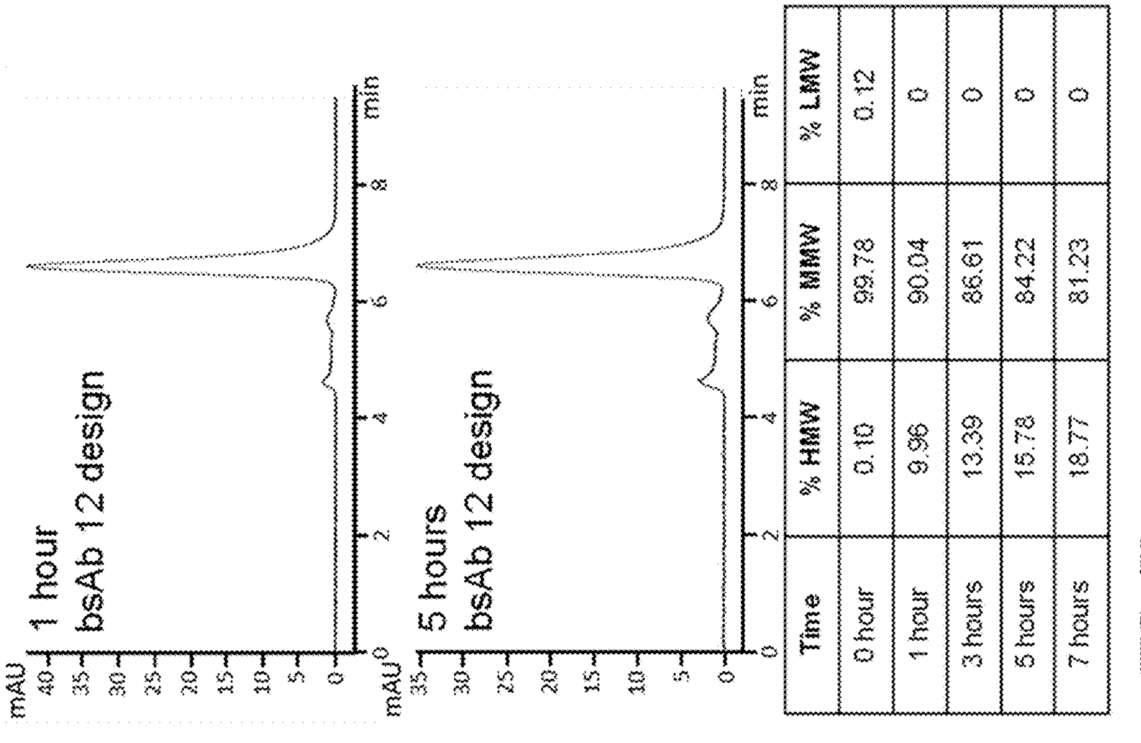
Figure 6H:
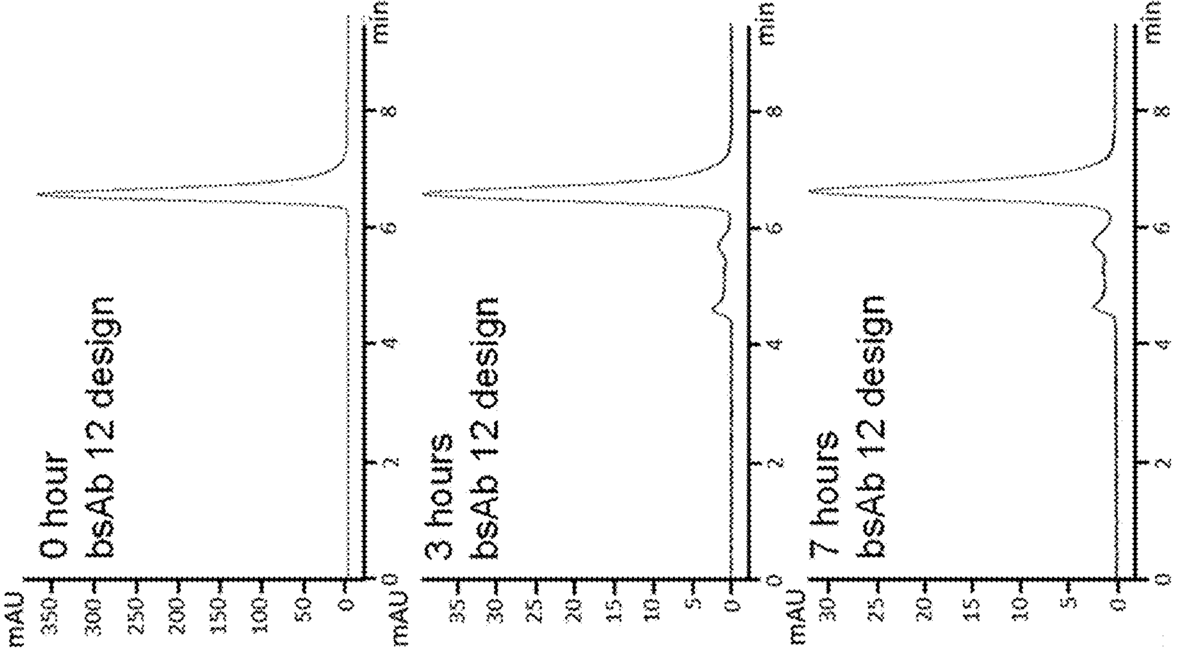

To assess the impact of the various pairs of shifted interchain disulfide bonds listed in Table 2 on the stability of a mAb, some of the groups of mutations (or namely designs) in Table 2 were introduced into mAb 1 on both arms. M1, M2, Z1 and Z2 which represent mutant designs from the patent literature (U.S. Pat. Nos. 9,527,927 B2 and 10,344,099 B2) were also introduced into mAb 1 on both arms for comparison. The mutant mAbs were expressed and purified using Protein A chromatography and hydrophobic interaction chromatography (HIC). Protein A chromatography was carried out using conventional methods. For HIC, protein A purified samples were buffer exchanged into PBS, and $(NH_4)_2SO_4$ was added to a final concentration of 800 mM. Samples were loaded onto a prepacked Source 15 PHE column (GE) pre-equilibrated with 50 mM MES pH6.0 and 1 M $(NH_4)_2SO_4$ buffer. Samples were eluted using a linear or stepwise gradient (Buffer A: 50 mM MES pH6.0, 1M $(NH_4)_2SO_4$; Buffer B: 50 mM MES pH6.0, 10% glycerol) with the main fraction eluting at 60% buffer B. Eluted fractions were analyzed by SDS-PAGE, and fractions containing primarily a 145 kDa band without lower molecular weight impurities were pooled as purified protein. FIGS. 4A-4H show the RP-HPLC profiles of the purified mutant mAbs containing different shifted interchain disulfide bonds under reducing or non-reducing condition; FIGS. 41-4J show the binding of the mutant mAbs containing different shifted interchain disulfide bonds to CD47 in an ELISA assay.

The purified mutant mAbs were analyzed for their thermostability. The mutant mAbs were buffer exchanged into DPBS (Corning, Cat: 21-031-CM) at 1 mg/mL and incubated at 55° C., 60° C., 65° C., 70° C. or 75° C. for 5 minutes on Thermo Cycler (Simpliamp, Thermo Fisher). After incubation, the mAbs were analyzed by SEC (size-exclusion chromatography). Each peak was quantified to determine the percentage of the antibody (medium molecular weight species). The results are shown in FIGS. 5A-5G. The mutant mAbs containing the bsAb 10 and bsAb 12 mutations, respectively, were more thermostable than any of the other mutant mAbs, including those containing the M1, M2, Z1, and Z2 mutations, respectively. These surprising findings indicate that the bsAb 10 and bsAb 12 designs are superior to any of the M1, M2, Z1 or Z2 design. The thermostability of an antibody is an important attribute that is required during the manufacturing process and storage. Good thermostability significantly improves the developability of an antibody and increases its chances to become a therapy.

The mutant mAbs were also tested for their pH stability or recovery from low pH incubation. The mAbs at 10 mg/mL were buffer exchanged into a buffer (pH3.0) containing 0.1 M citric acid and 0.1 M sodium chloride using Zeba™ Spin Desalting Columns (Thermo Fisher, Cat: 89882). The mAbs were diluted in the same buffer into 2 mg/mL and incubated for 1 hour, 3 hours, 5 hours, or 7 hours at room temperature, and then neutralized by adding 1.0 M Tris-HCl (pH9.0) to adjust the samples to a final pH of 6.0-7.0. After neutralization, the mAbs were diluted into DPBS to 1 mg/mL for SEC analysis. The results are shown in FIGS. 6A-6H. The mutant mAb containing the bsAb 12 design was more pH stable than any of the mutant mAbs containing the M1, M2, Z1, or Z2 mutations; it is also better than the rest of the mutant mAbs tested with respect to pH stability (FIGS. 6A-6H). The recovery from the pH stability study of the mutant mAb containing the bsAb 10 design was better than that of any of the mutant mAbs containing the M1, M2, Z1 or Z2 mutations. The data indicate that the bsAb 12 and bsAb 10 designs are superior to any of the M1, M2, Z1, or Z2 design with respect to pH stability or recovery from low pH incubation. In addition, the pH stability of the mutant mAb containing the bsAb 5 design was better than that of any of the mutant mAbs containing the M1, M2, Z1, or Z2 design when incubated at pH3.0 for 1 or 3 hours. These surprising findings indicate the bsAb 5, 10 and 12 designs are superior to any of the M1, M2, Z1, or Z2 design. The pH stability or recovery from low pH incubation of an antibody is an important attribute that is required during the manufacturing process. Good pH stability or recovery from low pH incubation, especially under 3-hour period of low pH condition, significantly improves the developability of an antibody and increases its chances to become a therapy.

TABLE 1

Sequences of various regions in mAb 1; mAb 2; human IgG2, IgG3 and IgG4 heavy chain (HC); and human lambda CL

| Name | Sequence | SEQ ID NO: |
|---|---|---|
| VH for mAb 1 | QVQLVQSGAEVKKPGASVKVSCKASGYTFTSYWMHWVRQAPGQG<br>LEWIGNIDPSDSETHYAQKFQGRVTLTVDKSTSTVYMELSSLRSEDT<br>AVYYCAGTDLAYWGQGTLVTVSS | 13 |
| VH for mAb 2 | EVQLVETGGGLIQPGGSLRLSCAASGFTFSDFGMHWIRQAPGKGLE<br>WVAYMSYTPGTFHYADTVKDRFTISRDNSKNTLYLQMNSLRAEDT<br>AVYYCARVHVGTVDYWGQGTLVTVSS | 14 |
| CH1 for mAb 1 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSC | 15 |
| CH1 for mAb 2 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSC | 16 |
| VL for mAb 1 | EIVLTQSPGTLSLSPGERATLSCHASQNINVWLSWYQQKPGQAPRLLI<br>YKASNLHTGIPDRFSGSGSGTDFTLTISRLEPEDFAVYYCQQGQSYPF<br>TFGQGTKVEIK | 17 |
| VL for mAb 2 | EVVLTQSPATLSLSPGERATLSCRASQNINNNLHWFQQKPGQAPRLL<br>IKYASQSISGIPARFSGSGSGTDFTLTISSLEPEDFAVYFCQQSNSWPA<br>LTFGQGTKVEIK | 18 |
| CL for mAb 1 | RTVAAPSVFIFPPSDEQLKSGTASVVCLLNNFYPREAKVQWKVDNA<br>LQSGNSQESVTEQDSKDSTYSLSSTLTLSKADYEKHKVYACEVTHQ<br>GLSSPVTKSFNRGEC | 19 |
| CL for mAb 2 | RTVAAPSVFIFPPSDEQLKSGTASVVCLLNNFYPREAKVQWKVDNA<br>LQSGNSQESVTEQDSKDSTYSLSSTLTLSKADYEKHKVYACEVTHQ<br>GLSSPVTKSFNRGEC | 20 |
| IgG2 CH1 | ASTKGPSVFPLAPCSRSTSESTAALGCLVKDYFPEPVTVSWNSGALTS<br>GVHTFPAVLQSSGLYSLSSVVTVPSSNFGTQTYTCNVDHKPSNTKVD<br>KTVERKCC | 21 |

TABLE 1-continued

Sequences of various regions in mAb 1; mAb 2; human IgG2, IgG3 and IgG4 heavy chain (HC); and human lambda CL

| Name | Sequence | SEQ ID NO: |
|---|---|---|
| IgG3 CH1 | ASTKGPSVFPLAPCSRSTSGGTAALGCLVKDYFPEPVTVSWNSGALT SGVHTFPAVLQSSGLYSLSSVVTVPSSSLGTQTYTCNVNHKPSNTKV DKRVELKTPLG | 22 |
| IgG4 CH1 | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVD KRVESKYG | 23 |
| lambda CL | QPKAAPSVTLFPPSSEELQANKATLVCLISDFYPGAVTVAWKADSSP VKAGVETTTPSKQSNNKYAASSYLSLTPEQWKSHRSYSCQVTHEGS TVEKTVAPTEC | 24 |
| VH for mAb 2b | EVQLVQSGAEVKKPGSSVKVSCKASGYAFSSSWMNWVRQAPGQGL EWIGRIYPGDGYTHYNGMFKGRASLTADKSTSTGYMELSSLRSEDT AVFFCTRHGDFPYWYFDVWGRGTLVTVSS | 33 |
| CH1 for mAb 2b | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSC | 34 |
| VL for mAb 2b | DIQMTQSPSTLSASVGDRVTITCRASENIDSYLAWYQQKPGRAPKLL VYAATNLAVGVPSRFSGSGSGTEYTLTISSLQPDDFATYYCQHHYST PPTFGQGTKLEIK | 35 |
| CL for mAb 2b | RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGEC | 36 |

TABLE 2

Amino acid substitutions on the mAb 1 arm of the mAb 1/mAb 2 bispecific antibody (bsAb) for shifted interchain disulfide bond

| | VH | CH1 | VL | CL |
|---|---|---|---|---|
| bsAb 1 | G44C | C220S | G101C | C214S |
| bsAb 2 | H58C | C220S | Y94C | C214S |
| bsAb 3 | A60C | C220S | P95C | C214S |
| bsAb 4 | W103C | C220S | P44C | C214S |
| bsAb 5 | | S131C; C220S | | P119C; C214S |
| bsAb 6 | | F170C; C220S | | S176C; C214S |
| bsAb 7 | | P171C; C220S | | S162C; C214S |
| bsAb 8 | | V173C; C220S | | Q160C; C214S |
| bsAb 9 | | A129C; C220S | | S121C; C214S |
| bsAb 10 | | K133C; C220S | | K207C; C214S |
| bsAb 11 | | K133C; C220S | | I117C; C214S |
| bsAb 12 | | K133C; C220S | | F209C; C214S |
| M1 | | F126C; C220S | | S121C; C214S |
| M2 | | A141C; C220S | | F116C; C214S |
| Z1 | | F126C; C220S | | Q124C; C214S |
| Z2 | | F170C; C220S | | S162C; C214S |

Note:
Kabat numbering is used for the VH and VL regions; EU numbering is used for the CH1 and CL regions.

The bispecific antibodies in the examples are on the IgG1 HC and kappa LC framework (Kabat numbering for the VH and VL regions; EU numbering for the CH1 and CL regions). Some bispecific antibodies were constructed using mAb 1 and mAb 2, including bsAb 1, bsAb 2, bsAb 3, bsAb 4, bsAb 5, bsAb 6, bs Ab 7, and bsAb 8 (bsAb 1 refers to the bispecific antibody with the mAb 1 arm containing the corresponding mutations in Table 2 that is expected to result in the relocation (or "shifting") of the HC/LC interchain disulfide bond, and with mAb 2 as the second arm; the other bispecific antibodies in this group follow the same naming rule). No mutation on the VH, CH1, VL or CL region of the mAb 2 arm was introduced. Mutation G44C refers to the conversion of the native glycine at residue 44 (G44) to cysteine; all the other mutations adopt the same naming rule. Other bispecific antibodies were constructed using mAb 1 and mAb 2b, including bsAb 5b, bsAb 10, and bsAb 12 (bsAb 5b refers to the bispecific antibody with the mAb 1 arm containing the corresponding bsAb 5 mutations in Table 2 and with mAb 2b as the second arm; bsAb 10 refers to the bispecific antibody with the mAb 1 arm containing the corresponding bsAb 10 mutations in Table 2 and with mAb 2b as the second arm; bsAb 12 refers to the bispecific antibody with the mAb 1 arm containing the corresponding bsAb 12 mutations in Table 2 and with mAb 2b as the second arm). Sequences of the CH1, CL, VH and VL regions of the mAb 1 arm of the bispecific antibodies are listed in Table 3. In addition, charged amino acid pairs were introduced at Q39 (Kabat numbering) on HC and Q38 (Kabat numbering) on LC of each arm of a given bispecific antibody. These bispecific antibodies were named as follows: bsAb 5b (E/K) refers to the bispecific antibody with Q39E (Q is changed to E; the same naming rule applies to the other mutations below) on the HC and Q38K on the LC of the mAb 1 arm and Q39K on the HC and Q38E on the LC of the mAb 2b arm of bsAb 5b; bsAb 10 (E/K) and bsAb 12 (E/K) follow the same naming rule. Further, bsAb 5b (K/E) refers to the bispecific antibody with Q39K on the HC and Q38E on the LC of the mAb 1 arm and Q39E on the HC and Q38K on the LC of the mAb 2b arm of bsAb 5b; bsAb 10 (K/E) and bsAb 12 (K/E) follow the same naming rule. The mAb 1 HC has the T366W (EU numbering) mutation to form a "knob" and the mAb 2 or mAb 2b HC has the mutations T366S, L368A, and Y407V to form a "hole." In addition, a S354C cysteine mutation was introduced on mAb 1 HC and a Y349C cysteine mutation was introduced on mAb 2 or mAb 2b HC to stabilize the heterodimeric pairing.

TABLE 3

Sequences of the CH1, CL, VH and VL regions of the mAb 1 arm of the bispecific antibodies

| Clone name | Sequence | SEQ ID NO: |
|---|---|---|
| bsAb 1 VH | QVQLVQSGAEVKKPGASVKVSCKASGYTFTSYWMHWVRQAPGQCL EWIGNIDPSDSETHYAQKFQGRVTLTVDKSTSTVYMELSSLRSEDTAV YYCAGTDLAYWGQGTLVTVSS | 1 |
| bsAb 1 CH1 | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSS | 2 |
| bsAb 1 VL | EIVLTQSPGTLSLSPGERATLSCHASQNINVWLSWYQQKPGQAPRLLI YKASNLHTGIPDRFSGSGSGTDFTLTISRLEPEDFAVYYCQQGQSYPFT FGQCTKVEIK | 3 |
| bsAb 1 CL | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTKSFNRGES | 4 |
| bsAb 5 or 5b CH1 | ASTKGPSVFPLAPCSKSTSGGTAALGCLVKDYFPEPVTVSWNSGALTS GVHTFPAVLQSSGLYSLSSVVTVPSSSLGTQTYICNVNHKPSNTKVDK KVEPKSS | 5 |
| bsAb 5 or 5b CL | RTVAAPSVFIFCPSDEQLKSGTASVVCLLNNFYPREAKVQWKVDNAL QSGNSQESVTEQDSKDSTYSLSSTLTLSKADYEKHKVYACEVTHQGL SSPVTKSFNRGES | 6 |
| bsAb 6 CH1 | ASTKGPSVFPLAPSSKSTSGGTAALGCLVKDYFPEPVTVSWNSGALTS GVHTCPAVLQSSGLYSLSSVVTVPSSSLGTQTYICNVNHKPSNTKVDK KVEPKSS | 7 |
| bsAb 6 CL | RTVAAPSVFIFPPSDEQLKSGTASVVCLLNNFYPREAKVQWKVDNAL QSGNSQESVTEQDSKDSTYSLCSTLTLSKADYEKHKVYACEVTHQGL SSPVTKSFNRGES | 8 |
| bsAb 7 CH1 | ASTKGPSVFPLAPSSKSTSGGTAALGCLVKDYFPEPVTVSWNSGALTS GVHTFCAVLQSSGLYSLSSVVTVPSSSLGTQTYICNVNHKPSNTKVDK KVEPKSS | 9 |
| bsAb 7 CL | RTVAAPSVFIFPPSDEQLKSGTASVVCLLNNFYPREAKVQWKVDNAL QSGNSQECVTEQDSKDSTYSLSSTLTLSKADYEKHKVYACEVTHQGL SSPVTKSFNRGES | 10 |
| bsAb 8 CH1 | ASTKGPSVFPLAPSSKSTSGGTAALGCLVKDYFPEPVTVSWNSGALTS GVHTFPACLQSSGLYSLSSVVTVPSSSLGTQTYICNVNHKPSNTKVDK KVEPKSS | 11 |
| bsAb 8 CL | RTVAAPSVFIFPPSDEQLKSGTASVVCLLNNFYPREAKVQWKVDNAL QSGNSCESVTEQDSKDSTYSLSSTLTLSKADYEKHKVYACEVTHQGL SSPVTKSFNRGES | 12 |
| bsAb 9 CH1 | ASTKGPSVFPLCPSSKSTSGGTAALGCLVKDYFPEPVTVSWNSGALTS GVHTFPAVLQSSGLYSLSSVVTVPSSSLGTQTYICNVNHKPSNTKVDK KVEPKSS | 25 |
| bsAb 9 CL | RTVAAPSVFIFPPCDEQLKSGTASVVCLLNNFYPREAKVQWKVDNAL QSGNSQESVTEQDSKDSTYSLSSTLTLSKADYEKHKVYACEVTHQGL SSPVTKSFNRGES | 26 |
| bsAb 10 CH1 | ASTKGPSVFPLAPSSCSTSGGTAALGCLVKDYFPEPVTVSWNSGALTS GVHTFPAVLQSSGLYSLSSVVTVPSSSLGTQTYICNVNHKPSNTKVDK KVEPKSS | 27 |
| bsAb 10 CL | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTCSFNRGES | 28 |
| bsAb 11 CH1 | ASTKGPSVFPLAPSSCSTSGGTAALGCLVKDYFPEPVTVSWNSGALTS GVHTFPAVLQSSGLYSLSSVVTVPSSSLGTQTYICNVNHKPSNTKVDK KVEPKSS | 29 |
| bsAb 11 CL | RTVAAPSVFCFPPSDEQLKSGTASVVCLLNNFYPREAKVQWKVDNAL QSGNSQESVTEQDSKDSTYSLSSTLTLSKADYEKHKVYACEVTHQGL SSPVTKSFNRGES | 30 |
| bsAb 12 CH1 | ASTKGPSVFPLAPSSCSTSGGTAALGCLVKDYFPEPVTVSWNSGALTS GVHTFPAVLQSSGLYSLSSVVTVPSSSLGTQTYICNVNHKPSNTKVDK KVEPKSS | 31 |

TABLE 3-continued

| Sequences of the CH1, CL, VH and VL regions of the mAb 1 arm of the bispecific antibodies | | |
|---|---|---|
| Clone name | Sequence | SEQ ID NO: |
| bsAb 12 CL | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTKS**C**NRGE**S** | 32 |

Note:
The residues resulting from amino acid substitutions are in bold and underlined form.

Example 2: Characterization of Bispecific Antibodies

The simultaneous expression of the two heavy chains and the two light chains in the same cell led to the expression and assembly of a desired bispecific antibody, which contains the anti-CD47 arm and the anti-FRα arm. The bispecific antibodies were purified using protein A chromatography. Some samples were further purified using hydrophobic interaction chromatography (HIC).

Figure 7A:
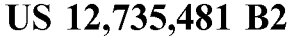
FIGS. 7A-7D show the SDS-PAGE images of bispecific antibodies purified using Protein A chromatography.
Figure 7A:
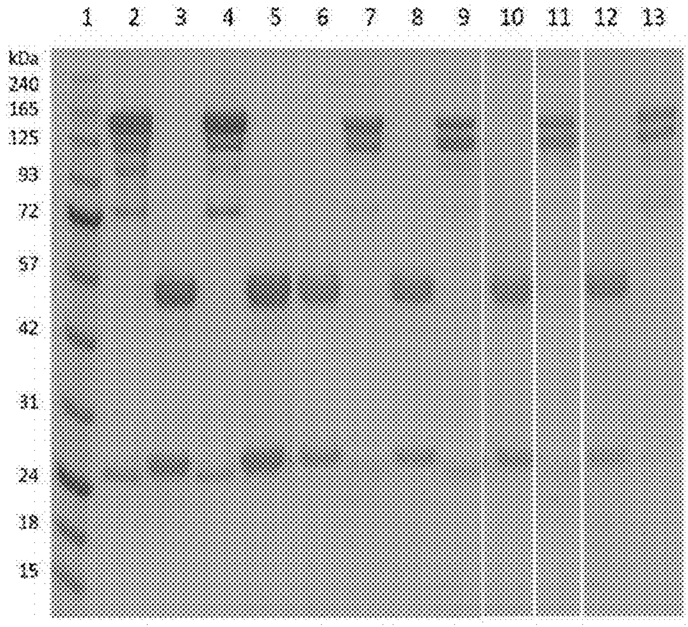
Figure 7B:
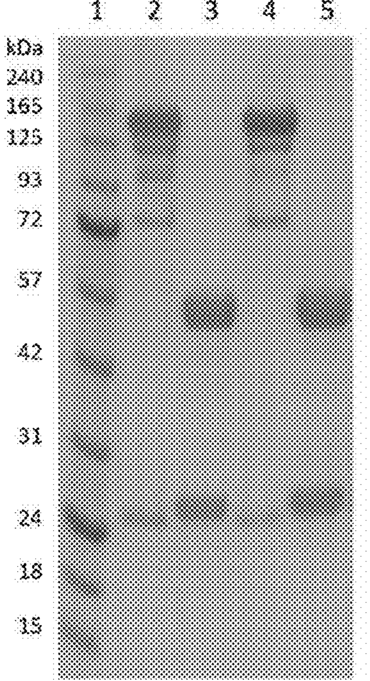
Figure 7C:
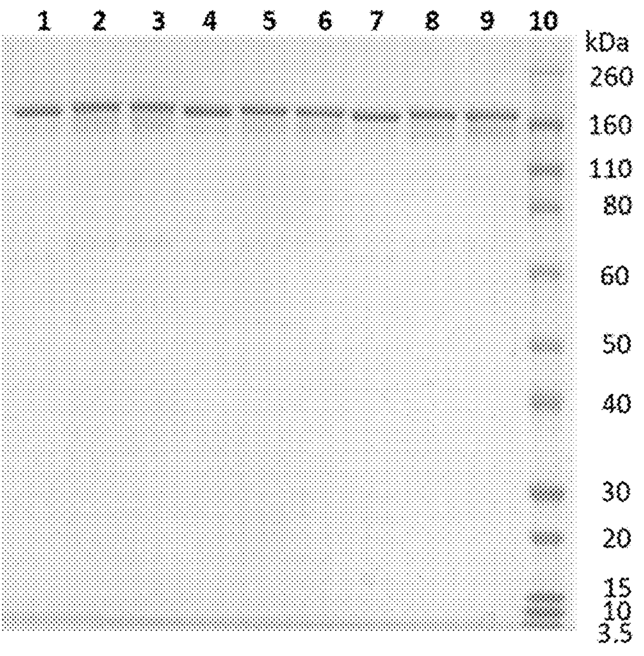
Figure 7D:
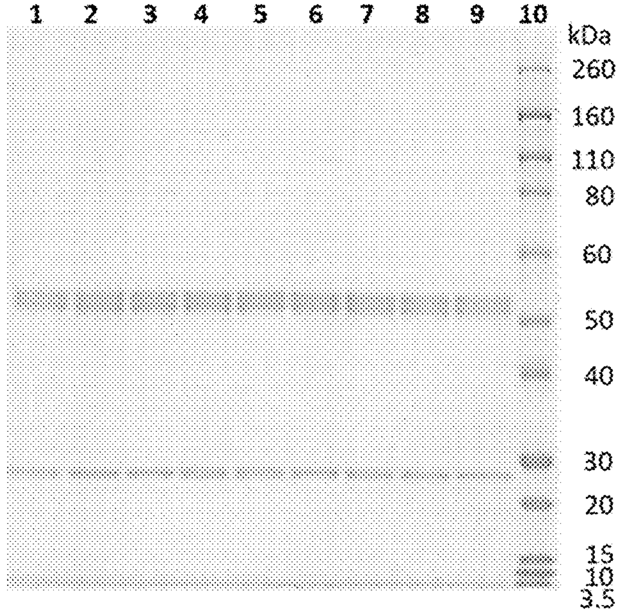
Figure 8A:
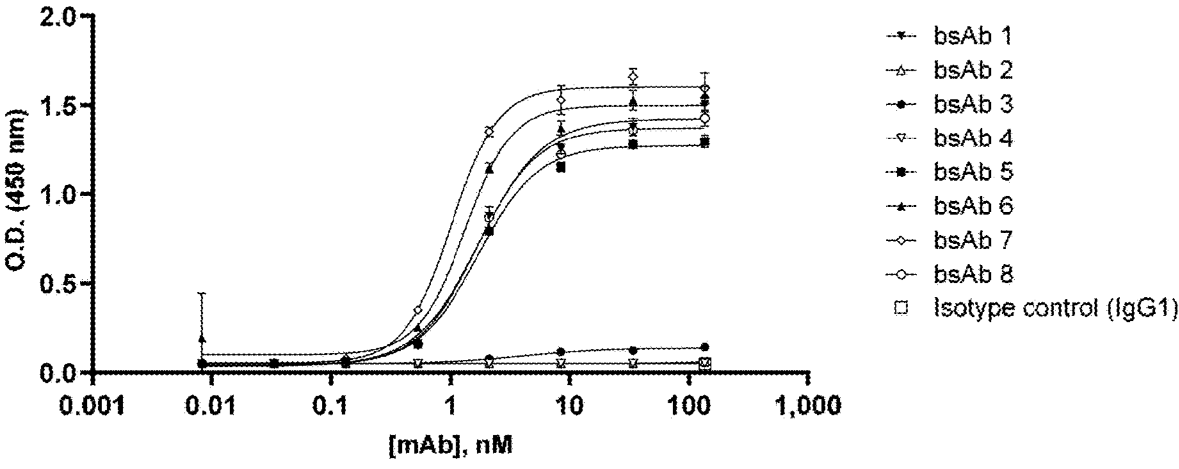
FIG. 8A-8J show graphs demonstrating the results for the binding of the Protein A purified bispecific antibodies to both antigens (i.e., CD47 and FRα) in a bridging ELISA assay.
Figure 8B:
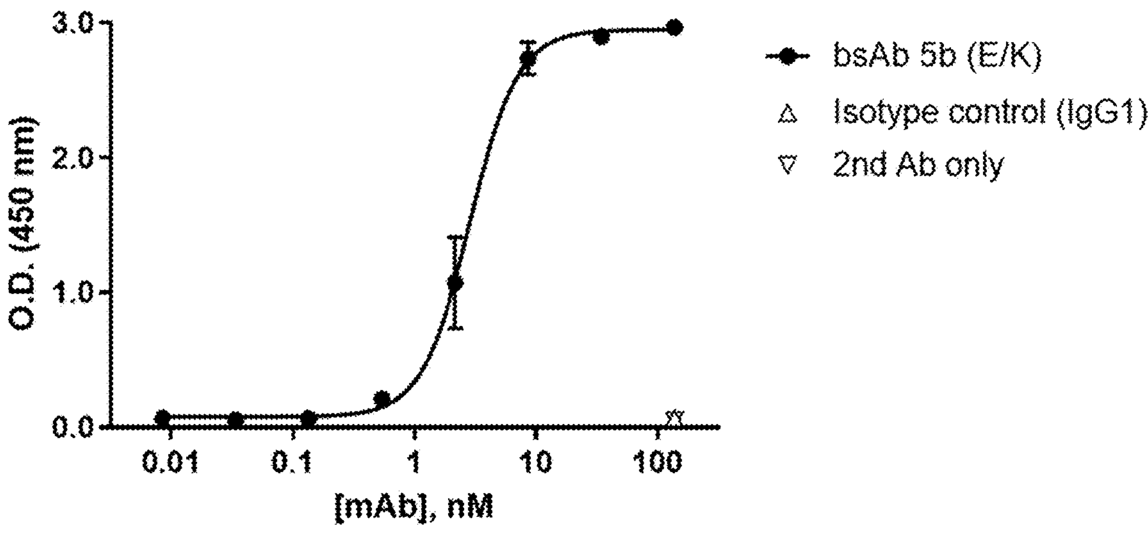
Figure 8C:
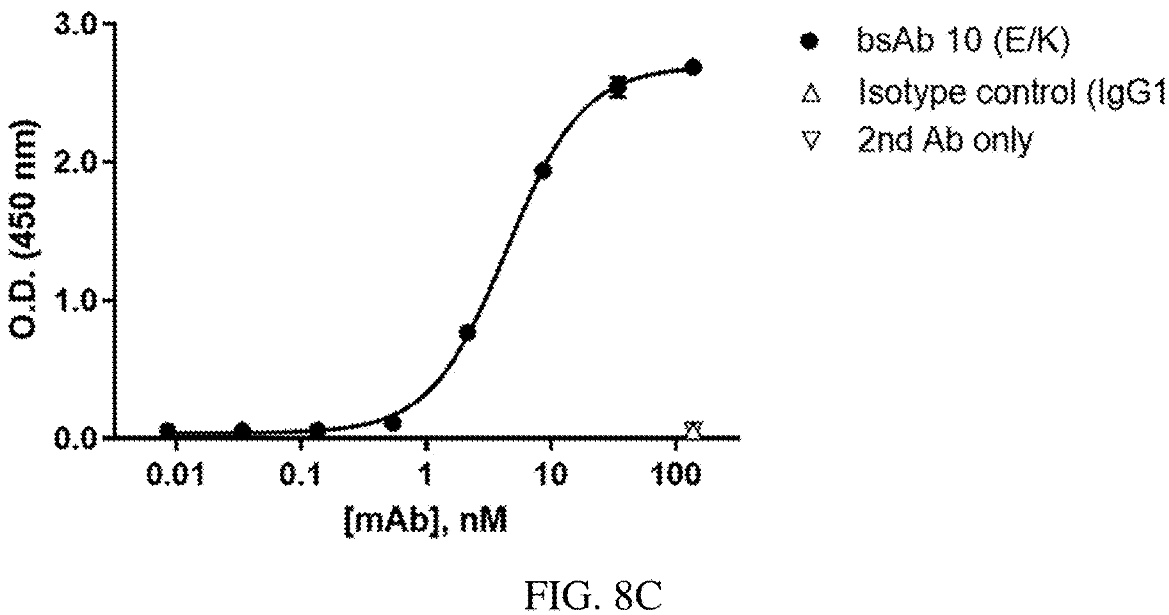
Figure 8D:
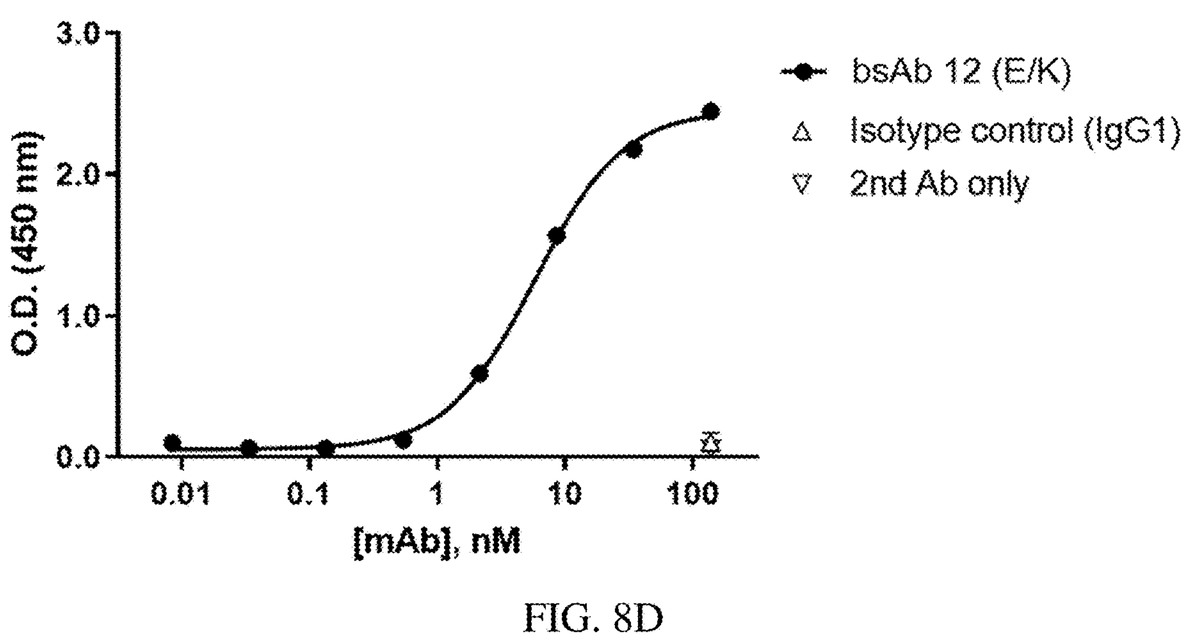
Figure 8E:
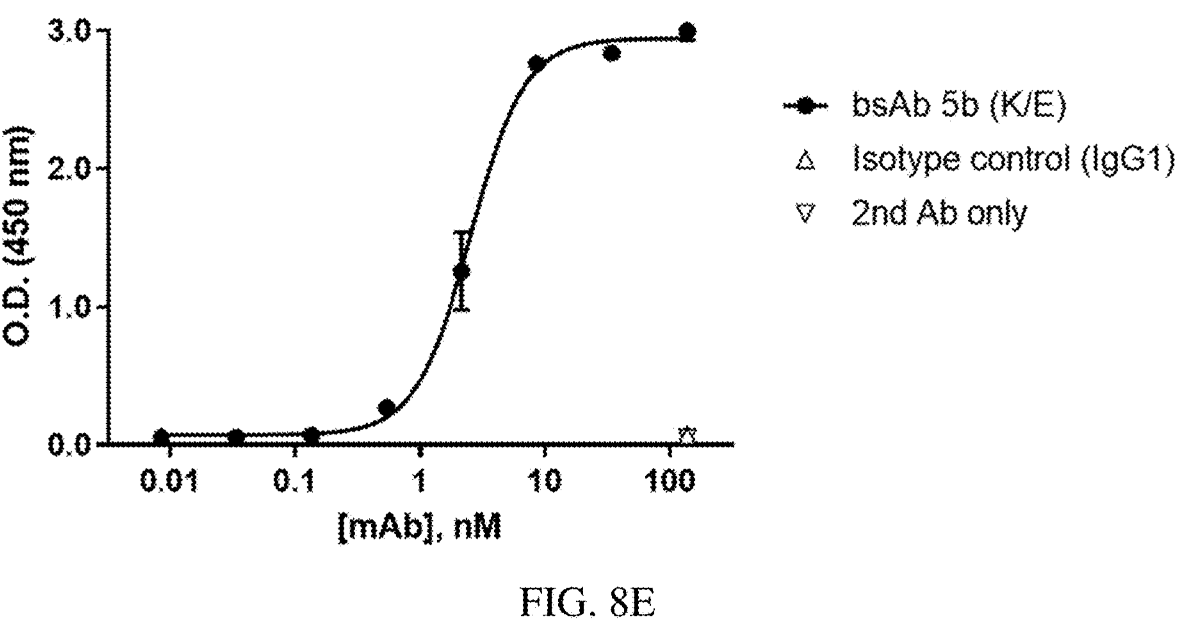
Figure 8F:
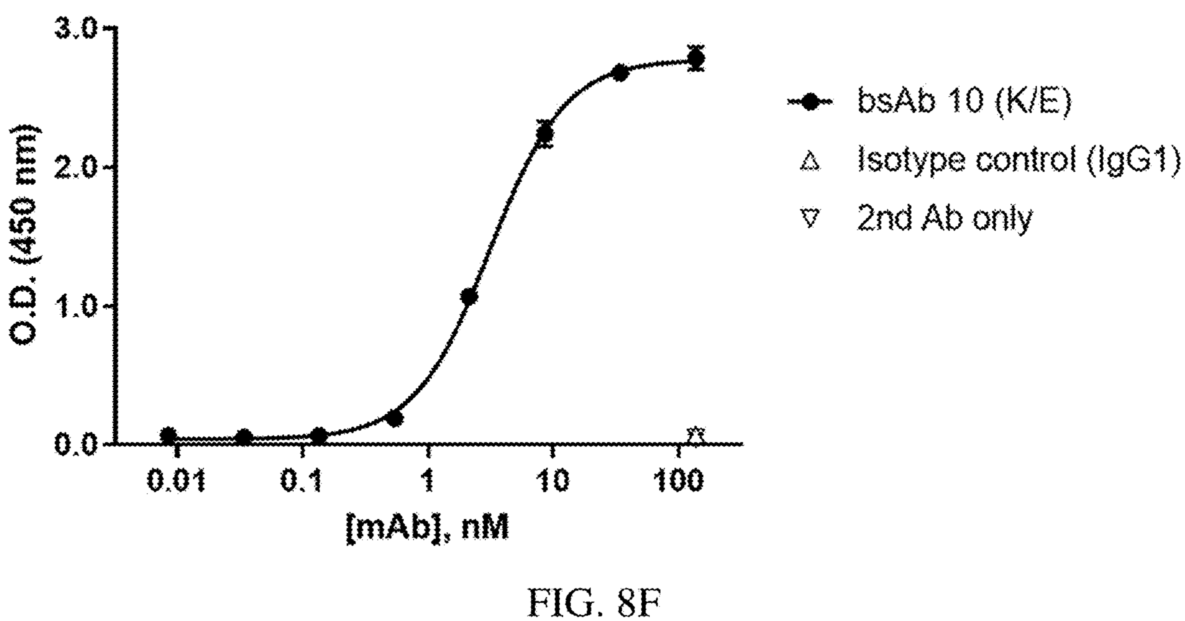
Figure 8G:
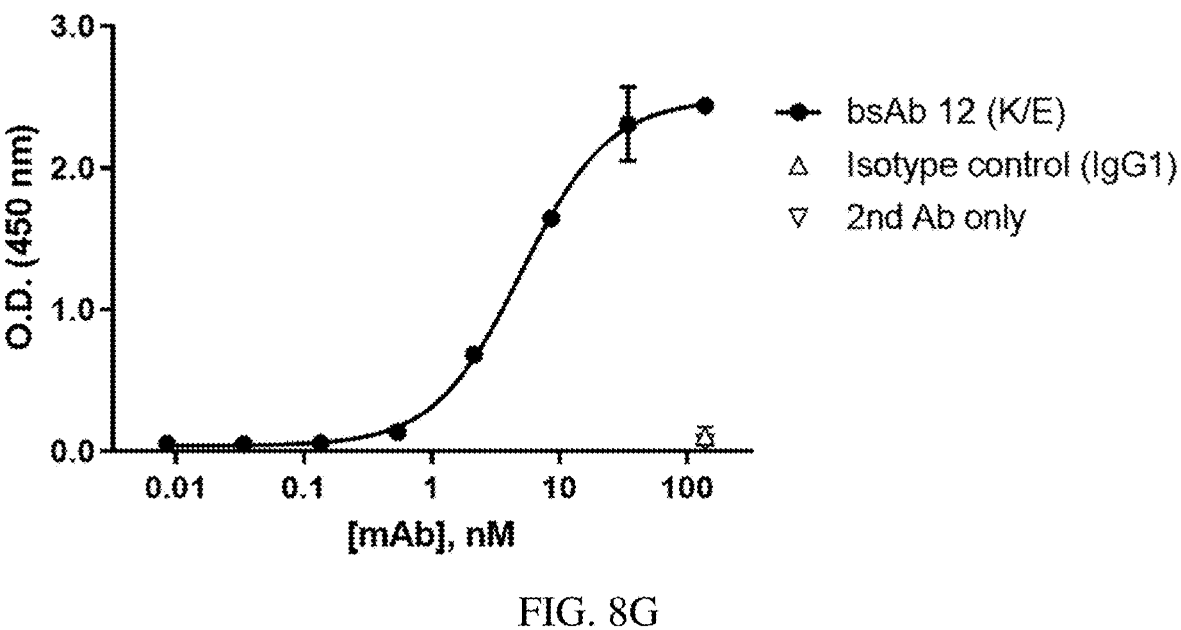
Figure 8H:
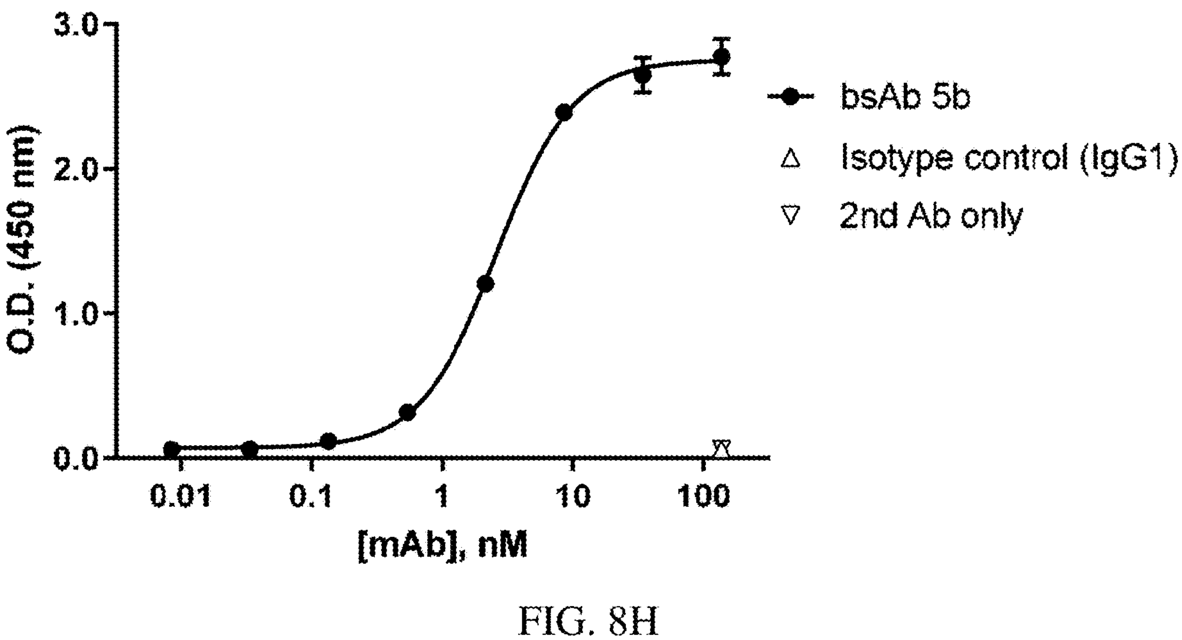
Figure 8I:
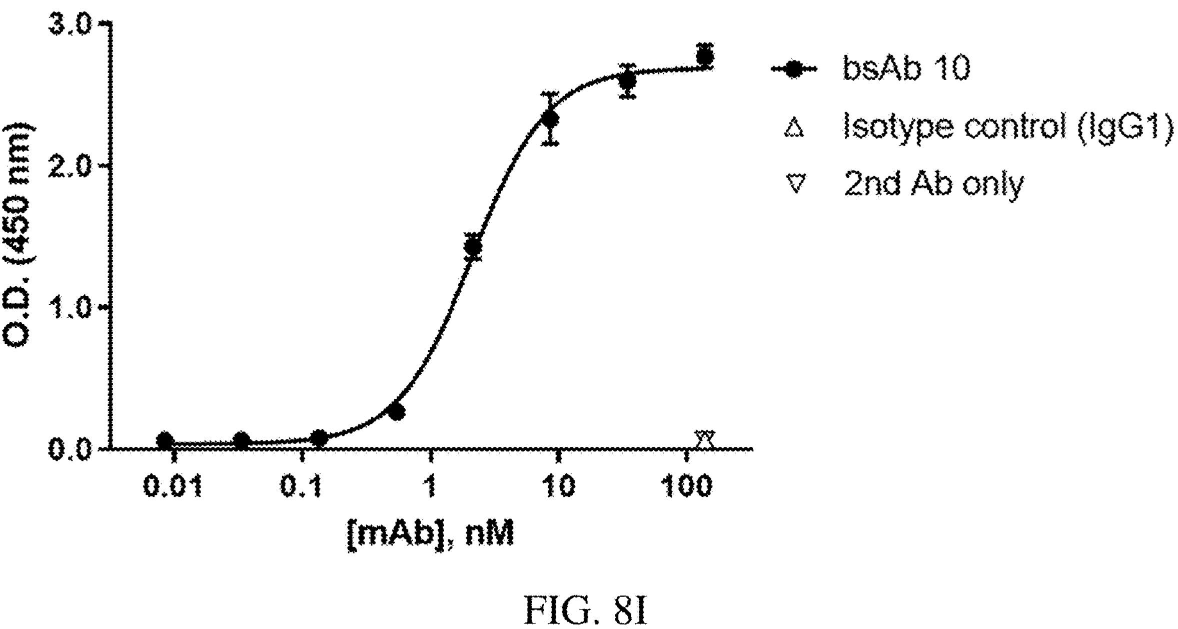
Figure 8J:
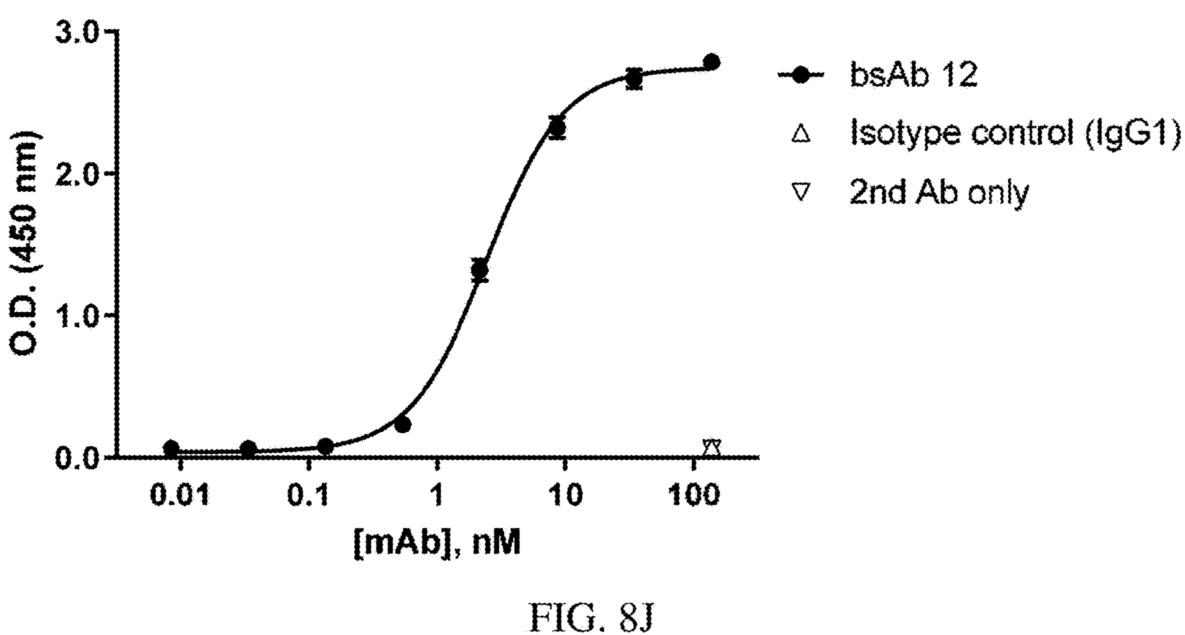
Figure 9A:
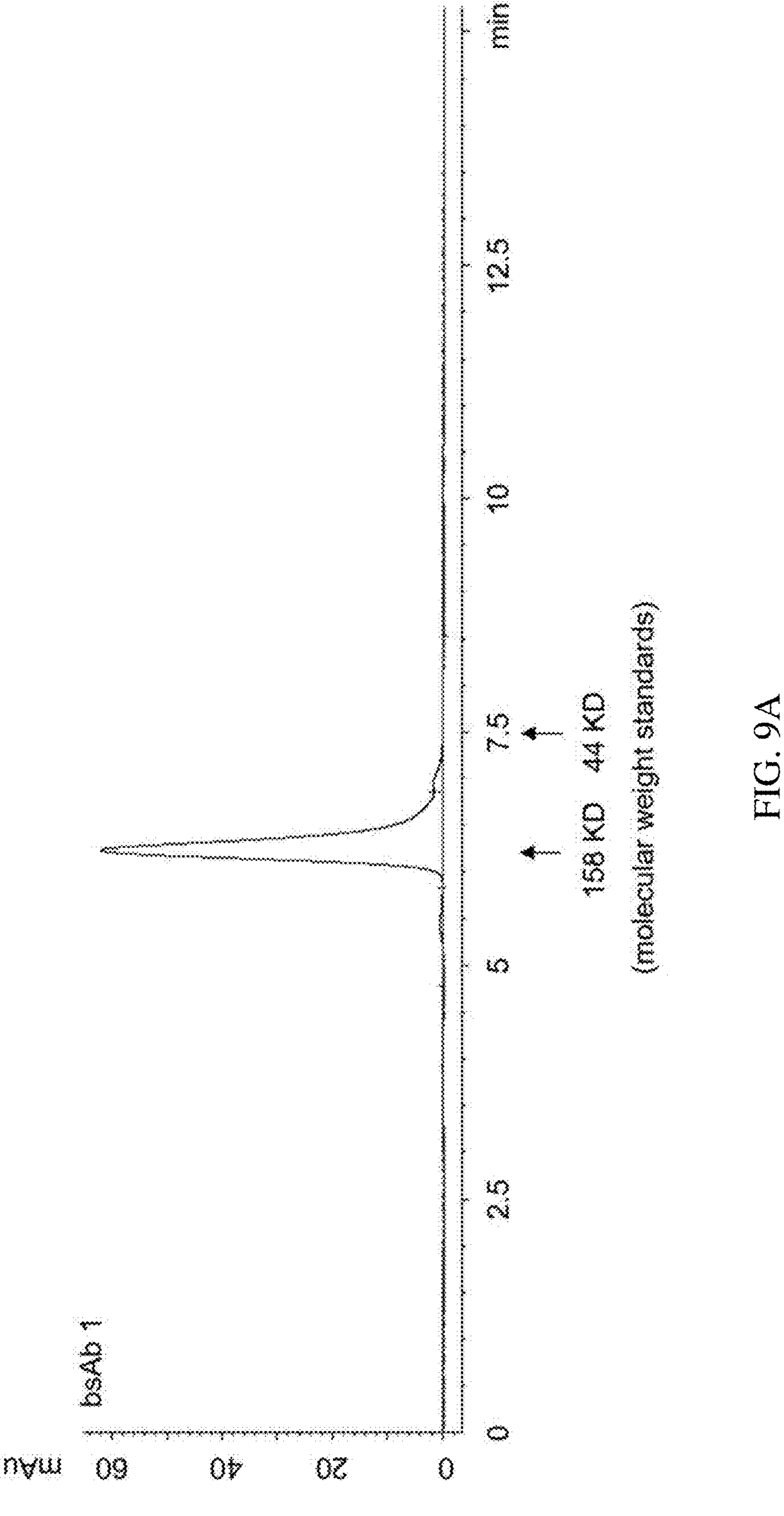
FIGS. 9A-9N show the size exclusion chromatography (SEC) profiles of the purified bispecific antibodies using Protein A chromatography (FIGS. 9A-9E), or bispecific antibodies purified using Protein A chromatography followed by hydrophobic interaction chromatography (HIC) (FIGS. 9F-9N).
Figure 9B:
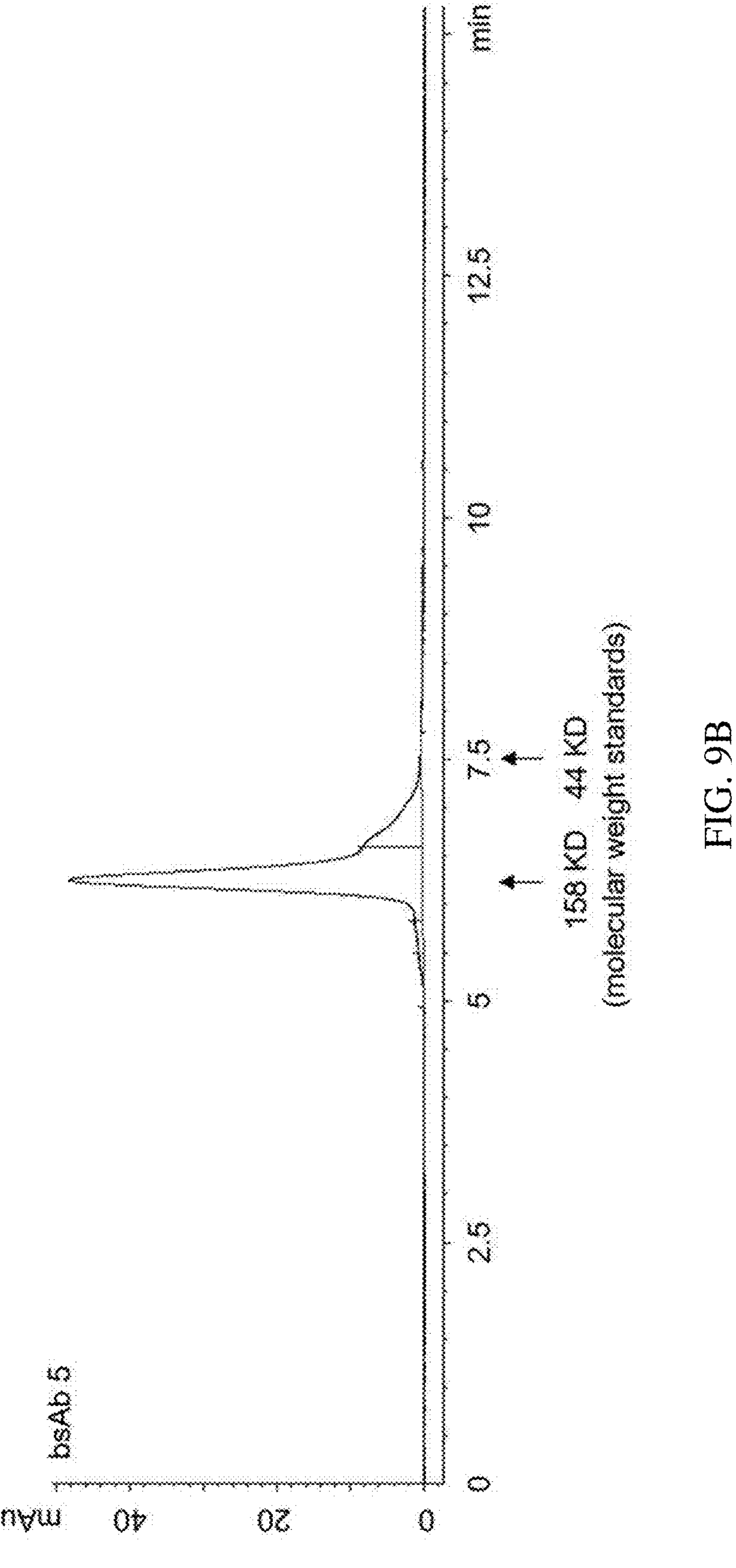
FIG. 9B, SEC profile of bsAb 5.
Figure 9C:
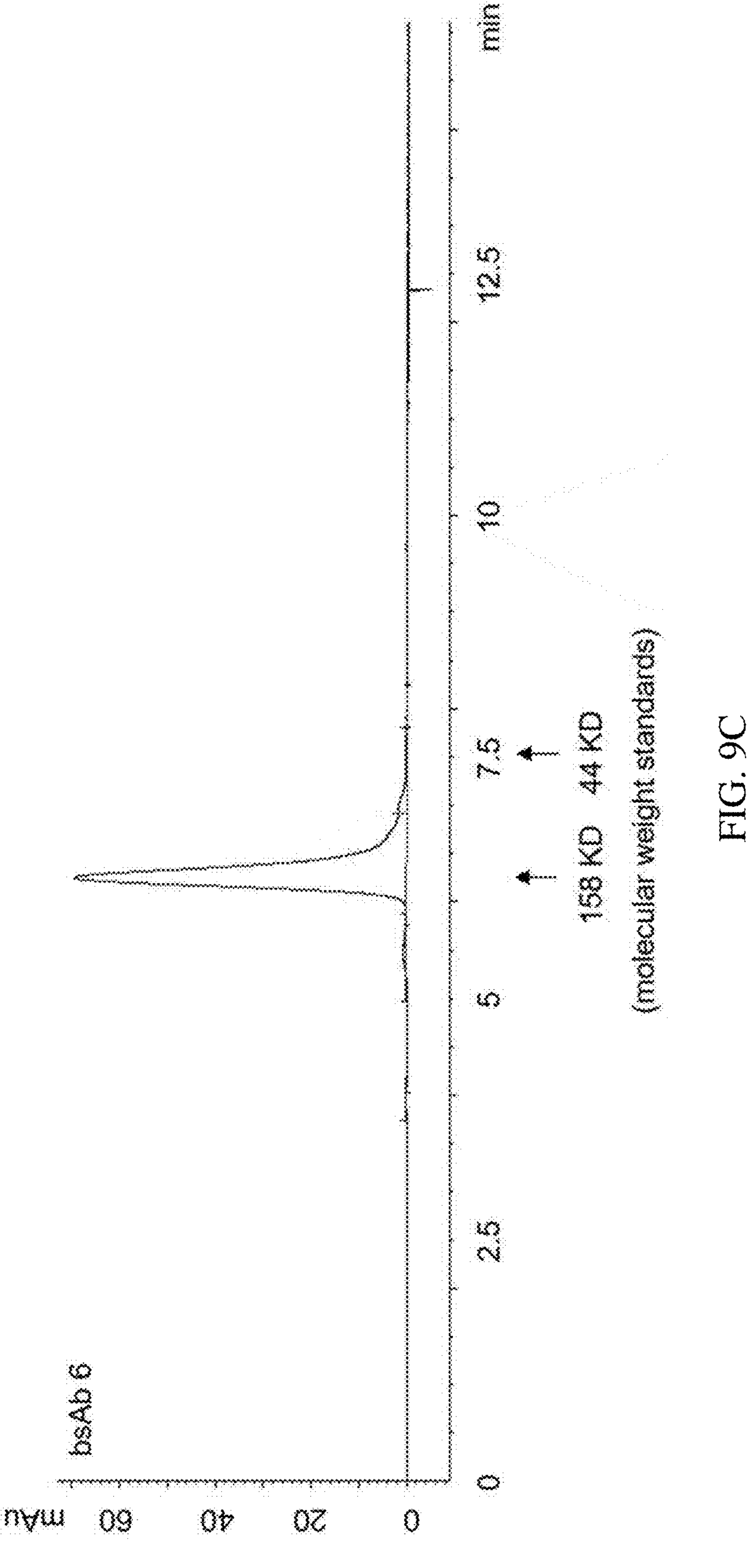
FIG. 9C, SEC profile of bsAb 6.
Figure 9D:
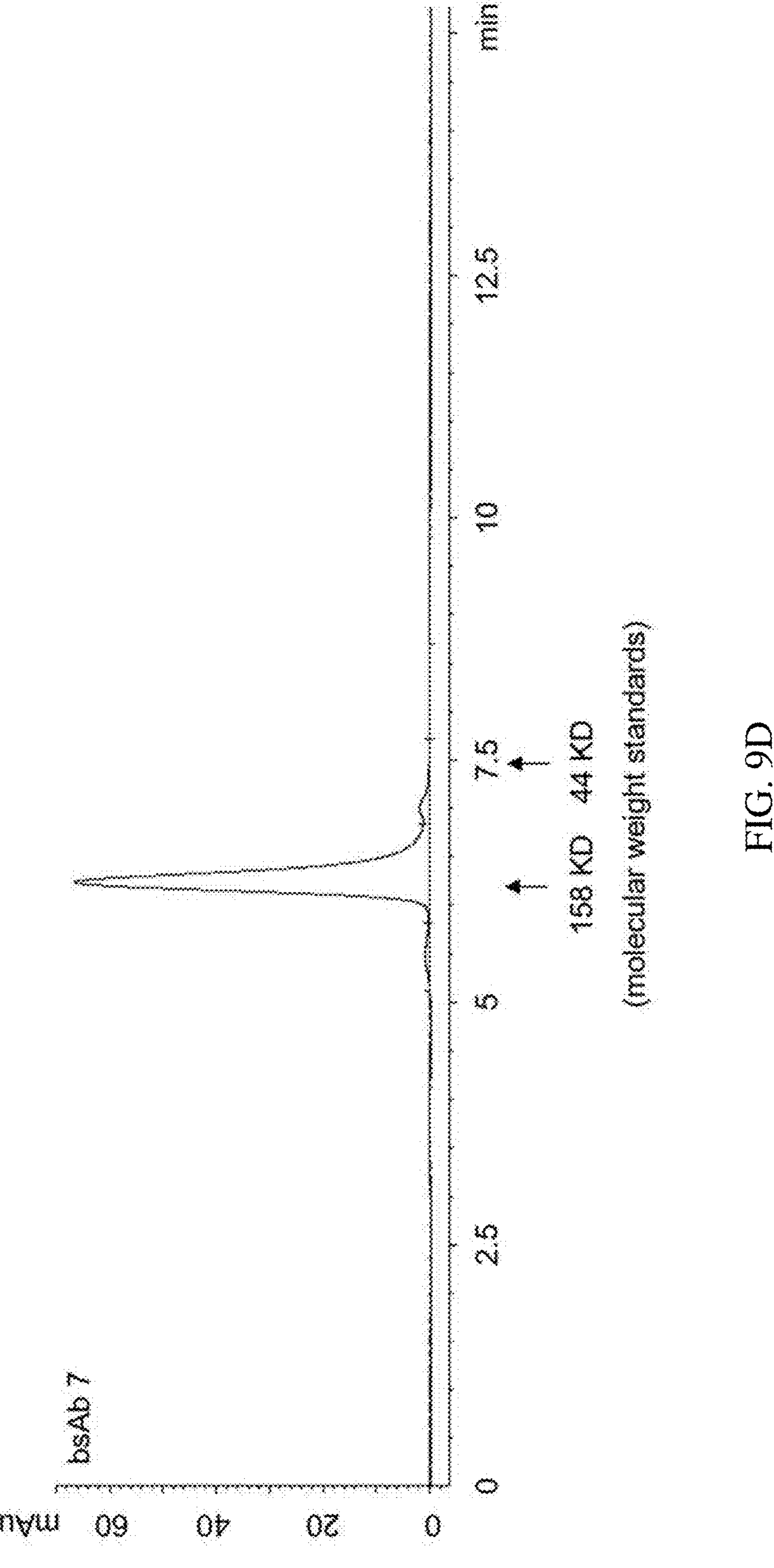
FIG. 9D, SEC profile of bsAb 7.
Figure 9E:
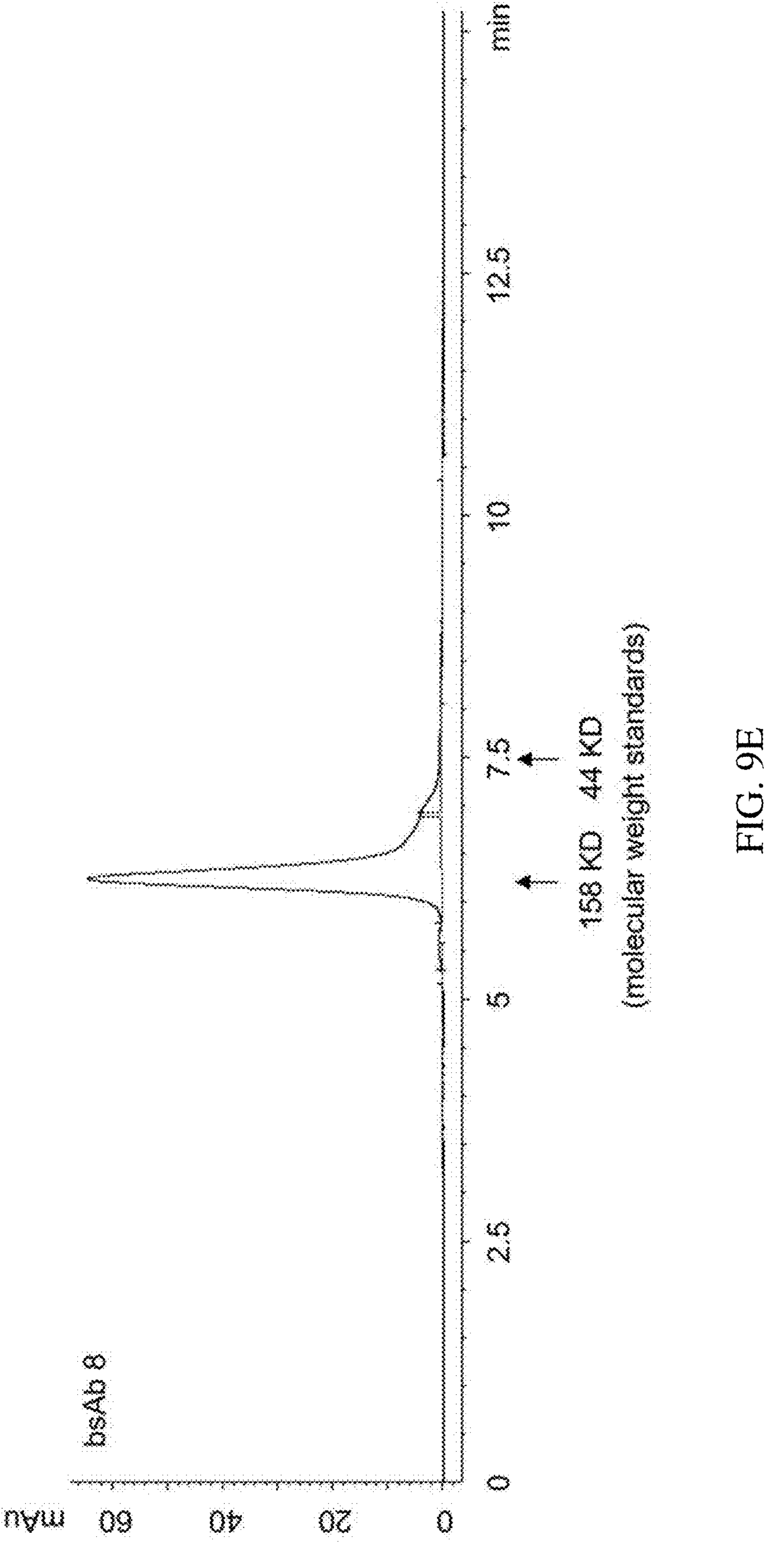
FIG. 9E, SEC profile of bsAb 8.
Figure 9F:
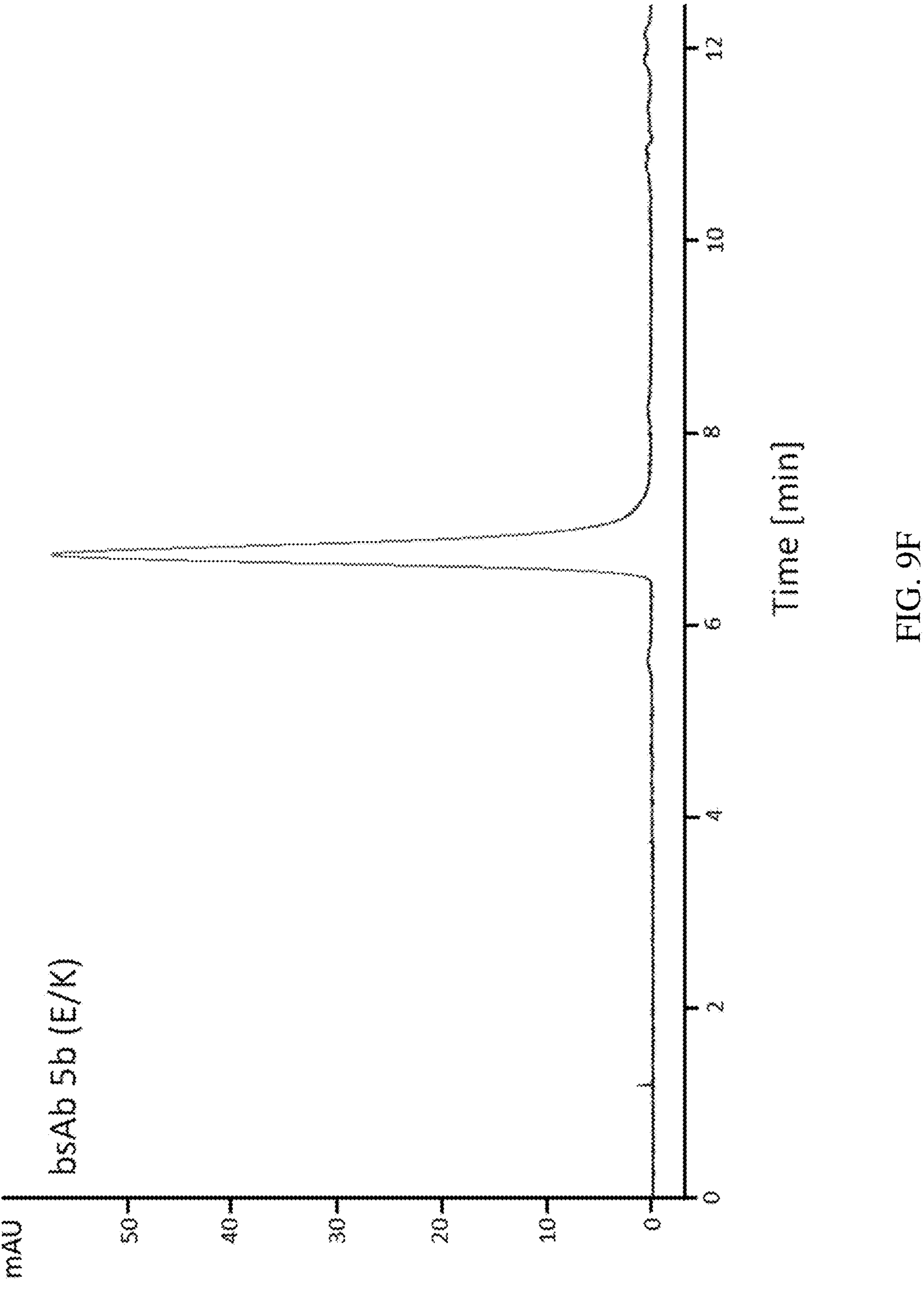
FIG. 9F, SEC profile of bsAb 5b (E/K)
Figure 9G:
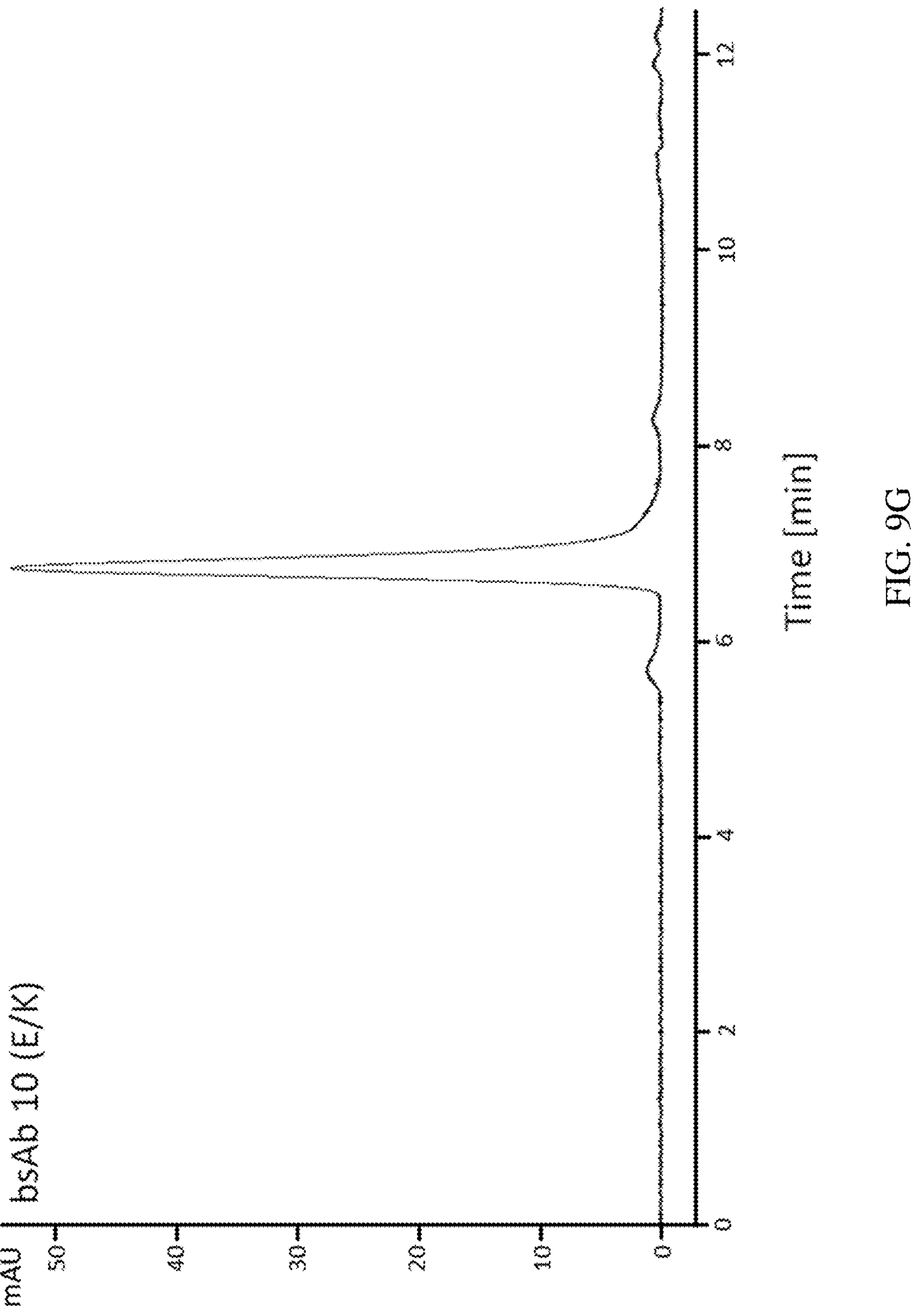
FIG. 9G, SEC profile of bsAb 10 (E/K)
Figure 9H:
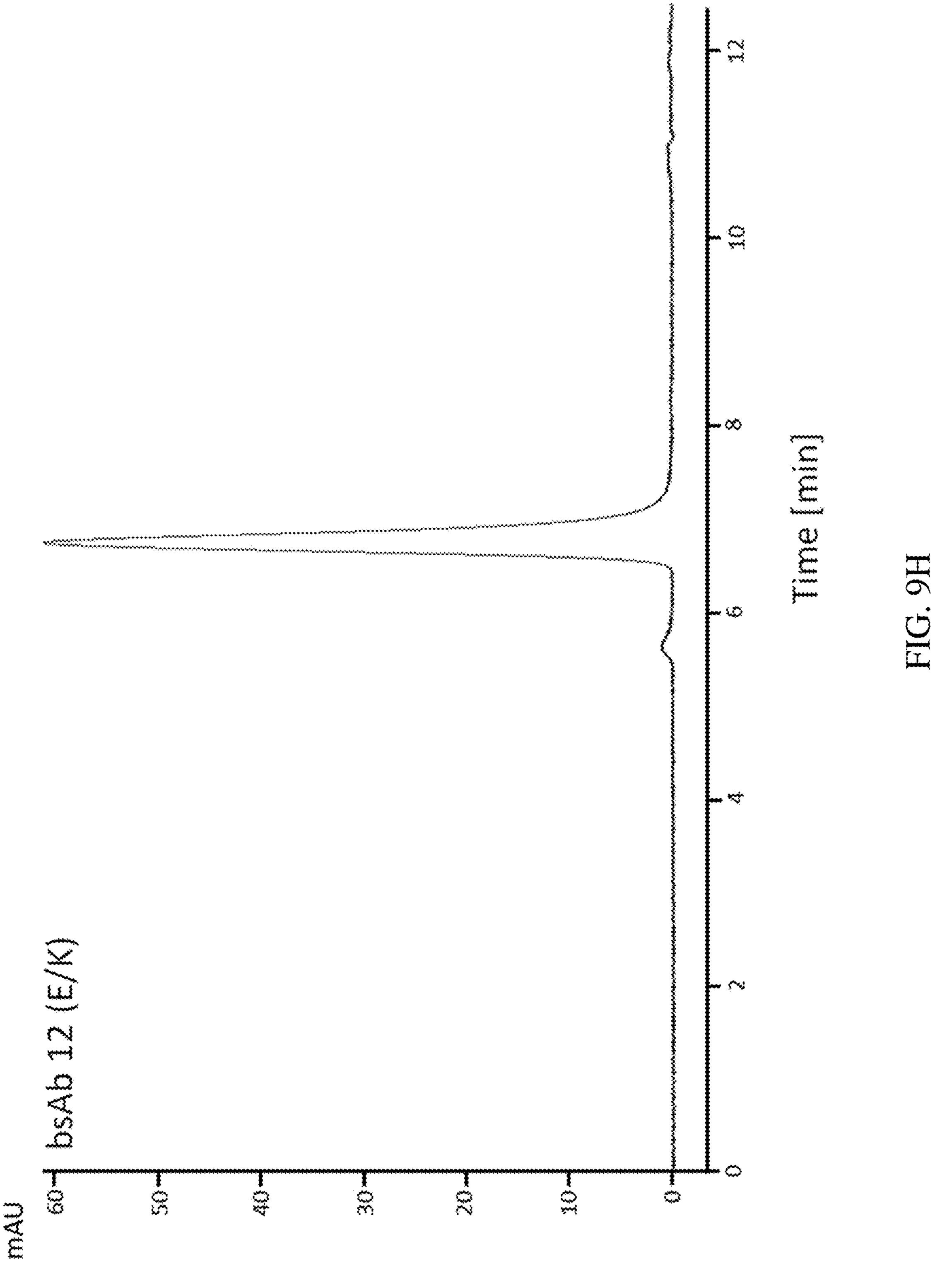
FIG. 9H, SEC profile of bsAb 12 (E/K)
Figure 9I:
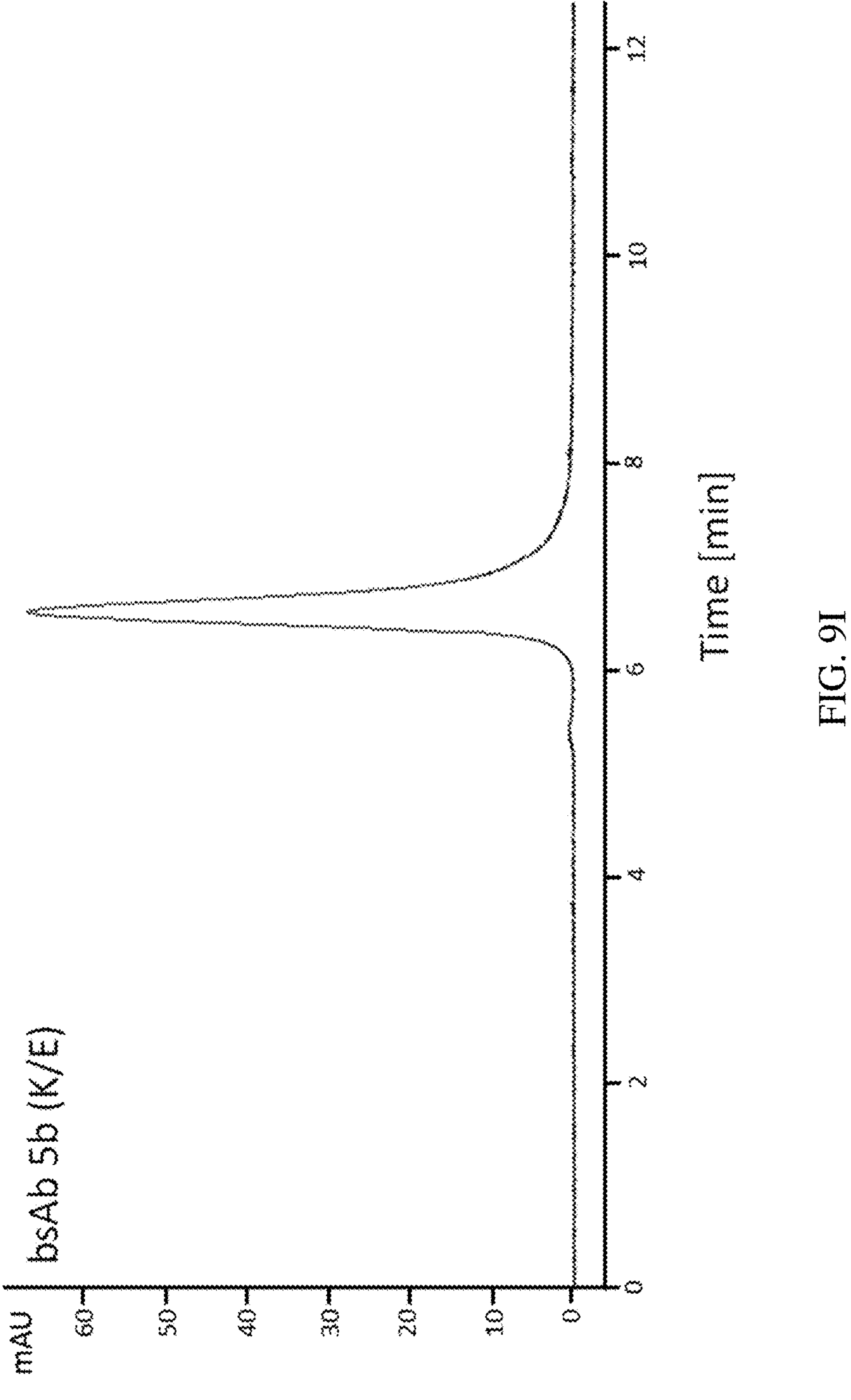
FIG. 9I, SEC profile of bsAb 5b (K/E)
Figure 9J:
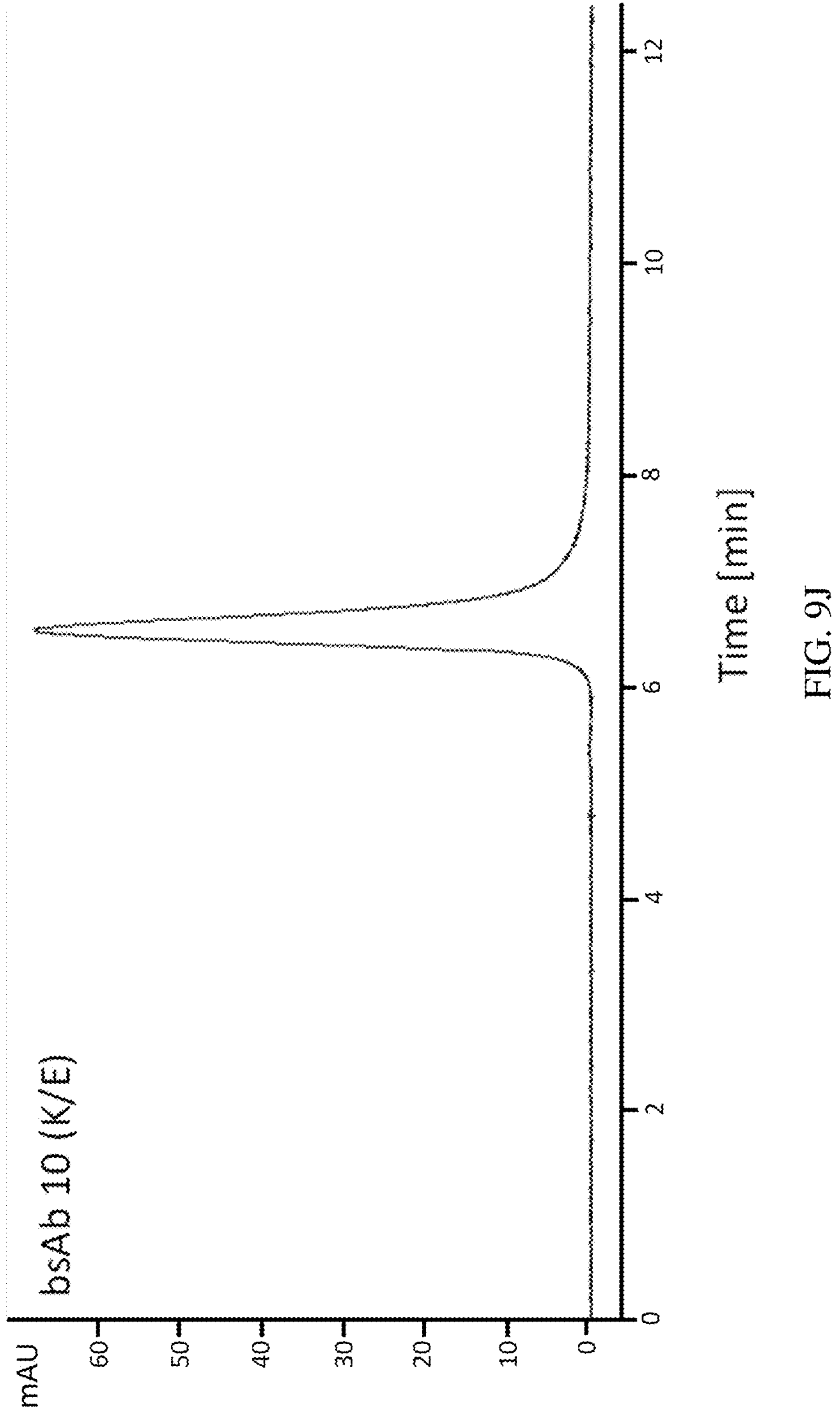
FIG. 9J, SEC profile of bsAb 10 (K/E)
Figure 9K:
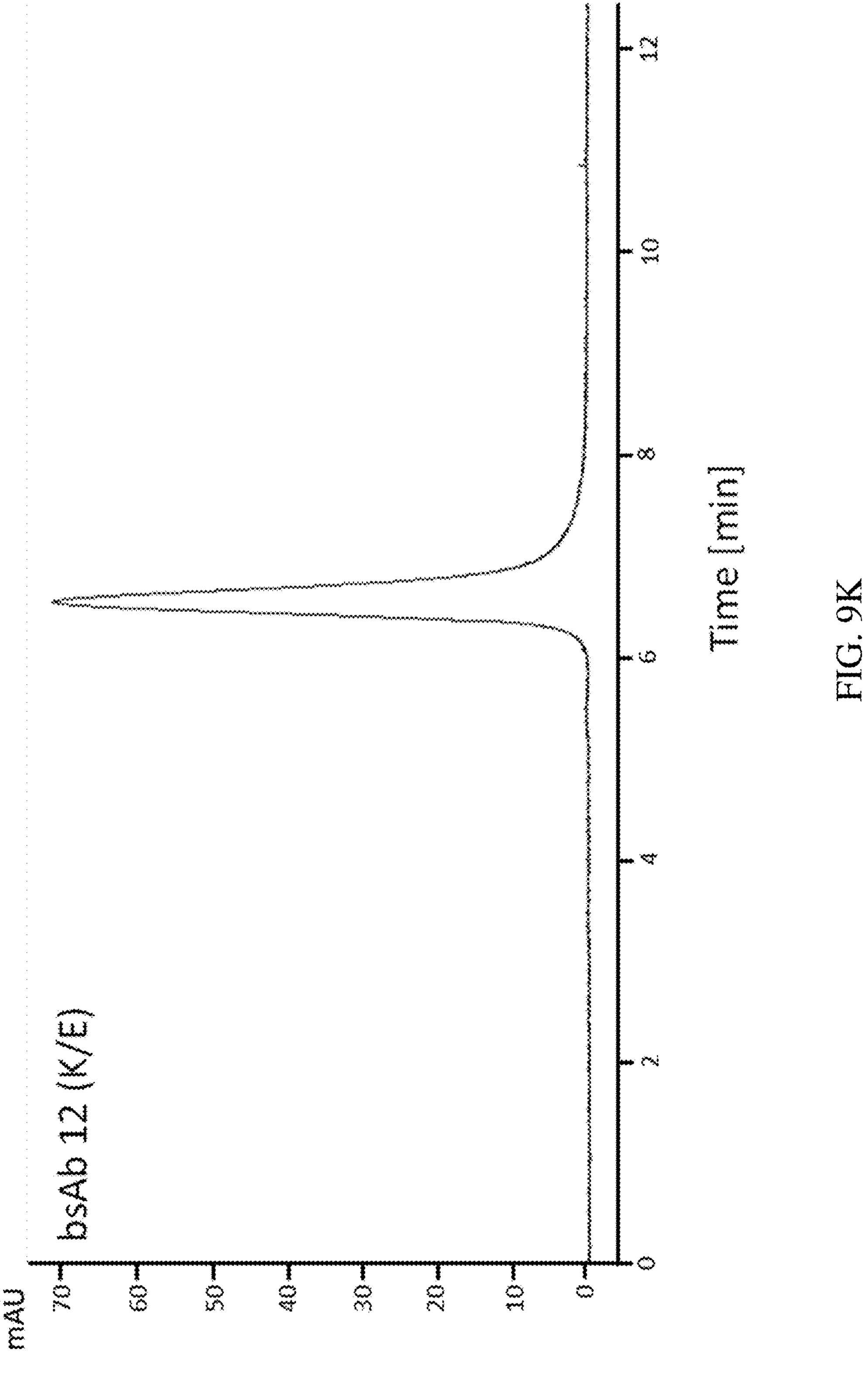
FIG. 9K, SEC profile of bsAb 12 (K/E)
Figure 9L:
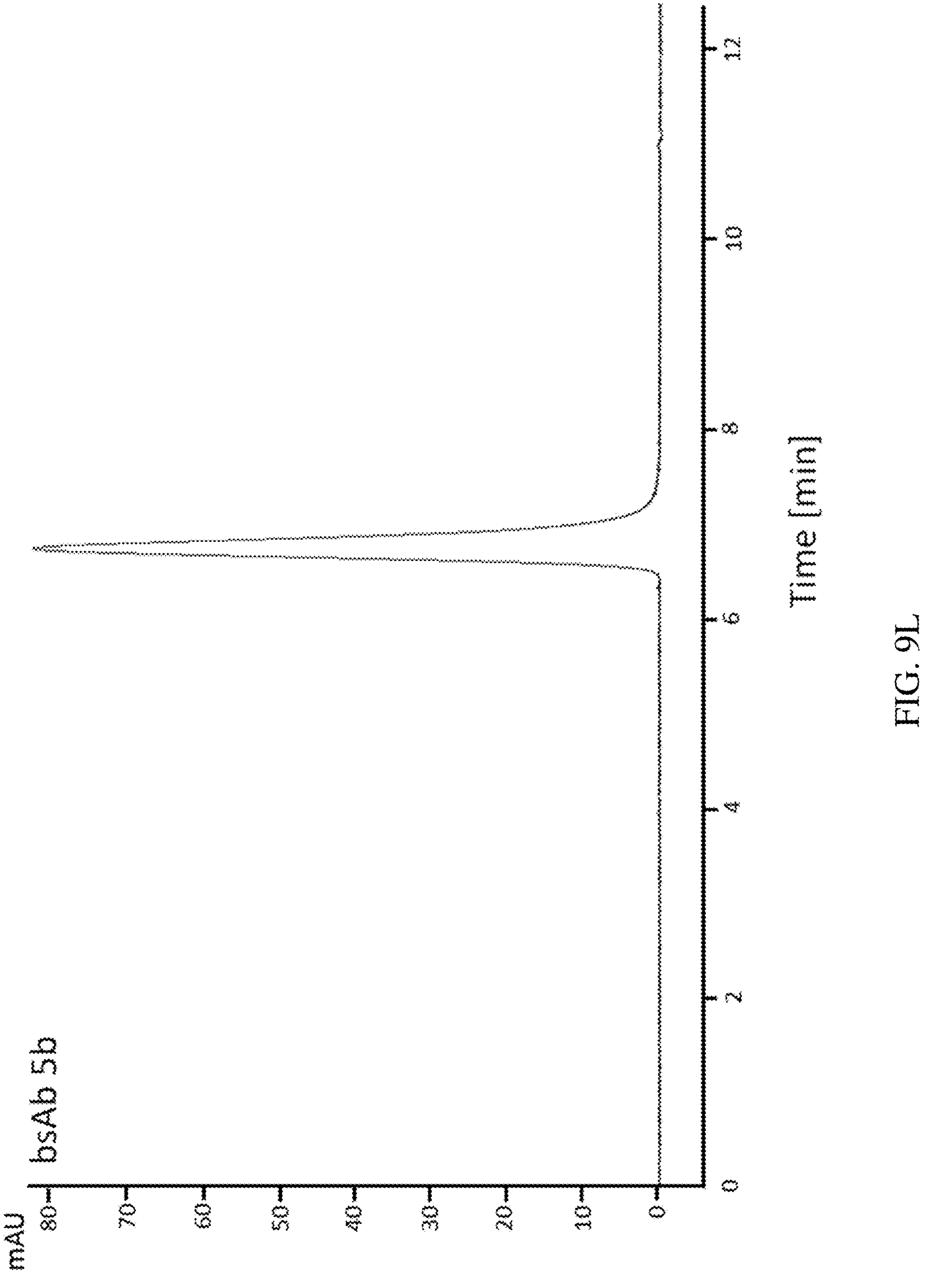
FIG. 9L, SEC profile of bsAb 5b.
Figure 9M:
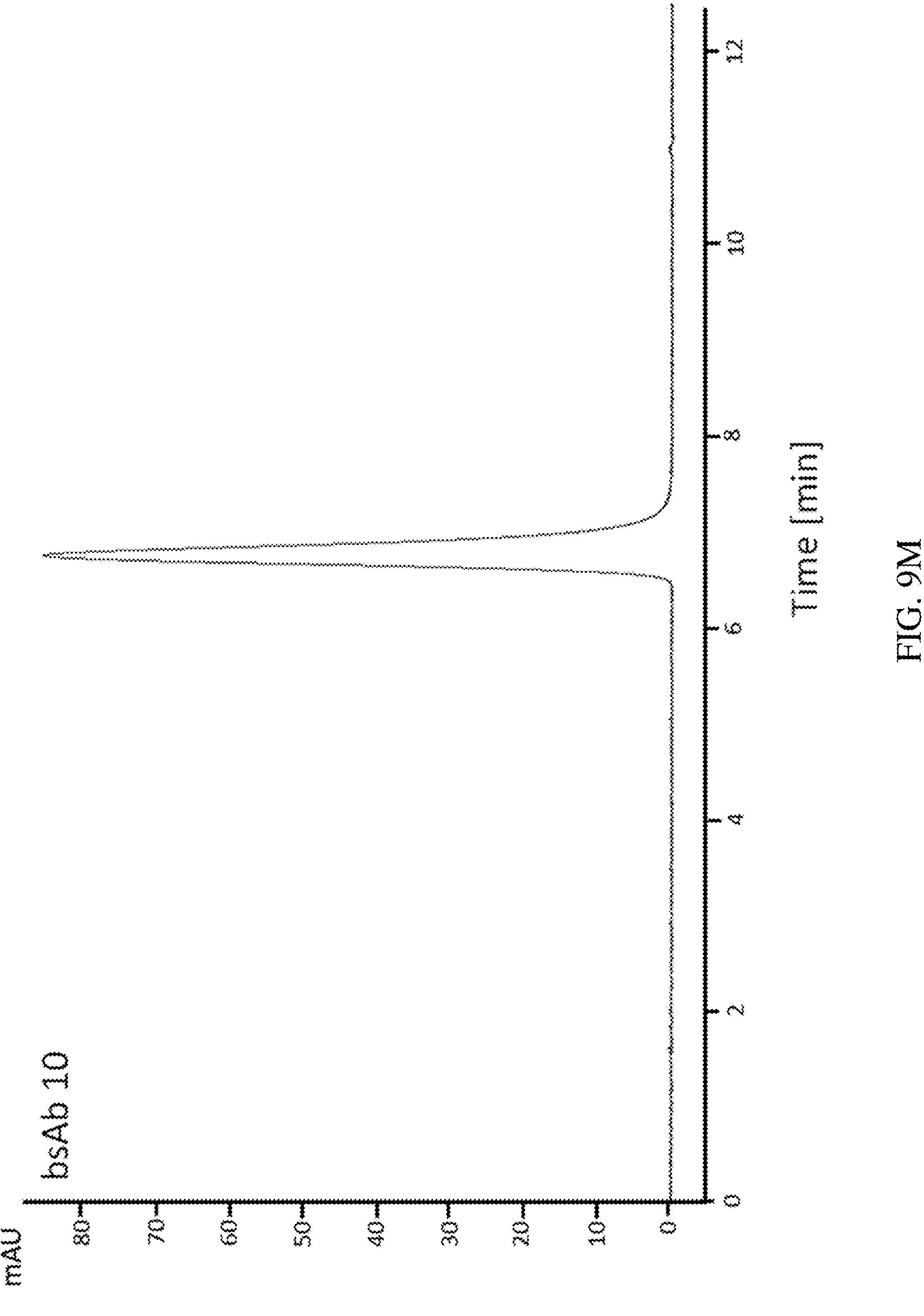
FIG. 9M, SEC profile of bsAb 10.
Figure 9N:
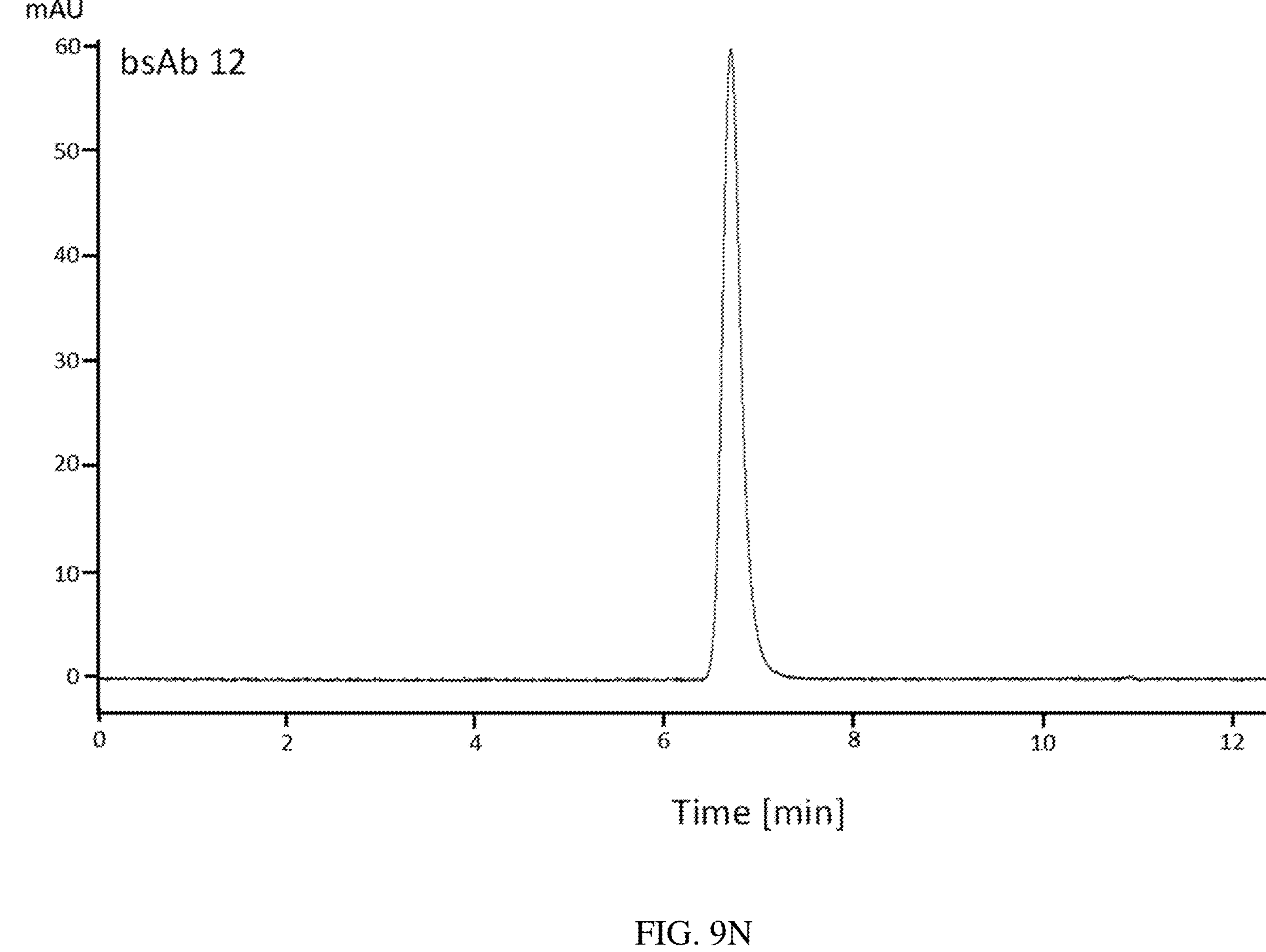
Figure 10A:
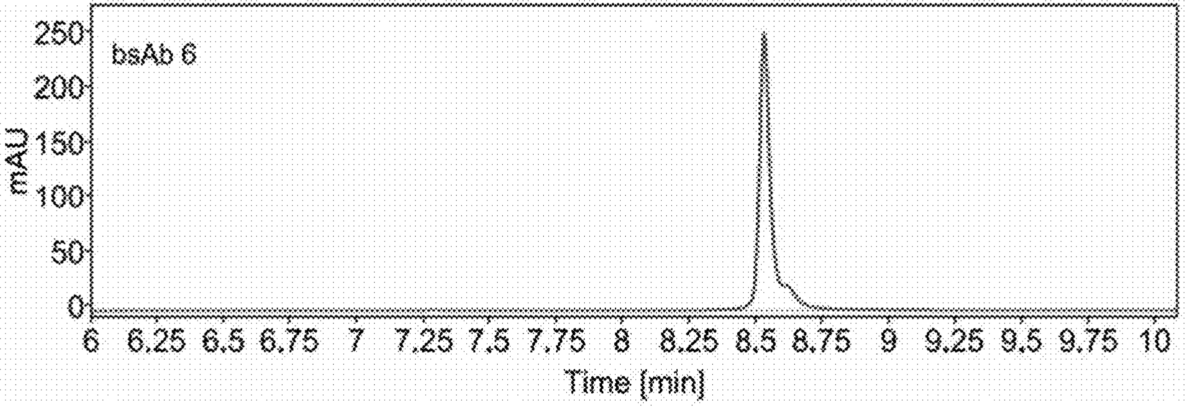
FIGS. 10A-10L show the RP-HPLC profiles of the HIC purified bispecific antibodies under non-reducing condition.
Figure 10B:
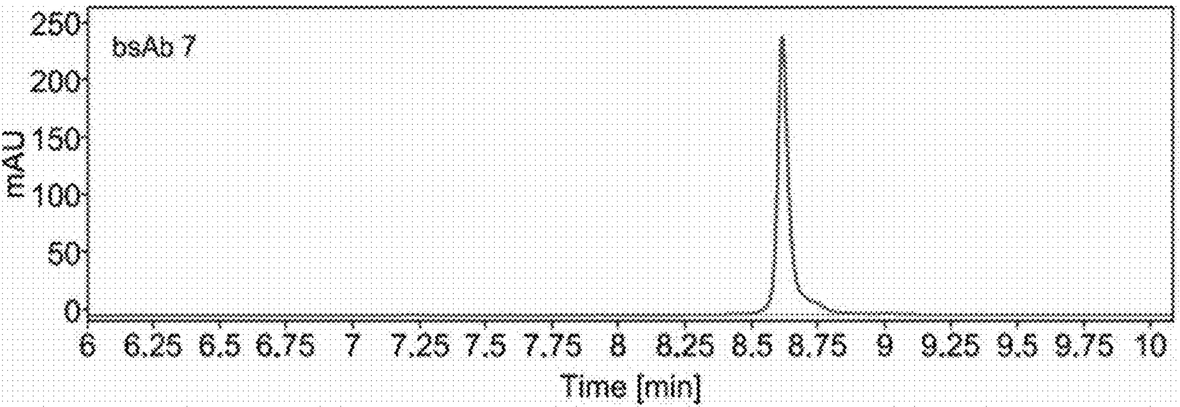
Figure 10C:
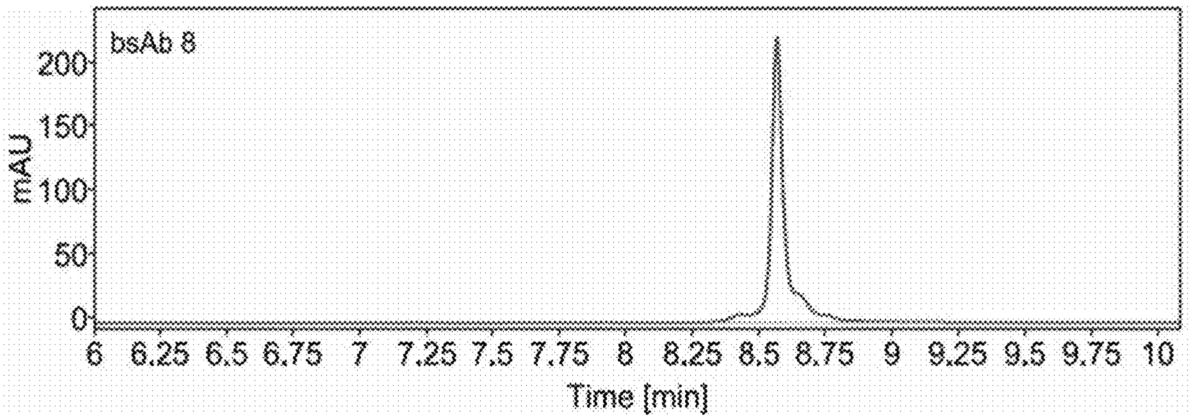
Figure 10D:
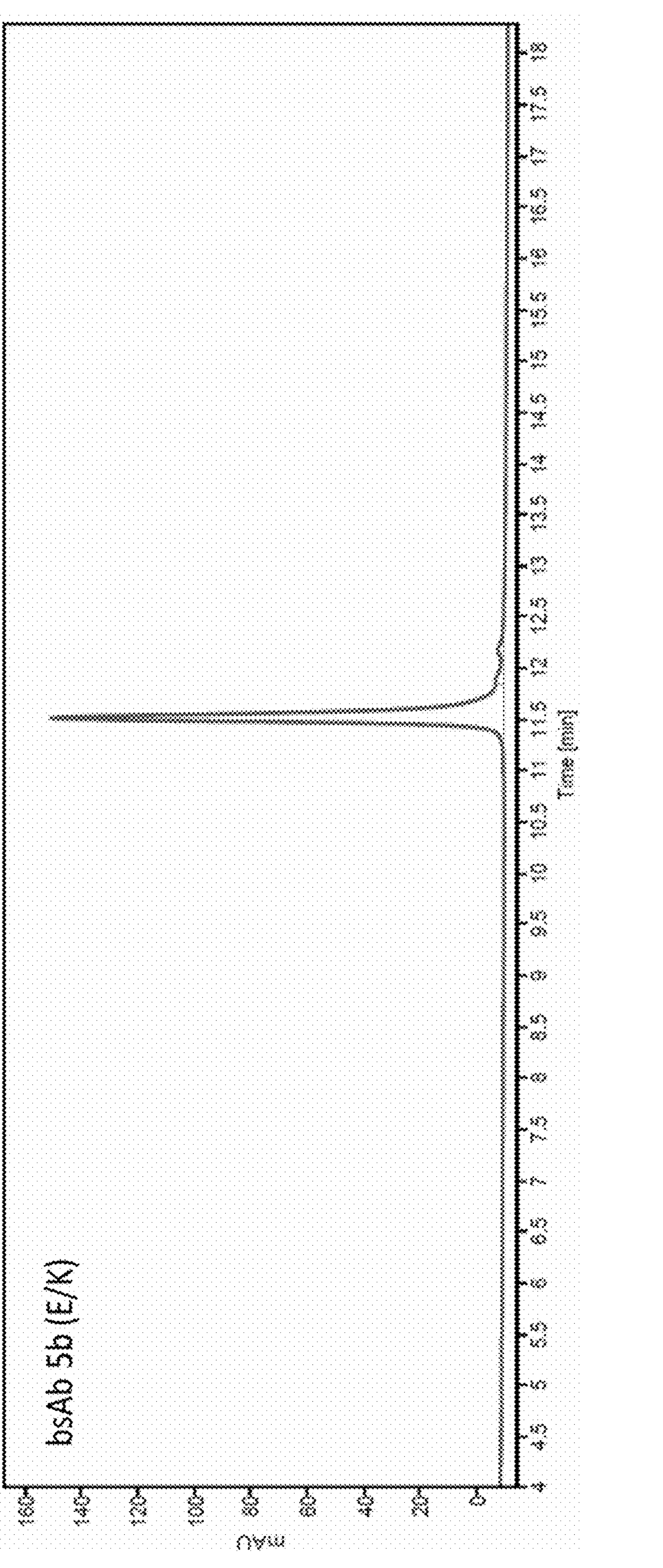
Figure 10E:
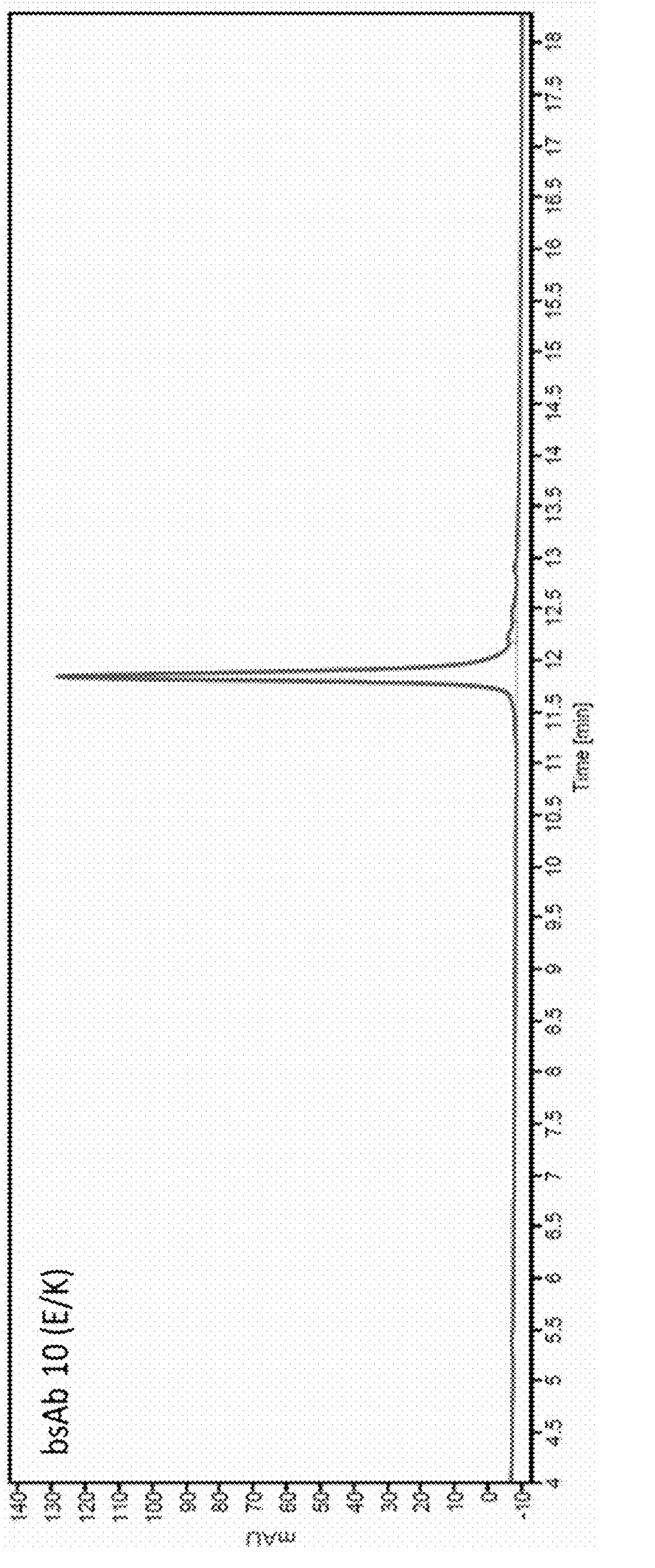
Figure 10F:
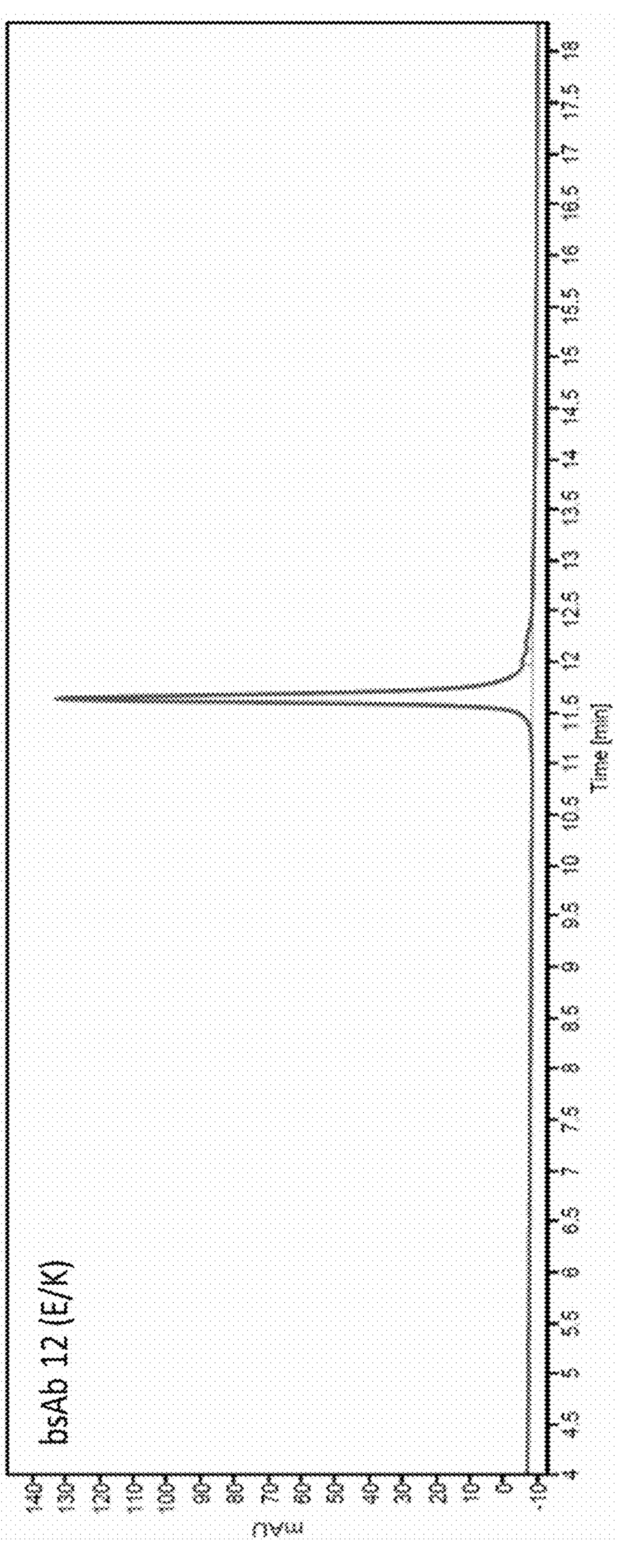
Figure 10G:
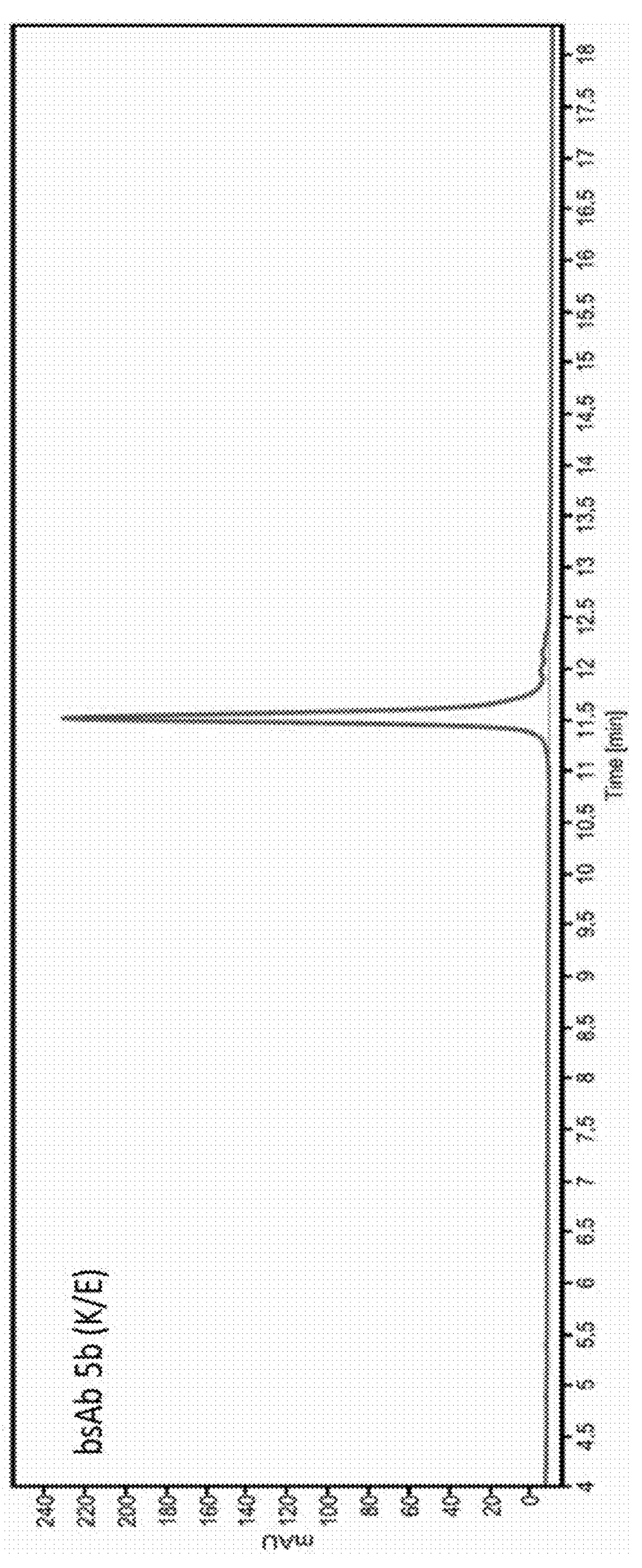
Figure 10H:
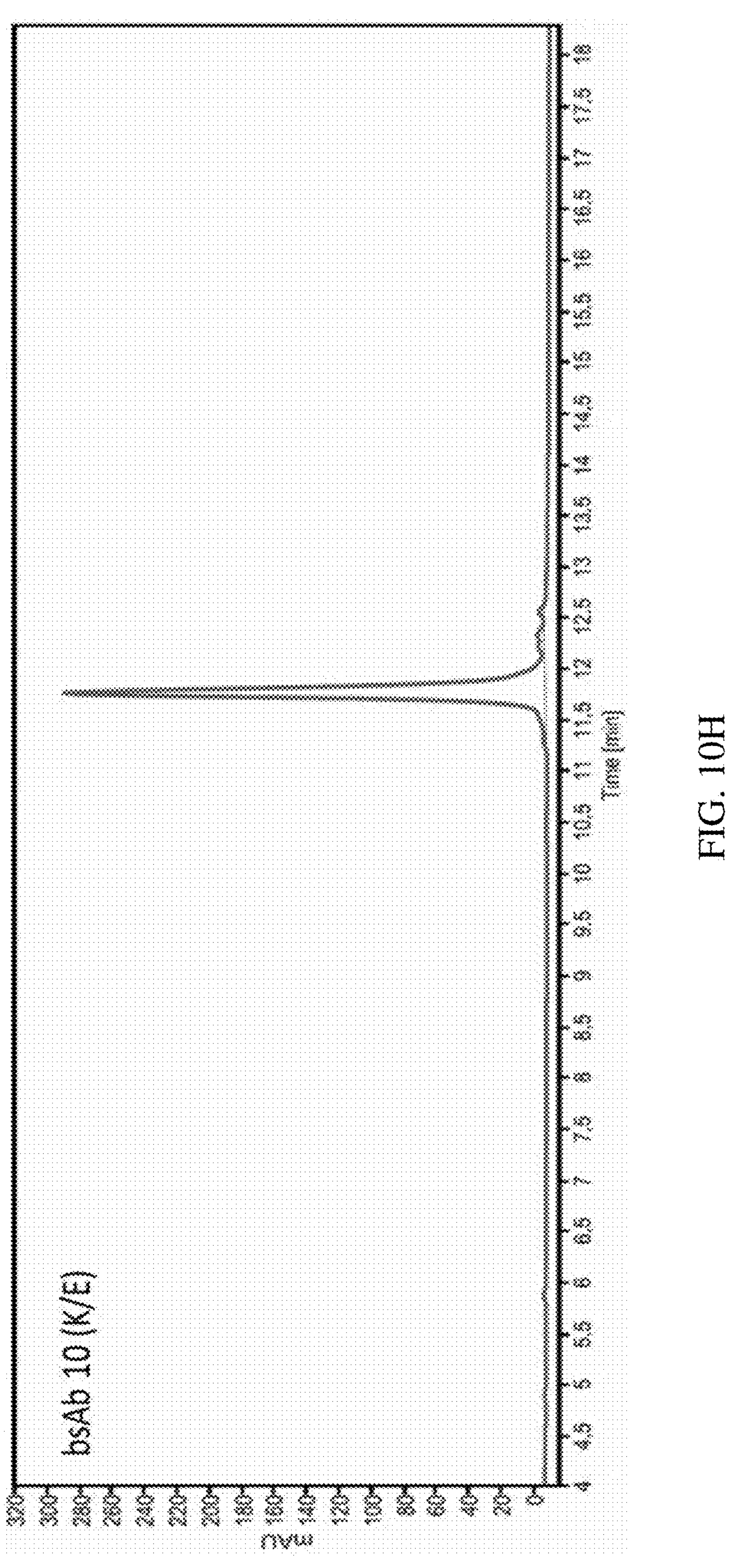
Figure 10I:
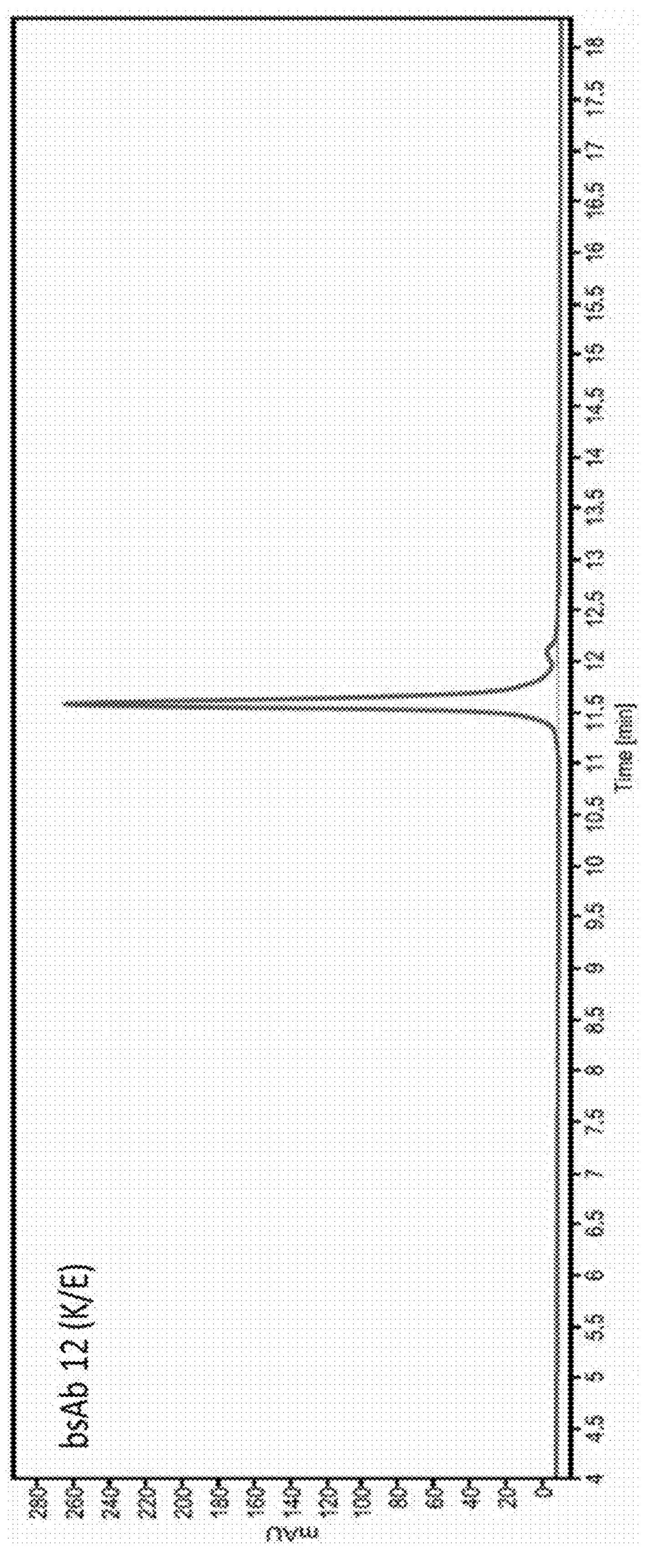
Figure 10J:
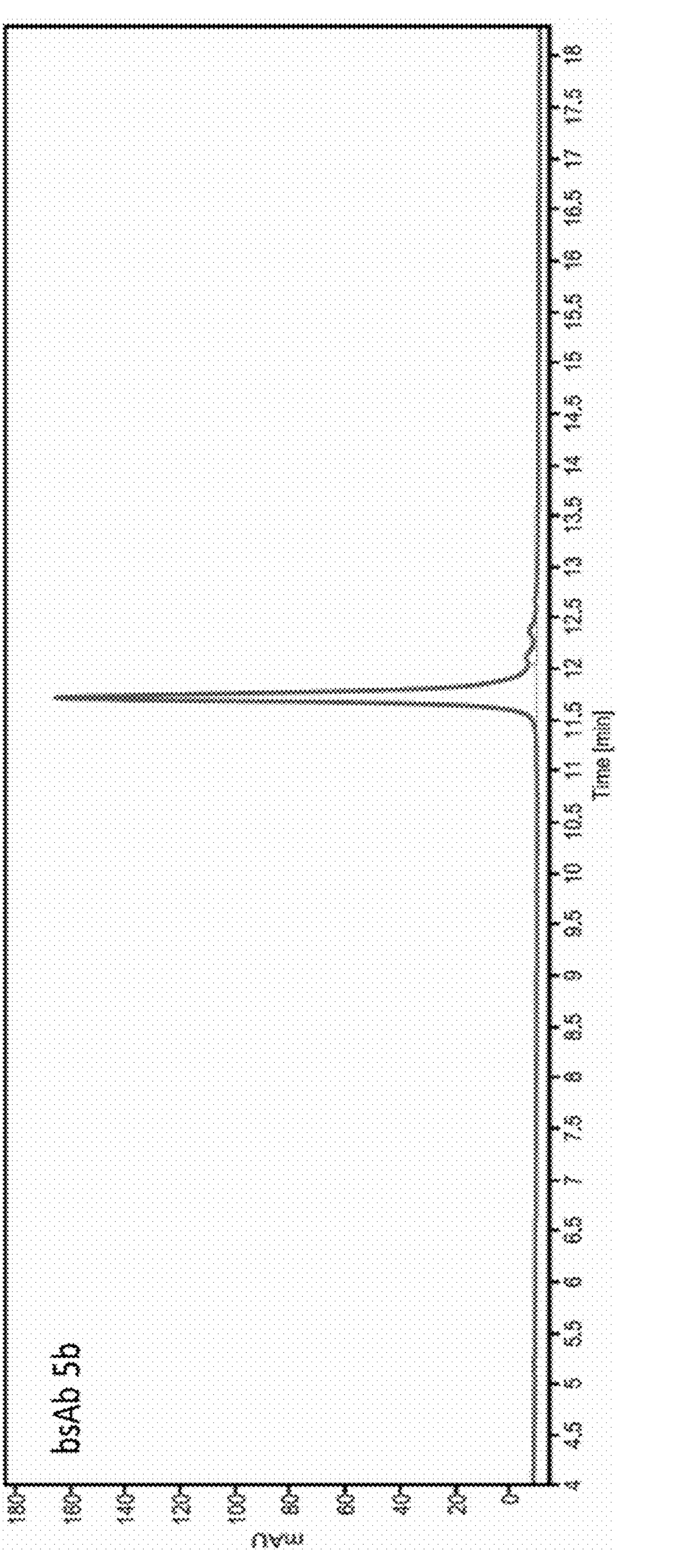
Figure 10K:
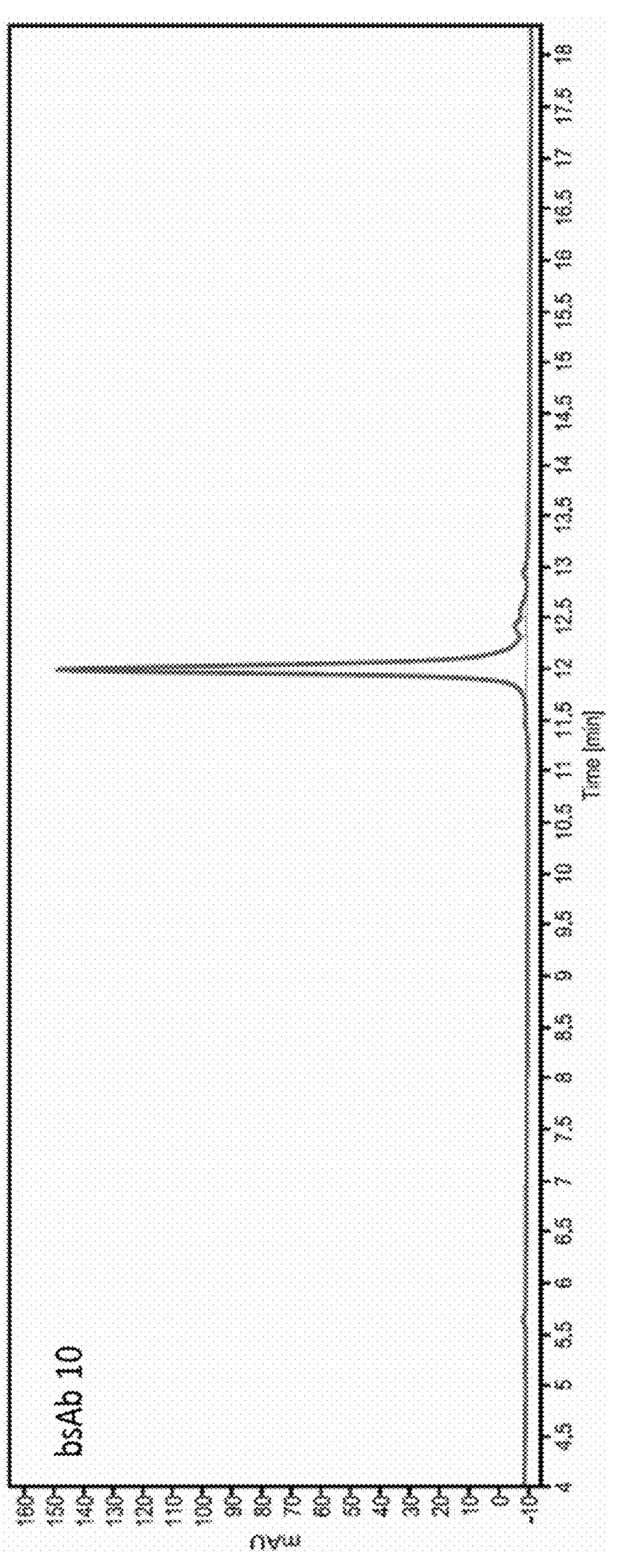
Figure 10L:
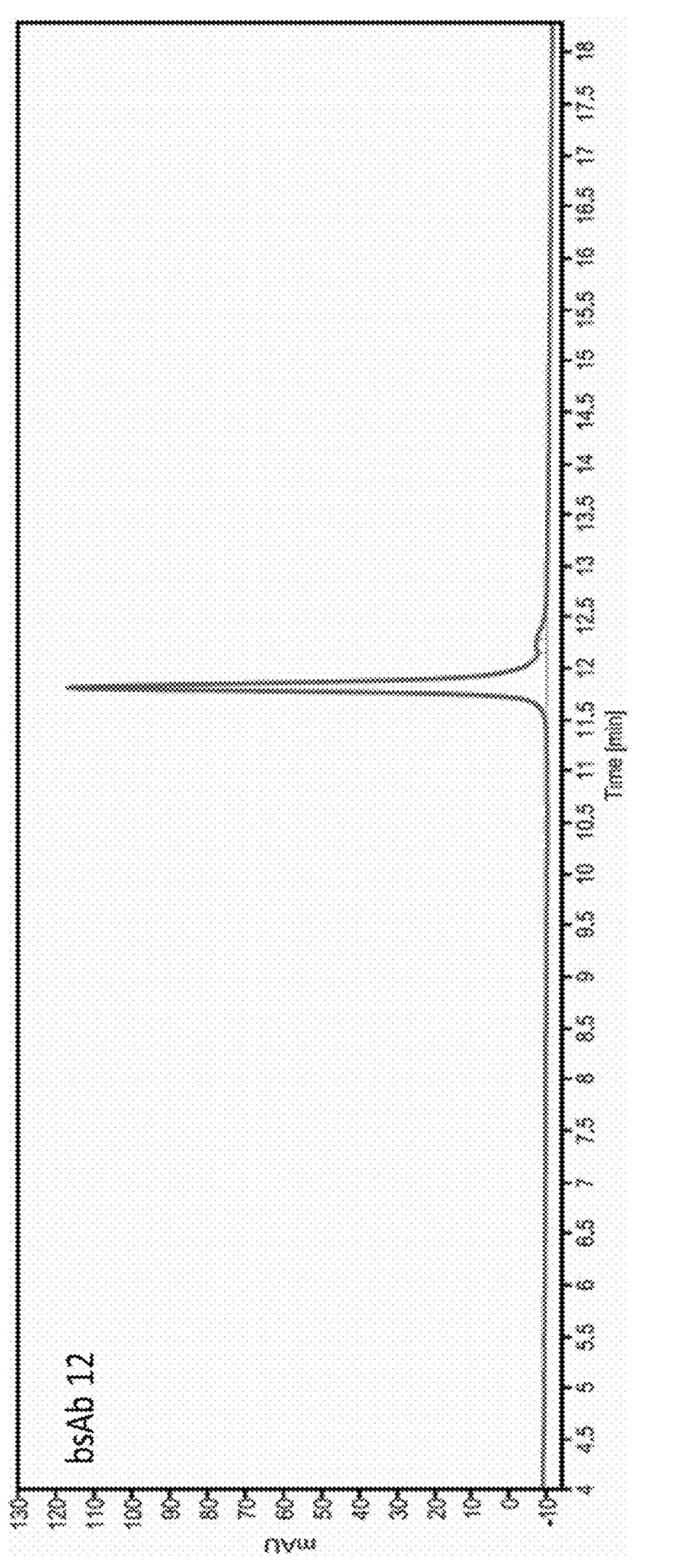

The Protein A purified bispecific antibodies were analyzed with SDS-PAGE. Protein samples were diluted to a concentration of 1 mg/mL. For non-reducing lanes, 3 μL protein was added to 4.5 μL water and 2.5 μL 4×LDS sample buffer (Thermo NP0007; Waltham, MA) and loaded onto the gel directly. For reducing lanes, 3 μL protein was added to 3.5 μL water, 2.5 μL 4×LDS sample buffer, and 1 μL 1 μL 1M DTT and heated at 95° C. for 3 min and loaded onto the gel. Bolt 4-12% bis-tris gels were used for all samples (Thermo NP0323BOX). Samples were electrophoresed for 30 min at 180 V and visualized with Coomassie G-250. FIGS. 7A-7B show the SDS-PAGE images of mAb 1/mAb 2 bispecific antibody samples purified using Protein A chromatography. Under reducing and denaturing conditions, all the samples displayed two bands with one corresponding to heavy chains (about 50 kDa) and the other corresponding to light chains (about 25 kDa). Under non-reducing and denaturing conditions, all the samples displayed multiple bands, of which the top band in each lane represents an intact antibody or a mixture of intact antibodies (about 150 kDa), although it is not clear if this is a mixture of the heterodimeric bispecific antibody (facilitated by H1H2 interaction) and homodimeric antibodies. The smaller bands represent a variety of non-intact antibodies on SDS-PAGE—for example, the second band (about 125 kDa) from the top in each lane likely represents an antibody lacking one light chain; this could be from an intact antibody where one light chain did not form an interchain disulfide bond so that on SDS-PAGE, the light chain is separated from the main antibody. FIGS. 7C-7D show the SDS-PAGE images of mAb 1/mAb 2b bispecific antibody samples purified using Protein A chromatography. Under non-reducing and denaturing conditions, all the samples displayed one main band corresponding to the molecular weights of the bispecific antibodies (FIG. 7C); under reducing and denaturing conditions, all the samples displayed two bands corresponding to the molecular weights of the two different heavy chains, and one band corresponding to the molecular weights of the two different light chains (FIG. 7D).

To assess the binding activities of the bispecific samples in a bridging ELISA assay, recombinant folate receptor 1 (Novoprotein C784; Summit, NJ) was diluted to a concentration of 0.25 μg/ml in PBS and used to coat a 96-well plate (Genesee Scientific 91-415F; San Diego, CA). 50 μL of antigen were added per well and coated overnight at 4° C. Plates were blocked with 5% BSA in TBST and washed with TBST. 50 μL of antibody in 5% BSA in TBST were added at the indicated concentrations, incubated at room temperature, and washed with TBST. Secondary recombinant biotinylated CD47 antigen (AcroBio CD47-H82E9-258g; Newark, DE) diluted to a concentration of 0.05 μg/mL in 5% BSA in TBST was added to each well, incubated at room temperature, and washed with TBST. Streptavidin HRP (JIR 016-030-084) diluted to a concentration of 0.2 or 0.5 μg/mL in 5% BSA in TBST was added to each well, incubated at room temperature, and washed. Plates were developed with TMB substrate (Thermo 34028) and quenched with stop solution (Thermo SS04), and wells were quantified by absorbance at 450 nm. FIGS. 8A-8J show the results for the binding of the purified bispecific antibodies to both antigens in a bridging ELISA assay. The data in FIG. 8A indicate that bsAb 1, 5, 6, 7, and 8 have anti-CD47/FRα bispecific activity, confirming the formation of the intended anti-CD47/FRα bispecific antibody by each of these constructs. All the bispecific antibodies tested in FIGS. 8B-8J exhibited bridging ELISA activity.

To determine the purity of the samples purified by Protein A chromatography or Protein A chromatography followed by HIC, size exclusion chromatography (SEC) was used. Protein samples were diluted to a concentration of 1 mg/mL and submicron filtered. 5 μL of protein was injected onto an AdvanceBio SEC column (300 mm, 2.7 um, 300 A, Agilent PL1580-5301). DPBS was used as the mobile phase and was flowed at 0.35 mL/min. Bio-rad gel filtration standards were used as the standard (Bio-rad 1511901; Hercules, CA). Samples were quantified by measuring absorbance at 280 nm. FIGS. 9A-9E show the SEC profiles of the samples purified by Protein A chromatography. The appearance of the main peak at about 150 kDa suggests the main species in the samples were full antibodies (or an antibody) with two heavy chains and two light chains. These data are consistent with the observation by SDS-PAGE shown in FIGS. 7A-7B. FIGS. 9F-9N show the SEC profiles of the samples purified by Protein A chromatography followed by HIC.

Figure 11A:
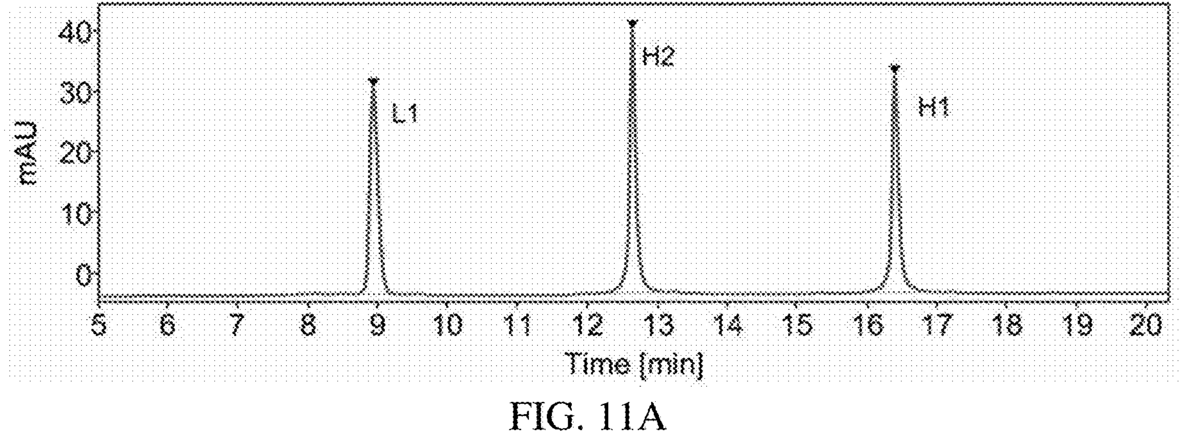
FIGS. 11A-11N show the RP-HPLC profiles of the HIC purified bispecific antibodies under reducing condition.
Figure 11B:
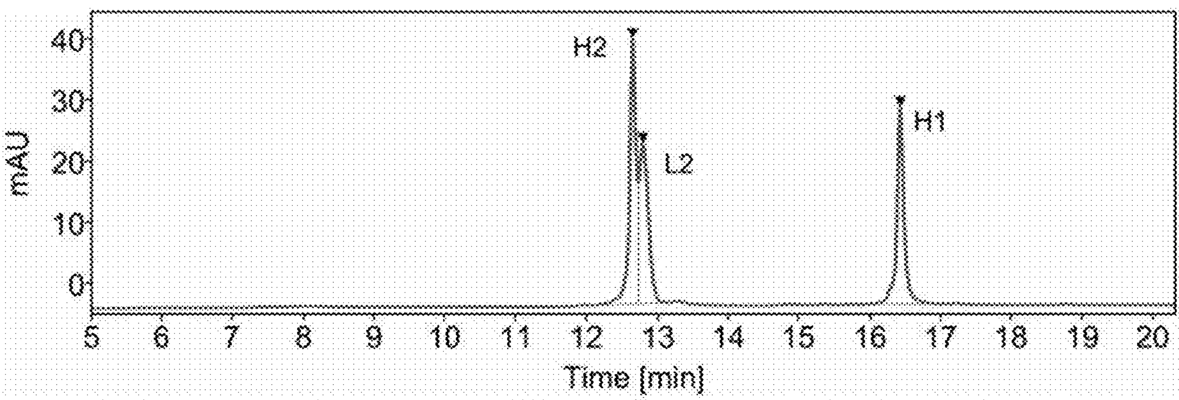
FIG. 11B, RP-HPLC profile of control antibody #2 assembled with H1, H2 and L2 of bsAb 7, and purified with Protein A chromatography.
Figure 11C:
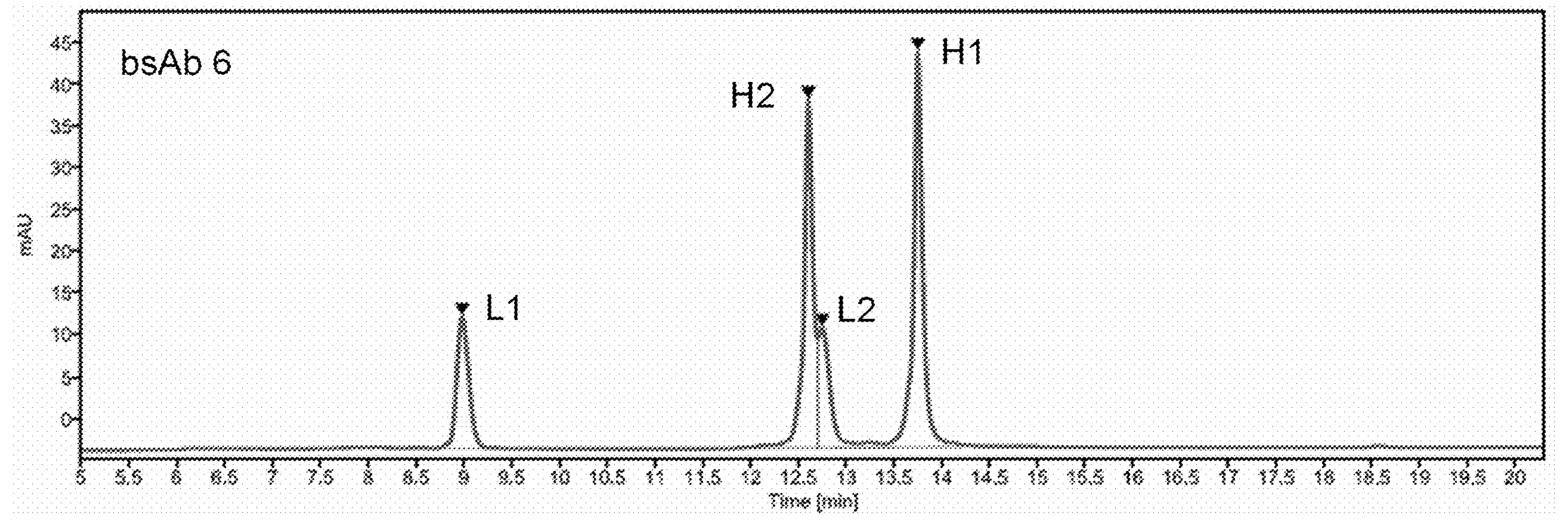
FIG. 11C, RP-HPLC profile of HIC purified bsAb 6.
Figure 11D:
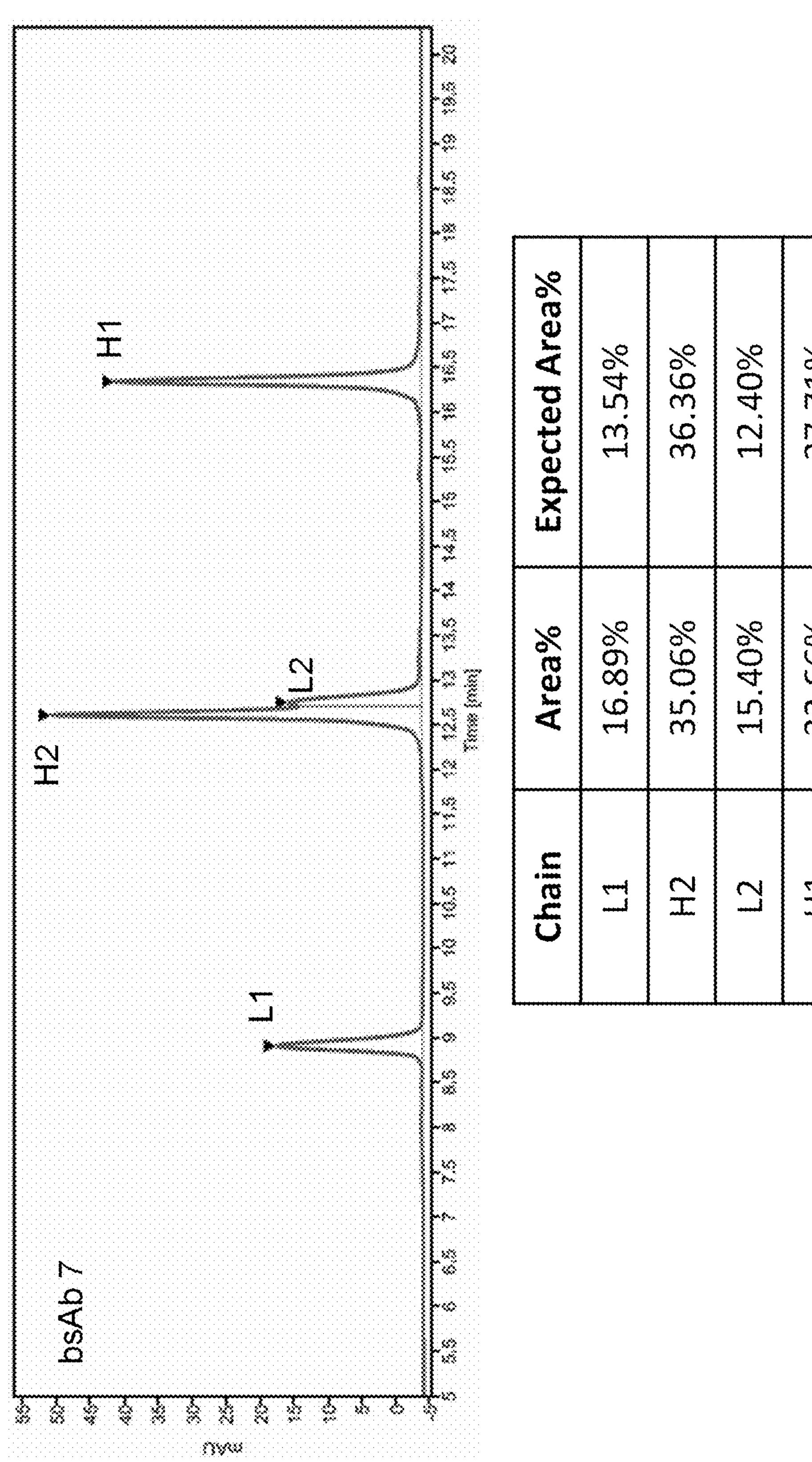
FIG. 11D, RP-HPLC profile of HIC purified bsAb 7.
Figure 11E:
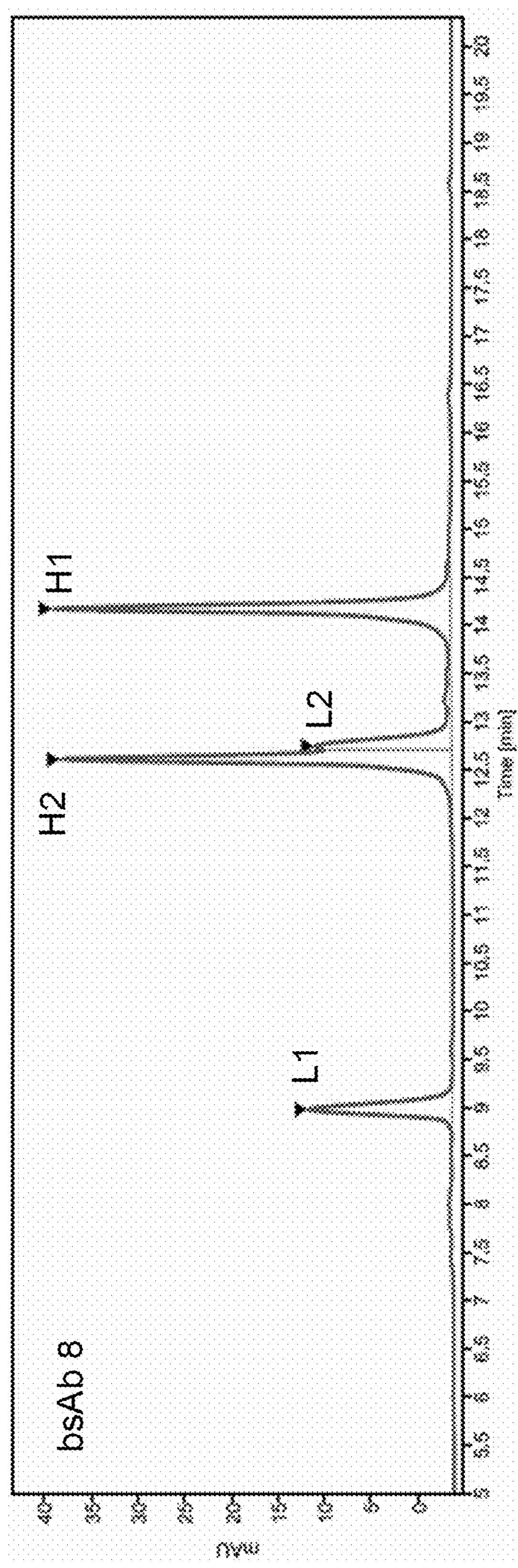
FIG. 11E, RP-HPLC profile of HIC purified bsAb 8.
Figure 11F:
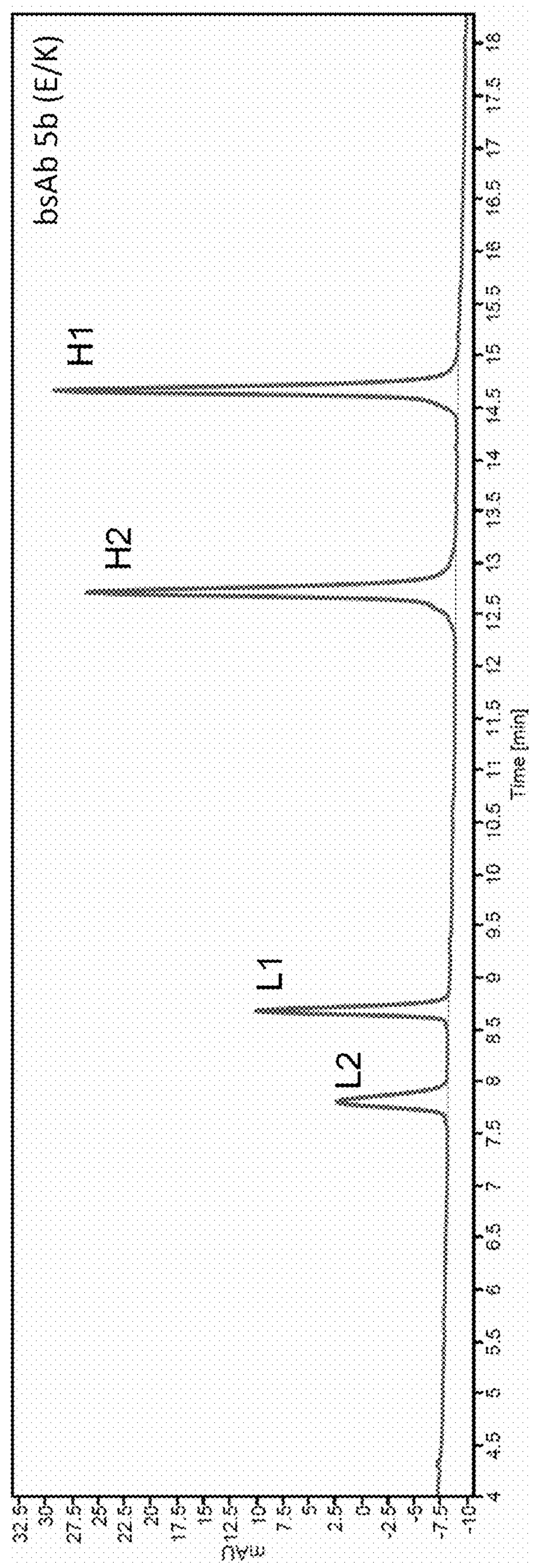
FIG. 11F, RP-HPLC profile of HIC purified bsAb 5b (E/K)
Figure 11G:
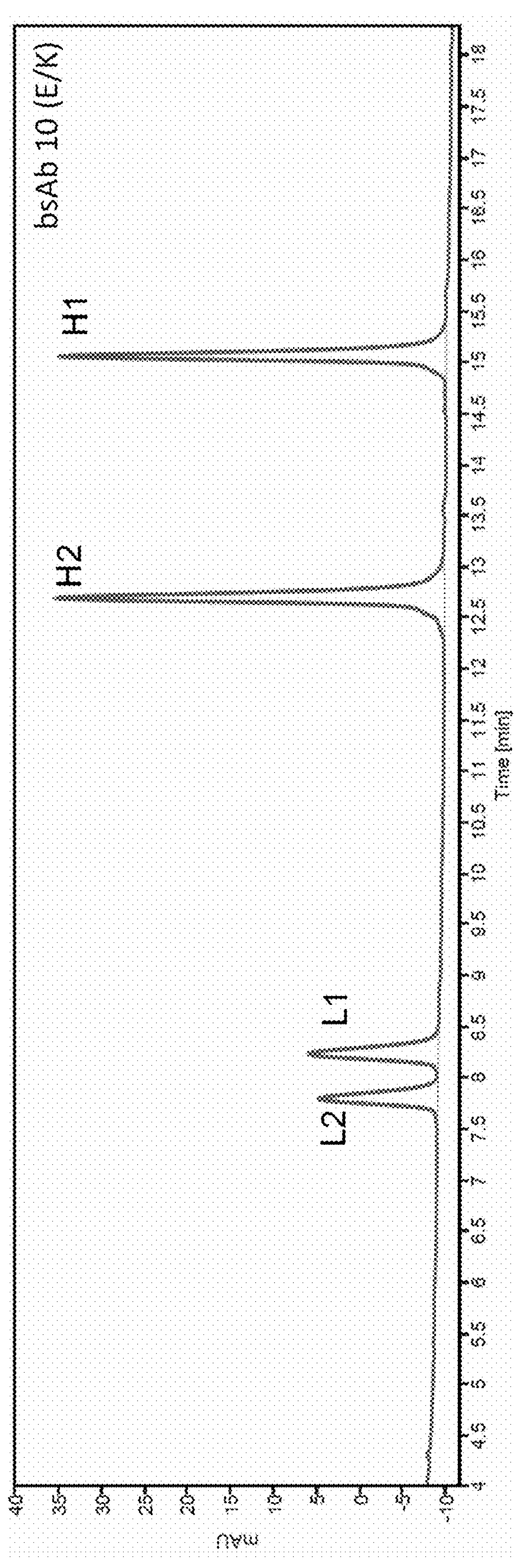
FIG. 11G, RP-HPLC profile of HIC purified bsAb 10 (E/K)
Figure 11H:
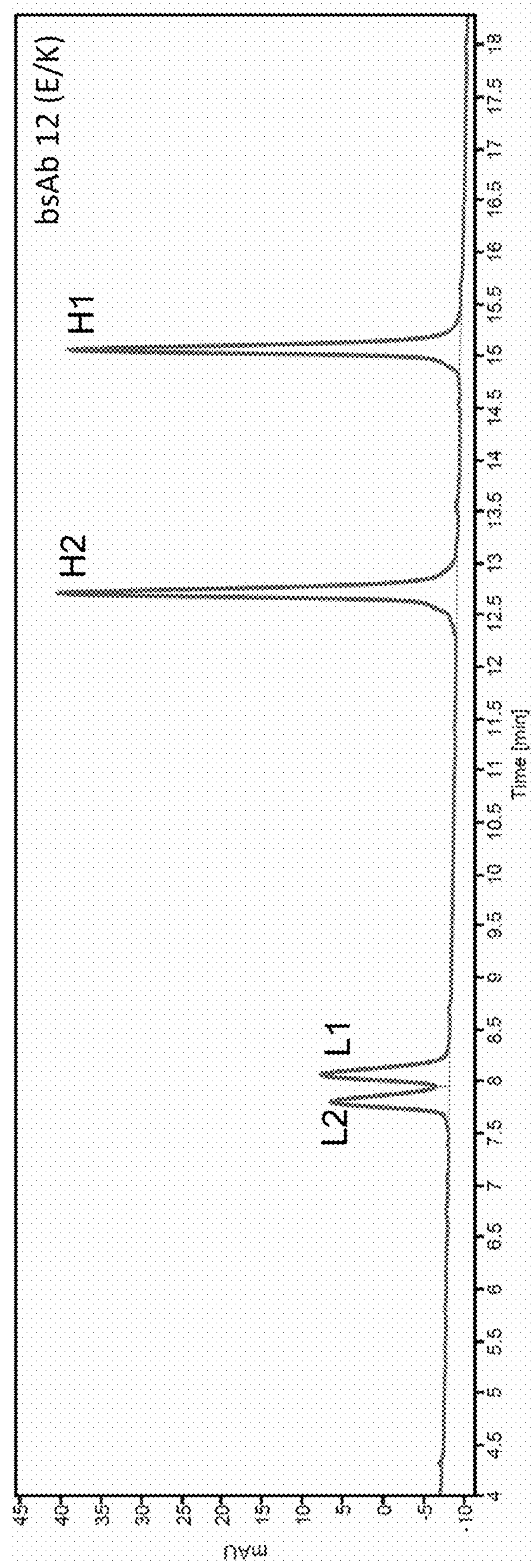
FIG. 11H, RP-HPLC profile of HIC purified bsAb 12 (E/K)
Figure 11I:
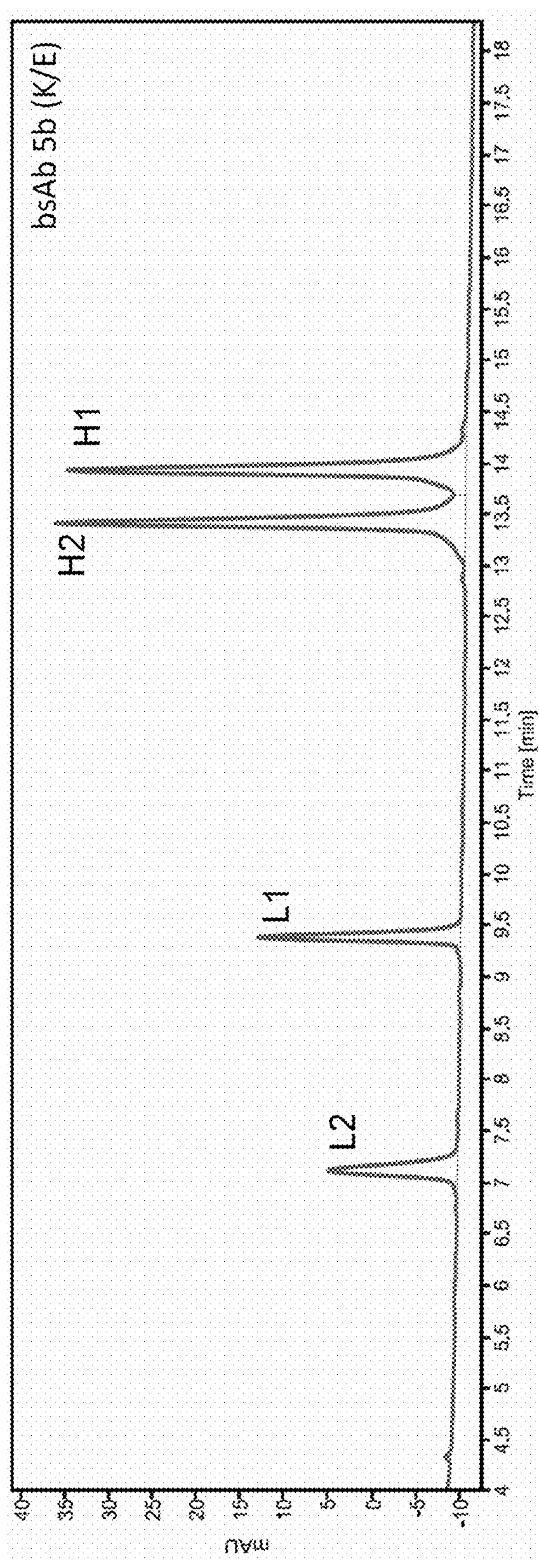
FIG. 11I, RP-HPLC profile of HIC purified bsAb 5b (K/E)
Figure 11J:
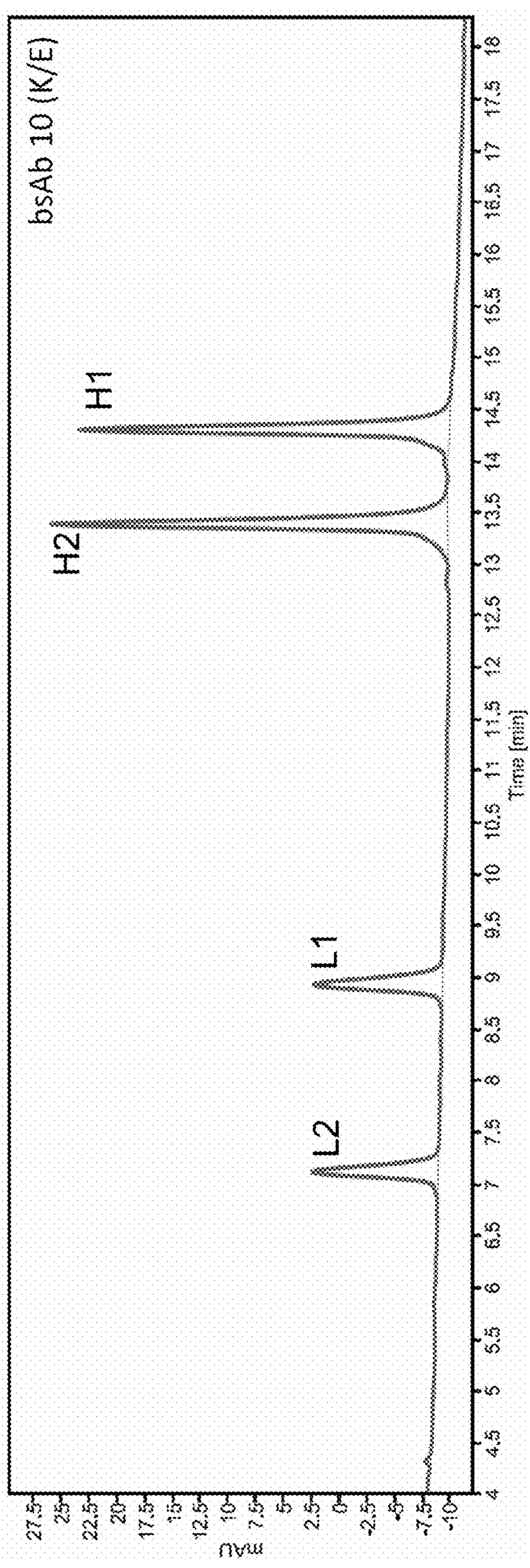
FIG. 11J, RP-HPLC profile of HIC purified bsAb 10 (K/E)
Figure 11K:
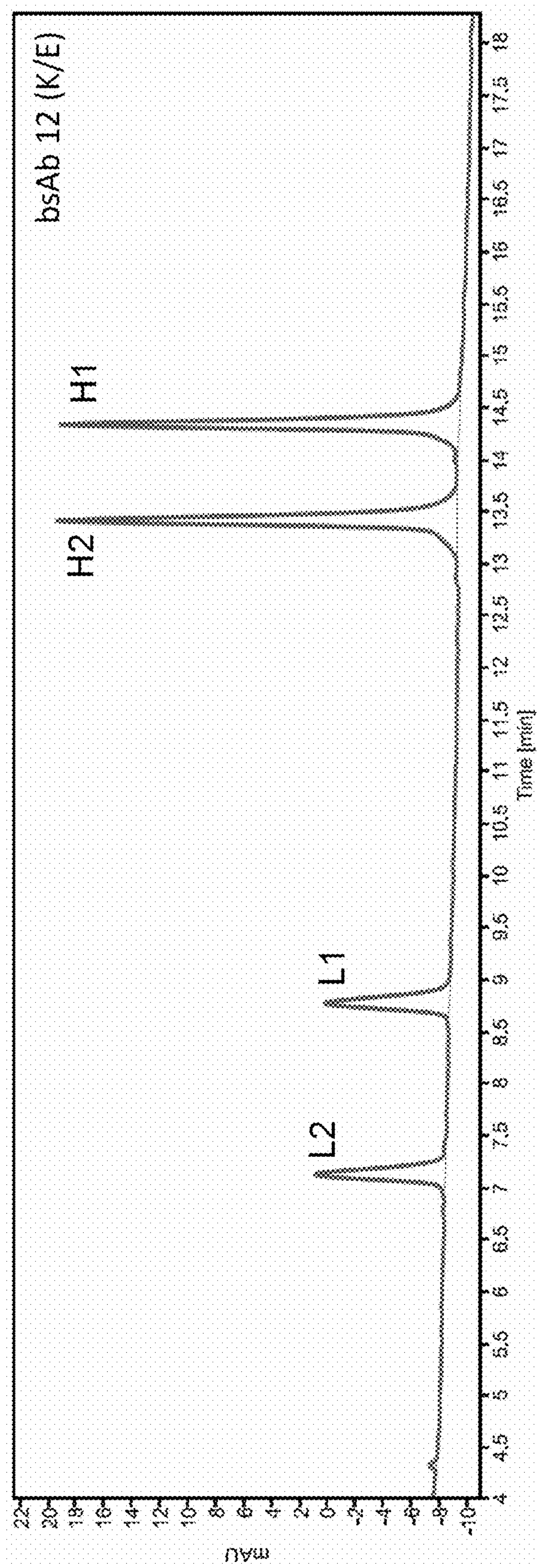
FIG. 11K, RP-HPLC profile of HIC purified bsAb 12 (K/E)
Figure 11L:
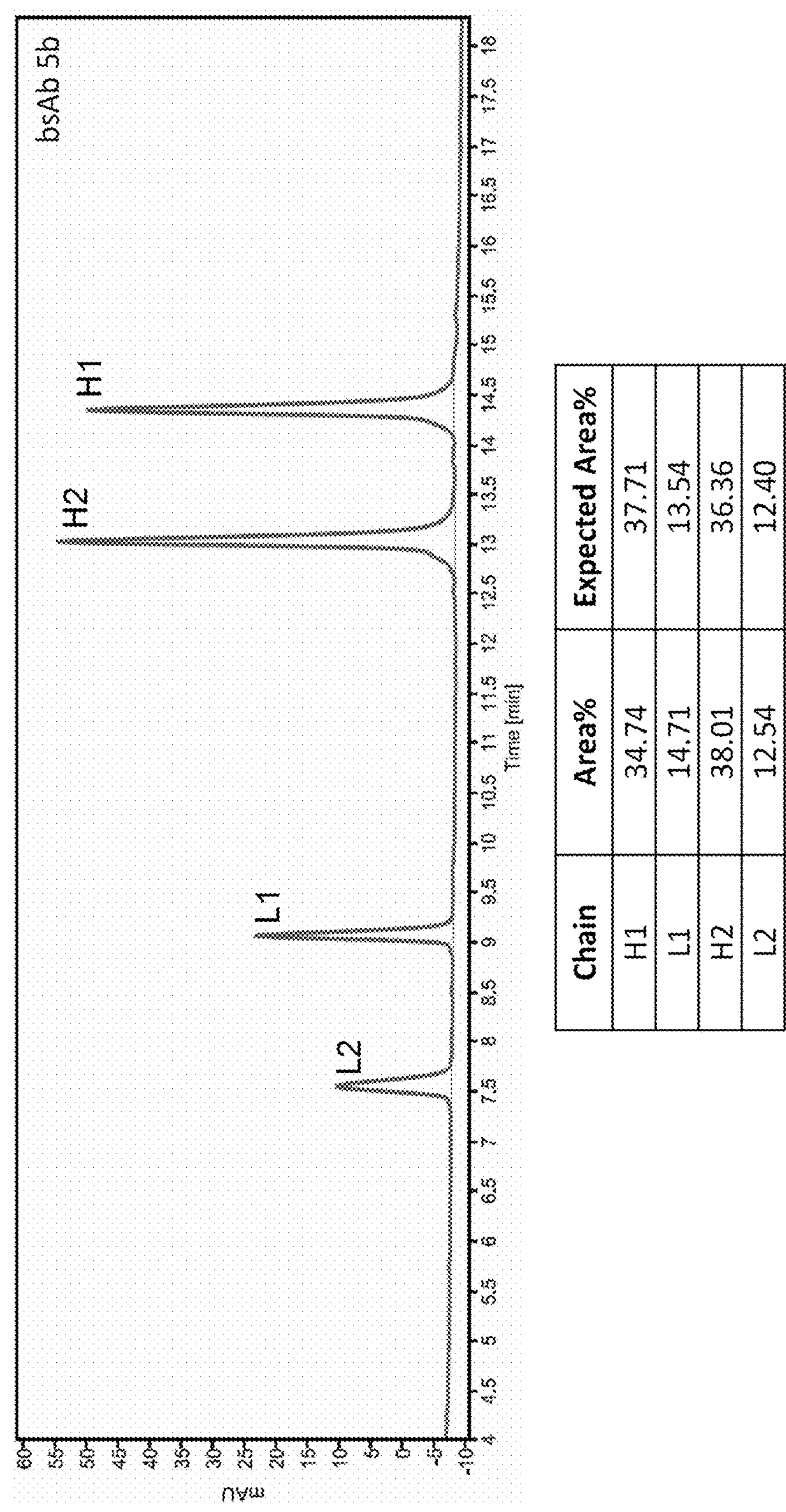
FIG. 11L, RP-HPLC profile of HIC purified bsAb 5b.
Figure 11M:
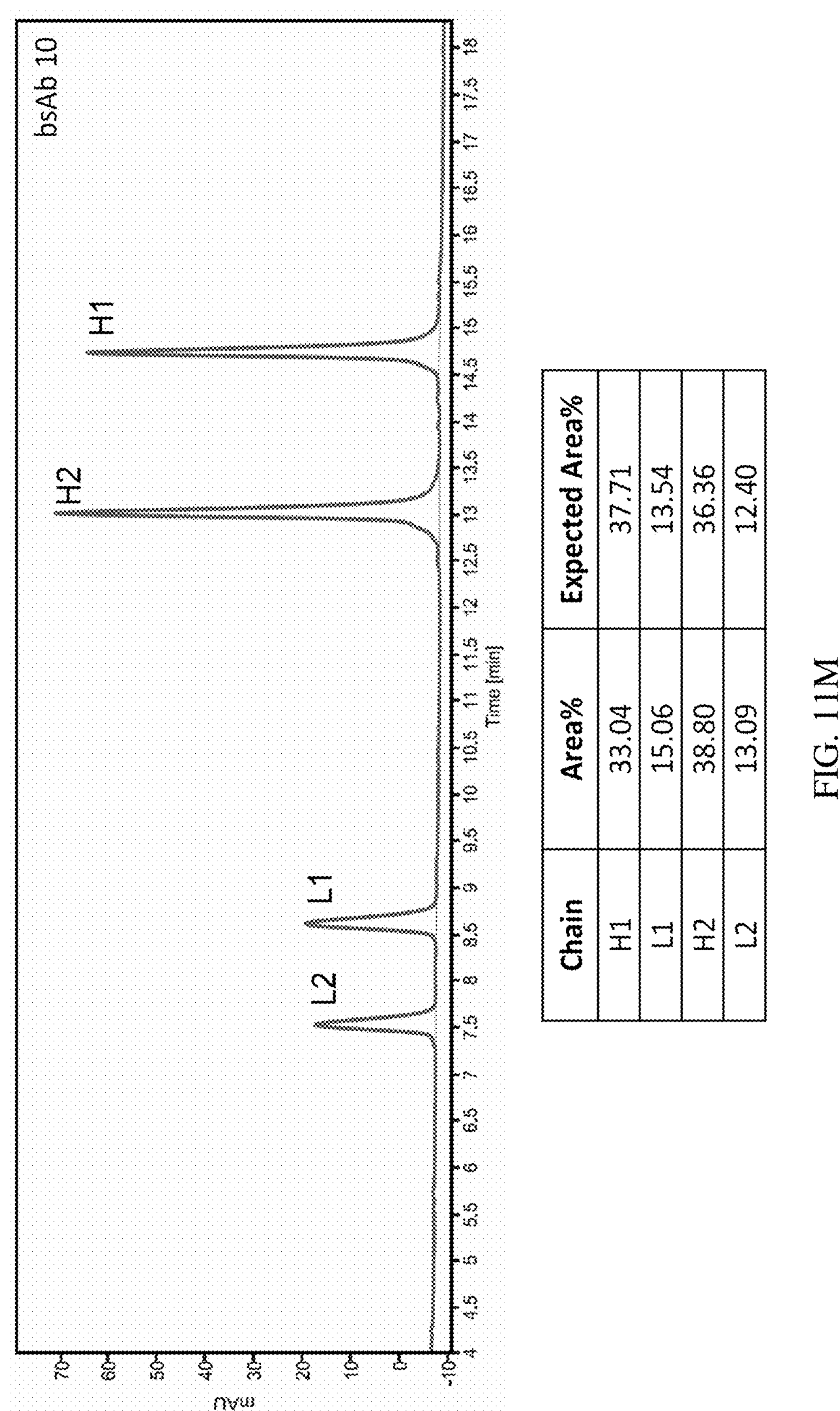
FIG. 11M, RP-HPLC profile of HIC purified bsAb 10.
Figure 11N:
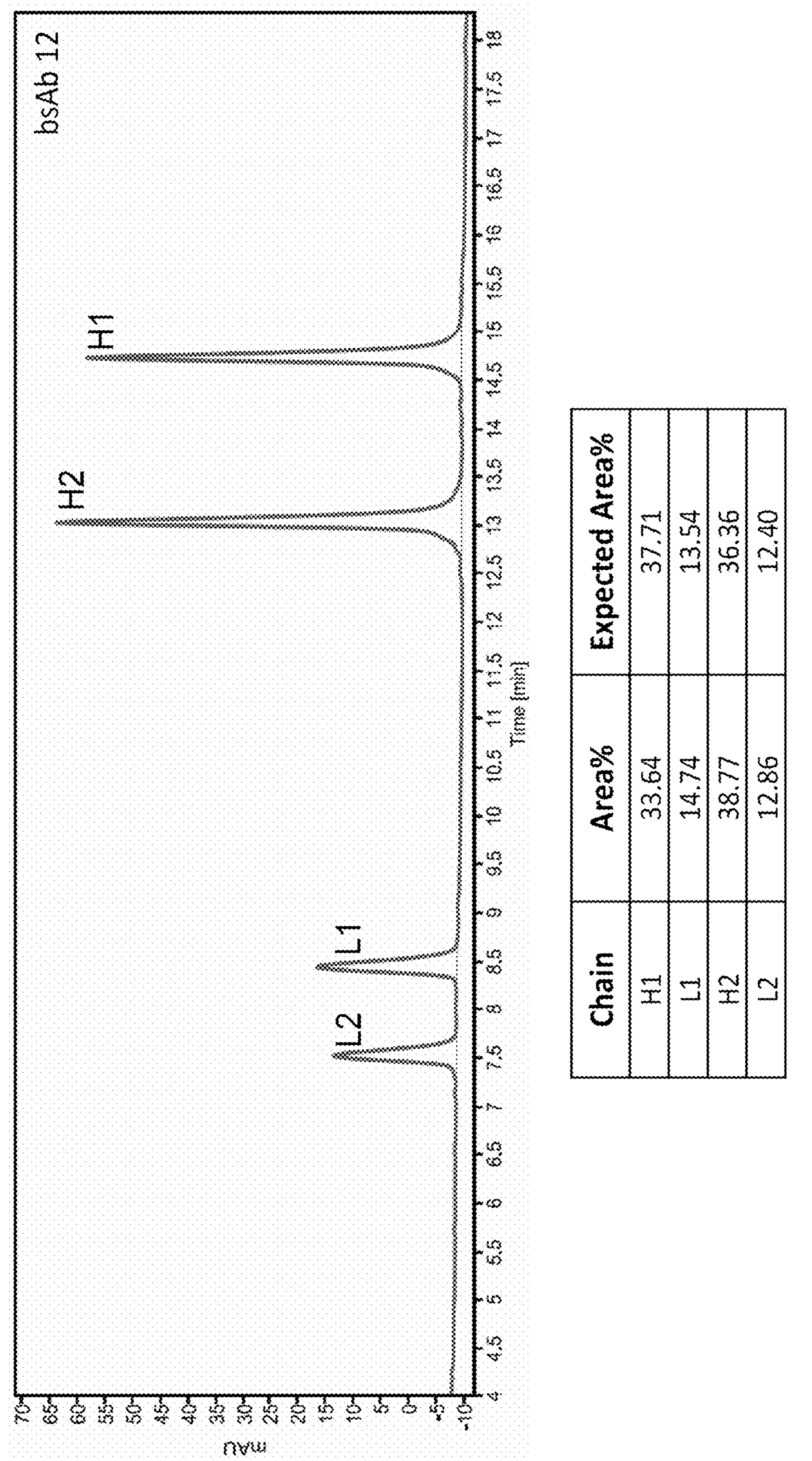
Figure 12A:
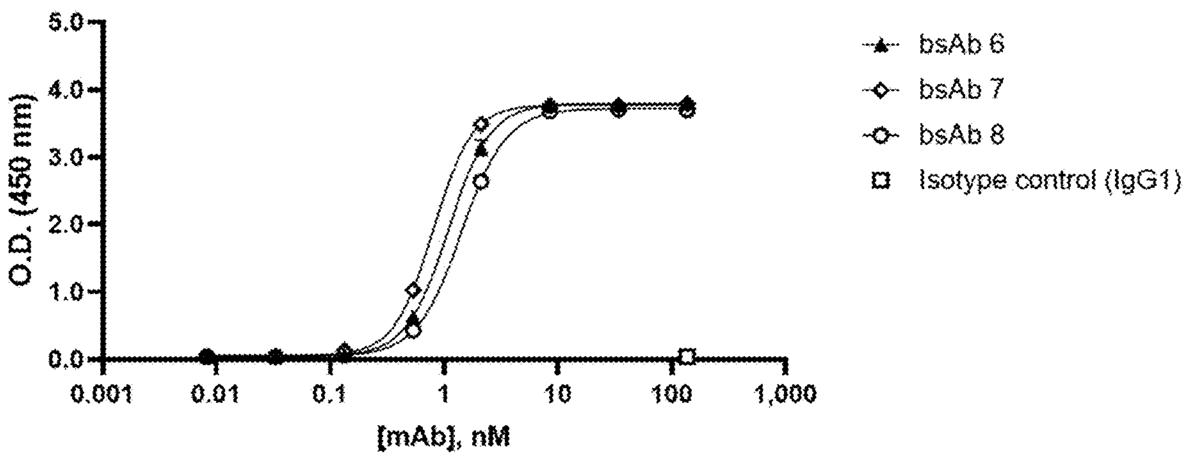
FIGS. 12A-12F show graphs demonstrating the results for the binding of the HIC purified bispecific antibodies to both antigens (i.e., CD47 and FRα) in a bridging ELISA assay.
Figure 12B:
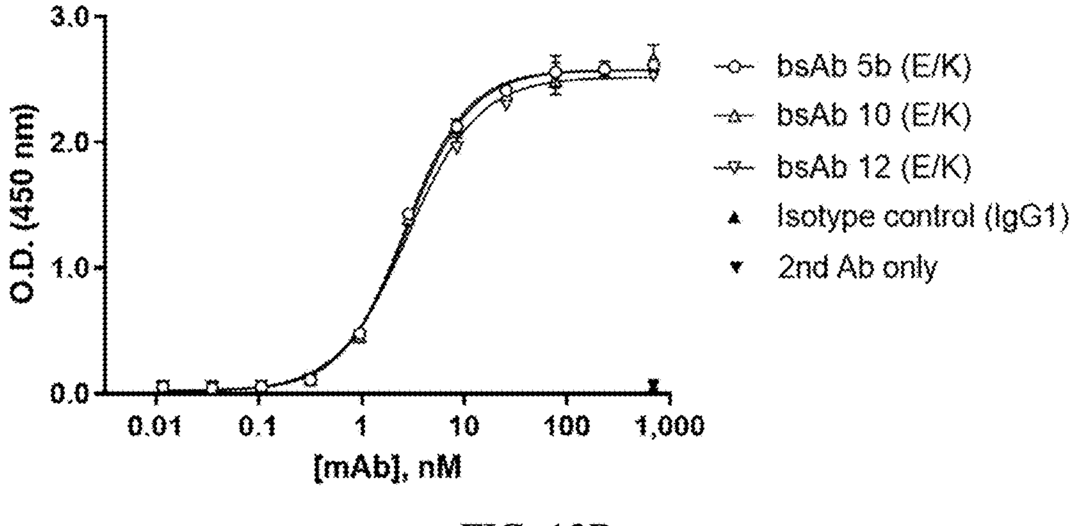
Figure 12C:
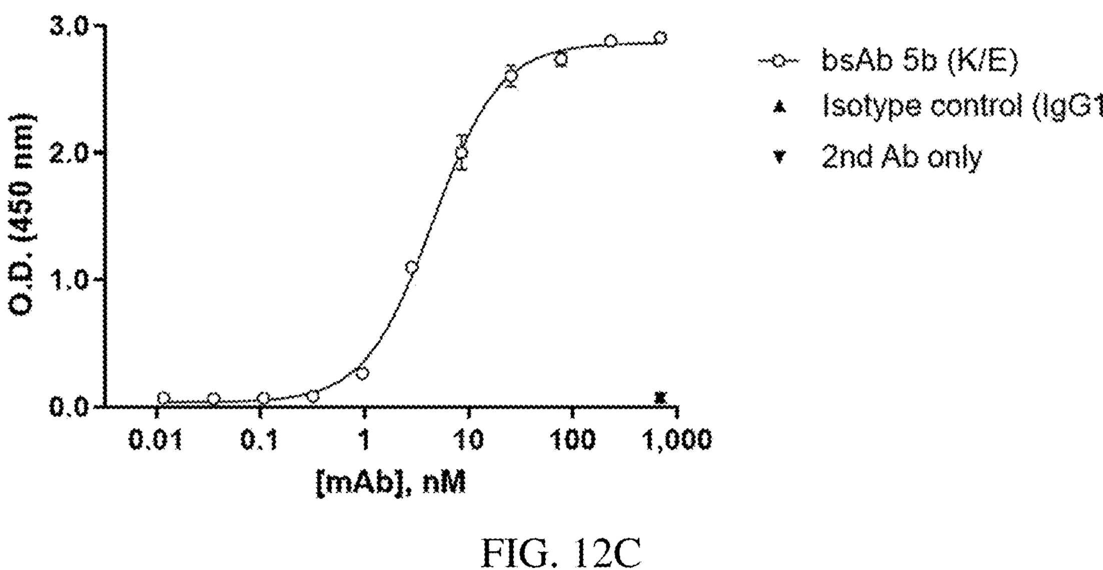
Figure 12D:
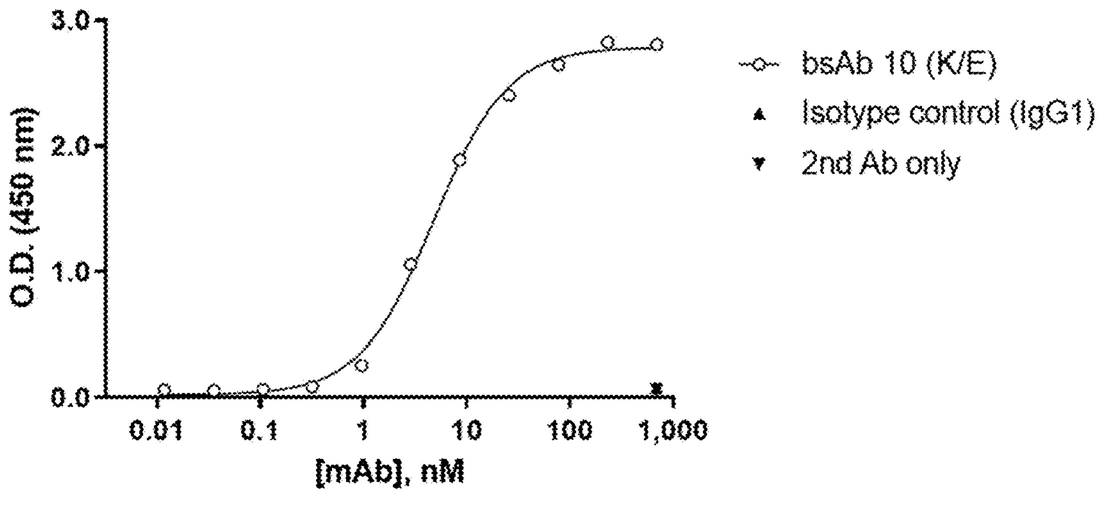
Figure 12E:
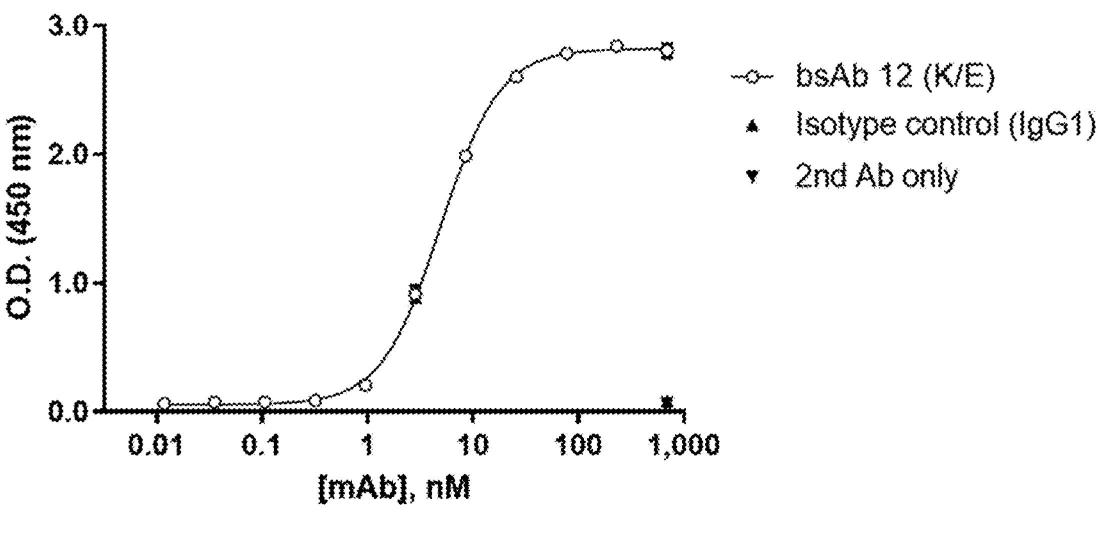
Figure 12F:
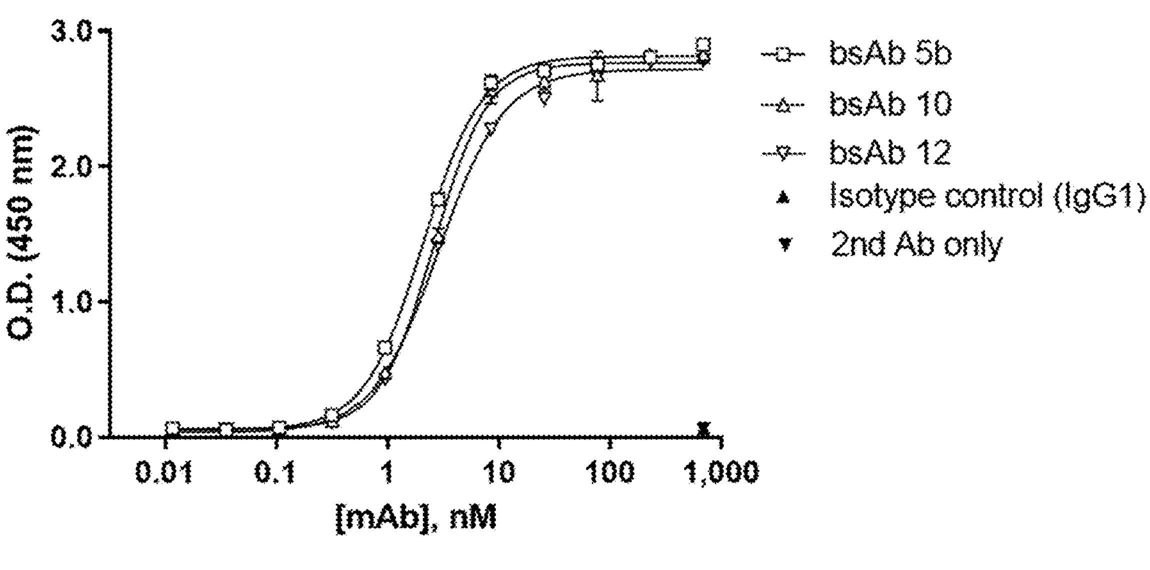

The purity of the HIC purified bispecific antibody samples were further analyzed using reversed-phase high-performance liquid chromatography (RP-HPLC) under non-reducing condition. FIGS. 10A-10L show the RP-HPLC profiles of the bispecific antibodies. In each case, there is one main species. RP-HPLC was also run under reducing condition to determine the existence of both HCs (H1 and H2) as well as both LCs (L1 and L2) of the intended bispecific antibody. Control antibody samples were produced by transiently expressing H1, H2 and L1 of bsAb 7 (control antibody #1), and H1, H2, and L2 of bsAb 7 (control antibody #2), respectively, followed by purification using Protein A chromatography. These samples served as controls to identify the LC peaks on RP-HPLC (FIGS. 11A and 11B). Combined with the RP-HPLC profiles of bsAb 6 (FIG. 11C), bsAb 7 (FIG. 11D), and bsAb 8 (FIG. 11E), the HC peaks (H1 and H2) and LC peaks (L1 and L2) were identified (FIGS. 11A-11E). FIGS. 11F-11N show the RP-HPLC profiles under reducing condition of the bispecific antibodies constructed with mAb 1 and mAb 2b. Appropriate control transfections with one of the two arms were used to identify the different HC and LC peaks for a given bispecific antibody (data not shown here). The area under the curve (AUC) of each HC or LC relative to the total AUC in the RP-HPLC profiles was quantified and shown in FIGS. 11C-11N. The ratios of the H1, L1, H2 and L2 are consistent with those of a heterodimeric bispecific antibody. These data indicate that the main species in the HIC purified bispecific samples were heterodimeric bispecific antibodies with the intended composition of HCs (H1 and H2) and LCs (L1 and L2). Importantly, the data in FIGS. 10A-10L and FIGS. 11A-11N suggested that there were interchain disulfide bonds between the HCs and between the HC and LC on each of the two arms of the bispecific antibodies.

Figure 13A:
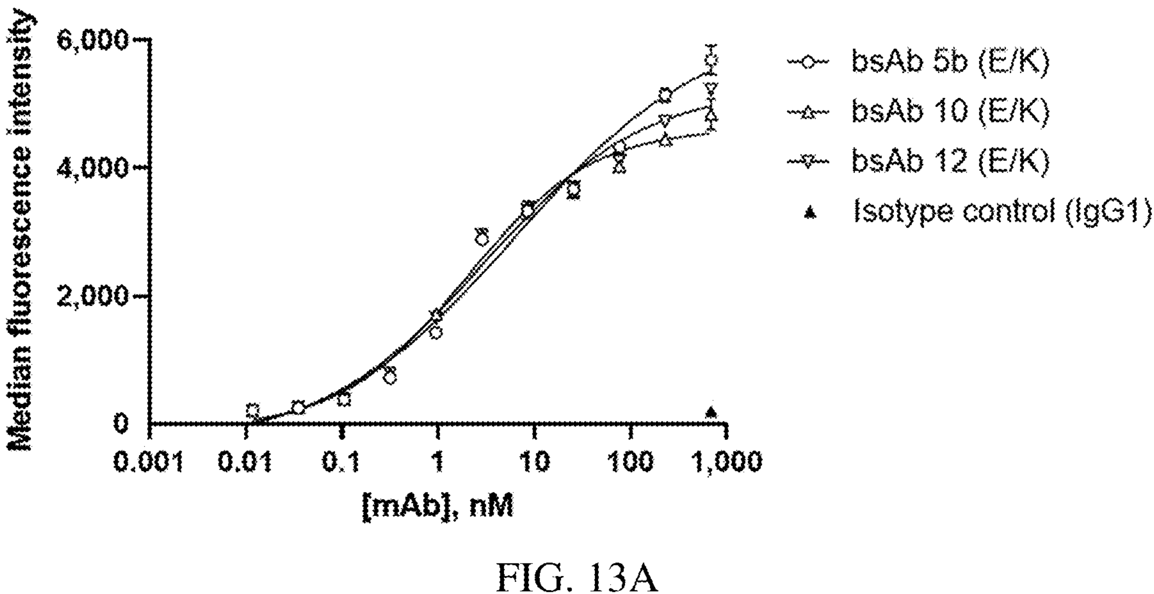
FIGS. 13A-13C show the binding of the HIC purified bispecific antibodies to SK-OV-3 cells which are known to express both CD47 and FRα.
Figure 13B:
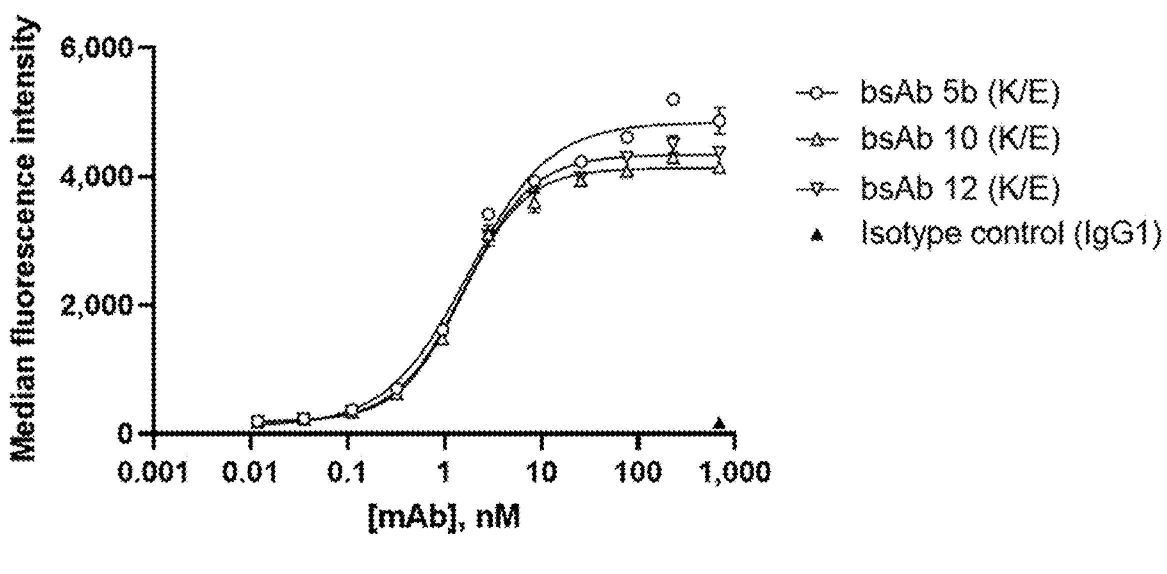
Figure 13C:
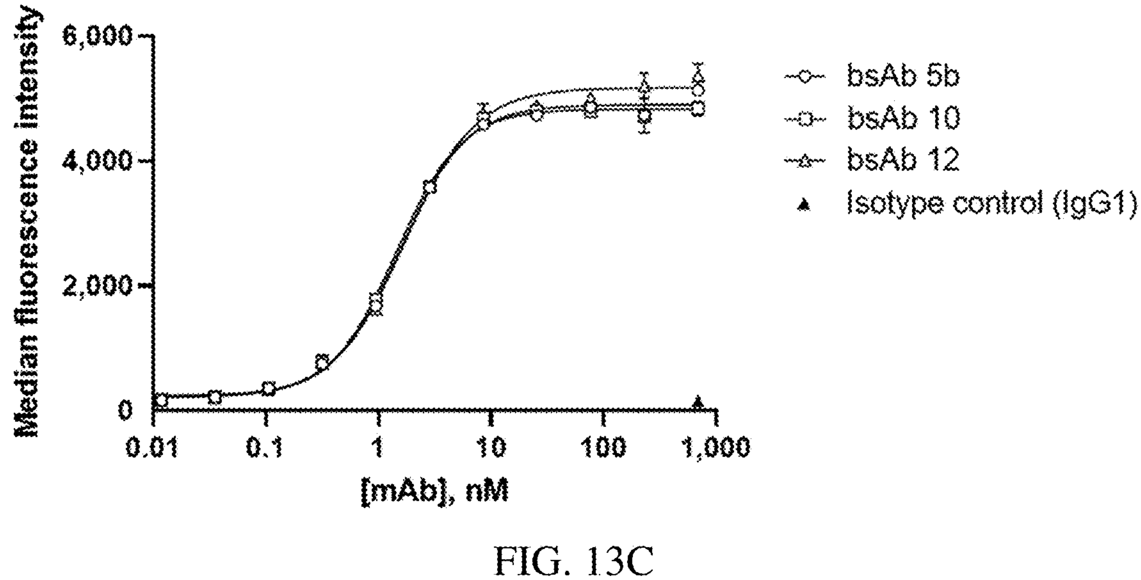

The same HIC purified bispecific antibody samples were analyzed for their ability to bind both antigens using bridging ELISA. Consistent with the analytical data above, all the bispecific antibodies were shown to be able to bind to both CD47 and FRα simultaneously, suggesting that each arm of the bispecific antibodies was properly formed with the right HC and LC (FIGS. 12A-12F). The bispecific antibodies were tested for their ability to bind to SK-OV-3 cells, which express both antigens (CD47 and FRα). In the assay, SK-OV-3 cells were incubated with bispecific antibodies at various concentrations for 15 minutes at 4° C. Cells were then centrifuged for 5 minutes and washed three times with FACS buffer (HBSS supplemented with 5% BSA and 0.05% sodium azide). The cells were then incubated with Alexa Fluor 488-conjugated anti-human IgG secondary antibody (ThermoFisher, Cat #: H10120) and incubated on ice for another 15 minutes. Cells were then washed with FACS buffer twice and resuspended in FACS buffer. Cells were then run through the Attune NxT and the data were analyzed by the Attune NxT software. The bispecific antibodies showed significant binding to SK-OV-3 cells in the FACS assay (FIGS. 13A-13C).

Figure 14A:
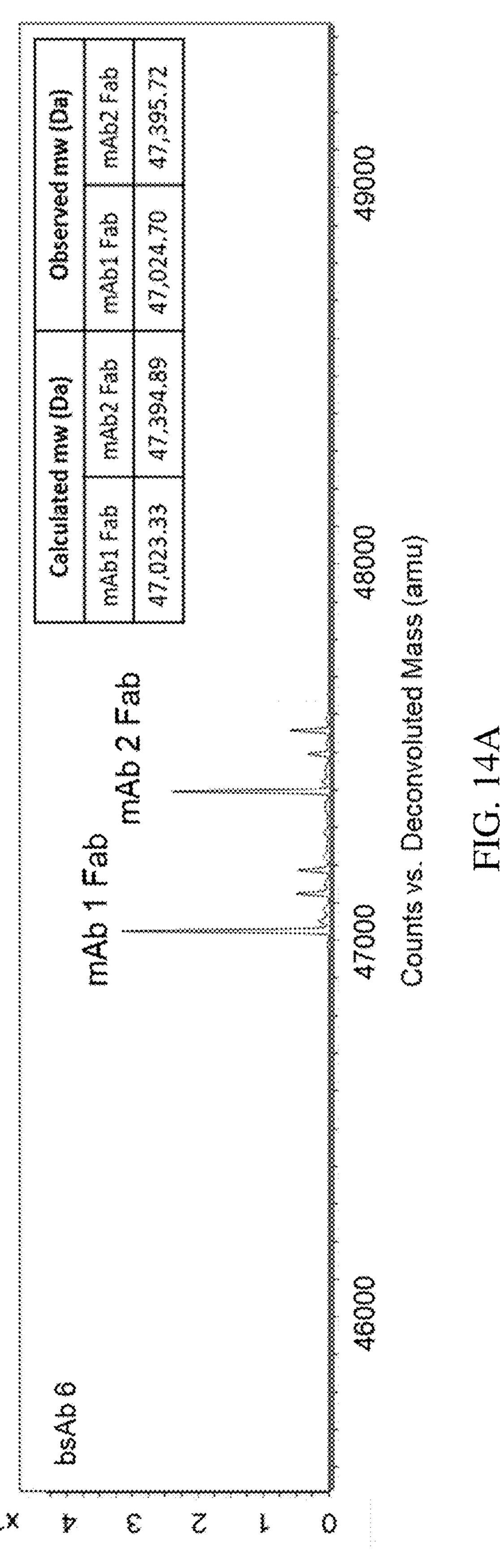
FIGS. 14A-14C show the mass spectrometry (MS) profiles of papain digested samples of the HIC purified bispecific antibodies. Fab fragments generated from both arms (mAb 1 arm and mAb 2 arm) of each bispecific antibody were identified.
Figure 14B:
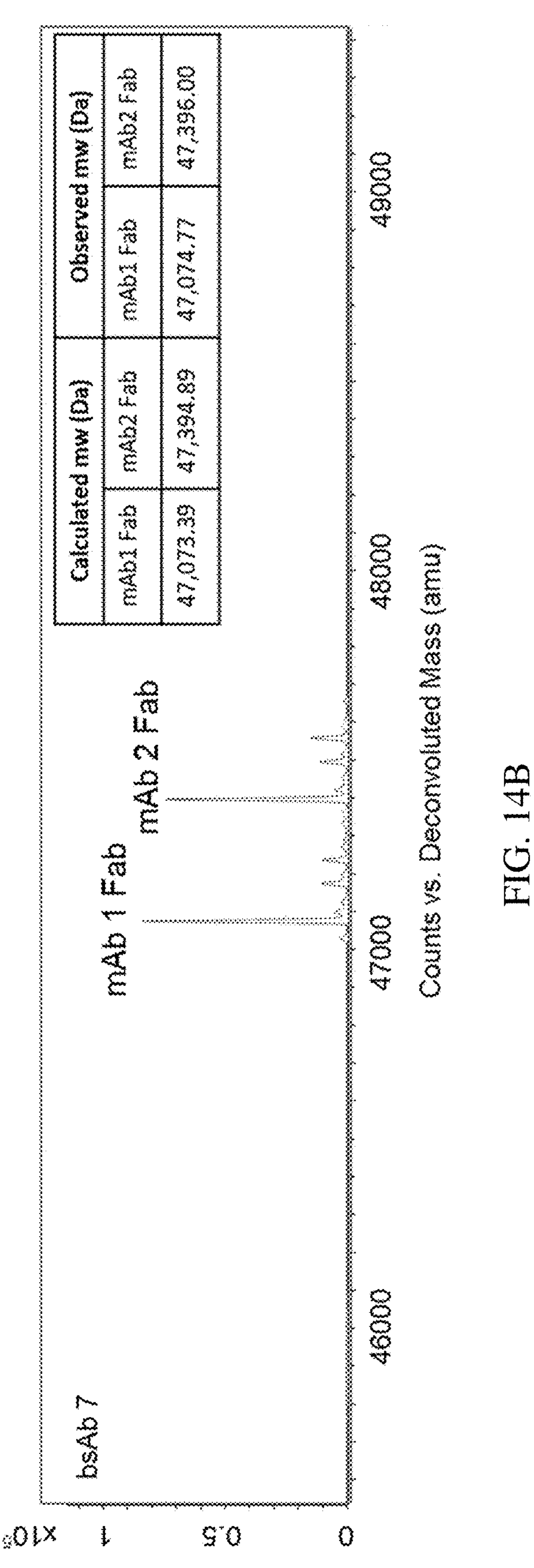
Figure 14C:
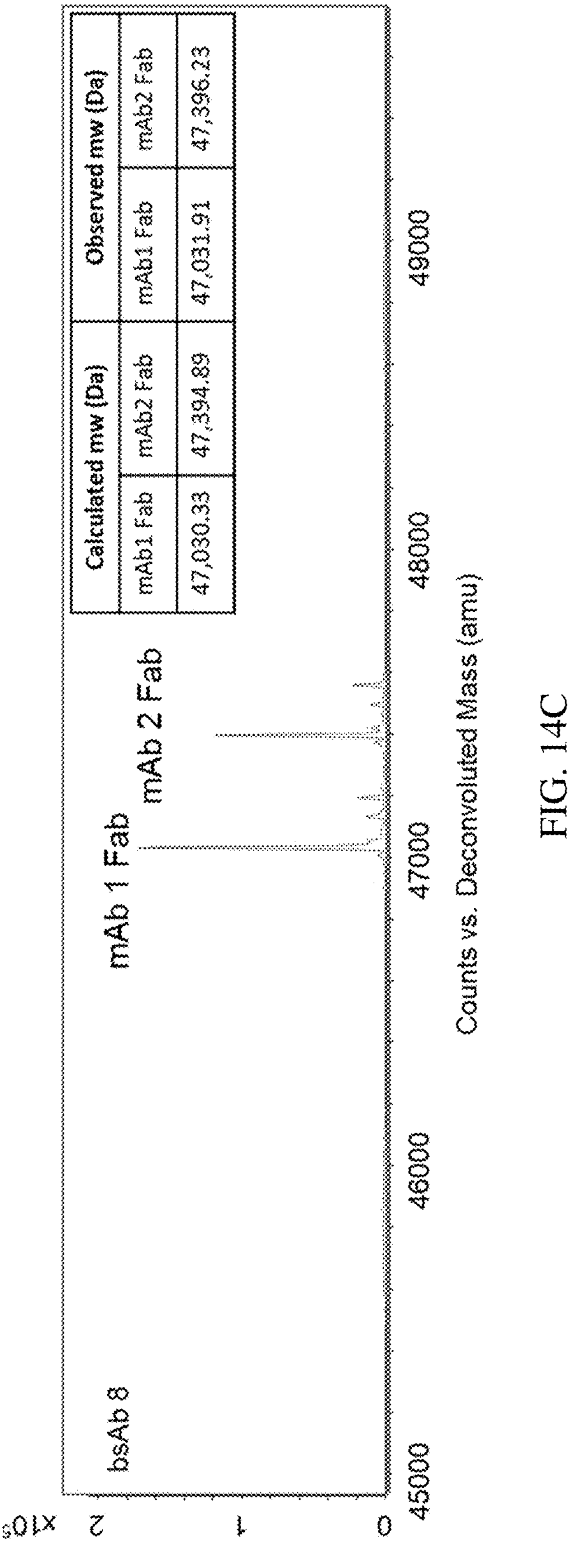

The HIC purified bispecific antibody samples were subjected to papain digestion under non-reducing condition to determine if the expected Fab fragments were generated from the bispecific antibodies. Samples were concentrated to a final concentration of 5-10 mg/mL and buffer exchanged into papain digestion buffer (20 mM cysteine, 20 mM sodium phosphate, 10 mM EDTA, pH 7.0). Agarose immobilized papain (Thermo 20341) was pre-equilibrated in papain digestion buffer and resuspended as a 50% slurry. Protein samples were added to the slurry at a 2:1 volume ratio and shaken overnight at room temperature. Supernatant was extracted and analyzed by mass spectrometry directly. The calculated molecular weight (mw) of each Fab fragment was shown along with its observed mw (FIGS. 14A-14C). The data indicated that the expected Fab fragments generated by papain digestion were detected on mass spectrometry and the intended bispecific antibodies formed properly.

Figure 15A:
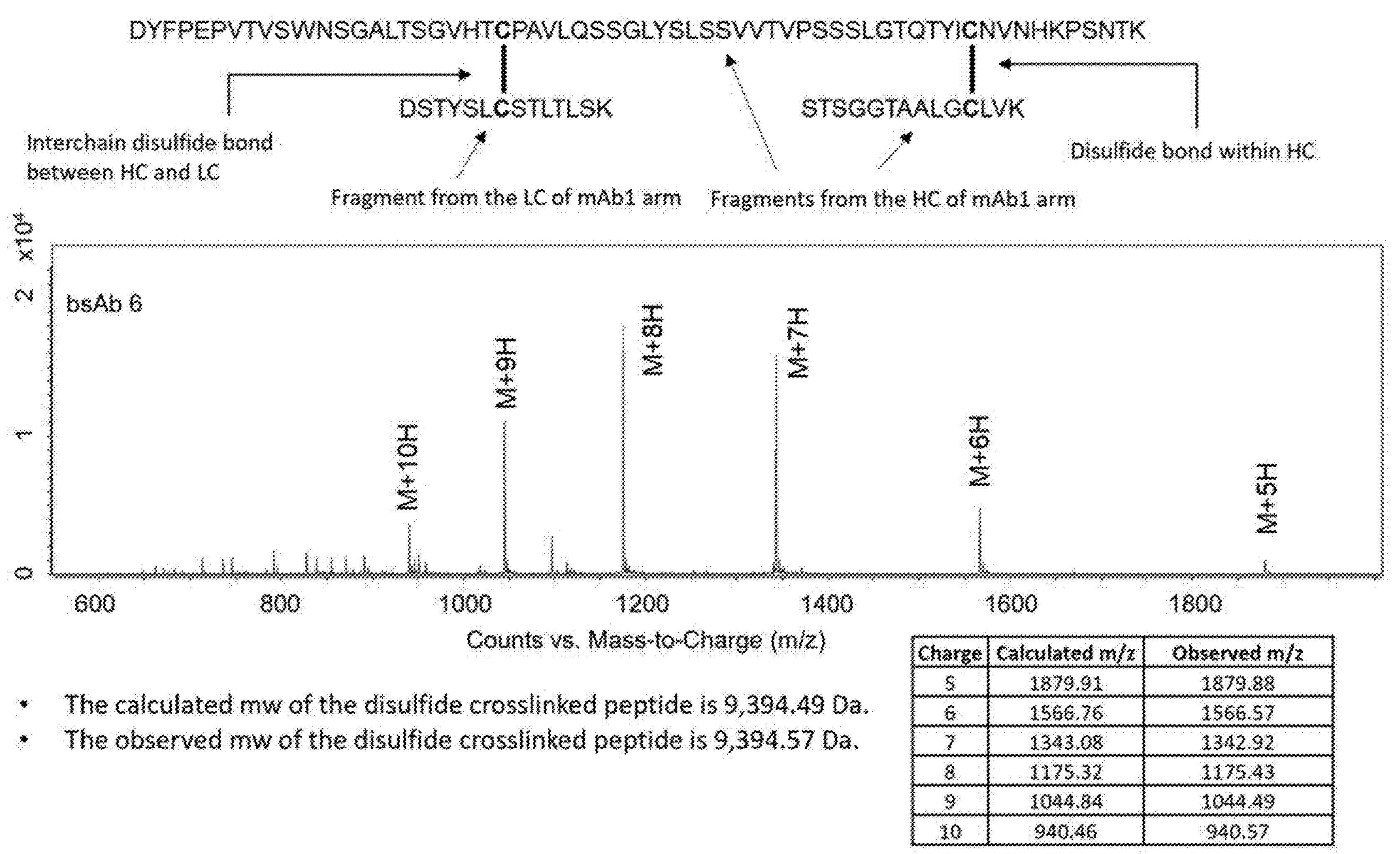
FIGS. 15A-15F show the MS profiles of trypsin digested samples of the HIC purified bispecific antibodies. The disulfide cross-linked peptide fragment generated from the mAb 1 arm of each bispecific antibody was identified. The disulfide bond forming cysteines are in bold form.
Figure 15B:
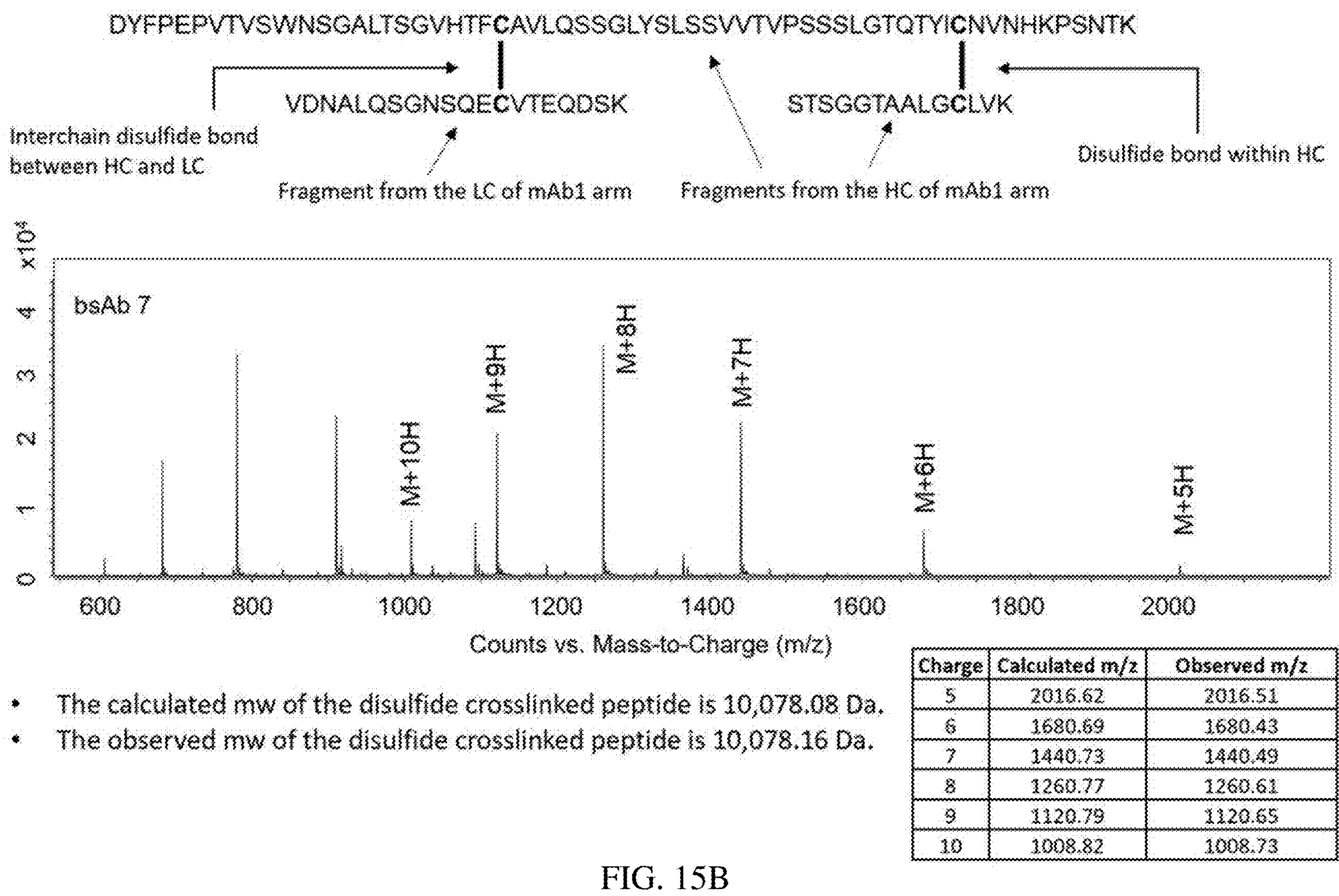
Figure 15C:
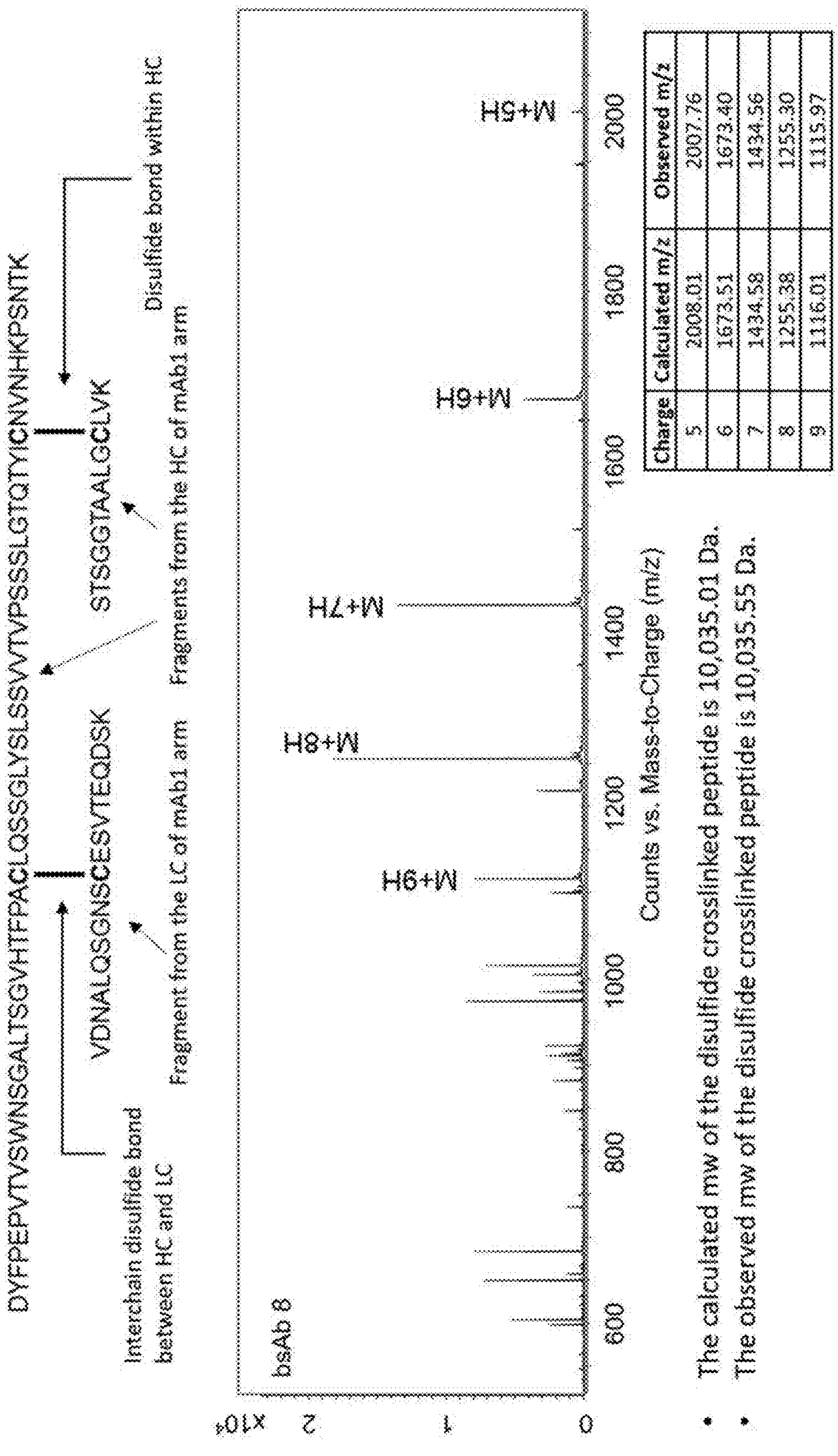
Figure 15D:
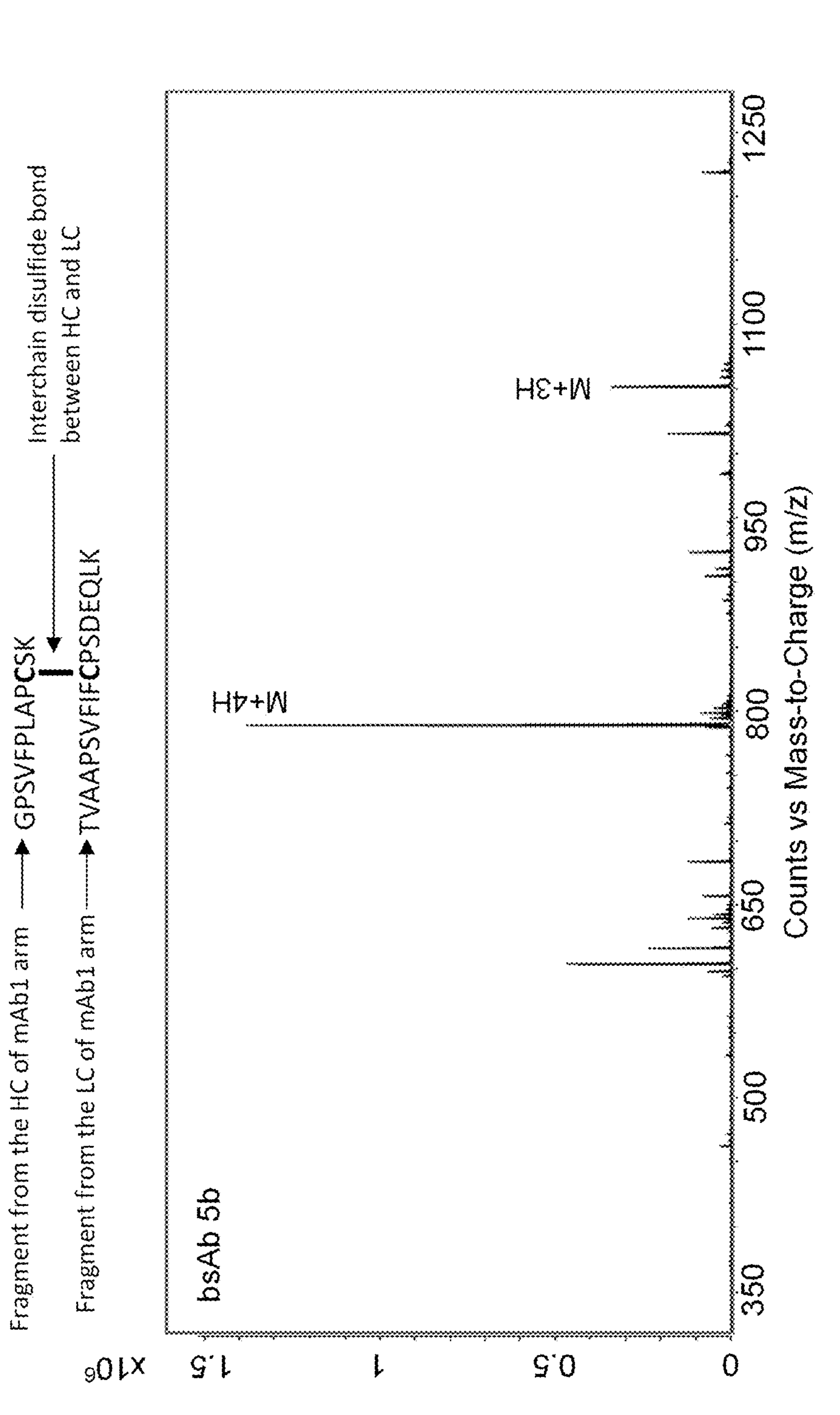
Figure 15E:
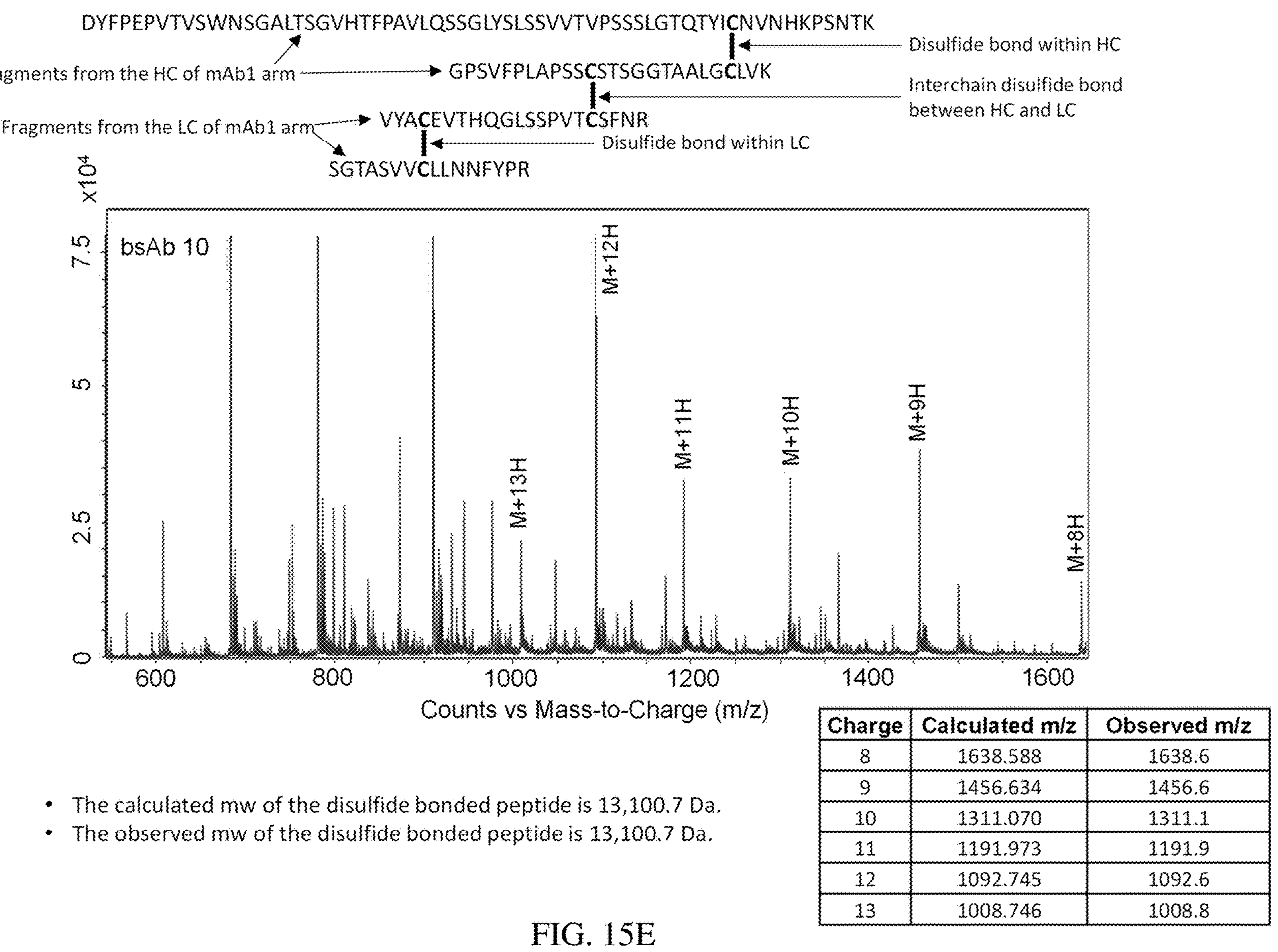
Figure 15F:
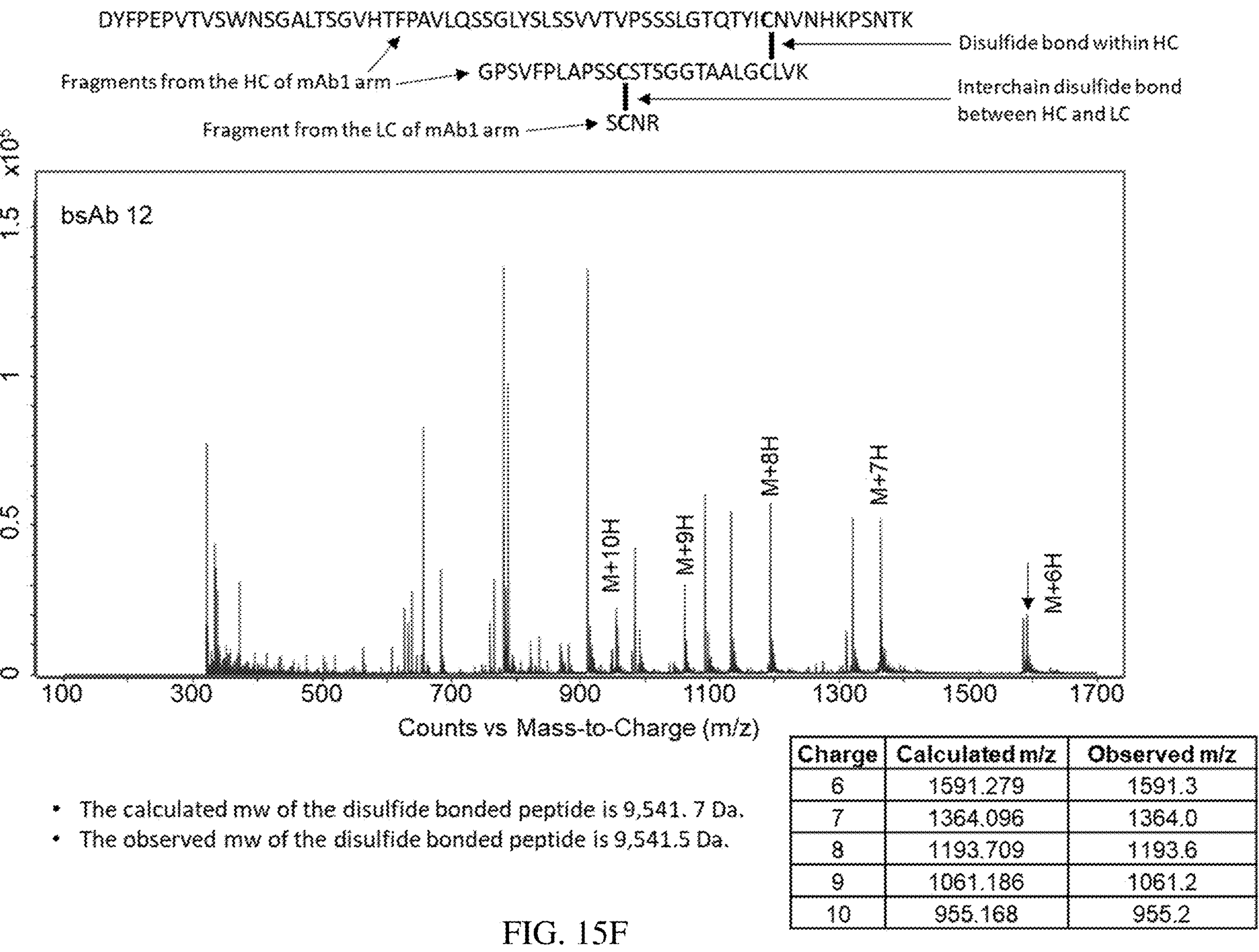

The HIC purified bispecific antibody samples were also subjected to trypsin digestion under non-reducing condition to determine if calculated tryptic digest peptide fragments from the mAb 1 arms of the intended bispecific antibodies were generated. Samples were diluted to a final concentration of 1 mg/mL in 200 mM guanidine HCl and heated at 95° C. for 1 minute. 2× trypsin digestion buffer was added at a 1:1 volume ratio (NEB P8101S) and 2 μg total trypsin ultra (NEB P8101S) was added. The resulting reaction was shaken at 37° C. for 4 hours and used directly for analysis by mass spectrometry. The amino acid sequences and the sites for disulfide linkage of a disulfide crosslinked peptide fragment that was expected to be produced from the tryptic digestion of the mAb 1 arm (the anti-CD47 arm) of bsAb 6 are shown in FIG. 15A. The cysteine residues forming the disulfide bonds are in bold form; the expected interchain disulfide bond formed by the knocked in cysteines is also indicated (FIG. 15A). Similar illustrations are also shown for bsAb 7 (FIG. 15B), bsAb 8 (FIG. 15C), bsAb 5b (FIG. 15D), bsAb 10 (FIG. 15E), and bsAb 12 (FIG. 15F), respectively. The MS results in FIGS. 15A-15F indicated that the expected disulfide crosslinked peptide fragment from the trypsin digested mAb 1 arm of each of the bispecific antibodies (bsAb 6, bsAb 7, bsAb 8, bsAb 5b, bsAb 10 and bsAb 12) can be identified on MS. These data further demonstrated that the knocked in cysteines allowed for the proper formation of the interchain disulfide bond in each of the bispecific antibodies bsAb 6, bsAb 7, bsAb 8, bsAb 5b, bsAb 10 and bsAb 12 (FIGS. 15A-15F).

Figure 16A:
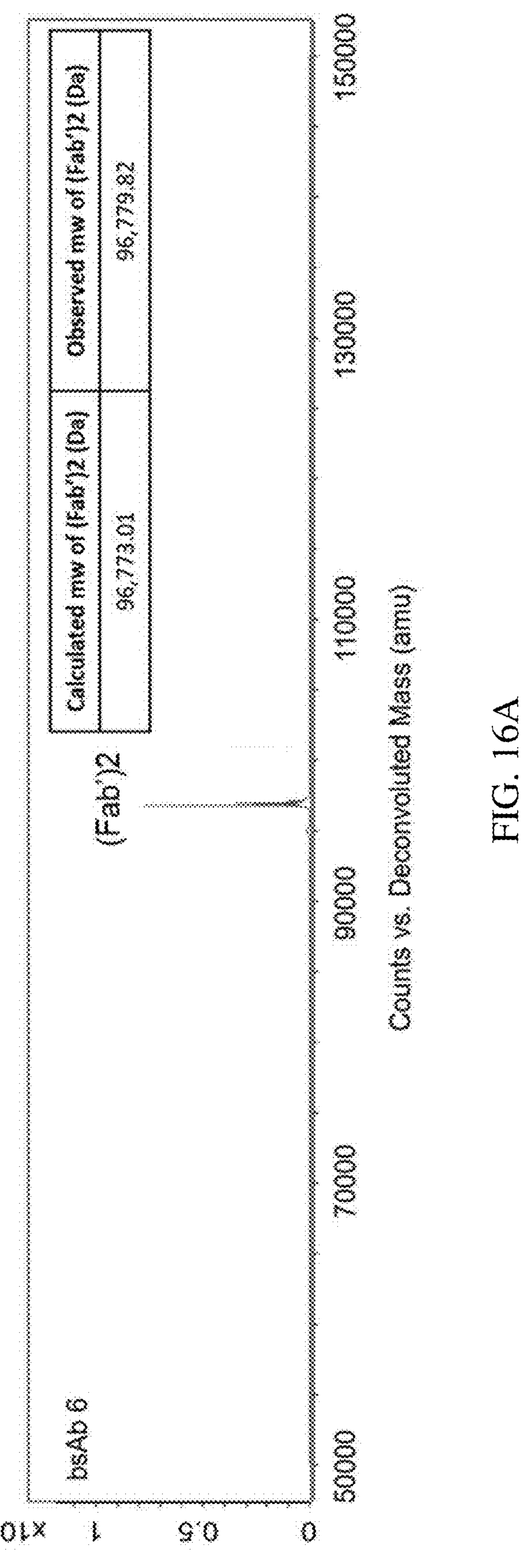
FIGS. 16A-16C show the MS profiles of IdeZ protease digested samples of the HIC purified bispecific antibodies. The (Fab')2 generated from each of the bispecific antibodies was identified.
Figure 16B:
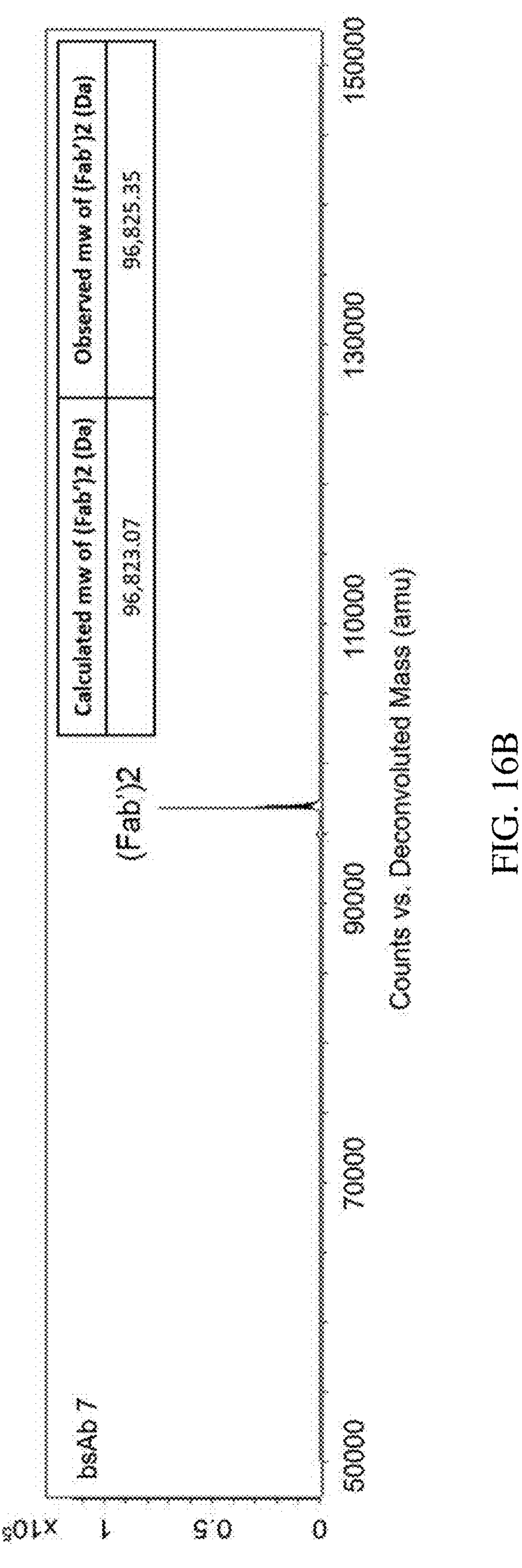
Figure 16C:
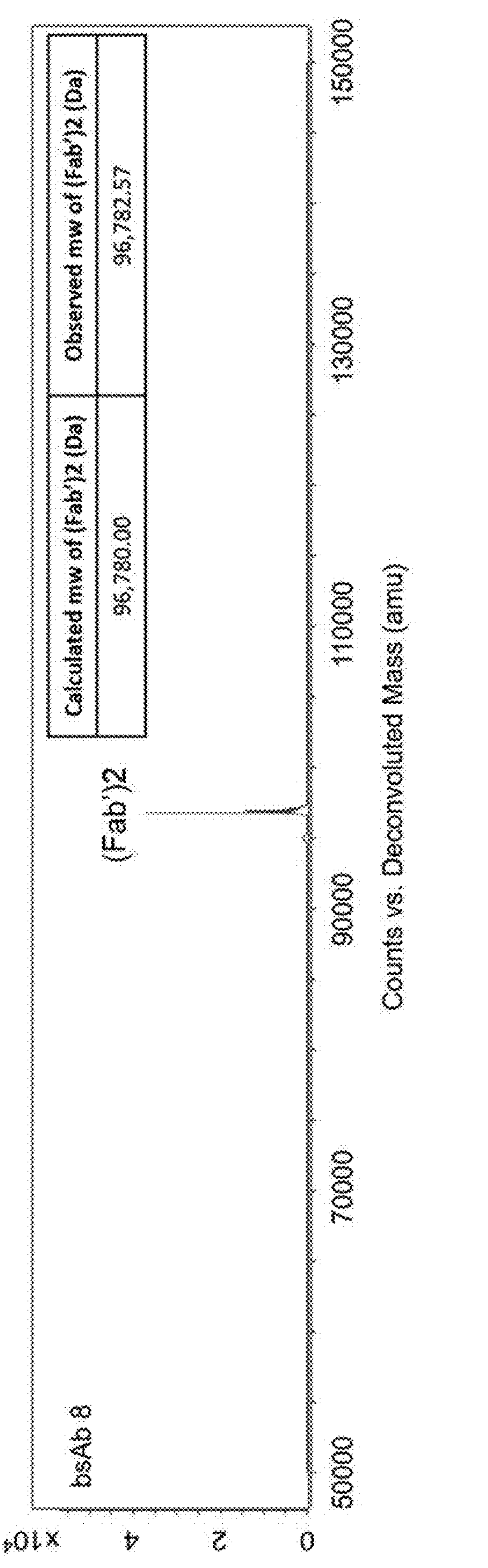

The HIC purified bispecific antibody samples were also subjected to IdeZ protease digestion under non-reducing condition to determine if the calculated (Fab')2 parts from the intended bispecific antibodies were generated. Samples were diluted to a final concentration of 0.5 mg/mL in 1× glycobuffer 2 (NEB). IdeZ protease was added at a ratio of 80 U protease per 12.5 μg antibody. The resulting mixture was incubated at 37° C. for 4 hours and used directly for analysis by mass spectrometry. FIGS. 16A-16C show the MS profiles of IdeZ protease digested samples of the HIC purified bispecific antibodies. The (Fab')2 generated from each of the bispecific antibodies was identified, indicating that the intended bispecific antibodies were formed with properly formed interchain disulfide bonds by the knocked in cysteines.

Figure 17A:
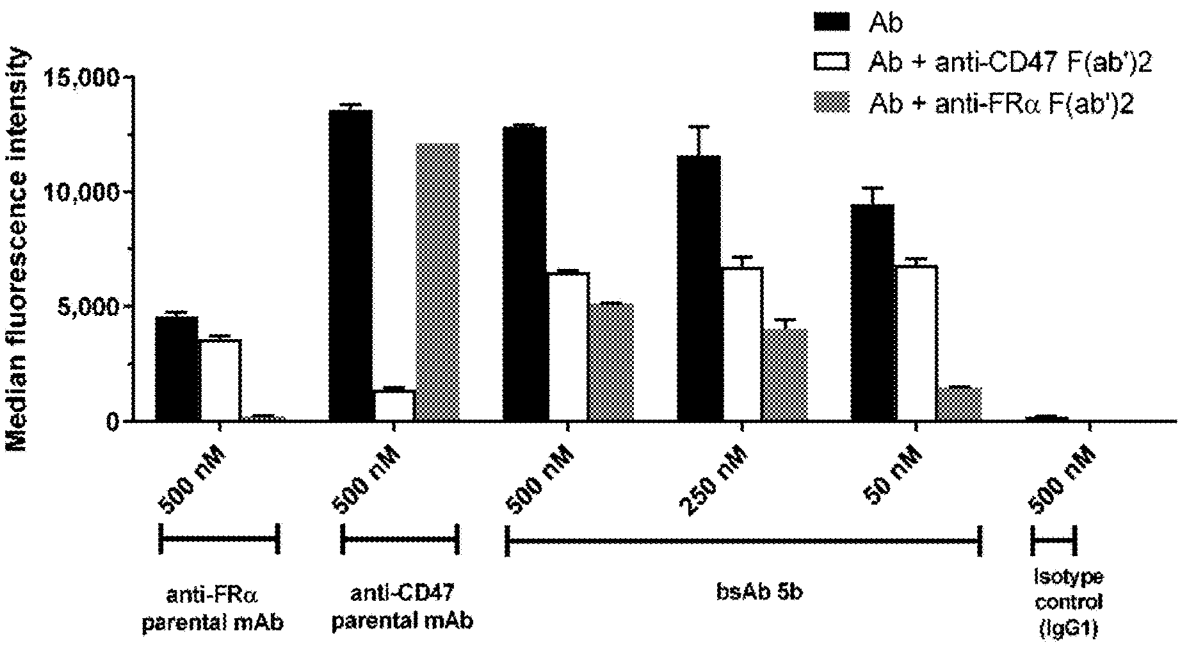
FIGS. 17A-17C show the inhibition of antibody binding to SK-OV-3 cells by F(ab')2 generated from the anti-CD47 or the anti-FRα parental mAb in a FACS assay.
Figure 17B:
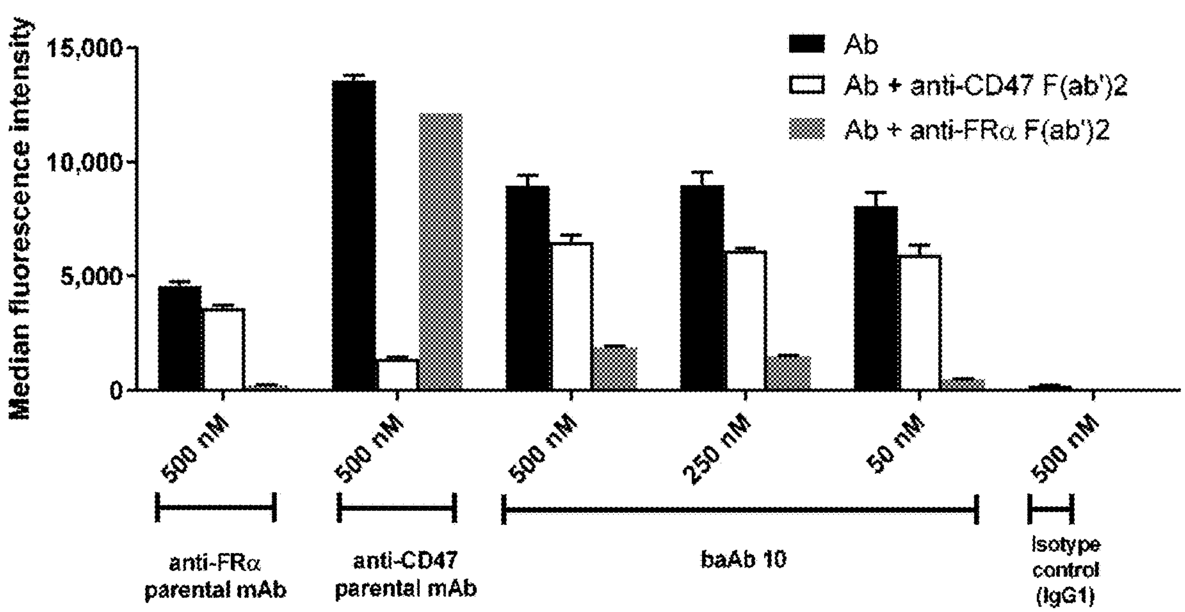
Figure 17C:
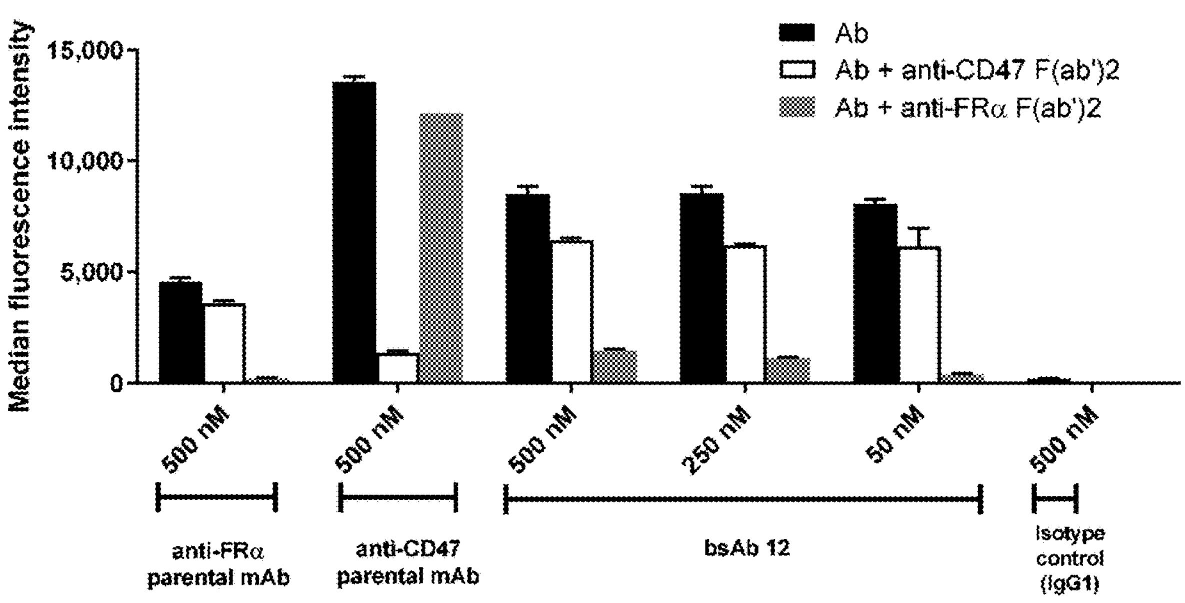
Figure 18A:
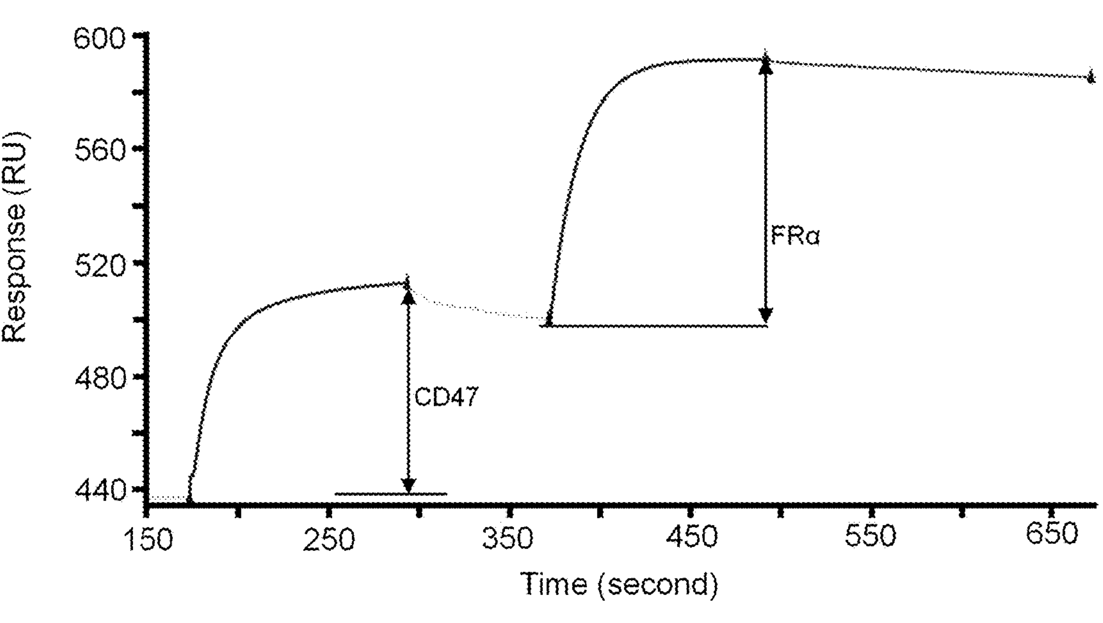
FIGS. 18A-18B show the sequential binding of the two antigens (CD47 and FRα) to the bispecific antibody bsAb 12 on Biacore.
Figure 18B:
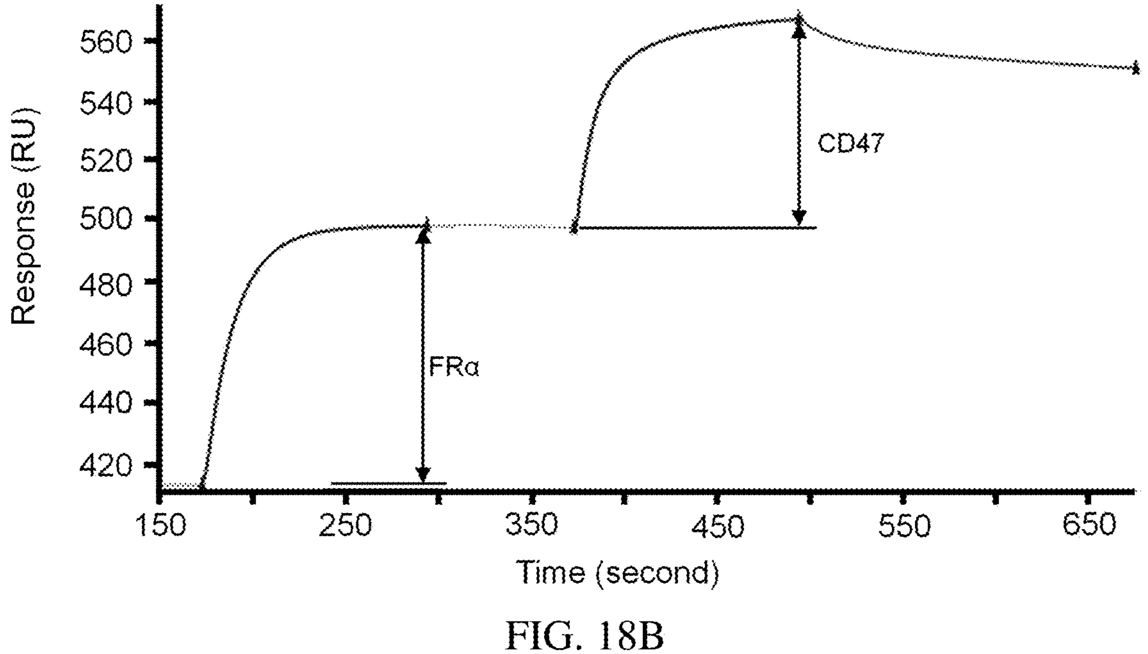

To demonstrate the contribution of both arms of the bispecific antibodies in binding to SK-OV-3 cells, which are known to express both antigens, the inhibition of antibody binding to the cells by F(ab')2 generated from the anti-CD47 or the anti-FRα parental mAb was assessed in a FACS assay. Ab (antibody) concentrations used in the assay are indicated below each graph in FIGS. 17A-17C. The inhibitory effect was tested with 5,000 nM F(ab')2 (FIGS. 17A-17C). Further, the sequential binding of CD47 and FRα to immobilized bsAb 12 was detected using Biacore (FIGS. 18A-18B).

Figure 19A:
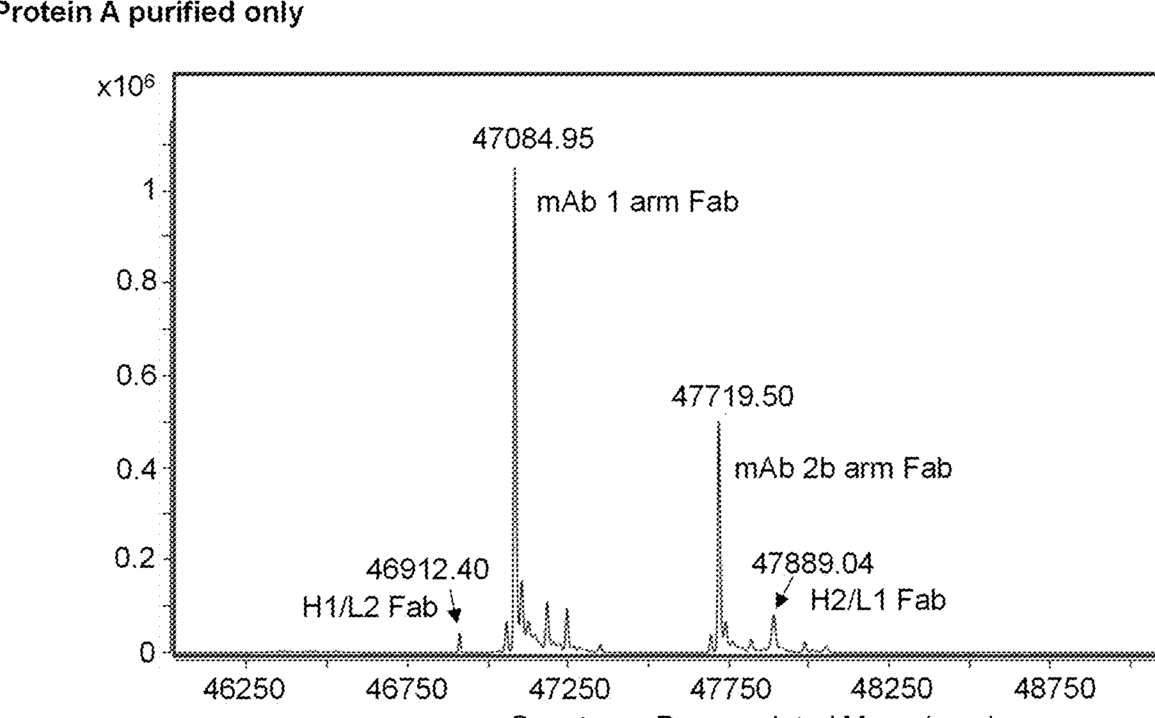
FIGS. 19A-19C show the MS profiles of the Fab fragments from papain digested samples of Protein A purified bispecific antibodies.
Figure 19B:
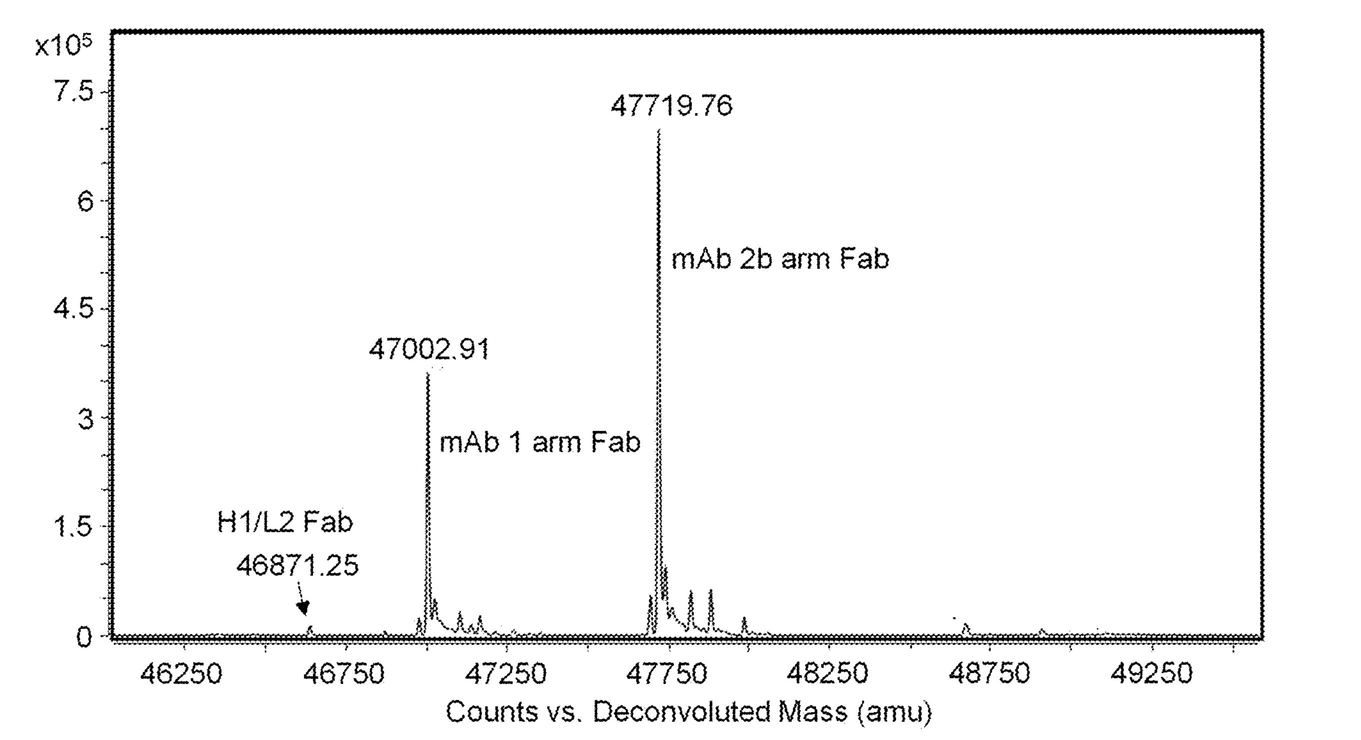
Figure 19C:
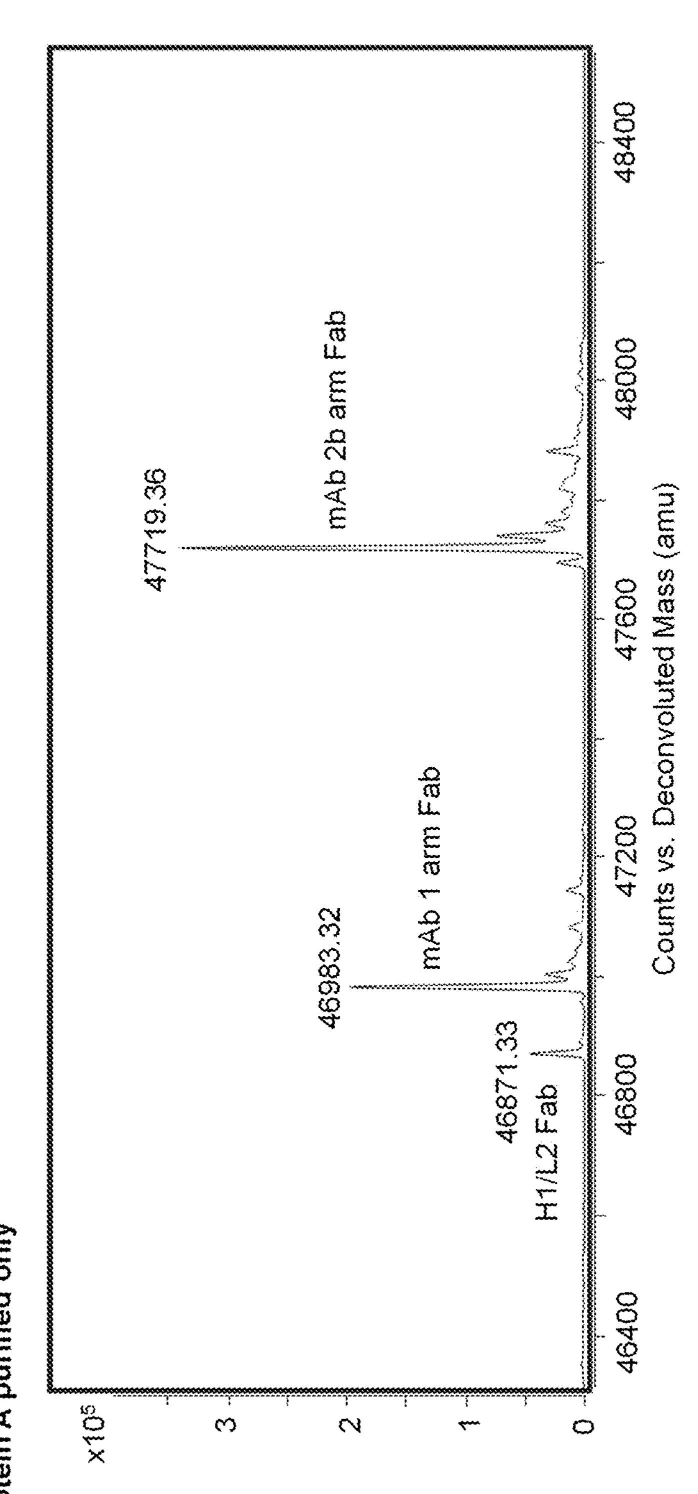
Figure 20:
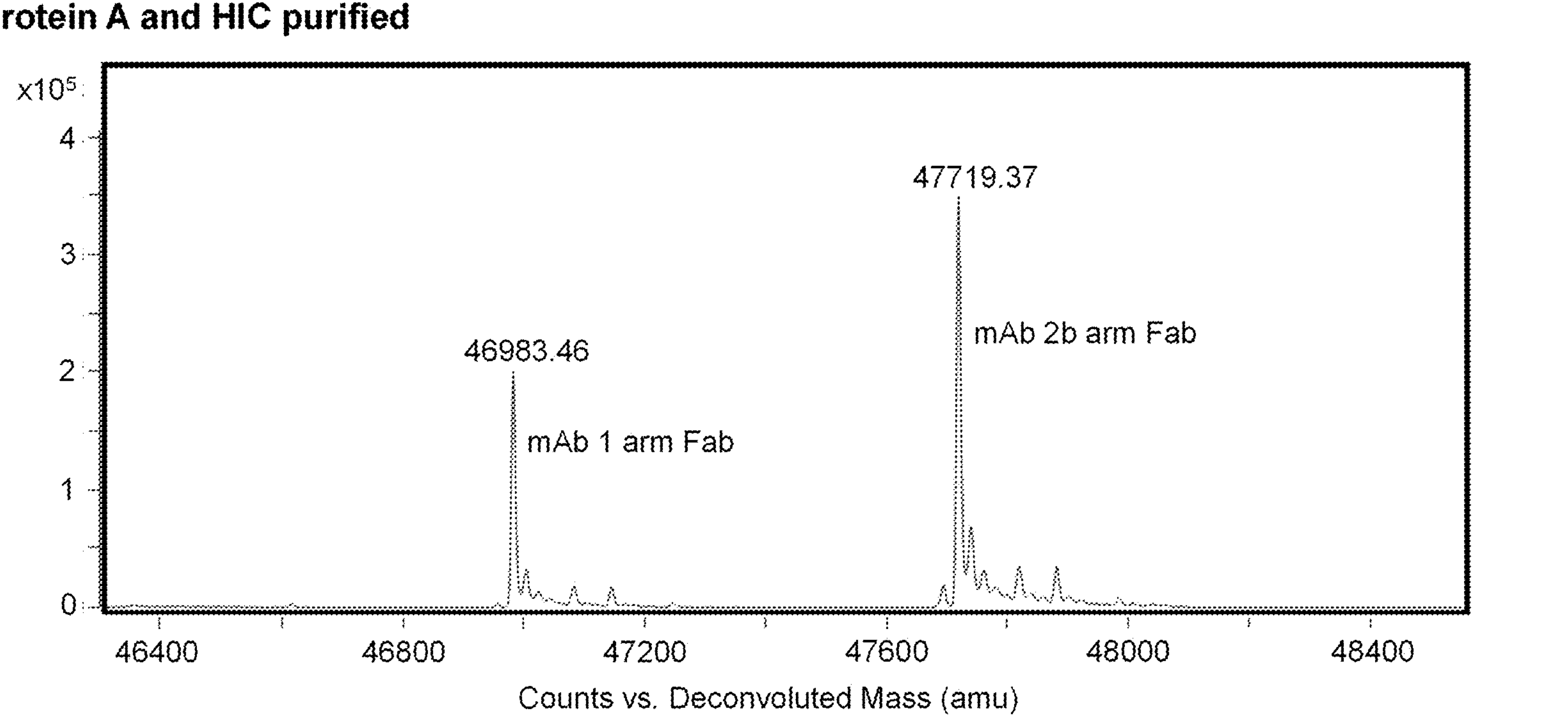
FIG. 20. The MS profile of the Fab fragments from papain digested bsAb 12 that was purified by Protein A followed by HIC purification. No mismatched species was detected.

The Protein A purified bispecific antibodies were digested with papain and the Fab fragments generated from the digestion were identified on MS (FIGS. 19A-19C). In the WT bispecific antibody sample, the Fab fragments from both correctly paired arms as well as those from the two mismatched arms (H1/L2 and H2/L1) were detected (FIG. 19A). However, in the bsAb 10 (FIG. 19B) and bsAb 12 (FIG. 19C) samples, only one of the two mismatched arms was detected. In the meantime, there is no HC/LC mismatched species in the bsAb 10 and bsAb 12 designs that did not form the HC/LC interchain disulfide bond because no LC band was found in these designs on non-reducing SDS-PAGE (FIG. 7C). Therefore, these data indicate that the bsAb 10 and bsAb 12 designs eliminated the formation of the H2/L1 mismatched species; further, the lack of the formation of the H2L1 pairing also supports the conclusion that the scrambled species H1L2/H2L1 did not form. Compared with other bispecific antibody designs using the strategy of shifted HC/LC interchain disulfide bond that have been revealed in the literature, the bsAb 10 and bsAb 12 designs are superior in that they prevent the formation of one mismatched species and the scrambled species. When the Protein A purified bsAb 12 was further purified by HIC, the mismatched H1/L2 Fab disappeared on the MS profile (FIG. 20). The purification process for bsAb 12 was optimized and is shown in Table 4. The yield was 77 mg from 500 mL culture of transiently transfected ExpiCHO cells, which is in the similar range for a mAb in the same transient transfection system.

TABLE 4

Optimization of the purification process for bsAb 12

| Steps | Procedure |
|---|---|
| 1 | Expression in CHO cells: Two 250 mL transiently transfected ExpiCHO cultures. Cultured for 10 days with one feed. |
| 2 | Protein A purification: 20 mL MabSelect PrismA in HiScale 16/40. Bind at 15 mL/min, wash at 15 mL/min with 200 mL PBS and elute at 5 mL/min with 50 mM NaCl in 50 mM citrate (pH 3.7). |
| 3 | Viral inactivation: Hold in the elution buffer for 1 hour. |
| 4 | Neutralization: Add 1M trisodium citrate (pH 6.5) slowly until pH 6.0. |
| 5 | AEX flowthrough: Poros GoPure XQ 5 mL, Flowthrough at 1.5 mL/min. Wash with 25 mM citrate (pH 6.0). Collect all flowthrough and wash fractions. |
| 6 | HIC bind and elute: 50 mL HP butyl resin (Cytiva 17543202) in HiScale 16/40. Buffer A: 1M $(NH_4)_2SO_4$, 50 mM Tris (pH 7.5). Buffer B: 50 mM Tris (pH 7.5). Step wash at 3 mL/min with 450 mL 36% buffer B. Elute with a linear gradient of 43%-50% buffer B over 100 mL. Collect all eluted fractions. The final yield was 77 mg. The purity was 98% by both HIC and SEC-HPLC. |

TABLE 5

Amino acid residues in the CH1 and CL regions for the formation of charged pairs

| Name | CH1 | CL |
|---|---|---|
| bsAb 5 CP | S131 | P119 |
| bsAb 9 CP | A129 | S121 |
| bsAb 10 CP | K133 | K207 |
| bsAb 11 CP | K133 | I117 |
| bsAb 12 CP | K133 | F209 |
| CP9 | G166 | S114 |
| CP10 | T187 | D170 |

Note:
EU numbering is used for the CH1 and CL regions. CP, charged pair.

To further facilitate the HC and LC pairing on each arm of a given bispecific antibody and/or enhance the feasibility of purification using the conventional manufacturing process, amino acid mutations are introduced at a pair of residues on the CH1 and CL regions, respectively, to form a charged pair. Each charged pair or any combination of more than one charged pair can be used to construct bispecific antibodies because they increase correct pairing of HC and LC and/or facilitate purification by introducing differential physical properties when compared with impurities (i.e., mismatched molecular species). Any charged pair or any combination of the charged pairs in Table 5 can be combined with other charged pairs (either known in the literature or newly designed) to achieve and/or enhance correct HC/LC pairing and/or facilitate purification by introducing differential physical properties when compared with impurities (i.e., mismatched molecular species). One of the two residues for the formation of charged pairs can be substituted with glutamate (E) and the other can be substituted with lysine (K), or vice versa. For example, on a given bispecific antibody consisting H1L1 and H2L2, if "E" is introduced on H1 and "K" is introduced on L1, then "K" is introduced on H2 and "E" is introduced on L2. The two residues for the formation of charged pairs can be replaced with acidic and basic amino acids, respectively, other than "E" and "K". For example, the residue where "E" is introduced can also be substituted with aspartate (D) if "E" is not used. Whenever the native amino acid at a given residue happens to be the intended substitution amino acid (i.e., E, D, or K), no mutation is needed. The amino acid residues in CH1 and CL regions for the formation of charged pairs are listed in Table 5. Each pair of these residues is selected through 3-D modeling based on a variety of factors including proximity.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated bispecific antibody or antigen-binding fragment thereof comprising:

a. a first heavy chain, H1;

b. a second heavy chain, H2;

c. a first light chain, L1; and d. a second light chain, L2;

wherein H1 and L1 form a first arm comprising a first antigen-binding domain that specifically binds a first antigen, wherein the first antigen-binding domain comprises a VH region and a VL region, and wherein H2 and L2 form a second arm comprising a second antigen-binding domain that specifically binds a second antigen, wherein the second antigen-binding domain comprises a VH region and a VL region, wherein (a) H1 comprises a CH1 region of human IgG1, IgG2, IgG3, or IgG4; and (b) L1 comprises a CL region of a human kappa light chain or a human lambda light chain;

wherein the CH1 region sequence of H1 is selected from the group consisting of SEQ ID NO:15, 21, 22, and 23; the CL region sequence of L1 is selected from SEQ ID NO:19 or 24; and wherein the CH1 and CL regions further comprise amino acid substitutions selected from:

(1) K133C and C220X in CH1, and F209C and C214X in CL;

(2) K133C and C220X in CH1, and K207C and C214X in CL;

(3) R133C and C131X in CH1, and K207C and C214X in CL;

(4) R133C and C131X in CH1, and F209C and C214X in CL;

(5) R133C and C131X in CH1, and V209C and C214X in CL; or (6) K133C and C220X in CH1, and V209C and C214X in CL;

wherein X is selected from S, A or G;

wherein the second arm comprising H2 and L2 does not comprise the amino acid substitutions of the first arm comprising H1 and L1, maintaining its native interchain disulfide bond, and wherein EU numbering is used for the CH1 and CL regions.

2. An isolated bispecific antibody or antigen-binding fragment thereof comprising:

a. a first heavy chain, H1;

b. a second heavy chain, H2;

c. a first light chain, L1; and d. a second light chain, L2;

wherein H1 and L1 form a first arm comprising a first antigen-binding domain that specifically binds a first antigen, wherein the first antigen-binding domain comprises a VH region and a VL region, and wherein H2 and L2 form a second arm comprising a second antigen-binding domain that specifically binds a second antigen, wherein the second antigen-binding domain comprises a VH region and a VL region, wherein (a) H1 comprises a CH1 region of human IgG1, IgG2, IgG3, or IgG4 and a heavy chain variable region (VH region); and (b) L1 comprises a CL region of a human kappa light chain or a human lambda light chain and a light chain variable region (VL region);

wherein the CH1 region sequence of H1 is selected from the group consisting of SEQ ID NO: 15, 21, 22, and 23, the VH region sequence of H1 is SEQ ID NO:13, the CL region sequence of L1 is selected from SEQ ID NO:19 or 24, and the VL region sequence of L1 is SEQ ID NO:17; and wherein the CH1, VH1, CL, and VL regions further comprise amino acid substitutions selected from:

(1) C220X in CH1, G44C in VH, C214X in CL, and G101C in VL; or (2) C131X in CH1, G44C in VH, C214X in CL, and G101C in VL;

wherein X is selected from S, A or G;

wherein the second arm comprising H2 and L2 does not comprise the amino acid substitutions of the first arm comprising H1 and L1, maintaining its native interchain disulfide bond, and wherein EU numbering is used for the CH1, VH, CL, and VL regions.

3. The isolated bispecific antibody or antigen-binding fragment thereof of claim 1, wherein the first antigen-binding domain is a CD47 binding domain.

4. The isolated bispecific antibody or antigen-binding fragment thereof of claim 3, wherein the VH region comprises the amino acid sequence of SEQ ID NO: 1, and the VL region comprises the amino acid sequence of SEQ ID NO: 3.

5. The isolated bispecific antibody or antigen-binding fragment thereof of claim 1, wherein (a) the two heavy chains H1 and H2 each comprise a VH region, a CH1 region, and a Fc region (containing CH2 and CH3 regions), wherein the VH regions have different amino acid sequences;

(b) the two heavy chains H1 and H2 each comprise a VH region, a CH1 region, and a Fc region (containing CH2 and CH3 regions), wherein the CH1 regions have different amino acid sequences;

(c) the two heavy chains H1 and H2 each comprise a VH region, a CH1 region, and a Fc region (containing CH2 and CH3 regions), wherein the Fc regions have different amino acid sequences;

(d) the two light chains L1 and L2 each comprise a VL region and a CL region, wherein the VL regions have different amino acid sequences; and/or (e) the two light chains L1 and L2 each comprise a VL region and a CL region, wherein the CL regions have different amino acid sequences.

6. The isolated bispecific antibody or antigen-binding fragment thereof of claim 5, wherein H1 and H2 form a heterodimer.

7. The isolated bispecific antibody or antigen-binding fragment thereof of claim 1, wherein (a) the VH region of H1 and the VL region of L1 have a Q39E and a Q38K substitution mutation, respectively, and the VH region of H2 and the VL region of L2 have a Q39K and a Q38E substitution mutation, respectively; or (b) the VH region of H1 and the VL region of L1 have a Q39K and a Q38E substitution mutation, respectively, and the VH region of H2 and the VL region of L2 have a Q39E and a Q38K substitution mutation, respectively.

8. The isolated bispecific antibody or antigen-binding fragment thereof of claim 1, wherein the isolated bispecific antibody or antigen-binding fragment is an anti-CD47/anti-FRα bispecific antibody or antigen-binding fragment thereof, wherein the first antigen-binding domain specifically binds CD47, and the second antigen-binding domain specifically binds folate receptor α (FRα).

9. The isolated bispecific antibody or antigen-binding fragment thereof of claim 1, wherein (a) the first antigen-binding domain has the VH sequence of SEQ ID: 13 and VL sequence of SEQ ID: 17, and the second antigen-binding domain has the VH sequence of SEQ ID: 33 and VL sequence of SEQ ID: 35; or (b) the first antigen-binding domain has the VH sequence of SEQ ID: 13 and VL sequence of SEQ ID: 17, and the second antigen-binding domain has the VH sequence of SEQ ID: 14 and VL sequence of SEQ ID: 18.

10. The isolated bispecific antibody or antigen-binding fragment thereof of claim 8, wherein the anti-CD47/anti-FRα bispecific antibody or antigen-binding fragment thereof is capable of blocking binding of signal regulatory protein alpha (SIRPα) to CD47 on cancer cells that express both FRα and CD47, inducing macrophage-mediated phagocytosis of cancer cells that express both FRα and CD47, and/or binding cancer cells that express both FRα and CD47 with minimal to undetectable binding to human red blood cells (RBCs).

11. An isolated nucleic acid encoding the bispecific antibody or antigen-binding fragment of claim 1.

12. A vector comprising the isolated nucleic acid of claim 11.

13. A host cell comprising the vector of claim 12.

14. A pharmaceutical composition, comprising the isolated bispecific antibody or antigen-binding fragment thereof of claim 1 and a pharmaceutically acceptable carrier.

15. A method of targeting FRα and CD47 that are both expressed on a cancer cell surface in a subject in need thereof, blocking the binding of SIRPα to CD47 on cancer cells that express both FRα and CD47 in a subject in need thereof, inducing macrophage-mediated phagocytosis of cancer cells that express both FRα and CD47 in a subject in need thereof, binding cancer cells that express both FRα and CD47 with minimal to undetectable binding to human red blood cells (RBCs) in a subject in need thereof, and/or treating cancer in a subject in need thereof, comprising administering to the subject a pharmaceutical composition comprising the isolated anti-CD47/anti-FRα bispecific antibody or antigen-binding fragment thereof of claim 8 and a pharmaceutically acceptable carrier, optionally the cancer is selected from the group consisting of a lung cancer, a gastric cancer, an esophageal cancer, a bile duct cancer, a cholangiocarcinoma, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

16. A method of producing the bispecific antibody or antigen-binding fragment thereof of claim 1, comprising culturing a cell comprising a vector comprising a nucleic acid encoding the bispecific antibody or antigen-binding fragment thereof under conditions to produce the bispecific antibody or antigen-binding fragment thereof, and recovering the bispecific antibody or antigen-binding fragment thereof from the cell or culture.

17. A method of producing a pharmaceutical composition comprising the bispecific antibody or antigen-binding fragment thereof of claim 1, comprising combining the bispecific antibody or antigen-binding fragment thereof with a pharmaceutically acceptable carrier to obtain the pharmaceutical composition.

18. The isolated bispecific antibody or antigen-binding fragment thereof of claim 1, wherein H1 and H2 comprise one or more mutations in CH3 region to promoter heterodimer formation.

19. The isolated bispecific antibody or antigen-binding fragment thereof of claim 1, wherein the amino acid substitutions allow the formation of a single disulfide bond between H1 and L1.

* * * * *